United States Patent
Wong et al.

(10) Patent No.: US 12,428,633 B2
(45) Date of Patent: Sep. 30, 2025

(54) INDUCIBLE DIMERIZATION OF RECOMBINASES

(71) Applicant: TRUSTEES OF BOSTON UNIVERSITY, Boston, MA (US)

(72) Inventors: Wilson W. Wong, Brookline, MA (US); Benjamin Harris Weinberg, Boston, MA (US)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 0 days.

(21) Appl. No.: 15/838,598

(22) Filed: Dec. 12, 2017

(65) Prior Publication Data

US 2018/0163195 A1 Jun. 14, 2018

Related U.S. Application Data

(60) Provisional application No. 62/432,916, filed on Dec. 12, 2016.

(51) Int. Cl.
C12N 9/00 (2006.01)
C12N 9/96 (2006.01)

(52) U.S. Cl.
CPC ............................ C12N 9/96 (2013.01); C12N 9/00 (2013.01)

(58) Field of Classification Search
None
See application file for complete search history.

(56) References Cited

U.S. PATENT DOCUMENTS

| 2009/0031441 A1 | 1/2009 | Matsuoka et al. |
| 2012/0003630 A1 | 1/2012 | Collins |
| 2014/0315310 A1 | 10/2014 | Lu |

(Continued)

FOREIGN PATENT DOCUMENTS

| WO | 2015/188191 A1 | 12/2015 | |
| WO | WO-2015188094 A1 * | 12/2015 | ............. C07K 14/00 |

OTHER PUBLICATIONS

Guo et al., Nature vol. 389, pp. 40-46, Sep. 1997.*
(Continued)

*Primary Examiner* — Richard G Hutson
(74) *Attorney, Agent, or Firm* — Nixon Peabody LLP; Ronald I. Eisenstein; Alissa R. Young

(57) ABSTRACT

The technology described herein relates to controlled chemically- or light-induced rejoinder of split-recombinases. In some embodiments, compositions, methods, kits and systems are provided that relate to a split-recombinase system, whereby protein complementation or rejoinder of split-recombinases is mediated by chemical-induced dimerization domains (CIDDs) or light-induced dimerization domains (LIDD) and rejoinder of the split-recombinases occur in the presence of one or more chemical inducers or light inducers, respectively. The split-recombinases systems as disclosed herein can be used in gene therapy, integrated logic and memory in living cells such as mammalian cells. The nucleic acid cassettes, switches, and systems described herein allow for controlled gene expression or gene regulation. The controlled chemically- or light-induced rejoinder of split-recombinases can be used in, for example, adopted T-cell therapy.

12 Claims, 48 Drawing Sheets

Specification includes a Sequence Listing.

(56) References Cited

U.S. PATENT DOCUMENTS

2016/0264665 A1  9/2016  Lim et al.
2017/0306336 A1* 10/2017  Lu ..................... A01K 67/0275

OTHER PUBLICATIONS

Roybal et al., "Precision Tumor Recognition by T Cells With Combinatorial Antigen-Sensing Circuits", Cell 164(4) 770-779 (2016).
Sajgo et al., "Dre-Cre sequential recombination provides new tools for retinal ganglion cell labeling and manipulation in mice", PLoS One 9(3) e91435 (2014).
Sarkar et al., "HIV-1 proviral DNA excision using an evolved recombinase", Science 316(5833) 1912-1915 (2007).
Sauer et al., "DNA recombination with a heterospecific Cre homolog identified from comparison of the pac-c1 regions of P1-related phages", Nuclec Acids 32(20) 6086-6095 (2004).
Schonhuber et al., "A next-generation dual-recombinase system for time- and host-specific targeting of pancreatic cancer", Nat Med 20(11) 1340-1347 (2014).
Shaikh et al., "Chimeras of the Flp and Cre recombinases: tests of the mode of cleavage by Flp and Cre", J Mol Biol 302(1) 27-48 (2000).
Shannon et al., "The Synthesis of Two-Terminal Switching Circuits", Bell Labs Technical Journal 28(1) 59-98 (1949).
Sirk et al., "Expanding the zinc-finger recombinase repertoire: directed evolution and mutational analysis of serine recombinase specificity determinants", Nucleic Acids Res 42(7) 4755-4766 (2014).
Situti et al., "Synthetic circuits integrating logic and memory in living cells", Nat Biotechnol 31(5) 448-452 (2013).
Slomovic et al., "DNA sense-and-respond protein modules for mammalian cells", Nat Methods 12(11) 1085-1090 (2015).
Stanton et al., "Genomic mining of prokaryotic repressors for orthogonal logic gates", Nat Chem Biol 10(2) 99-105 (2014).
Stricker et al., "A fast, robust and tunable synthetic gene oscillator", Nature 456(7221) 516-519 (2008).
Suzuki et al., "VCre/VloxP and SCre/SloxP: new site-specific recombination systems for genome engineering", Nucleic Acids Res 39(8) e49 (2011).
Tamsir et al., "Robust multicellular computing using genetically encoded NOR gates and chemical 'wires'", Nature 469(7329) 212-215 (2011).
Torella et al., "Rapid construction of insulated genetic circuits via synthetic sequence-guided isothermal assembly", Nucleic Acids Res 42(1) 681-689 (2014).
Torella et al., "Unique nucleotide sequence-guided assembly of repetitive DNA parts for synthetic biology applications", Nat Protoc 9(9) 2075-2089 (2014).
Torikai et al., "Toward eliminating HLA class I expression to generate universal cells from allogeneic donors", Blood 122: 1341-1349 (2013).
Weber et al., "A synthetic time-delay circuit in mammalian cells and mice", Proc Natl Acad Sci 104(8) 2643-2648 (2007).
Wei et al., "Bacterial virulence proteins as tools to rewire kinase pathways in yeast and immune cells", Nature 488 (7411) 384-388 (2012).
Xie et al., "Multi-input RNAi-based logic circuit for identification of specific cancer cells", Science 333(6047) 1307-1311 (2011).
Zhao et al., "Heterelogous expression of mutated HLA-G decreases immunogenicity of human embryonic stem cells and their epidermal derivatives", Stem Cell Res 13(2) 342-354 (2014).
Akopian et al., "Chimeric recombinases with designed DNA sequence recognition", Proc Natl Acad Sci USA 100(15) 8688-8691 (2003).
Appleton et al.,+55:78 "Interactive assembly algorithms for molecular cloning", Nat Methods 11(6) 657-662 (2014).
Blomfield et al., "The regulation of pap and type 1 fimbriation in Escherichia coli", Adv Microb Physiol 45: 1-49 (2001).
Bogorad et al., "Synthetic non-oxidative glycolysis enables complete carbon conservation", Nature 502(7473) 693-697 (2013).
Bonnet et al., "Amplifying genetic logic gates", Science 340(6132) 599-603 (2013).
Bonnet et al., "Rewritable digital data storage in live cells via engineered control of recombination directionality", Proc Natl Acad Sci USA 109(23) 8884-8889 (2012).
Branda et al., "Talking about a revolution: The impact of site-specific recombinases on genetic analyses in mice", Dev Cell 6(1) 7-28 (2004).
Brophy et al., "Principles of genetic circuit design", Nat Methods 11(5) 508-520 (2014).
Canton et al., "Refinement and standardization of synthetic biological parts and devices", Nat Biotechnol 26(7) 787-793 (2008).
Chakravarti et al., "Synthetic biology in cell-based cancer immunotherapy", Trends Biotechnol 33(8) 449-461 (2015).
Chavez et al., "Highly efficient Cas9-mediated transcriptional programming", Nat Methods 12(4) 326-328 (2015).
Chen et al., "Characterization of 582 natural and synthetic terminators and quantification of their design constraints", Nat Methods 10(7) 659-664 (2013).
Chen et al., "Synthetic Biology. Emergent genetic oscillations in a synthetic microbial consortium", Science 349 (6251) 986-989 (2015).
Courbert et al., "Detection of pathological biomarkers in human clinical samples via amplifying genetic switches and logic gates", Sci Transl Med 7(289) 289ra83 (2015).
Elowitz et al., "A synthetic oscillatory network of transcriptional regulators", Nature 403(6767) 335-338 (2000).
Farruggio et al., "Serine integrase chimeras with activity in *E. coli* and Hela cells", Bio Open 3(10) 895-903 (2014).
Fenno et al., "Targeting cells with single vectors using multiple-feature Boolean logic", Nat Methods 11(7) 763-772 (2014).
Friedland et al., "Synthetic gene networks that count", Science 324(5931) 1199-1202 (2009).
Gaber et al., "Designable DNA-binding domains enable construction of logic circuits in mammalian cells", Nat Chem Biol 10(3) 203-208 (2014).
Gardner et al., "Construction of a genetic toggle switch in Escherichia coli", Nature 403(6767) 339-342 (2000).
Gordley et al., "Synthesis of programmable integrases", Proc Natl Acad Sci USA 106(13) 5053-5058 (2009).
Green et al., "Toehold switches: de-novo-designed regulators of gene expression", Cell 159(4) 925-939 (2014).
Grupp et al., "Chimeric antigen receptor-modified T cells for acute lymphoid leukemia", N Engl J Med 368(16) 1509-1518 (2013).
Guilinger et al., "Fusion of catalytically inactive Cas9 to FokI nuclease improves the specificity of genome modification", Nature Biotechnology 32; 577-582 (2014).
Guinn et al., "Biological 2-input decoder circuit in human cells", ACS Synth Biol 3(8) 627-633 (2014).
Ham et al., "Design and construction of a double inversion recombination switch for heritable sequential genetic memory", PLoS One 3(7) e2815 (2008).
Hauber et al., "Highly significant antiviral activity of HIV-1 LTR-specific tre-recombinase in humanized mice", PLoS Pathology 9(9) e1003587 (2013).
Hsiao et al., "A population-based temporal logic gate for timing and recording chemical events", Mol Syste Biol 12(5) 869 (2016).
Huynh et al., "Automatic design of synthetic gene circuits through mixed integer non-linear programming", PLoS One 7(4) e35529 (2012).
Jayanthi et al., "Retroactivity controls the temporal dynamics of gene transcription", ACS Synth Biol 2(8) 431-441 (2013).
Johnson, "Chapter 13: Bacterial Site-Specific SNA Inversion Systems" Mobile DNA II, ASM Press, Washington, D.C., 2002.
Jullien et al., "Regulation of Cre recombinase by ligand-induced complementation of inactive fragments", Nucleic Acids Res 31(21) e131 (2003).
Karimova et al., "Vika/vox, a novel efficient and specific Cre/loxP-like site-specific recombination system", Nucleic Acids Res 41(2) e37 (2013).
Karpinski et al., "Directed evolution of a recombinase that excises the provirus of most HIV-1 primary isolates with high specificity", Nat Biotechnol 34(4) 401-409 (2016).

(56) References Cited

OTHER PUBLICATIONS

Khalil et al., "A synthetic biology framework for programming eukaryotic transcription functions", Cell 150(3) 647-658 (2012).
Khalil et al., "Synthetic biology: applications come of age", Nat Rev Genet 11(5) 367-379 (2010).
Lee et al., "Role of nucleotide sequences of loxP spacer region in Cre-mediated recombination", Gene 216(1) 55-65 (1998).
Leisner et al., "Rationally designed logic integration of regulatory signals in mammalian cells", Nat Nanotechnol 5(9) 666-667 (2010).
Madisen et al., "Transgenic mice for intersectional targeting of neural sensors and effectors with high specificity and performance", Neuron 85(5) 942-958 (2015).
Mercer et al., "Chimeric TALE recombinases with programmable DNA sequence specificity", Nucleic Acids Res 40 (21) 11163-11172 (2012).
Moon et al., "Genetic programs constructed from layered logic gates in single cells", Nature 491(7423) 249-253 (2012).
Morgan et al., "Case report of a serious adverse event following the administration of T cells transduced with a chimeric antigen receptor recognizing ERBB2", Mol Ther 18(4) 843-851 (2010).
Mutalik et al., "Quantitative estimation of activity and quality for collections of functional genetic elements", Nat Methods 10(4) 347-353 (2013).
Nagy, "Cre recombinase: the universal reagent for genome tailoring", Genesis 26(2) 99-109 (2000).
Neilsen et al., "Genetic circuit design automation", Science 352(6281) aac7341 (2016).
Regot et al., "Distributed biological computation with multicellular engineered networks", Nature 469(7329) 207-211 (2011).
Ro et al., "Production of the antimalarial drug precursor artemisinic acid in engineered yeast", Nature 440(7086) 940-943 (2006).
Rodrigo et al., "AutoBioCAD: full biodesign automation of genetic circuits", ACS Synth Biol 2(5) 230-236 (2013).
Roquet et al., "Synthetic recombinase-based state machines in living cells", Science 353(6297) aad8559 (2016).

\* cited by examiner

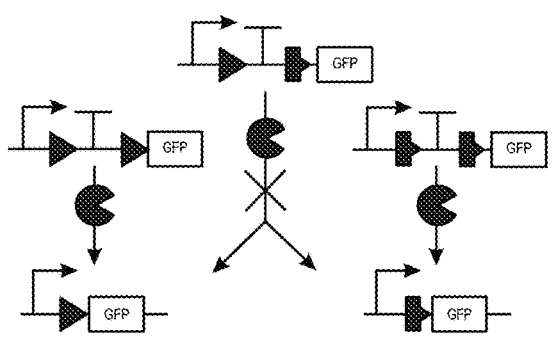
FIG. 9
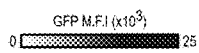
FIG. 10A
FIG. 10B

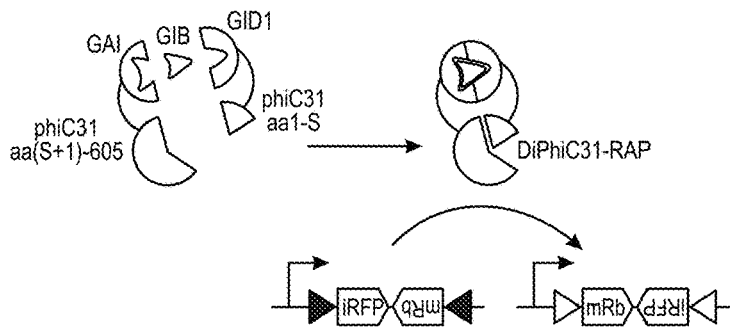
FIG. 39A
| | mean mRuby2 (a.u.) | | mean iRFP (a.u.) | |
|---|---|---|---|---|
| Rapalog: | − | + | − | + |
| S = 233 | 539 | 22169 | 62867 | 19480 |
| 300 | 67 | 4525 | 48701 | 32004 |
| 314 | 73 | 1857 | 50947 | 37892 |
| 349 | 70 | 2460 | 46570 | 40066 |
| 379 | 68 | 1198 | 34868 | 36636 |
| 396 | 79 | 13489 | 50282 | 22561 |
| 428 | 162 | 13828 | 47478 | 18923 |
| 571 | 73 | 12063 | 41061 | 13253 |
| PhiC31 | 14775 | 14526 | 8804 | 8398 |
| NLS-PhiC31 | 16901 | 16431 | 29014 | 30132 |
| PhiC31- | 31311 | 29053 | 10522 | 10662 |
| Blank | 93 | 76 | 47863 | 38703 |
FIG. 39B
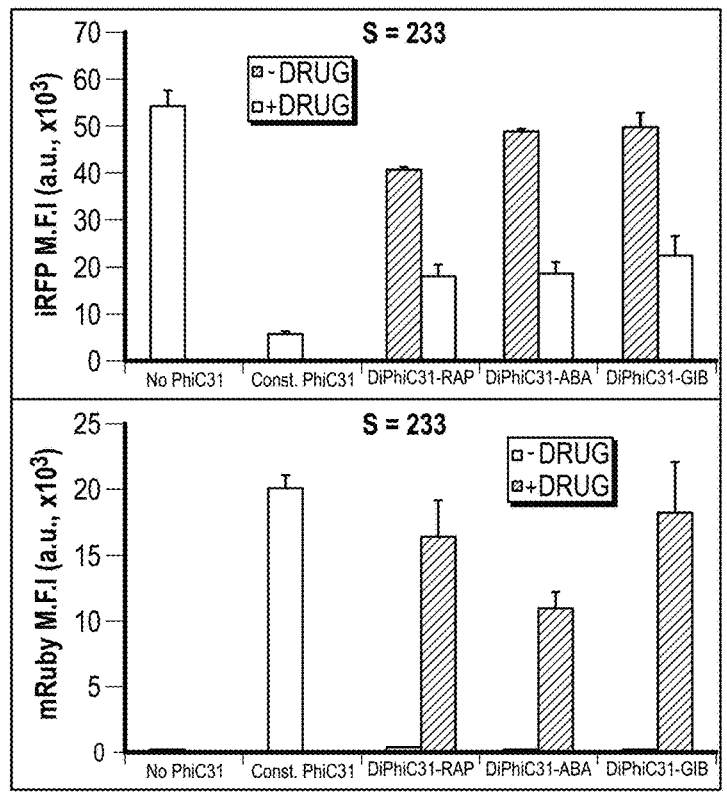
FIG. 39C

PHAGE-DERIVED TYROSINE RECOMBINASES
(Vcre aligned to Cre)

Cre Ribbon Model

| Cre (42): | Flp (20): | PhiC31 (13): | VCre (20): | B3 (28): | Bxb1 (1): |
|---|---|---|---|---|---|
| 37 | 27 | 44 | 58 | 27 | 468 |
| 61 | 49 | 81 | 82 | 49 | |
| 66 | 74 | 113 | 87 | 74 | |
| 83 | 81 | 233 | 103 | 84 | |
| 105 | 106 | 300 | 125 | 106 | |
| 128 | 112 | 314 | 154 | 122 | |
| 134 | 132 | 349 | 172 | 146 | |
| 152 | 150 | 379 | 192 | 164 | |
| 172 | 168 | 396 | 210 | 206 | |
| 190 | 234 | 428 | 220 | 220 | |
| 200 | 249 | 484 | 227 | 230 | |
| 207 | 257 | 520 | 249 | 234 | |
| 229 | 264 | 571 | 257 | 250 | |
| 251 | 275 | | 269 | 254 | |
| 256 | 290 | | 277 | 259 | |
| 275 | 301 | | 285 | 285 | |
| 280 | 349 | | 303 | 345 | |
| 287 | 374 | | 312 | 378 | |
| 305 | 392 | | 330 | 394 | |
| 316 | 396 | | 366 | 403 | |
| 94 | | | | 428 | |
| 125 | | | | 439 | |
| 131 | | | | 495 | |
| 163 | | | | 504 | |
| 184 | | | | 512 | |
| 219 | | | | 527 | |
| 248 | | | | 539 | |
| 270 | | | | 549 | |
| 298 | | | | | |
| 327 | | | | | |
| 26 | | | | | |
| 47 | | | | | |
| 74 | | | | | |
| 119 | | | | | |
| 144 | | | | | |
| 177 | | | | | |
| 195 | | | | | |
| 210 | | | | | |
| 263 | | | | | |
| 309 | | | | | |
| 321 | | | | | |
| 334 | | | | | |

INDUCIBLE DIMERIZATION OF RECOMBINASES

CROSS-RELATED APPLICATIONS

This application claims under 35 U.S.C. 119(e) claims the benefit of U.S. Provisional Patent Application Ser. No. 62/432,916 filed on Dec. 12, 2016, the contents of which is incorporated herein in its entirety by reference.

GOVERNMENT SUPPORT

This invention was made with Government Support under Contract No. CA186574 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Dec. 12, 2017 is named 701586-088161-US_SL.TXT and is 116,787 bytes in size.

TECHNICAL FIELD

The present invention relates generally to controlled gene expression, engineered gene circuits, and adoptive T cell therapies.

BACKGROUND OF THE INVENTION

Methods of genome engineering permitting controlled regulation of gene expression have been increasingly important in a wide range of areas, including but not limited to gene therapy, synthetic biology, plant management, environmental clean-up, bacterial and microbial management and synthetic genetic circuits. Synthetic genetic circuits hold vast potential at revolutionizing therapeutics, animal models, and biotechnological processes and are useful to integrate multiple input signals and deliver multiple outputs for cell-based therapy and animal model development. Despite rapid advances in recent years, genome regulation required for example, for engineering complex genetic circuits remains a challenge due to difficult circuit performance predictability stemming from unintended interactions between cascading biological components, such as transcription factors, chaperonins, or miRNAs.

In particular, without greater precision in gene regulation, for example, engineering even simple circuits in mammalian cells often requires extensive fine-tuning. A fundamental goal in synthetic biology and cellular engineering is to predictably and efficiently reprogram cells to perform novel tasks[1]. Genetically engineered cells hold great promise for advancing therapeutics[2-4], diagnostics[5,6], animal models[7,8], and biotechnological processes[9,10]. Synthetic gene circuits with multiple inputs and outputs are increasingly relied upon to endow cells with new decision-making capabilities and carry out the desired tasks. Despite rapid advances and encouraging results in cell consortia[11-19], building even simple gene circuits in single cells remains challenging due to inadvertent reactions between cascading biological parts[20]. In addition, no reliable framework is available to aid the design of synthetic circuits in mammalian cells. As such, genetic circuit designs are usually done in an ad hoc fashion and not generalizable. Extensive fine-tuning is often required to engineer functional circuits, which has hampered the deployment of genetic circuits to non-specialists. Moreover, the number of transcription units, and hence the effort required to balance input-output responses, increases significantly when the number of inputs and outputs of the circuits grows. While substantial efforts in curating genetic parts in prokaryotes and developing automation design software are underway to address this challenge[21-25], such resources remain lacking in mammalian cells. Furthermore, it is unclear how transferrable some of these technologies are to higher organisms. Consequently, a generalizable platform for reliably creating multi-input-multi-output genetic devices with minimal interconnecting layers and optimization would greatly accelerate cell engineering.

Some of the most powerful genetic engineering tools in mammalian cell are site-specific DNA recombinases[26]. Site-specific DNA recombinase is a class of DNA-modifying enzymes that recognize a specific DNA sequence, and perform cleavage and reunion of DNA. These genome-modifying enzymes are routinely used as versatile gene expression regulators that act as transcription activators or repressors depending on the placement of recombination sites. For instance, recombinase-mediated gene expression can be achieved through tyrosine recombinase-mediated excision of a transcription terminator before a gene of interest (GOI) or serine integrase-mediated inversion of a GOI (analogous to a buffer BUF gate) (see., FIG. 1A for example). Conversely, termination of gene expression can be accomplished via the placement of recombination sites around a GOI and elimination of expression through tyrosine recombinase-mediated excision or serine integrase inversion (analogous to a NOT gate). Increasingly, optogenetics, animal disease models, and stem cell engineering have relied on recombinase-based strategies to achieve temporal or tissue-specific gene expression or disruption, utilizing drug-inducible systems or tissue-specific promoters to drive recombinase expression in combination with a BUF or NOT gate containing a GOI[27,28].

DNA recombinase-based systems have also shown promise in creating computation devices[29,30]. However, current successes remain largely confined to 2-input-1-output Boolean circuits[7,31-33] or multi-input recombinase-based circuits that only modified DNA without generating any functional output[34]. Moreover, most work has involved the use of serine integrases in prokaryotes, enzymes which have not been widely used in mammalian cells in comparison to the popular tyrosine recombinases, such as Cre and Flp, and circuits have not been demonstrated to work with the monocistronic restriction of eukaryotic translation machinery. In addition, it remains uncertain how to reliably design circuits that can access all possible higher-order logic behaviors with many inputs and outputs, and thus phenotypic space with a minimal number of circuit layers.

Additionally, a common strategy for restricting gene expression in a specific cell type is to identify a single cell type specific promoter and use it to control recombinase expression. Although some cell type specific promoters have been identified, they do not cover the diversity represented by all the different cell types in complex organs, such as the mammalian brain. It is, however, more efficient to identify a set of promoters that collectively define a specific subset of cells rather than relying on one promoter. Extensive gene expression profiling in different brain regions and cells had allowed researchers to identify promoters that can define different type of brain cells. What is lacking is a complementary strategy and genetic tools to incorporate different promoters input to regulate gene expression—genetic logic gates that can integrate different recombinase inputs.

SUMMARY OF THE INVENTION

Recombinases can be used in genome engineering to regulate gene expression, both for exogenous and endogenous genes. The excision reaction by a recombinase can lead to both activation and inhibition of gene expression. In previous research, the inventors demonstrated the BLADE platform with gene expression of site-specific DNA recombinases, which can be used to activate or inhibit expression of genes. The inventors previously demonstated a robust, generalizable, and scalable biocomputing platform for creating decision-making devices in mammalian cells using site-specific recombinases called Boolean Logic and Arithmetic through DNA Excision (BLADE) for engineering diverse genetic circuits in human cells with minimal optimization. BLADE integrates cellular signals on a single transcriptional layer encoded in a DNA sequence using recombinase technology. In the inventors previous BLADE platform, as disclosed on WO 2015/188191, which is incorporated herein in its entirety by reference, over 100 novel multi-input-multi-output gentic circuits were created and functionally evaluated using novel quantitative metrics. Furthermore, the inventors previously interfaced BLADE with small biomolecules for temporal inducible control and the CRISPR/Cas9 system for modulation of endogenous gene expression. Overall, the inventors developed a robust, single-stage gene circuit platform for executing diverse sophisticated cellular computation in mammalian cells with applications in cell and tissue engineering.

Typically, in the BLADE platform as disclosed in WO 2015/188191 or other genetic circuits, gene expression of a gene of interest (GOI) is controlled by the recombinase. The expression of the recombinsae protein is dependent on the promoter to which it is operatively linked to. Thus, the efficiency of the BLADE platform or other genetic circuits is impacted by the control of the expression of the recombinase, which is dependent on its promoter. Promoters have their limitations, and are often tissue or cell specific which prevents the BLADE platform being used in all cells, or are inducible promoters which can be leaky. In order to circumvent this, the inventors have developed split-recombinases which come together by drug-mediated protein-complementation, therefore broadening the use of the BLADE platform and other genetic circuits to all cells, regardless of origin. Thus the present invention enables, in instances of gene expression, for example, gene therapy, genetic circuits, to be independent of recombinase expression, and be dependent on the coming together of two fragments of a recombinase enzyme by protein-complementation, where the protein complementation is only triggered in the presence of a specific drug or agent (i.e., an inducer).

By controlling how and when the recombinases become functional for a desired goal by protein complementation in the presence of an inducer agent, it provides an additional level of control of expression of the recombinasaes in a wide range of systems, including in genetic circuits. For example, a recombinase protein that is split into at least two inactivated polypeptide fragments, each fragment associated with a complementary protein pair. The complementary proteins, when brought together by the presence of an inducer agent or drug, form a fully active recombinant protein, and can immediately be used to control gene expression of the gene of interest in the genetic circuit, e.g., BLADE platform. Stated another way, a recombinant protein can be split into at least two inactive fragments, i.e., R' and R", where R' and R" are each conjugated (or otherwise attached) to complementary chemical-induced dimerization domains (CIDDs, also referred to as "binding motifs") C' and C". In the presence of a specific inducer inducer agent or drug, the chemical-induced dimerization domains (CIDDs) C' and C" come together, and as a result of being conjugated to C' and C", R' and R" come together by complementary base pairing to reconstitute a fully functional recombinase protein that can recognize the Recombinase recognition sequence (RRS) and direct gene expression in a genetic circuit.

Accordingly, the inventors herein demonstrate a drug inducible split Flp, PhiC31, VCre, BxB1, and B3 system that permits regulatable control of their activity, which will allow them to control gene expression in a range of areas, including gene therapy, synthetic biology, plant management, environmental clean-up, bacterial and microbial management and synthetic genetic circuits, such as but not exclusively genetic circuits disclosed in WO 2015/188191. In particular, the inventors demonstrate reconstituting two halves of the Flp, PhiC31, VCre, Bxb1 and B3 recombinases and their protein recombination can be used to in combination for use in genetic logic gates. These recombinases are large proteins, and it was not clear prior to the present discovery, that a split of these recombinases can be successfully reconstituted by protein complementation, particularly where protein complementation results in strong activity after reconstitution in vivo.

In some embodiments, the recombinase split-proteins are reconstituted by coming together of attached proteins (also referred to as chemically-induced dimerization domains, or CIDDs), such as, e.g., FKBP/FRB proteins, which come together in the presence of Rapalog. In other embodiments, the recombinase split-proteins are reconstituted by the coming together of attached proteins, such as, e.g., PYL/ABI proteins, which come together in the presence of Abscisic acid. In other embodiments, the recombinase split-proteins are reconstituted by bringing together attached proteins, such as, e.g., GAI/GID1 proteins, which come together in the presence of Gibberellin Ester.

In some embodiments, the recombinase split-proteins are reconstituted by coming together of light-inducible dimerization domains (or LIDDs), such as, e.g., pMag/nMag and CIBN/CRY2 proteins, Other forms of recruiting the two split recombinases can also be used to reconstitute the recombinase, such as through inteins and leucine zippers. In addition, the multiple split proteins can be expressed under different conditional promoters, thus forming an AND gate.

Herein, the inventors demonstrate several split sites on the Flp, PhiC31, B3, BxB1 and VCre recombinases proteins, where their activity can be reconstituted with chemical inducible dimerization system. In particular, the inventors have demonstrated herein, that reconstitution of split recombinases, and therefore recombinase activity induced with Rapalog, abscisic acid, and/or Gibberellins in mammalian cells.

Recombinase, such as Cre, Flp B3 and PhiC31, are extremely powerful genome engineering tools and are often used to control gene expression in eukaryotic and mammalian animals. Therefore, this system of split-recombinases provides a powerful tool for controlling gene expression in many eukaryotic cells, including human cell. In addition, some of the recombinases, such as Flp, are known to have less cytotoxicity than Cre.

Accordingly, in one aspect, the technology herein relates to a split-recombinase polypeptide, comprising: (a) a recombinase protein split into at least two recombinase polypeptide fragments, wherein each recombinase polypeptide fragment is conjugated to a chemically-induced dimerization domain (CIDD), and wherein each recombinase polypeptide fragment is not active by itself, but can rapidly complement with the one or more recombinase polypeptide fragments to reconstitute the active recombinase protein; and (b) at least one chemically-induced dimerization domain pair (CIDD pair), comprising a first chemically-induced dimerization domain (CIDD$^A$) and at least a second complementary CIDD (CIDD$^B$) wherein the first CIDD (CIDD$^A$) and the second complementary CIDD (CIDD$^B$) come together in the presence of a target agent or target signal, resulting in protein complementation of the at least two recombinase polypeptide fragments to form the active recombinase protein in the presence of the target agent.

Stated in a different way, and exemplified in FIG. 40A, the technology herein relates to a split recombinase that can be split into two or more fragments (e.g., $R^1$ and $R^2$ and optionally $R^3$), where each fragment is conjugated to one of two domains (i.e., $R^1$ is conjugated to Y also referred to as CIDD$^A$; and $R^2$ is conjugated to Z also referred to CIDD$^B$), where the two domains (Y and Z) come together in the presence of a target agent (e.g, X) or light signal (e.g., target signal). As a result of Y and Z coming together in the presence of X, recombinase fragments $R^1$ and $R^2$, each of which are attached to the Y and Z domains reconstitute (e.g., protein complement) to form an active recombinase protein. In some embodiments, the recombinase is split into two polypeptide fragments, as exemplified in FIG. 40A. In some embodiments, the recombinase is split into three polypeptide fragments, as exemplified in FIG. 41A.

In some embodiments, where the recombinase is split into two fragments (see, e.g., FIG. 40A), the split-recombinase polypeptide comprises a recombinase protein split into two fragments, wherein the split-recombinase polypeptide comprises (a) at least a first recombinase polypeptide fragment ($R^1$) and at least a second recombinase polypeptide fragment ($R^2$), where the first and second recombinase polypeptide fragments are not active by themselves and rapidly complement to reconstitute the active recombinase protein; and (b) at least a first chemically-induced dimerization domain (CIDD) (CIDD$^A$) and at least a second complementary CIDD (CIDD$^B$) wherein the first CIDD (CIDD$^A$) and the second complementary CIDD (CIDD$^B$) can bind to a target agent, or come together in the presence of a target signal (e.g., a light signal), wherein the first CIDD (CIDD$^A$) is conjugated to the first recombinase polypeptide fragment ($R^1$), and the second complementary CIDD (CIDD$^B$) is conjugated to the second recombinase polypeptide fragment ($R^2$), resulting in protein complementation of the first recombinase polypeptide fragment with the second polypeptide recombinase fragment to form the active recombinase protein in the presence of the target agent or target signal.

In alternative embodiments, where the recombinase is split into three fragments (see, e.g, FIG. 41A), the the split-recombinase polypeptide comprises a recombinase protein split into three fragments, wherein the split-recombinase polypeptude comprises: (a) a first recombinase polypeptide fragment ($R^1$), a second recombinase polypeptide fragment ($R^2$), and a third recombinase polypeptide fragment ($R^3$), wherein $R^1$, $R^2$ and $R^3$ recombinase polypeptide fragments are not active by themselves and rapidly complement to reconstitute the active recombinase protein; and (b) at least two CIDD pairs comprising: (i) at least a first chemically-induced dimerization domain pair (CIDD1 pair) comprising a first CIDD1 (CIDD1$^A$) and the second complementary CIDD1 (CIDD1$^B$) which can dimerize on binding to first target agent, and (ii) a second CIDD pair (CIDD2 pair) comprising a second CIDD2 (CIDD2$^A$) and the second complementary CIDD2 (CIDD2$^B$) which can dimerize on binding to a second target agent, where $R^1$ is conjugated to the CIDD1$^A$ and the CIDD2$^A$,
$R^2$ is conjugated to the CIDD1$^B$, and
$R^3$ is conjugated to the CIDD2$^B$,
and protein complementation of $R^1$ with $R^2$ occurs in the presence of the first inducer, and protein complementation of $R^2$ with $R^3$ occurs in the presence of the second inducer to form the active recombinase protein in the presence of both the first and second target agent.

In all aspects of the technology described herein, the split-recombinase polypeptide can comprise a recombinase protein selected from the group consisting of: Flp, PhiC31, VCre, Bxb1, Cre and B3 recombinases, or proteins with at least 85% sequence identity thereto. Appropriate split sites are disclosed herein.

In all aspects of the disclosure described herein, a chemically-induced dimerization domain pair (CIDD pair) comprises a CIDD$^A$ and CIDD$^B$ selected from any one or more of: (i) a CIDD$^A$ comprising a GID1 domain or a fragment thereof, and a CIDD$^B$ comprising a GAI domain, wherein the GID1 domain and GAI domain bind to the target agent Gibberlin Ester (GIB); (ii) a CIDD$^A$ comprising a FKBP domain or a fragment thereof, and a CIDD$^B$ comprising a FRB domain, wherein the FKBP domain and FRB domain bind to the target agent Rapalog (RAP); a CIDD$^A$ comprising a PYL domain or a fragment thereof, and a CIDD$^B$ comprising a ABI domain, wherein the PLY domain and ABI domain bind to the target agent Absorbic acid (ABA); CIDD$^A$ comprising a Light-inducible dimerization domain (LIDD), wherein a LIDD dimerizes with a complementary LIDD (CIDD$^B$) upon exposure to a light signal of an appropriate wavelength.

In some embodiments, a LIDD is nMag or CIBN, wherein nMag can dimerize with the complementary LIDD pMag upon exposure to a blue light signal, and wherein CIBN can dimerize with the complementary CRY2 upon exposure to a blue light signal. In some embodiments, the light signal is a pulse light signal.

In all aspects of the technology described herein, the active recombinase protein (but not the split-recombinase fragments) can recognize the recombinant recognition sequence (RRS) of the recombinase protein.

Another aspect of the technology herein relates to fusion proteins comprising a split-recombinase protein fragment fused to a CIDD as disclosed herein. An exemplary embodiment of such fusion proteins comprises a split-recombinase polypeptide fragment (e.g., a split recombinase polypeptude fragment selected from any of Flp, PhiC31, B3, Bxb or VCre) fused to at least one chemically-inducible dimerization domain (CIDD), wherein the split-recombinase polypeptide fragment is selected from any of: (i) a N-terminal polypeptide comprising a fragment of any of SEQ ID NO: 1 (Flp), SEQ ID NO: 12 (PhiC31), SEQ ID NO: 16 (VCre), SEQ ID NO: 19 (B3) or SEQ ID NO: 41 (Bxb1) with the C-terminus ending at an appropriate split site (S) as disclosed herein, or (ii) a C-terminal polypeptide comprising a fragment of any of SEQ ID NO: 1 (Flp), SEQ ID NO: 12 (PhiC31), SEQ ID NO: 16 (VCre), SEQ ID NO: 19 (B3) or SEQ ID NO: 41 (Bxb1) with the N-terminus beginning at Split site+1 amino acid (S+1); and wherein the CIDD is selected from any of: a GID1 domain or GAI domain; a FKBP domain or a FRB domain; or a PYL domain or a ABI domain.

Another aspect of the technology herein relates to nucleic acids encoding the fusion proteins, or the split-recombinases as disclosed herein, as well as cells and vectors comprising the nucleic acids. Additional embodiments relate to kits comprising the split-recombinases as disclosed herein, or the fusion proteins described herein.

In the past, protein complementation has been used as a detection method, such as for detection of a particular analyte (such as nucleic acid or protein), where in the presence of the analyte, e.g., nucleic acid, two or more split-proteins are brought together to produce a detectable protein. For example, protein-complementation of a split-GFP protein or split-luciferase protein can be used detect the presence of a particular nucleic acid or nucleic acid species. In contrast, the technology described herein is distinct in that it relates to a controlled method for controlling gene transcription and protein expression. That is, the split-recombinase fragments come together (reconstitute) in the presence of an inducer to control gene transcription. Accordingly, the presence of the inducer results in recombination of the split-recombinase fragments and depending on the nucleic construct and the recombinase being rejoined, can turn on or off gene expression. Additionally, in contrast to inducible Cre, where Cre is present in a construct such as $ER^{T2}$-Cre-$ER^{T2}$ (see FIG. 27) and is located in the cytoplasm, induction of Cre occurs in the presence of 4OHT and results in translocation of the $ER^{T2}$-Cre-$ER^{T2}$ fusion protein from the cytoplasm to the nucleus to control gene expression. Such a system is not optimal in immediate control of gene transcription, as it dependent on protein translocation of the conjugate into the nucleus and therefore such a system has a lag-time from induction and does not allow for quick-controlled gene expression by Cre. Additionally, while a dimerizable Cre (DiCre) has been previously reported (Jullien et al., Nucleic Acids Research 2003, 31(21); e131), the technology disclosed herein relates to less cytotoxic recombinases, which can be reconstituted by an inducer, or in the presence of two or more inducers (e.g., inducer 1 and inducer 2), or by a light signal and light-inducible dimerization domains.

Accordingly, it is envisioned that the split-recombinase system as disclosed herein will have applications in cell-based therapy and animal model development. Additionally, many commercial applications would benefit by the use of drug inducible gene expression system, including but not limited to, adoptive T cell therapy as discussed in more detail below. For example, the split-recombinase system as disclosed herein are encompassed for use as powerful genetic tools for investigating and manipulating genetic functions, including but not limited to, expression of optogenetic proteins for optical control and study of very specific cell types in the brain, generation of animal models for study of diseases (e.g. cancer, neurological diseases, and other genetic pathologies), as well as serve as ON/OFF switch for cell-based therapeutics (e.g. adoptive T cell therapy or stem cell therapy) and the like.

Accordingly, the recombinase-split proteins, that are inducably reconstituted in the presence of a drug, can be combined with in a BLADE platform provides the first generalizable framework that enable the engineering of complex logic circuits in mammalian cells with minimal optimization from the user. Unlike most circuit designs demonstrated, the platform disclosed herein can readily yield circuits with multiple inputs or outputs without increasing the number of transcription units. To demonstrate the application of the BLADE platform in mammalian genetic circuit engineering, the inventors designed and assembled more than 100 functionally distinct circuits, including some of the most complex logical operations engineered any living cell, prokaryotic or eukaryotic, such as a three-input, two-output Full Adder and six-input, one-output Boolean Logic Look Up Table. A vast majority of the circuits (up to 88%) yielded the correct specified behavior without any optimization. Furthermore, the platform disclosed herein accommodates multiple outputs without significantly incurring additional design complexity and it can be adapted to regulate the expression of messenger RNAs from Pol II promoters or non-coding regulatory RNAs from Pol III promoters, such as guide RNAs for use with CRISPR/Cas9. The ability to control multiple different guide RNAs with advanced logic circuits allows us to assert sophisticated control over the regulation of endogenous human genes, thus expanding the explorable phenotypic space. The robustness, simplicity, accessibility, scalability, and generalizability of BLADE far exceed all circuit design strategies currently available in mammalian cells.

DETAILED DESCRIPTION OF THE FIGURES

FIGS. 1A-1C show examples of orthogonal site-specific tyrosine recombinases and serine integrases enable implementation of multi-input AND gates in mammalian cells. FIG. 1A shows that recombinases can perform simple BUF logic operations, either by tyrosine recombinase-mediated excision (left) or serine integrase-mediated inversion (right). FIG. 1B shows that recombinases are tested for their recombination efficiency and orthogonality on all BUF logic reporters. FIG. 1C shows an example of a 6-input AND-gate that produces GFP when all inputs are present. M.F.I.=mean fluorescence intensity from n=3 independent transfections; a.u.=arbitrary units. Error bars represent standard error of the mean.

FIGS. 2A-2B show 2-input BLADE platform can produce four distinct output functions based on two inputs. FIG. 2A shows an embodiment with a 2-input BLADE template on one plasmid with a single transcriptional unit. This template contains four distinct regions of DNA (addresses) downstream of a promoter. Each address corresponds to an output function and is accessed or deleted via site-specific DNA recombination. Each address can be programmed from different configurations ranging from zero-inputs to Boolean functions. The first address ($Z_{00}$), which is the closest to the promoter, corresponds to a state where no recombinase is expressed (A=0, B=0). If the $Z_{00}$ address contains a protein coding sequence, then that gene will be expressed. Gene expression from the other addresses downstream of $Z_{00}$ will be blocked by the presence of $Z_{00}$ protein coding region. In the presence of recombinase A, which corresponds to state (A=1, B=0), addresses $Z_{00}$ and $Z_{01}$ will be removed, thus moving address $Z_{10}$ directly downstream of the promoter and allowing gene expression of address $Z_{10}$ only to occur. Similarly, when only recombinase B is present (A=0, B=1), addresses $Z_{00}$ and $Z_{10}$ are excised, allowing $Z_{01}$ to be moved directly downstream of the promoter. Finally, when both recombinases are expressed (A=1, B=1), addresses $Z_{00}$, $Z_{01}$, $Z_{10}$ are all excised, thus placing $Z_{11}$ downstream of the promoter unobstructed by the other addresses. FIG. 2B shows an integrated 2-input BLADE decoder with tagBFP, EGFP, iRFP720, and mRuby2 as addresses $Z_{00}$, $Z_{10}$, $Z_{01}$, and $Z_{11}$ respectively. Plasmids constitutively expressing Cre and/or Flp are then stably integrated in. Three days of doxycycline (DOX) treatment is used to permit the rtTA-VP48 protein to bind to the tetracycline response elements promoter (pTRE) to activate gene expression. Mean fluorescence intensity (MFI) is plotted of either one or two replicate integrations. a.u.=arbitrary units.

FIG. 3A-3C shows one hundred and thirteen distinct gene circuits with up to two inputs and two outputs implemented using the 2-input BLADE template. FIG. 3A shows that to generate 2-input, 2-output circuits, a 2-input BLADE template can be configured with different combinations of output functions: zero-output (transcription termination sequence), one-output (GFP or mCherry) or two-output (GFP-T2A-mCherry). FIG. 3B shows a diverse library of >100 gene circuits, each shown as an individual column with predicted truth table GFP/mCherry ON/OFF behavior (black=no output, green=GFP ON, red=mCherry ON) and corresponding experimental averaged single-cell results obtained from flow cytometry. FIG. 3C shows Angles between each Signal Vector and corresponding Intended Truth Table Vectors are plotted versus worst-case dynamic range values for GFP ($\delta_G$) and mCherry ($\delta_M$) signals. Shown above is an expanded view of one of the logic gates made using this platform. M.F.I.=mean fluorescence intensity from n=3 independent transfections. Error bars represent standard error of the mean.

FIG. 4 shows an embodiment of a field-programmable storage and retrieval of logic and memory using a Boolean Logic Look-Up Table (LUT). The Boolean Logic LUT is a six-input-one-output genetic device that receives two data inputs, A and B, and is controlled by four select inputs, $S_1$, $S_2$, $S_3$, and $S_4$, producing an output of GFP. The select inputs are used to change data input-output behavior; each combination configures the device to any of the sixteen Boolean logic gates. F.I.=fluorescence intensity from n=3 independent transfections. Error bars represent standard error of the mean.

FIGS. 5A-5B shows a 3-input BLADE template can be applied to create 3-input arithmetic computational circuits. FIG. 5A shows the 3-input BLADE template can receive up to three inputs and produce eight distinct output functions. FIG. 5B shows a Three 3-input-2-output binary arithmetic computational circuits made using the 3-input BLADE template. The full adder can add A+B+C while the full subtractor calculates A−B−C. For addition, input C, output P, and output Q represent Carry In, Carry Out and Sum, respectively. For subtraction, input C, output P, and output Q signify Borrow In, Borrow Out and Difference, respectively. The half adder-subtractor performs either binary addition of A+B or binary subtraction of A−B depending on the presence of select input C. F.I.=fluorescence intensity from n=3 independent transfections. Error bars represent standard error of the mean.

FIGS. 6A-6B show an interfacing BLADE with biologically relevant inputs and outputs. FIG. 6A shows that small molecules, 4-hydroxytamoxifen (4OHT) and abscisic acid (ABA), are used to induce Cre and Flp recombination activities, respectively, on a decoder circuit containing four fluorescent protein outputs. Chemical induction of Cre recombination is achieved through 4OHT-mediated translocation of a Cre protein fused to mutated estrogen nuclear receptors ($ER^{T2}$) from the cytoplasm to the nucleus. Chemical induction of Flp recombination is achieved through a split Flp recombinase construct fused to ABA-binding domains ABI and PYL. Mean fluorescence intensity is plotted from n=3 independent transfections and error bars indicate the standard error of the mean. FIG. 6B shows that small molecules, 4OHT and ABA, are used to induce Cre and Flp recombination activities on a decoder circuit interfaced with a dCas9-VPR (VP64, p65, Rta) transcription activator. Four human genomic promoters are targets for activation via association of corresponding guide RNAs (gRNA) with dCas9-VPR. Total RNA was collected and averaged relative fold changes in target mRNA expression were obtained through quantitative real-time PCR of three biological replicates. Error bars represent the standard error of the mean.

FIG. 7A-7B shows embodiments of orthogonal site-specific tyrosine recombinases and serine integrases enable implementation of multi-input AND gates in mammalian cells. FIG. 7A shows recombinases are tested for their recombination efficiency and orthogonality on all BUF logic reporters. FIG. 7B shows a 6-input AND-gate that produces GFP when all inputs are present. % Cells ON calculated from n=3 independent transfections; a.u.=arbitrary units. Error bars represent standard error of the mean.

FIG. 8A-8C show recombinase cross-reactivity dose-response profile of Cre, Dre, VCre and Vika. FIG. 8A is a summary of intended and unintended recombination of Cre, Dre, VCre and Vika site-specific recombinases. Cre and Dre are mutually cross-reactive, whereas VCre can recombine Vika's recombination sites, but not the other way around. FIG. 8B shows the dose-response profile of Cre (left) and Dre (right) on both Cre and Dre reporter constructs. FIG. 8C shows the dose-response profile of VCre (left) and Vika (right) on both VCre and Vika reporter constructs.

FIG. 9 shows a recombinase-based 2-input, 1-output Boolean logic gates using Cre and Flp recombinases. Recombination sites for Cre and Flp are placed around termination sequences or GFP to enable or disable GFP expression. In this fashion all sixteen Boolean logic functions were created in mammalian cells.

FIGS. 10A-10B shows an embodiment of heterospecific recombination placed around a terminal sequence. FIG. 10A shows a schematic of heterospecific recombination sites where heterospecific recombination sites for Cre, Flp, and VCre are placed around termination (or a STOP) sequences before a GFP sequence. FIG. 10B shows a table shematic of when GFP is expressed (visualized by green-blocks or a ✓ mark) with different recombinase sites and recombinase enzymes.

FIG. 11 shows a unique Nucleotide Sequence guided assembly provides a fast and modular approach for creating DNA constructs. Genes are first cloned into part entry vectors that contain 40 bp unique nucleotide sequences (UNSes). These part vectors are then digested with either Ascl+Not1 or Ascl+Nhe1 restriction endonucleases to expose UNSes. The part fragments are then gel purified and assembled into a linearized destination vector using Gibson isothermal assembly. Details are described in[1].

FIG. 12 shows a 2-input BLADE platform can produce four distinct output functions based on two inputs. Integrated 2-input BLADE decoder with tagBFP, EGFP, iRFP720, and mRuby2 as addresses $Z_{00}$, $Z_{10}$, $Z_{01}$, and $Z_{11}$ respectively. Plasmids constitutively expressing Cre and/or Flp are then stably integrated in. Three days of doxycycline (DOX) treatment is used to permit the rtTA-VP48 protein to bind to the tetracycline response elements promoter (pTRE) to activate gene expression. % Cells ON is plotted of either one or two replicate integrations. a.u.=arbitrary units.

FIGS. 13A-13B show the construction of two-input BLADE constructs using Unique Nucleotide Sequence Guided Assembly. FIG. 13A shows that to create a two-input BLADE construct, part vectors are created that contain output states for each address. The part vectors, along with a destination (DEST) vector, are digested and gel purified to expose unique nucleotide sequences (UNSes). FIG. 13B shows that the part fragments and linearized destination vector are then assembled together in order of UNS via Gibson isothermal assembly to form the final expression vector.

FIG. 14 shows fluorescence histograms for 2-input decoder in non-induced Jurkat T lymphocytes. 2-input decoder produces a particular fluorescent protein for each row of the truth table. Grey histograms indicate wildtype Jurkat cells, unshaded colored histograms indicate OFF states and shaded colored histograms indicate ON states. Data is shown for one of the replicates.

FIG. 15 shows fluorescence histograms for 2-input decoder in doxycycline-induced Jurkat T lymphocytes. 2-input decoder produces a particular fluorescent protein for each row of the truth table. Grey histograms indicate wild-type Jurkat cells, unshaded colored histograms indicate OFF states and shaded colored histograms indicate ON states. Data is shown for one of the replicates.

FIG. 16 shows the output response of integrated doxycycline-inducible decoder in Jurkat T cells can be easily modulated by dosage of doxycycline. 2-input decoder produces a particular fluorescent protein for each row of the truth table. Unshaded colored dots indicate OFF states and shaded colored dots indicate ON states. Data is indicated for number of replicates (n=1 or n=2) plotted.

FIG. 17 shows the functionality of integrated doxycycline decoder in Jurkat T cells can be maintained over a couple weeks. 2-input decoder produces a particular fluorescent protein for each row of the truth table. Unshaded colored circles indicate OFF states and shaded colored circles indicate ON states; cells here were maintained with doxycycline induction starting from day 0. Unshaded colored squares indicate OFF states and shaded colored squares indicate ON states; cells here were maintained with doxycycline induction starting from day 14 and were not induced with doxycycline prior to that point. Data is indicated for number of replicates (n=1 or n=2) plotted.

FIG. 18A-18B shows a fluorescence bar charts and histograms for 2-input decoder in HEK293FT cells. 2-input decoder produces a particular fluorescent protein for each row of the truth table. FIG. 18A shows a 2-input BLADE template with tagBFP, EGFP, iRFP720, and mRuby2 as addresses $Z_{00}$, $Z_{10}$, $Z_{01}$, and $Z_{11}$ respectively. Mean fluorescence intensity from n=3 independent transfections. a.u.=arbitrary units. Error bars represent standard error of the mean. FIG. 18B shows gene expression; Grey histograms indicate wildtype HEK293FT, unshaded colored histograms indicate OFF states and shaded colored histograms indicate ON states. Data is shown for one of the replicates.

FIGS. 19A-19C show one hundred and thirteen distinct gene circuits with up to two inputs and two outputs implemented using the 2-input BLADE template. FIG. 19A shows that to generate 2-input, 2-output circuits, a 2-input BLADE template can be configured with different combinations of output functions: zero-output (transcription termination sequence), one-output (GFP or mCherry) or two-output (GFP-T2A-mCherry). FIG. 19B shows a diverse library of >100 gene circuits, each shown as an individual column with predicted truth table GFP/mCherry ON/OFF behavior (black=no output, green=GFP ON, red=mCherry ON) and corresponding experimental averaged single-cell results obtained from flow cytometry. FIG. 19C shows Angles between each Signal Vector and corresponding Intended Truth Table Vectors are plotted versus worst-case dynamic range values for GFP ($\delta_G$) and mCherry ($\delta_M$) signals. Shown above is an expanded view of one of the logic gates made using this platform. % Cells ON is calculated from n=3 independent transfections. Error bars represent standard error of the mean.

FIGS. 20A-20C show the determination of angular global rank amongst possible 255 truth tables for circuits made using the 2-input-2-output BLADE platform. For a particular genetic circuit, angles between the Intended Truth Table vector and all 255 (up to 2-input, up to 2-output, excluding the 0-input-0-output FALSE) truth tables vectors were found (Theoretical Angle), where an angle of zero indicates the intended truth table vector (squared in blue). Similarly, the angles between the signal vector and all possible truth table vectors were found (Measured Angle), where the lowest angle indicates the best truth table match. The global rank n is determined by how many (n) other truth tables were closer than the intended truth table. FIG. 20A and FIG. 20B indicate two circuits (Gate 89 and Gate 71, respectively) that achieved a global rank 0 and VP angle scores around 0° and 10°, respectively. FIG. 20C indicates Gate 94, where the signal vector was closer to one other truth table than the intended truth table (VP global rank 1); this circuit had a higher VP angle score as well around 20°.

FIG. 21 shows a field-programmable storage and retrieval of logic and memory using a Boolean Logic Look-Up Table (LUT). The Boolean Logic LUT is a six-input-one-output genetic device that receives two data inputs, A and B, and is controlled by four select inputs, $S_1$, $S_2$, $S_3$, and $S_4$, producing an output of GFP. The select inputs are used to change data input-output behavior; each combination configures the device to any of the sixteen Boolean logic gates. F.I.=fluorescence intensity from n=3 independent transfections. Error bars represent standard error of the mean.

FIG. 22A-22B shows alternative versions of the Boolean Logic Look-up Table (LUT). FIG. 22A shows a Boolean Logic LUT using Dre, Vika, B3 and VCre as select inputs. Red circles indicate areas where cross-reactivity made detectable changes in circuit response. FIG. 22B shows the same Boolean LUT using low amounts of select inputs to reduce cross-reactivity effects of Cre/Dre and VCre/Vika, as noticeably illustrated in the AND and A gates. Red circles indicate areas where cross-reactivity was resolved.

FIG. 23 shows the three-input BLADE template can be used to generate eight distinct output functions. The three-input BLADE template uses Cre, Flp, and VCre to generate eight distinct configurations of DNA that each code for a distinct output function.

FIGS. 24A-24B show the construction of three-input BLADE constructs using Unique Nucleotide Sequence Guided Assembly. FIG. 24A shows that to create a three-input BLADE construct, part vectors are created that contain output states for each address. The part vectors, along with a destination (DEST) vector, are digested and gel purified to expose unique nucleotide sequences (UNSes). FIG. 24B shows the part fragments and linearized destination vector are then assembled together in order of UNS via Gibson isothermal assembly to form the final expression vector.

FIG. 25 shows a 3-input BLADE template can be applied to create 3-input arithmetic computational circuits. FIG. 25 shows a 3-input BLADE template can receive up to three inputs and produce eight distinct output functions, and also shows a three 3-input-2-output binary arithmetic computational circuits made using the 3-input BLADE template. The full adder can add A+B+C while the full subtractor calculates A−B−C. For addition, input C, output P, and output Q represent Carry In, Carry Out and Sum, respectively. For subtraction, input C, output P, and output Q signify Borrow In, Borrow Out and Difference, respectively. The half adder-subtractor performs either binary addition of A+B or binary subtraction of A−B depending on the presence of select input C. % Cells ON is calculated from n=3 independent transfections. Error bars represent standard error of the mean.

FIG. 26 shows recursive construction of BLADE templates to form up to N-input, N-output combinatorial logic. A BLADE template with and an alternate orthogonal version can be placed into a 1-input BLADE template to increase the input order by one. This approach can be repeated for generating N-input, M-output logic with $2^N$ addresses.

FIG. 27 shows interfacing BLADE with biologically relevant inputs and outputs. Small molecules, 4-hydroxytamoxifen (4OHT) and abscisic acid (ABA), are used to induce Cre and Flp recombination activities, respectively, on a decoder circuit containing four fluorescent protein outputs. Chemical induction of Cre recombination is achieved through 4OHT-mediated translocation of a Cre protein fused to mutated estrogen nuclear receptors ($ER^{T2}$) from the cytoplasm to the nucleus. Chemical induction of Flp recombination is achieved through a split Flp recombinase construct fused to ABA-binding domains ABI and PYL. Calculated % Cells ON is plotted from n=3 independent transfections and error bars indicate the standard error of the mean.

Figure 30:
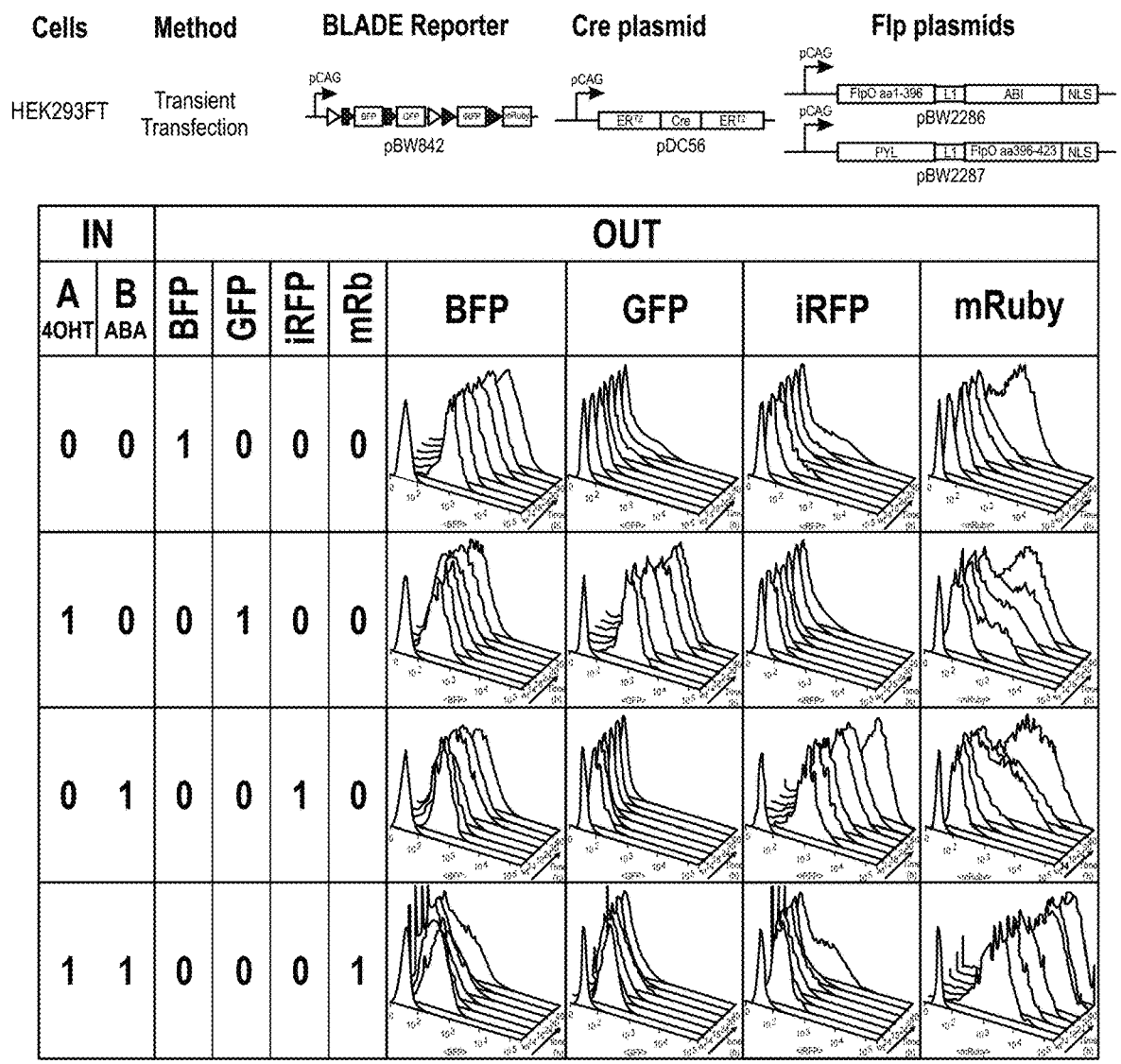

FIG. 30 shows fluorescence histograms for 2-Input 4-hydroxytamoxifen and abscisic acid-inducible decoder in HEK293FT cells over two days. 2-Input decoder produces a particular fluorescent protein for each row of the truth table. Grey histograms indicate wildtype HEK293FT, unshaded colored histograms indicate OFF states and shaded colored histograms indicate ON states. Data is shown for one of the replicates and for six time points in the z-axis.

Figure 31:
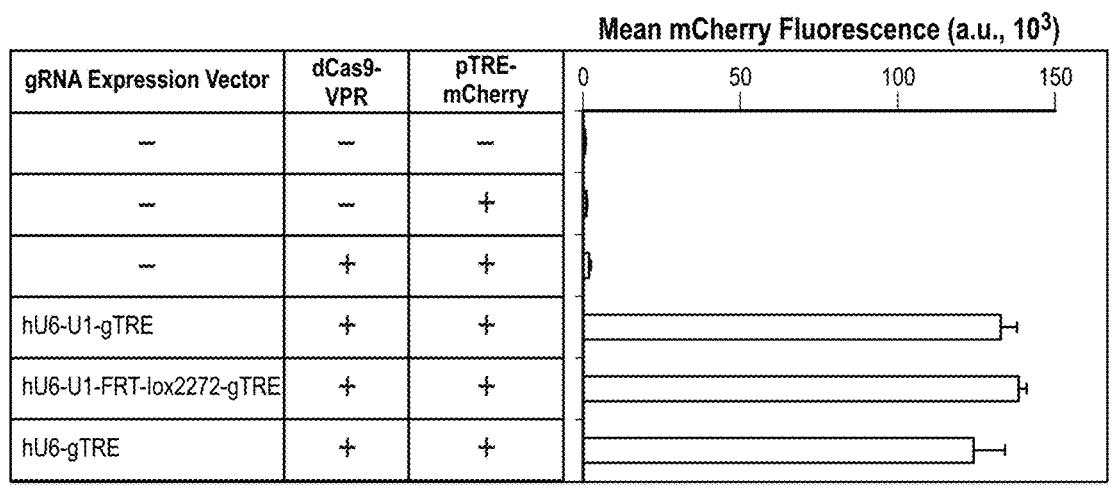

FIG. 31 shows the 5' recombination site additions do not diminish dCas9-VPR transcription activation. Co-transfection of guide RNA expression plasmids that contain cloning scars (U1 UNS sequence) or FRT and lox2272 sites do not show diminished dCas9-VPR activation of a plasmid containing target sequences upstream a minimal promoter and an mCherry fluorescent protein sequence.

Figures 32A, 32B:
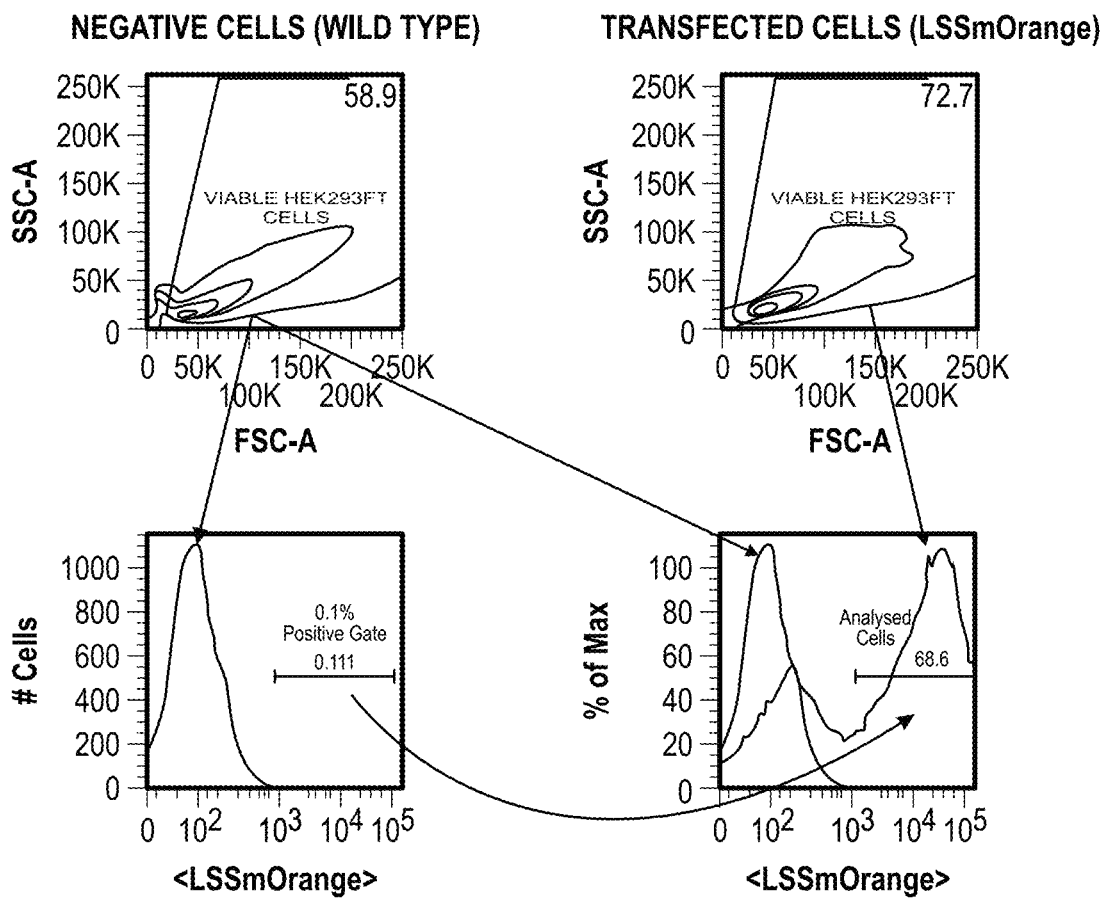

FIG. 32A-32B shows flow cytometric gating procedures for transient transfection of HEK293FT human embryonic kidney cells. FIG. 32A shows that the instruments are set initially with an FSC threshold of 500 arbitrary units which filters out a small part of the debris population. All cells are then gated for viable HEK293FT cells as depicted in the pink gates above. Next, a transfection positive gate is made by gating for the top 0.1% transfection marker-expressing (LSS-mOrange or BFP) wild type HEK293FT cells. This gate is then applied to transfected cells and all analyses are done from cells within this gate. FIG. 32B is an example of a compensation matrix generated through FlowJo's auto-compensation tool using single positive fluorescent cells and universal negative wild type cells.

Figure 33:
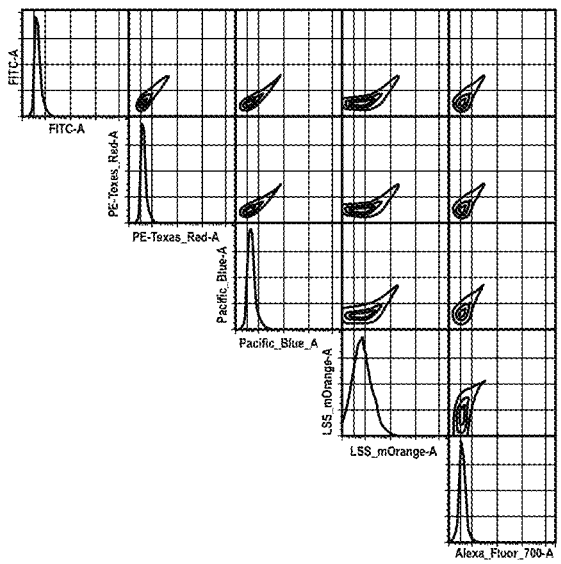
Figure 33:
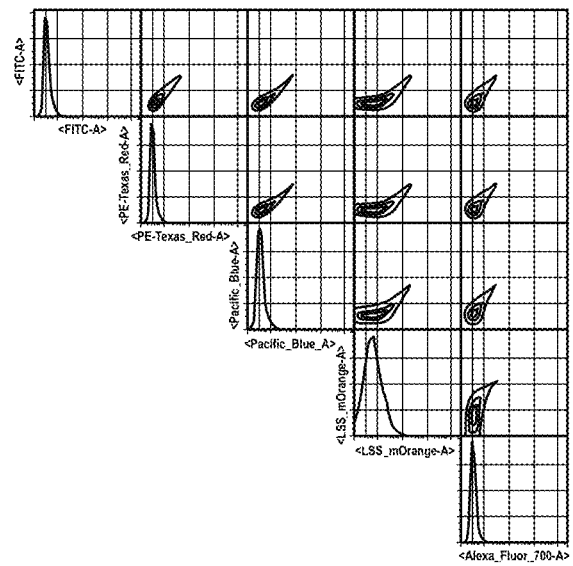
Figure 33:
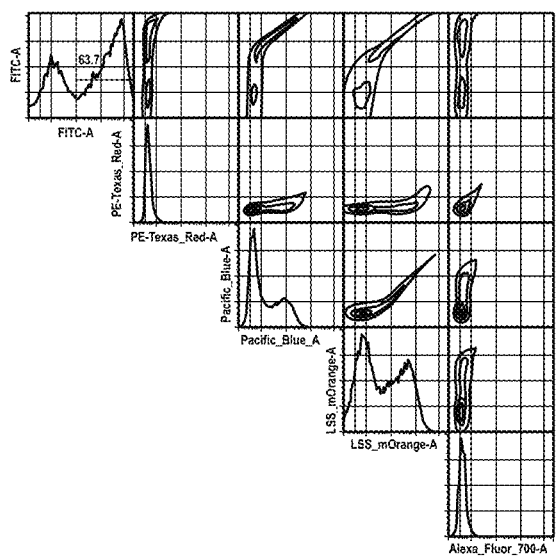
Figure 33:
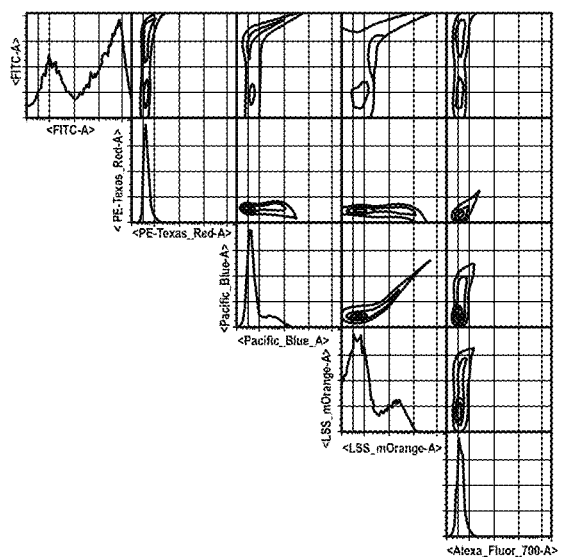

FIG. 33 shows a comparison of uncompensated (left) and compensated (right) universal negative and GFP+ HEK293FT cells. Wild type HEK293FT cells are used as a universal negative and cells transfected with pCAG-EGFP are used for GFP+control.

Figure 34:
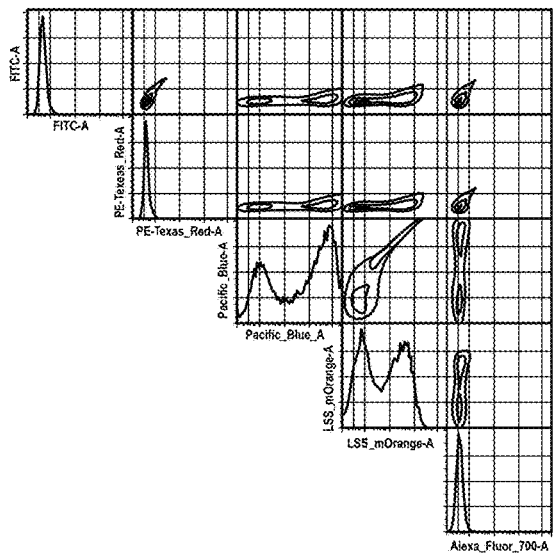
Figure 34:
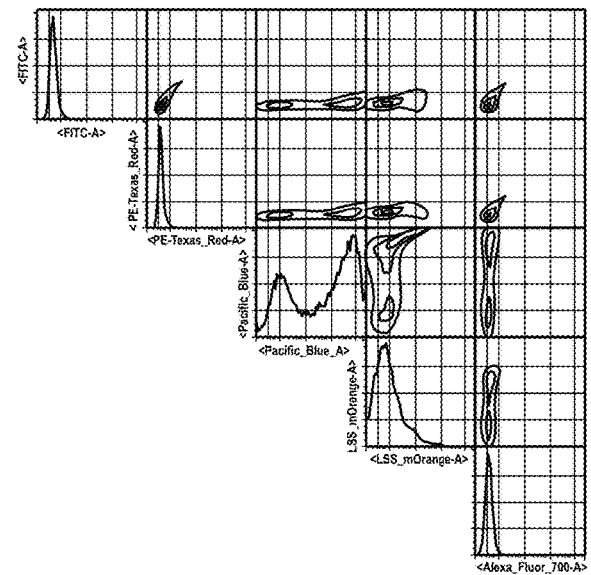
Figure 34:
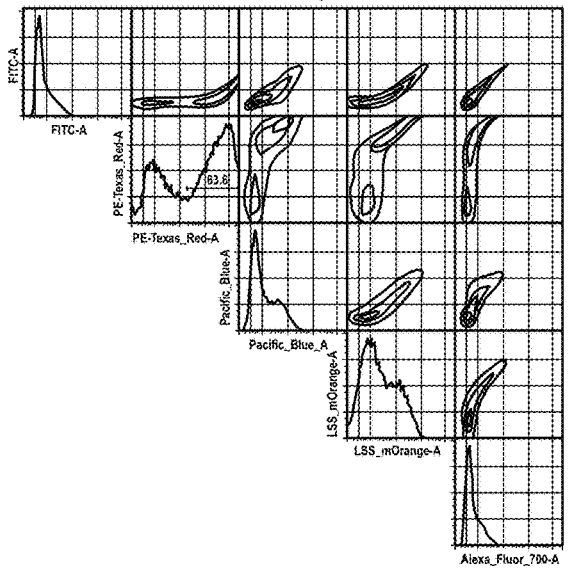
Figure 34:
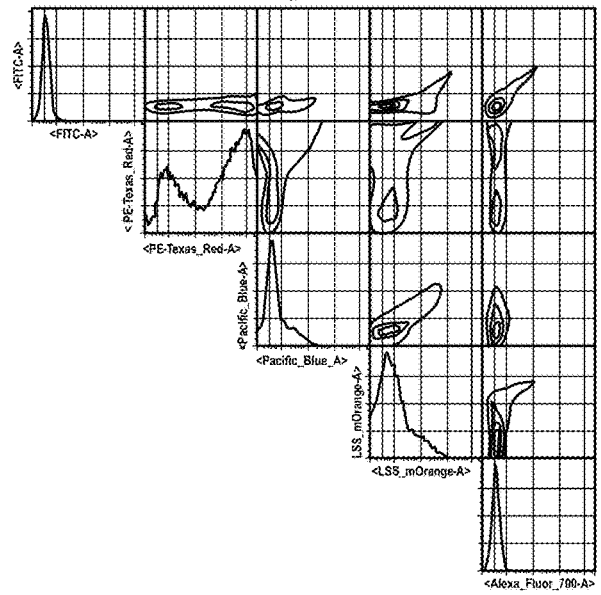

FIG. 34 is a comparison of uncompensated and compensated BFP+ and mRuby2+HEK293FT cells. Cells transfected with pCAG-tagBFP are used for BFP+control and cells transfected with pCAG-mRuby2 are used for mRuby2+ control.

Figure 35:
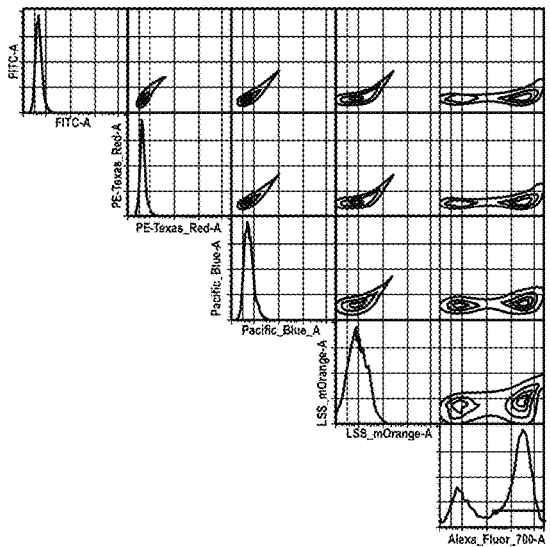
Figure 35:
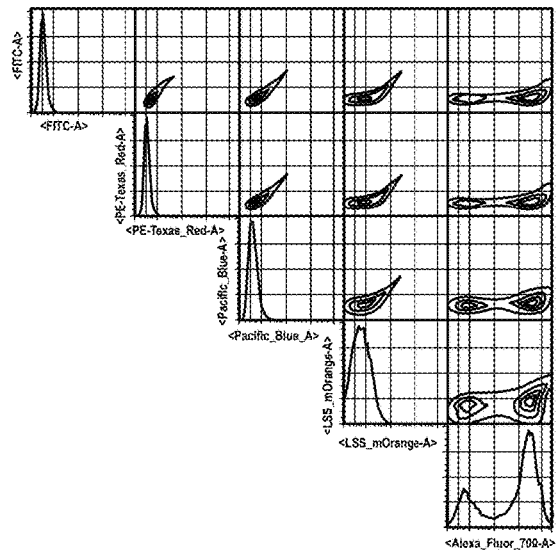
Figure 35:
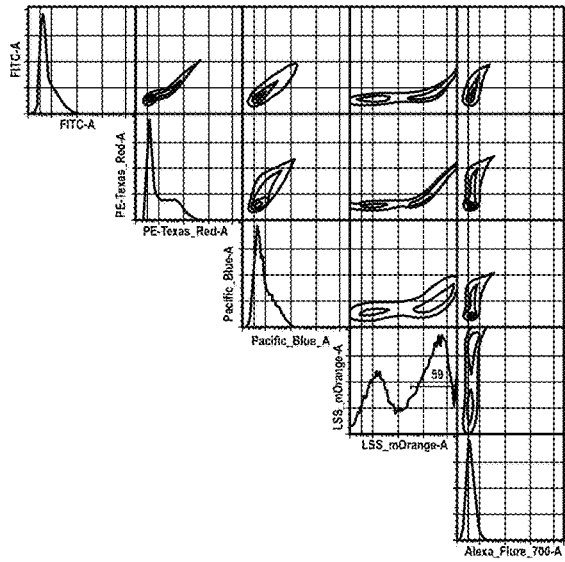
Figure 35:
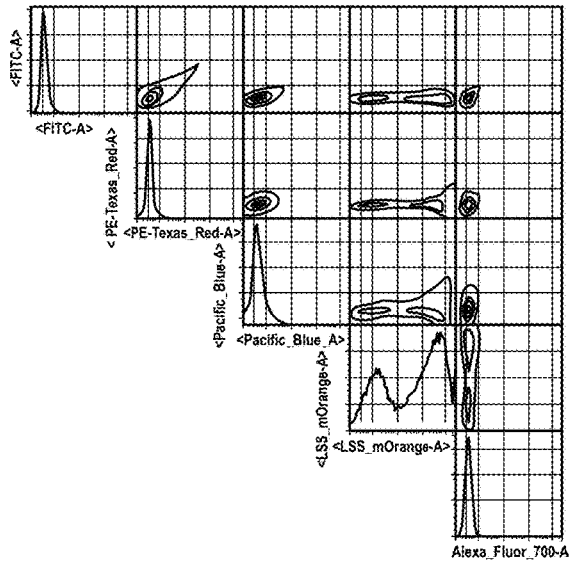

FIG. 35 is a comparison of uncompensated and compensated iRFP+ and LSSmOrange+HEK293FT cells. Cells transfected with pCAG-iRFP720 are used for iRFP+control and cells transfected with pCAG-LSSmOrange are used for LSSmOrange+control.

Figure 36A:
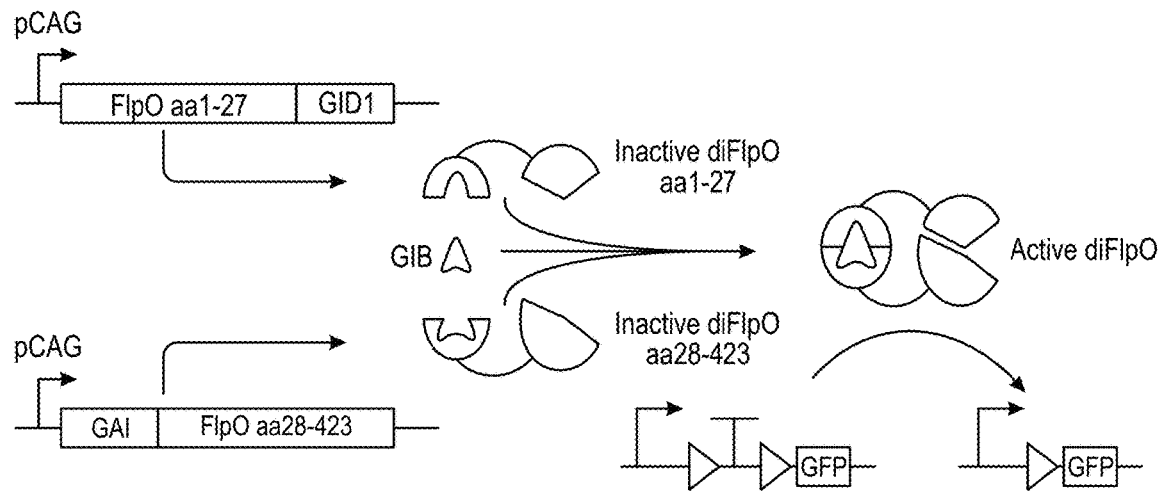
Figure 36B:
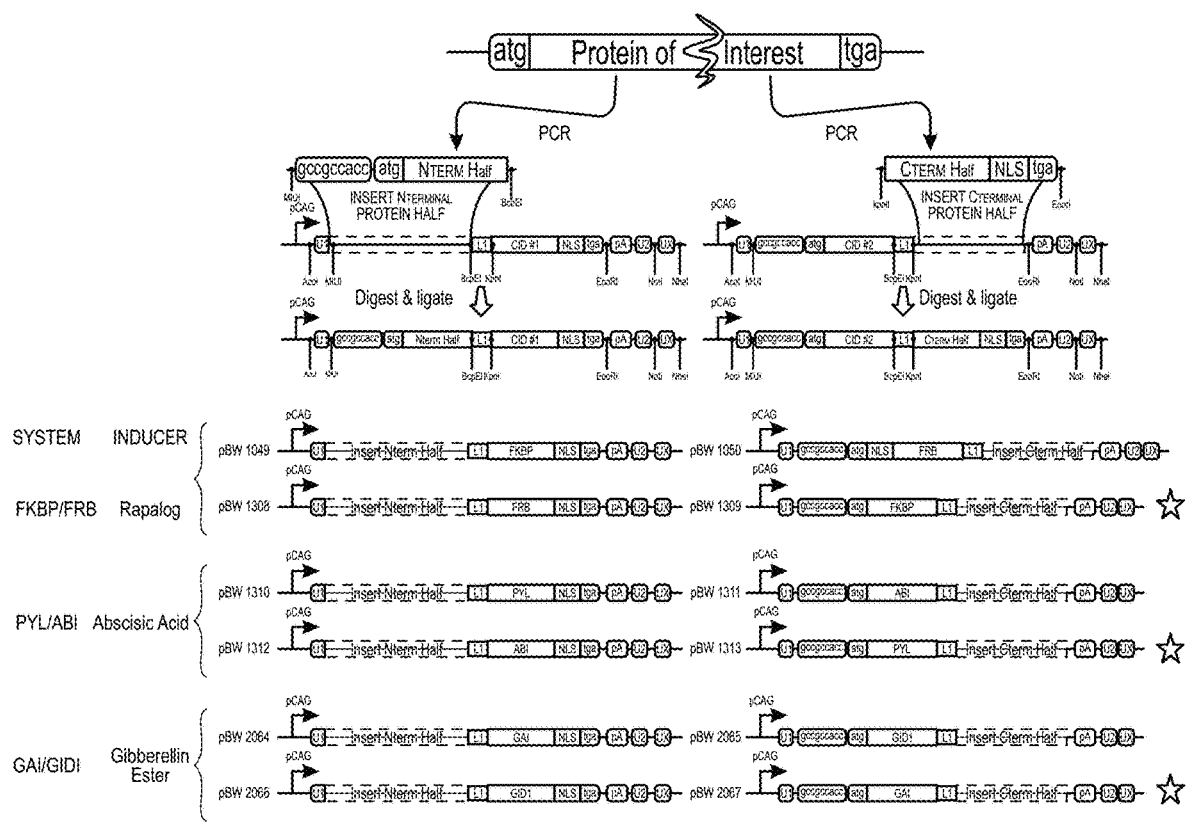

FIG. 36A-36B is a schematic of chemically induced split recombinases. FIG. 36A is a shematic showing an overview of reconstitution of recombinase activity via chemically induced heterodimerization. Here, two halfs of Flp recombinase are fused to the GID1 and GAI heterodimerization domains, which inhibit the recombination activity of Flp via disrupting the protein structure. Upon addition of an esterified gibberellin (GIB) molecule, the GAI and GID1 domains associate with the drug bringing the halves of the Flp together and promoting Flp recombinase activity. FIG. 36B is a cloning schematic of split chemically-inducible recombinases. Fragments are PCRed from a full length DNA sequence of the protein and cloned into two vectors, one for the N-terminal portion of the expressed protein and the second for the C-terminal. Starred vector pairs indicate vectors primarily used for this work. NLS indicates the presence of a nuclear localization signal. L1 (SEQ ID NO: 36) is a glycine/serine rich flexible linker. pA indicates a bovine growth polyadenylation sequence. U1, U2, and UX are cloning scar sequences. All proteins are expressed using a CAGGS (pCAG) promoter.

Figure 37:
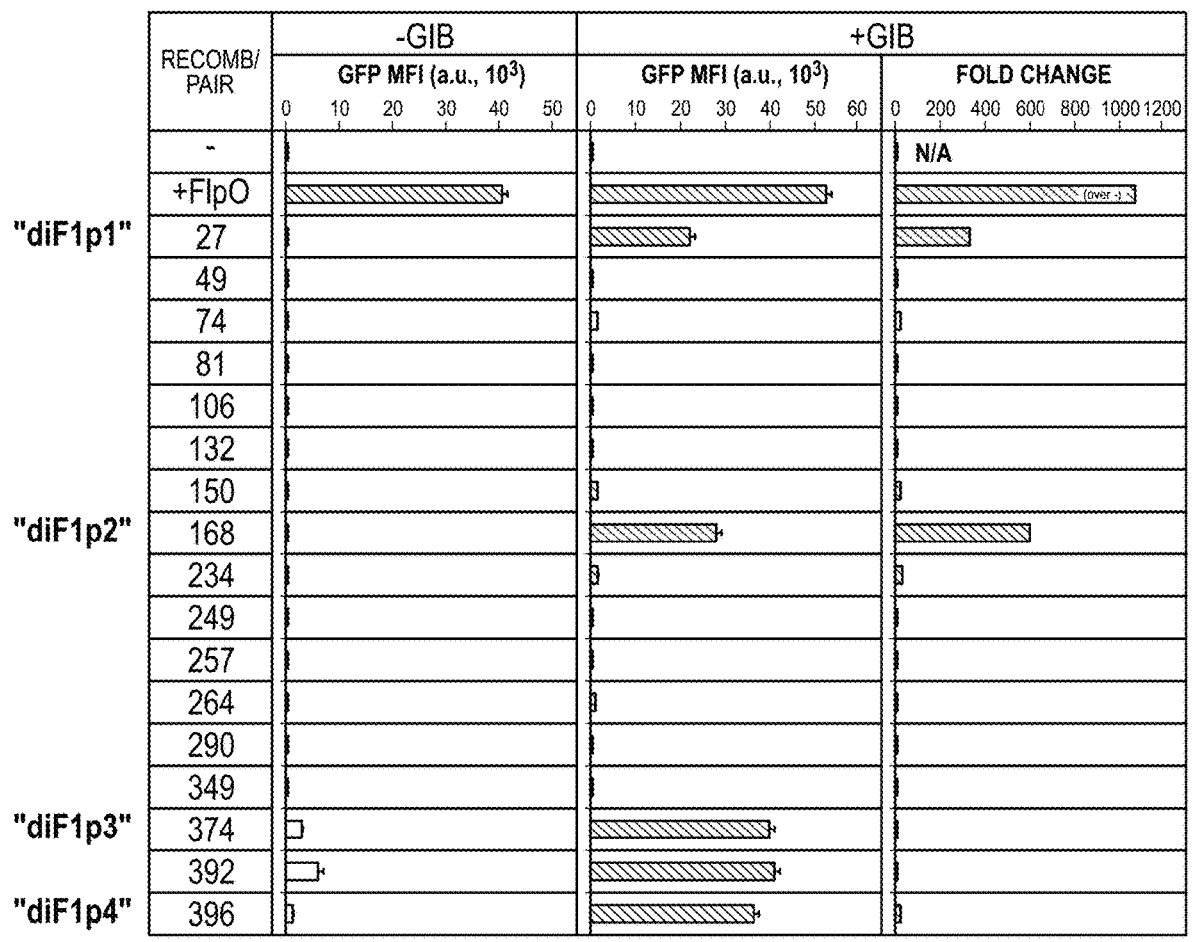

FIG. 37 shows Gibberellin-induced split Flp activity. Full length FlpO and split Flp vectors were tested for induction of recombinase activity on a pCAG-FRT-Neo-FRT-GFP reporter with and without the presence of gibberellin ester (GIB). Values on the left column indicate the amino acid location of the fission (e.g. 27 means amino acid 1 through 27 for the N-terminal portion and amino acid 28 through the end of the protein for the C-terminal portion. Blue shadings indicate split proteins that demonstrate an appreciable increase in GFP expression upon addition of the small molecule drug and four that were further characterized were termed "diFlp."

Figure 38:
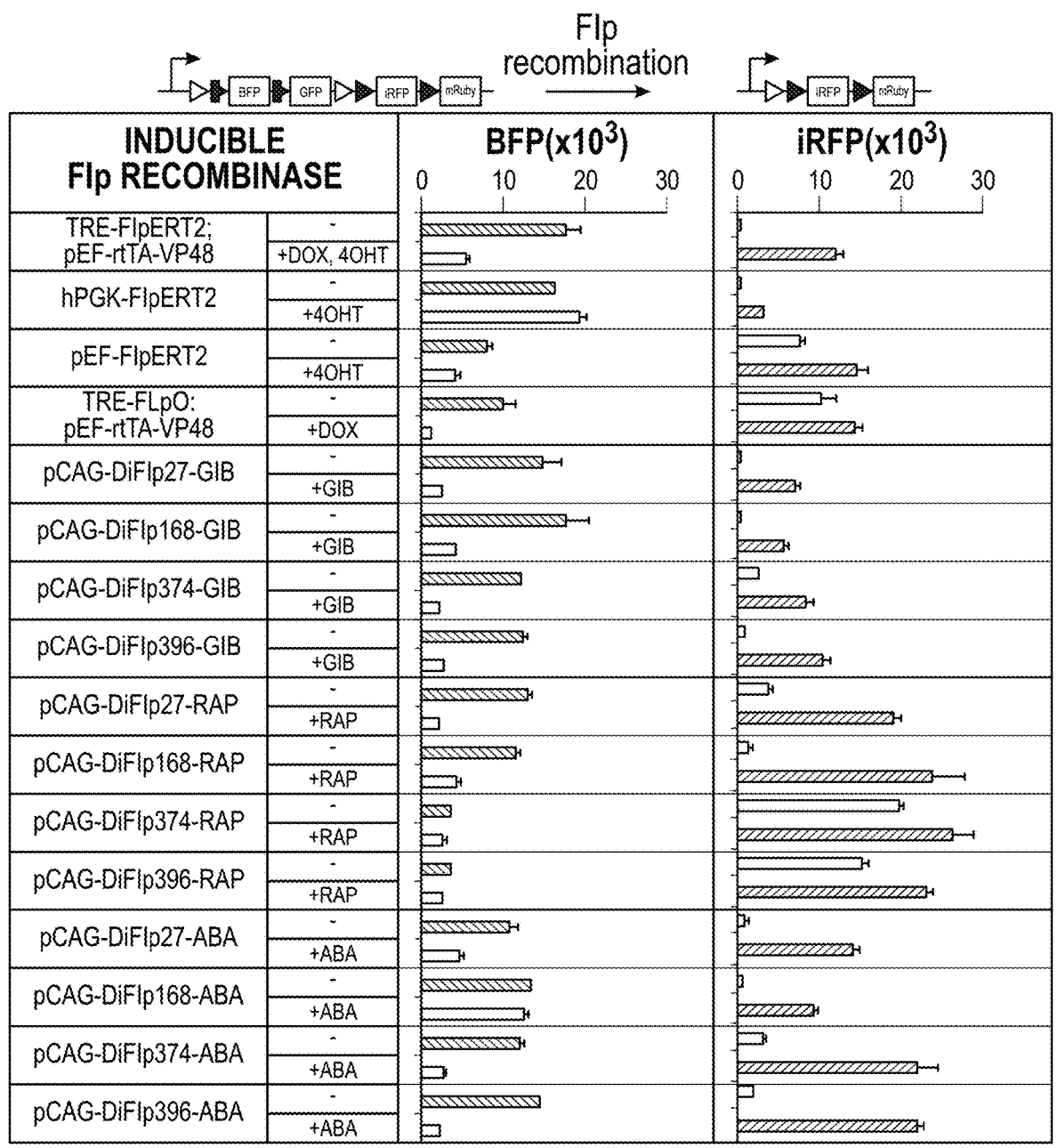

FIG. 38 is a comparison of split Flp protein systems in comparison to doxycycline (DOX) and 4-hydroxytamoxifen (4OHT) controlled Flp systems. Four split locations of Flp recombinase were tested in gibberellin (GIB), rapalog (RAP), and abscisic acid (ABA) chemically dimerization domain vectors in comparison with Flp constructs under control of a DOX/rtTA-VP48 controlled pTRE promoter and/or directly fused to the 4OHT nuclear translocation-responsive estrogen receptor (ERT2). Increase production of iRFP and decrease production of BFP indicate induction of Flp recombination activity.

FIGS. 39A-39C show an embodiment of Gibberlin-induction of a split-PhiC31 recombinase, with Gibberlin inducer binding to the GIA and GID1 CIDD for rejoinder of the split-PhiC31 fragments. FIG. 39A is a schematic for N-terminal PhiC31 (i.e., aa 1-S) conjugated to GIA, and the C-terminal PhiC31 fragment (i.e., aa (S+1)-605) conjugated to GID1, where reconstitution occurs in the presence of gibberlin. When reconstitution occurs, iRFP gene is inverted to a 3' to 5' direction (the incorrect direction) and iRFP expression is turned OFF, and mRuby2 gene is inverted to the 5' to 3' direction (the correct) and mRuby2 gene expression is turned ON. FIG. 39B shows a table of turning ON Ruby2 expression, and turning OFF iRFP expression with PhiC31 N-terminal fragments having a C-terminal amino acid at positions S 233, 396, 428 and 571 in the presence of Rapalog. FIG. 39C shows iRFP expression and mRuby expression of the recombination of PhiC31 N-terminal fragment 1-233, and C-terminal PhiC31 fragment of 234-605 when these fragments are conjugated to CIDDs pairs FKBP/FRB in the presence of Rapalog, or PYL/ABL in the presence of Abscisic acid (ABA), or GAI/GIB in the presence of gibberlin (GIB).

Figure 40A:
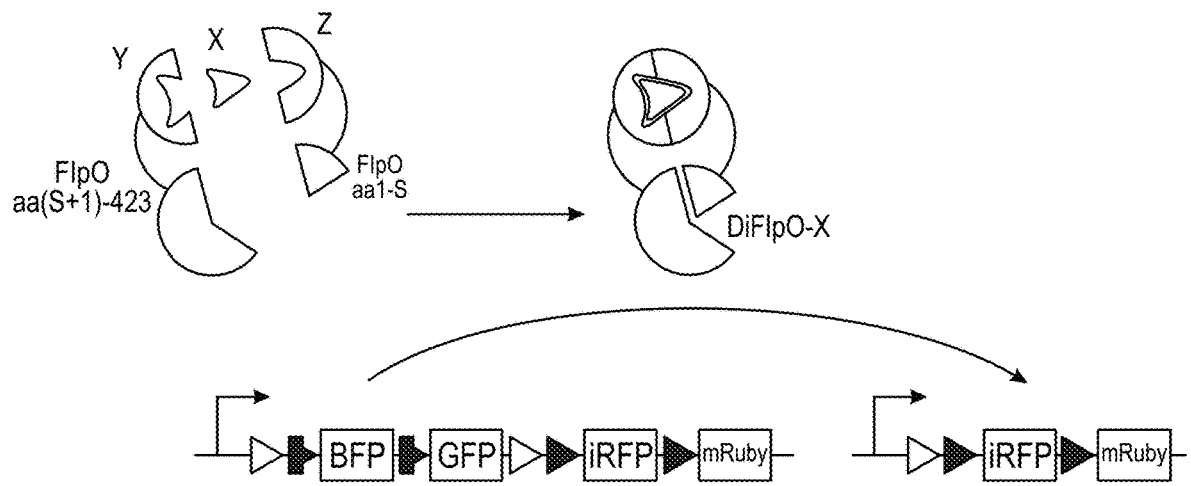
Figure 40B:
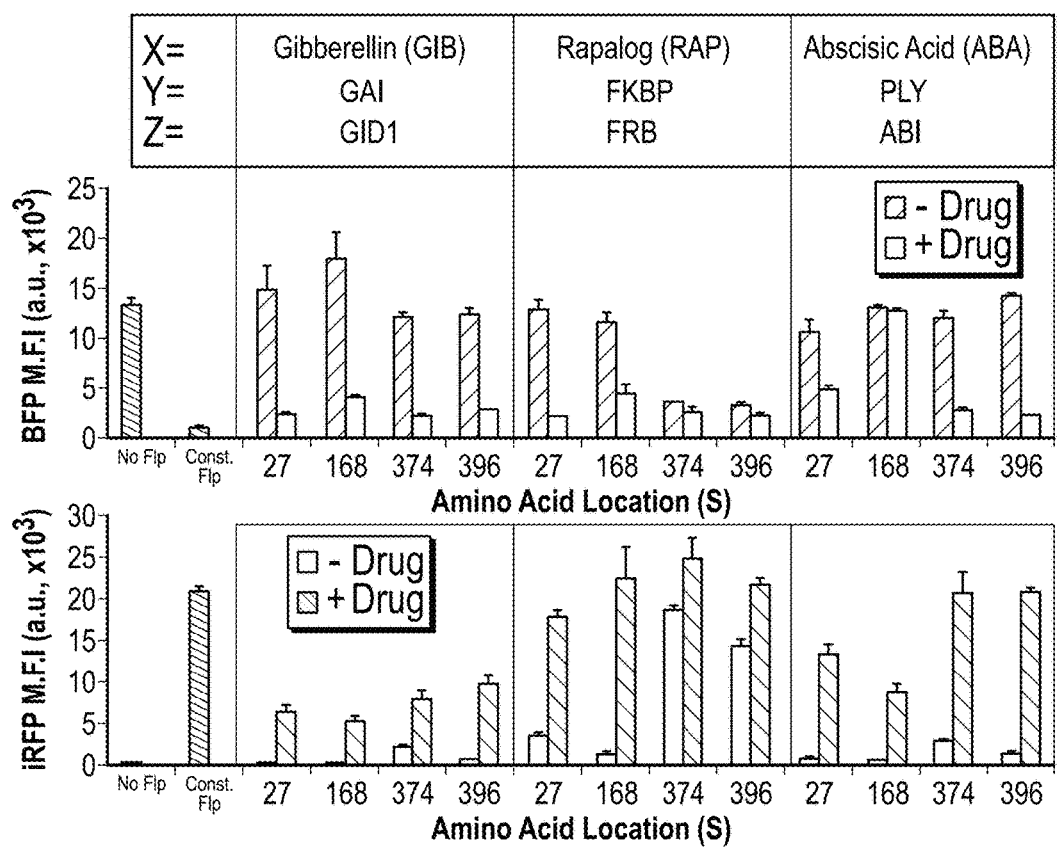

FIGS. 40A-40B controlled induced rejoinder of a split-Flp recombinase. FIG. 40A shows a schematic embodiment of a N-terminal Flp fragment conjugated to a CIDD Y (CIDD$^A$), and a C-terminal fragment conjugated to the complementary CIDD partner, Z (or CIDD$^B$), that in the presence of X (the target agent or inducer to the CIDD pair), recombination occurs of Y and Z (also referred to as CIDD$^A$ and CIDD$^B$) and BFB and GFP expression are turned off, and iRFP expression is turned ON. FIG. 40B shows iRFP and BFP expression on the recombination of different N-terminal Flp fragments with different C-terminal Flp fragments when these fragments are conjugated to CIDDs pairs FKBP/FRB in the presence of the target agent Rapalog, or PYL/ABL in the presence of the target agent Abscisic acid (ABA), or GAI/GIB in the presence of the target agent gibberlin (GIB).

Figure 41A:
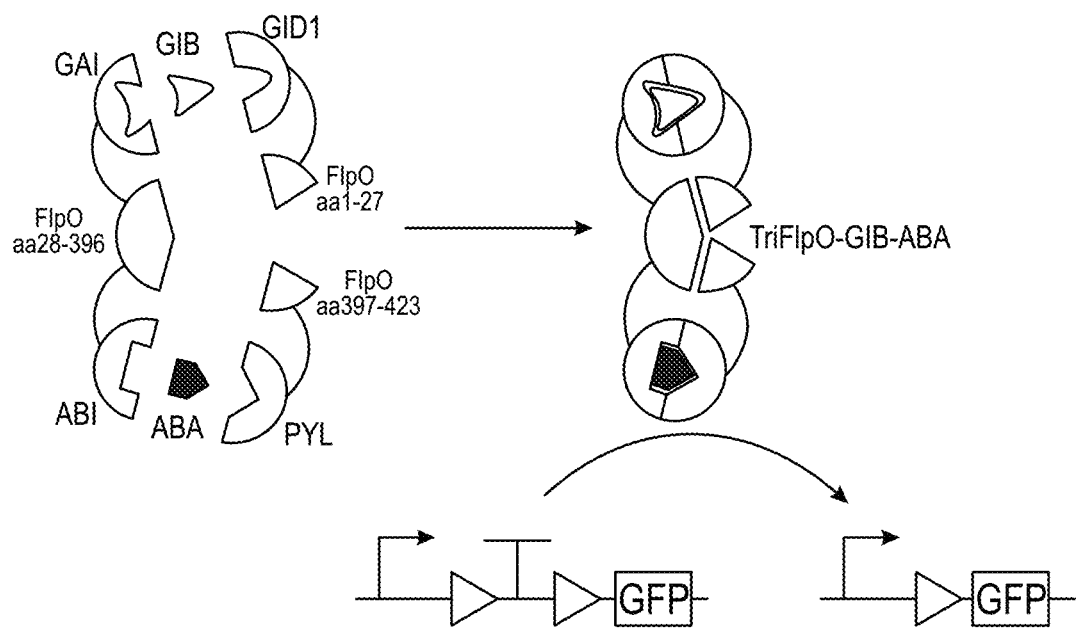
Figure 41B:
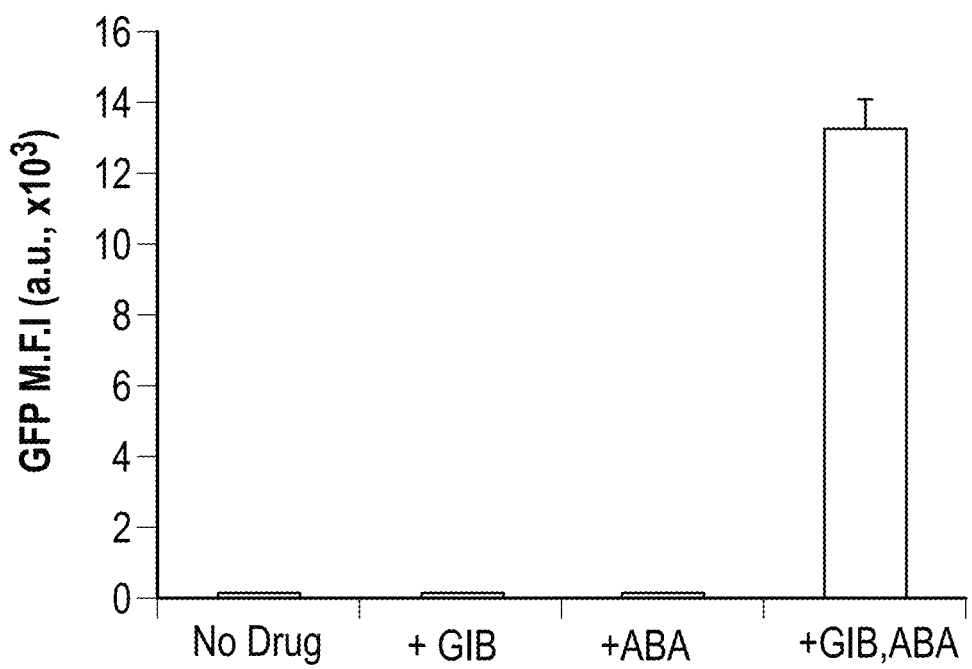

FIG. 41A-41B shows an embodiment of a three-split Flp recombinase, that is controlled by presence of two inducer agents. FIG. 41A is a shematic of an exemplary Flp recombinase split into three fragments (e.g., Flp$^A$, Flp$^B$ and Flp$^C$). In this embodiment, a middle Flp fragment (R$^1$ corresponds to Flp$^B$ of aa 28-396 of SEQ ID NO: 1) is conjugated to GAI (i.e., a first CIDD1 or CIDD1$^A$) and to ABI (i.e., a second CIDD2 or CIDD2$^A$). This middle fragment is represented as ABI-Flp(28-396)-GAI. An N-terminal Flp fragment (aa 1-27 of SEQ ID NO: 1, i.e., R$^2$ which corresponds to Flp$^A$) is conjugated to GID1 (i.e., the complementary pair of CIDD1 or CIDD1$^B$), and is represented as Flp(1-27)-GID1. A C-terminal Flp fragment (aa 397-423 of SEQ ID NO: 1, i.e., R$^3$ which corresponds to Flp$^C$) is conjugated to PYL (i.e., the complementary pair of CIDD2, i.e., CIDD2$^B$) and is represented by Flp(397-423aa)-PYL. In the presence of GIB (the target agent or inducer of CIDD1), GAI and GID1 bind and dimerize, resulting in the rejoinder of the N-terminal Flp fragment (1-27aa, also referred to as R$^2$, Flp$^A$) with the middle fragment (aa 28-396, i.e., R$^1$, or Flp$^B$). For complete recombination of active Flp protein, ABI and PYL bind and dimerize the presence of the target agent ABA, resulting in the rejoinder of the C-terminal Flp fragment (aa 397-423, i.e., R$^3$ or Flp$^C$ fragment) with the middle Flp1 fragment (aa 28-396, e.g., R$^1$ or Flp$^B$ fragment), to produce the active protein, which can catalyze the excision of the stop codon and turn ON GFP gene expression. FIG. 41B shows GFP expression in the presence of both GIB and ABA iducers, demonstrating controlled induced rejoinder in the presence of both inducers.

Figure 42A:
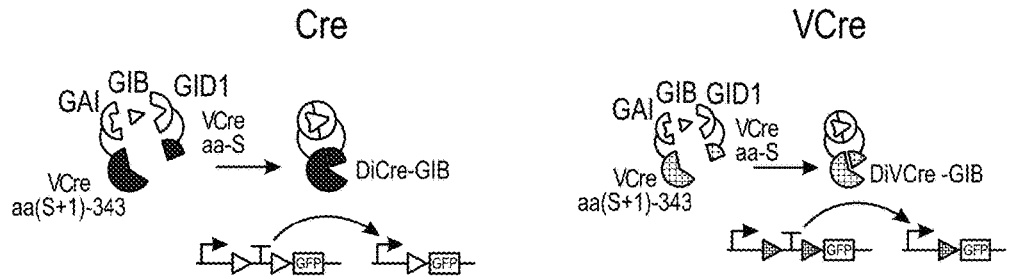
Figure 42B:
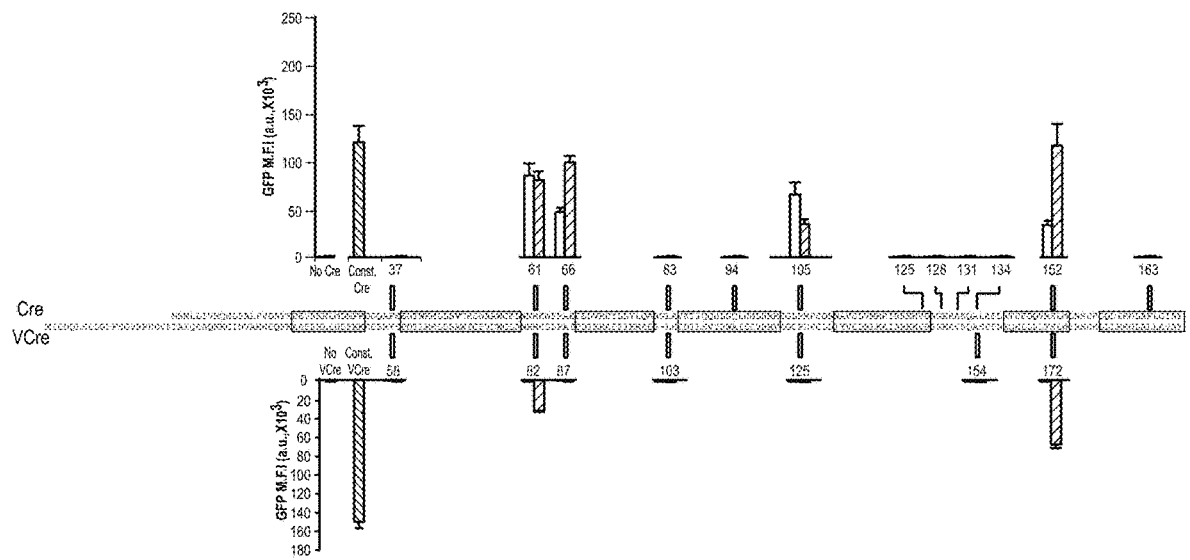
Figure 42B:
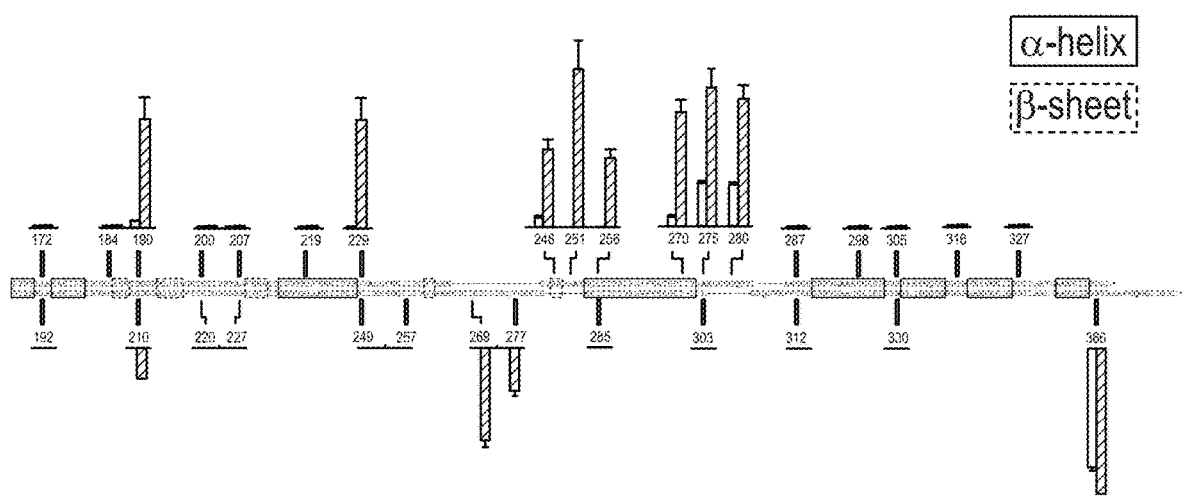

FIGS. 42A-42B show results of gene expression of different split-recombinase Cre (SEQ ID NO: 74) or VCre fragments (SEQ ID NO: 16). FIG. 42A shows a schematic of a split-Cre system and a split-VCre system conjugated to the GAI/GID1 CIDD pair, that in the presence of GIB inducer result in excision of a stop codon upstream of a GFP gene and turn ON expression from the downstream GFP gene. FIG. 42B shows the GFP expression levels of different amino acid residue of split sites (S) of the Cre amino acid sequence (top; shown in red), and different amino acid residue of split sites (S) of VCre amino acid sequence (below, shown in yellow). Split sites (S) of Cre that result in GFP expression in the presence of GIB are aa 190, 229, 248, 251, 256, 270, 275 and 280 of Cre. Split sites (S) of VCre that result in GFP expression in the presence of GIB are: 82, 172, 210, 269 and 277.

Figure 43A:
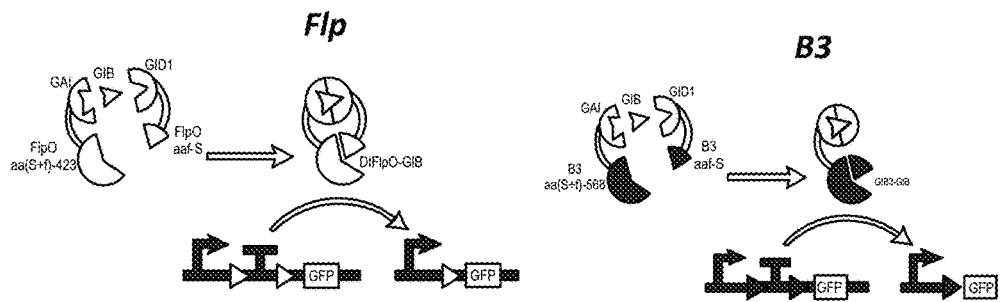
Figure 43B:
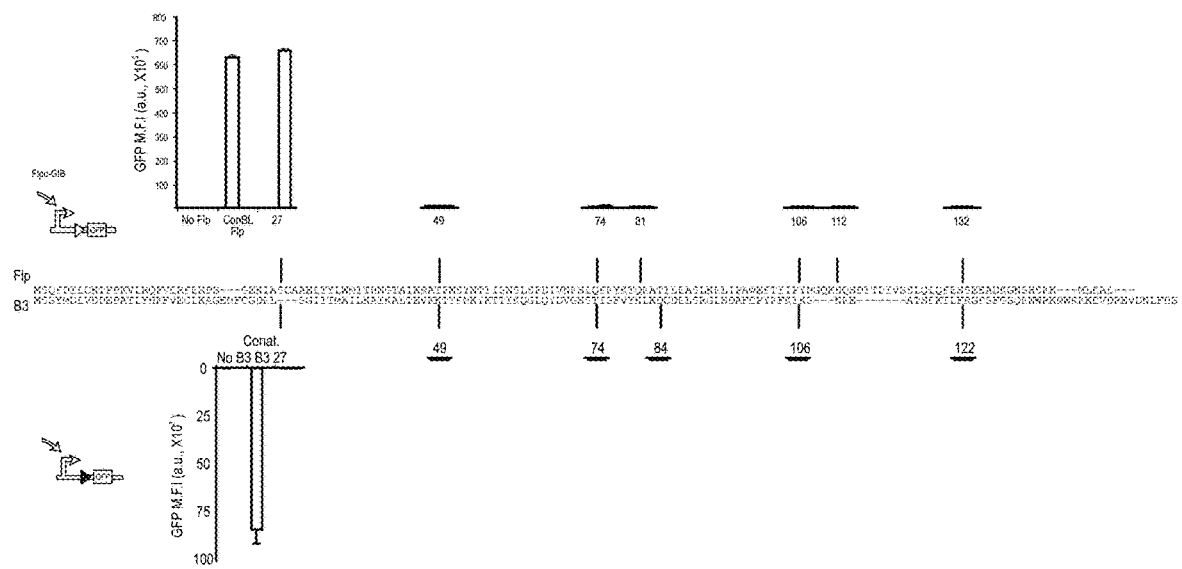
Figure 43C:
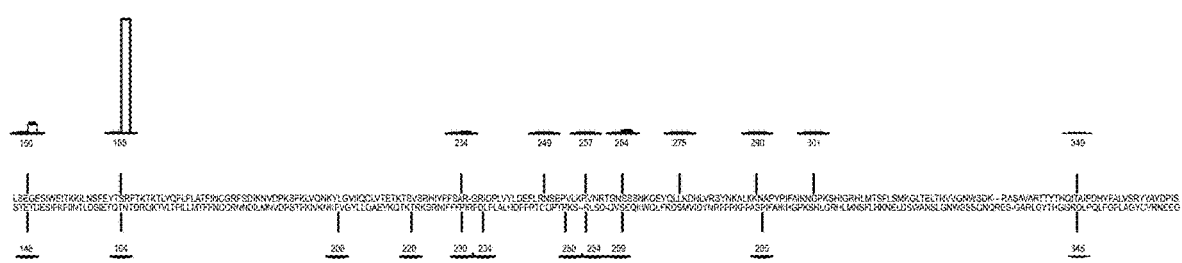
Figure 43D:
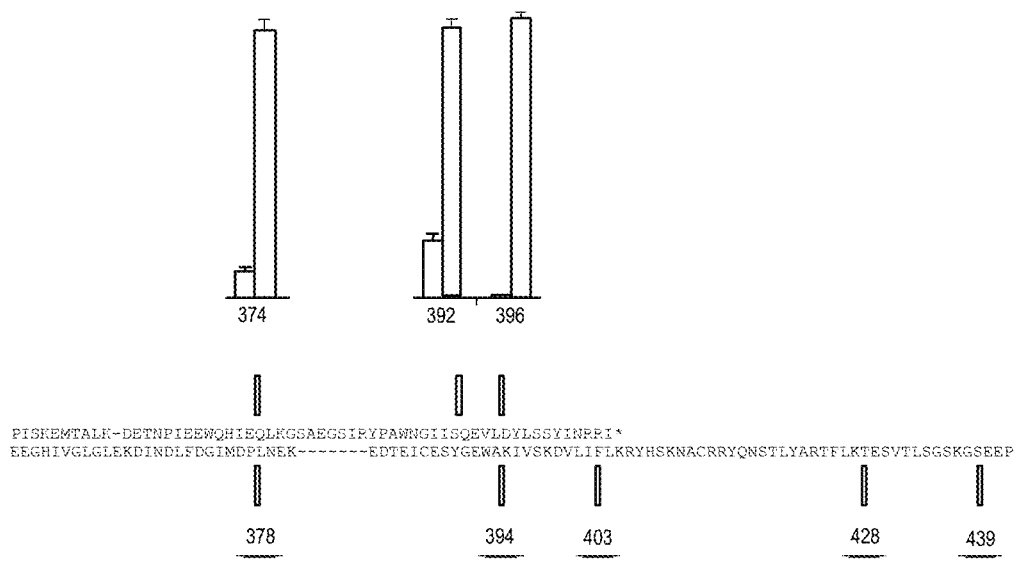
Figure 43E:
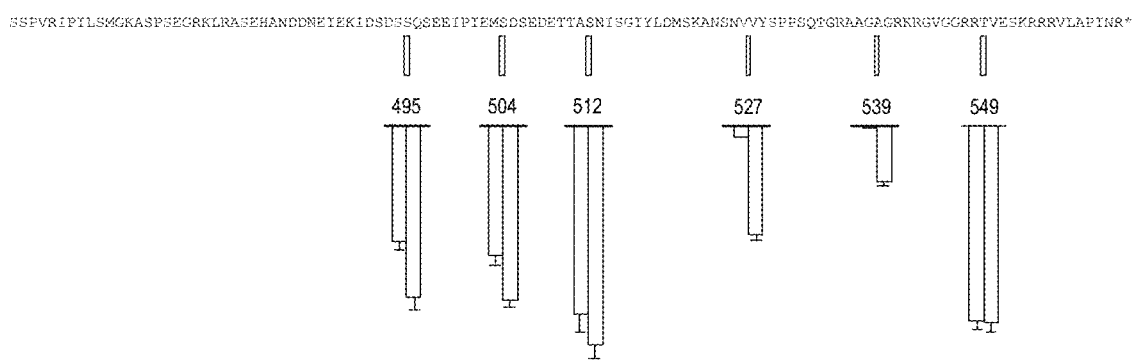

FIGS. 43A-43E show results of gene expression of different split-recombinase Flp (SEQ ID NO: 1) or B3 fragments (SEQ ID NO: 19). FIG. 43A shows a schematic of a split-Flp system and a split-B3 system conjugated to the GAI/GID1 CIDD pair, that in the presence of GIB inducer result in excision of a stop codon upstream of a GFP gene and turn ON expression from the downstream GFP gene. FIGS. 43B-43E show the GFP expression levels of different amino acid residue of split sites (S) of Flp amino acid sequence (top; shown in blue) and amino acid residue of split sites (S) of B3 amino acid sequence (below, shown in orange). Split sites (S) of Flp that result in GFP expression in the presence of GIB are aa 27, 150, 168, 374, 392 and 396 of Flp. Split sites (S) of B3 that result in GFP expression in the presence of GIB are: 527 and 539.

Figure 44:
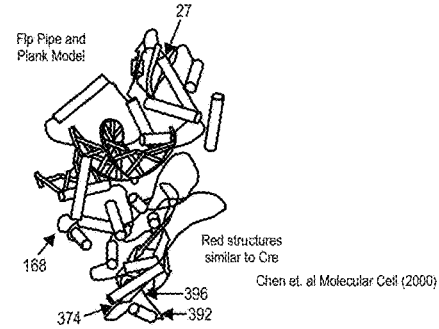

FIG. 44 is an alignment of B3 (SEQ ID NO: 75) and Flp (SEQ ID NO: 76) protein sequences, showing examples of suitable split sites (S) and secondary protein structure regions.

Figure 45:
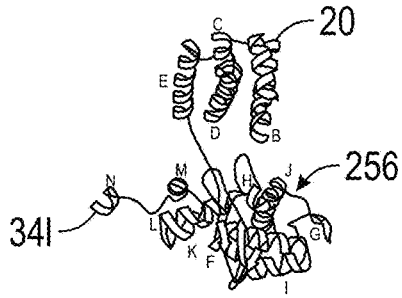

FIG. 45 is an alignment of Cre (SEQ ID NO: 77) and VCre (SEQ ID NO: 78) protein sequences, showing examples of suitable split sites and secondary protein structure regions, identifying regions suitable for split by one of ordinary skill in the art.

Figure 46:
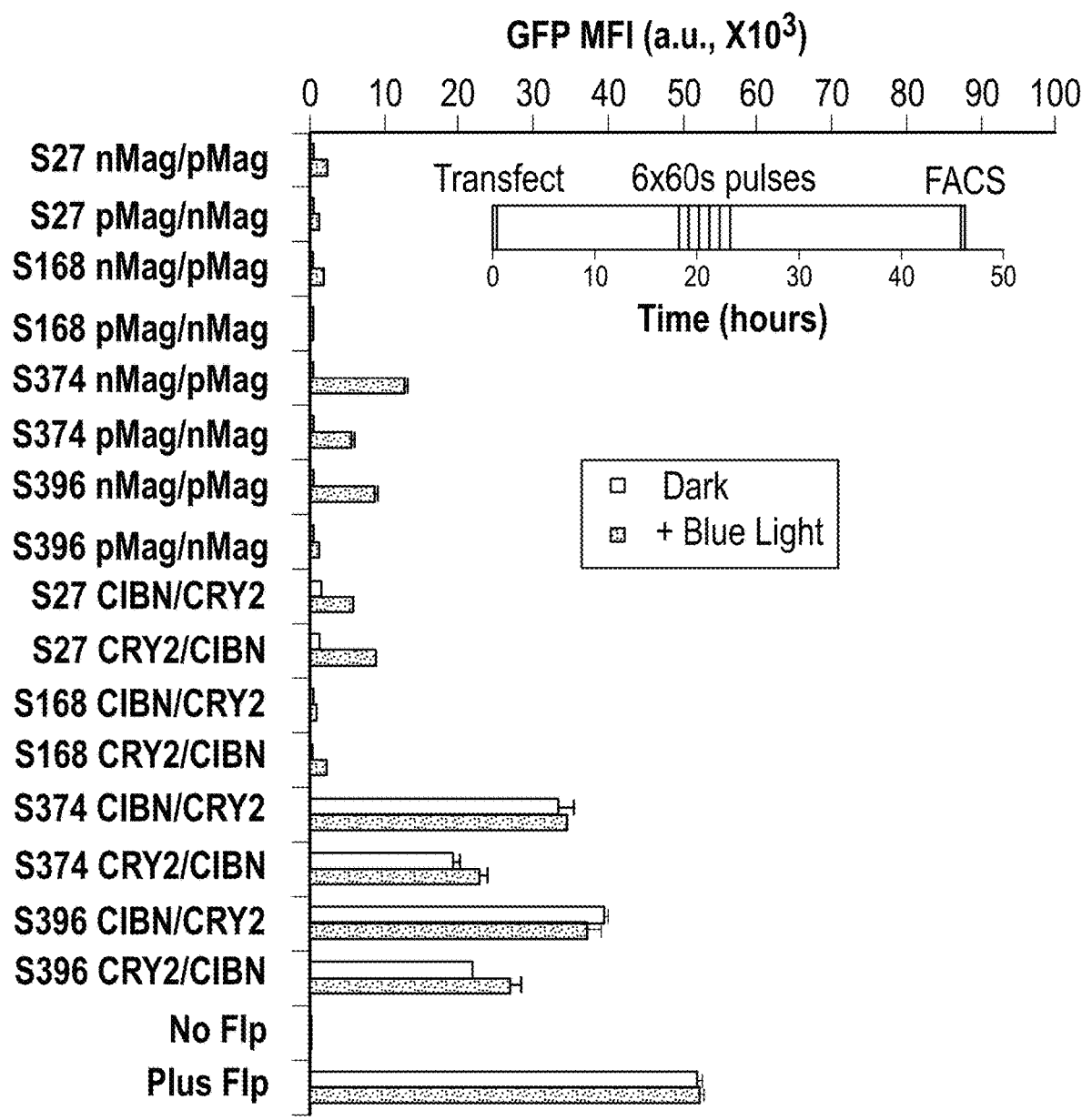

FIG. 46 shows rejoinder of split-Flp fragments conjugated to light inducible dimerization domains (LIDD), nMag/pMag or CRY/CIBN and recombination and GFP expression in the presence of a target signal that is blue light. The LIDD can be fused in different configurations, e.g., nMag to either the N-terminal or C-terminal Flp polypeptide fragments, and vice versa, pMag fused to either the N-terminal or C-terminal Flp polypeptide fragments. The transfected cells were either kept in the dark or stimulated with blue light (i.e., a light signal or target signal) using an IOrodeo large blue LED transilluminator. Pulsed Light (a target signal) was performed at 18 hours post-transfection, with a 60 second pulse of light exposure every hour for the next six hours. Alternative pulse light regimines are encompassed for inducing recombination or light-induced rejoinder of the split-recombinase polypeptide fragments. S374 nMag/pMag configuration (where the N-terminal Flp fragment (1-374aa corresponding to SEQ ID NO: 6) is conjugated to nMag, and the C-terminal Flp fragment (375-423aa corresponding to SEQ ID NO: 7) is conjugated to pMag) showed the largest fold change on pulse light induction.

Figure 47:
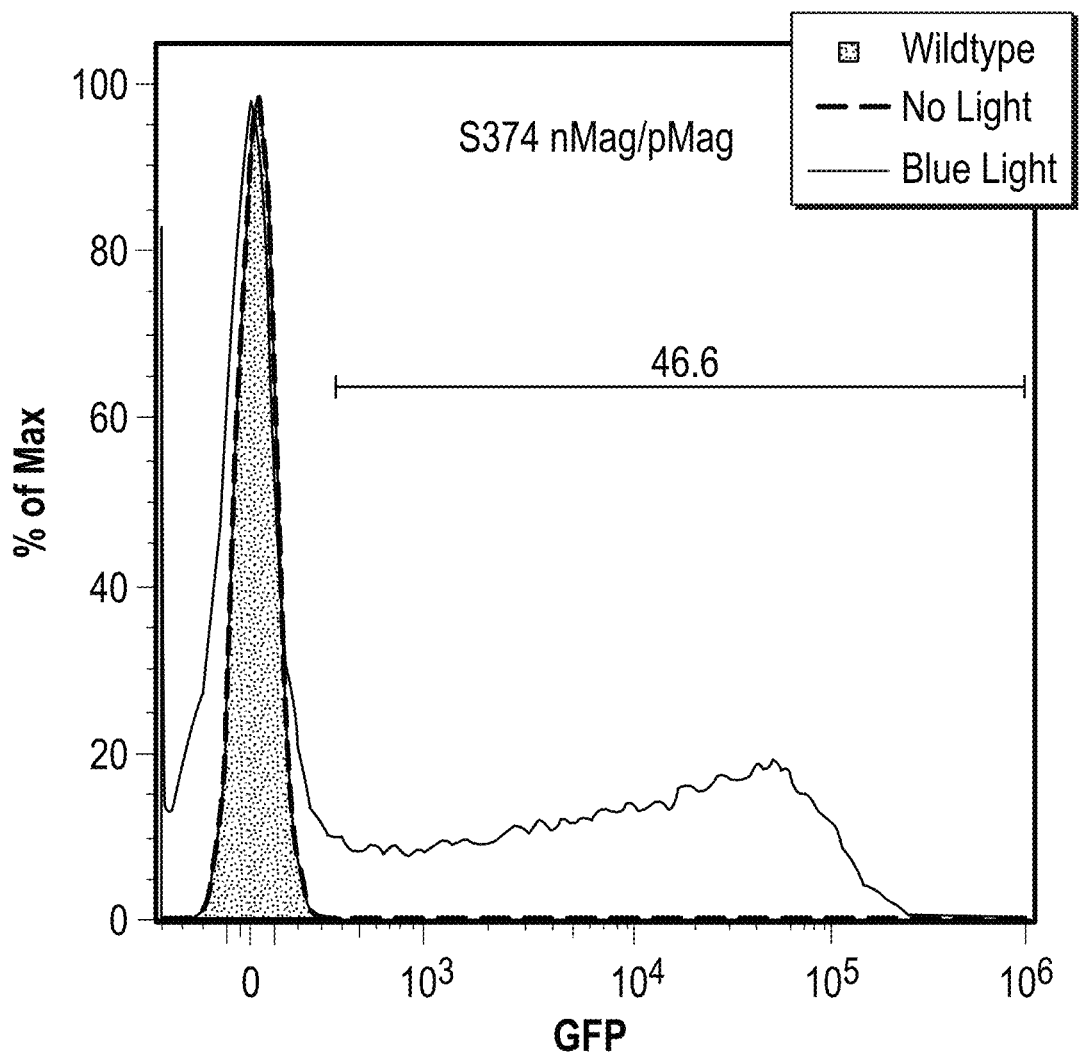

FIG. 47 shows a flow cytometry histogram plot of GFP expression on blue light induction of split-recombinase S374 nMag/pMag configuration, where the N-terminal Flp fragment (1-374aa corresponding to SEQ ID NO: 6) is conjugated to nMag, and the C-terminal Flp fragment (375-423aa corresponding to SEQ ID NO: 7) is conjugated to pMag.

Figure 48A:
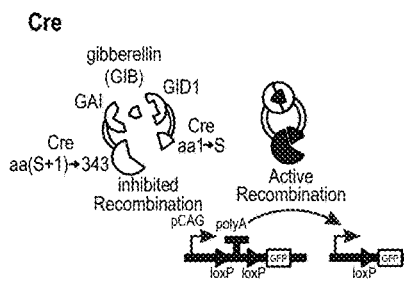
Figure 48C:
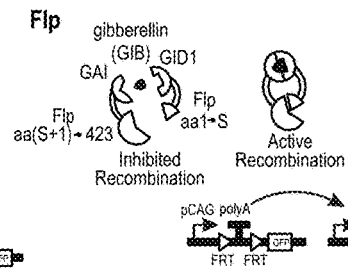
Figure 48E:
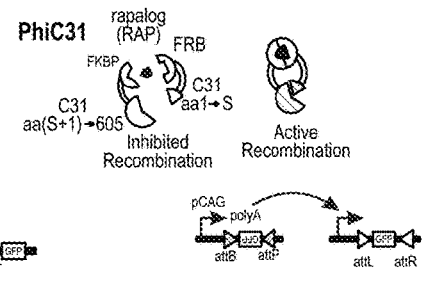
Figure 48B:
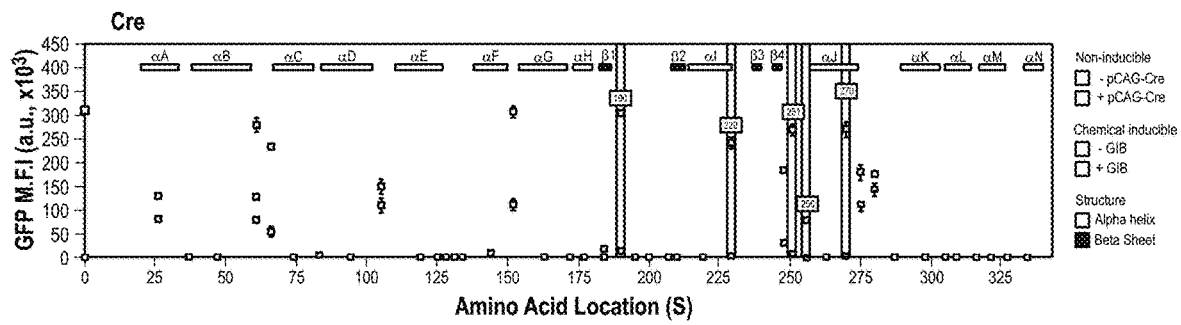

FIG. 48A-48G shows embodiments of different split sites in Cre, Flp and PhiC31 that function to recombine to form an active recombinase, versus non-effective split sites. FIG. 48A shows an embodiment of Cre split into two fragments, Cre$^1$ (aa 1-Split) and Cre$^2$ (aa Split+1 to 343), where Cre$^1$ is conjugated to CIDD$^A$ of GID1, and Cre$^2$ is conjugated to GAI (CIDD$^B$), and in the presence of target agent GIB, GID1 (CIDD$^A$) and GAI (CIDD$^B$) come together to reconstitute Cre$^1$ and Cre$^2$ fragments into the active Cre recombinase protein, thereby removing the Stop signal which is flanked by LoxP (e.g., Cre recombinase target sites) and gene expression (e.g., GFP) expression is turned ON. FIG. 48B shows split sites (S) of Cre that result in GFP expression in the presence of GIB are aa 190, 229, 251, 256, 270 of Cre. FIG. 28B also shows split sites (S) of Cre that do not result in the significant expression of GFP in the presence of GIB (+GIB) (as compared to the absence of GIB; –GIB) are amino acids are listed in the white boxes in FIG. 48G or located in amino acid split sites in alpha helicies αA, αB αB, αD, αE, αF, αG, αH; αK; αL and αM.

Figure 48D:
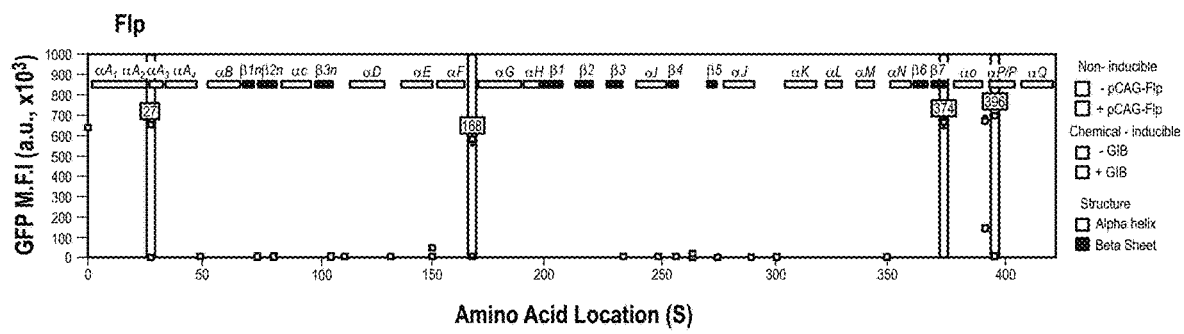

FIG. 48C shows an embodiment of Flp split into two fragments, Flp$^1$ (aa 1-Split) and Flp$^2$ (aa Split+1 to 423), where Flp$^1$ is conjugated to CIDD$^A$ of GID1, and Flp$^2$ is conjugated to GAI (CIDD$^B$), and in the presence of target agent GIB, GID1 (CIDD$^A$) and GAI (CIDD$^B$) come together to reconstitute Flp1 and Flp$^2$ fragments into the active recombinase Flp protein, thereby removing the Stop signal which is flanked by FRT (e.g., Flp recombinase target sites) and gene expression (e.g., GFP) expression is turned ON. FIG. 48D shows split sites(S) of Flp that result in GFP expression in the presence of GIB are aa 27, 168, 374 and 396 of Flp. FIG. 48D also shows split sites(S) of Flp that do not result in the significant expression of GFP in the presence of GIB (+GIB) (as compared to the absence of GIB; –GIB) are listed in the white boxes in the Table shown FIG. 48G or where the amino acid split sites are located in alpha helicies αA$_1$, αA$_2$, αA$_4$, or αB, αC, αD, αE, αF, αG, αH; αI, αJ, αK; αL, αM, αN, αO, or beta-sheets β1n, β2n, β3n, β3, β4, β5.

Figure 48F:
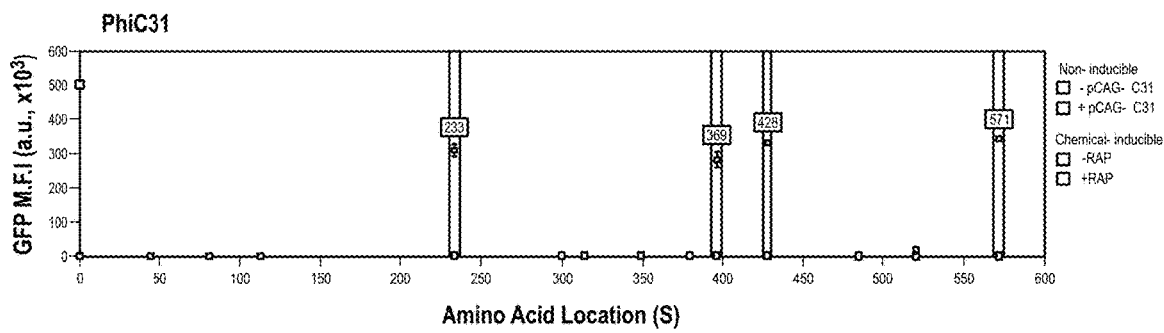

FIG. 48E shows an embodiment of PhiC31 split into two fragments, PhiC31$^1$ (aa 1-Split) and PhiC31$^2$ (aa Split+1 to 605), where PhiC31$^1$ is conjugated to CIDD$^A$ of GID1, and PhiC31$^2$ is conjugated to GAI (CIDD$^B$), and in the presence of target agent GIB, GID1 (CIDD$^A$) and GAI (CIDD$^B$) come together to reconstitute PhiC31$^1$ and PhiC31$^2$ fragments into the active recombinase PhiC31 protein, thereby inverting the GFP gene which is flanked by attB and attP (e.g., PhiC31 recombinase target sites) and gene expression (e.g., GFP) expression is turned ON as attP converted to attL and attB is converted to attR. FIG. 48F shows split sites(S) of PhiC31 that result in GFP expression in the presence of GIB are aa 233, 396, 428, 571 of PhiC31. FIG. 48F also shows split sites(S) of PhiC31 that do not result in the significant expression of GFP in the presence of GIB (+GIB) (as compared to the absence of GIB; –GIB) are listed in the white boxes in the Table shown FIG. 48G.

Figures 48G, 49:
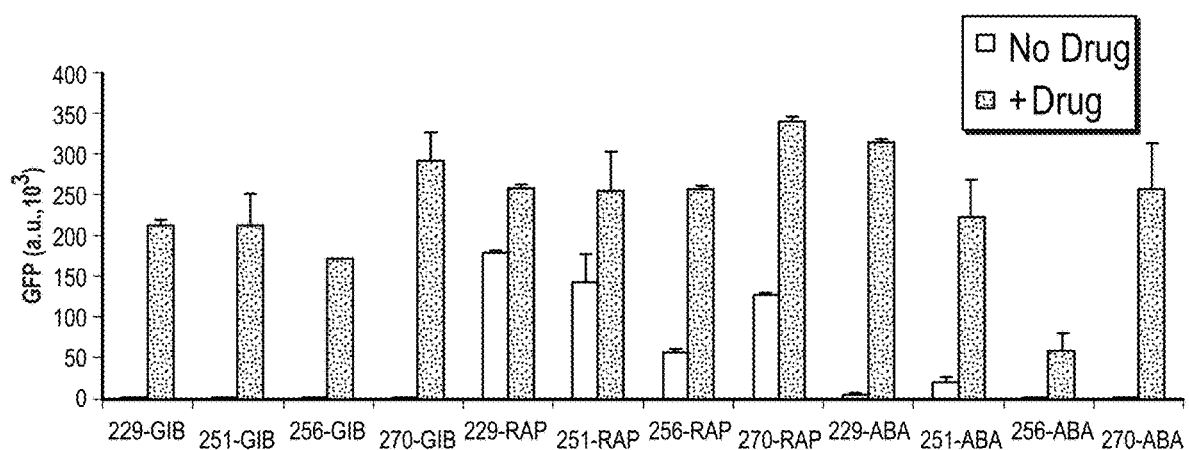

FIG. 48G is a table of Split-sites (S) assesd in Cre, Flp, PhiC31, VCre, B3 and Bxb1. Shown in bold and grey boxes are optimal split site (S) amino acids that allow rejoinder or reconugation to the active recombinase protein. The non-grey amino acids are split sites that were not optimal, i.e., allowed spontaneous rejoinder or recombination of the split-fragments in the absence of the target agent, or did not recombine in the presence of the target agent.

FIG. 49 shows GFP expression of different Cre fragments. Shown is the GFP expression in the presence of the target agent with split sites of Cre at 229, 251, 256 and 270 of Cre (i.e., a N-terminal fragment of Cre, (i.e., Cre$^1$) can be aa 1-229, 1-251, 1-256 or 1-270, and can recombine with C-terminal fragments (i.e., Cre$^2$) as aa 300-343, aa 252-343, aa 257-342 or aa 271-342, respectively. GFP expression is detected when Cre$^1$ is conjugated to any of GIB, RAP or ABA as the CIDD$^A$, in the presence of the corresponding Cre$^2$ and CIDD$^B$ protein, and in the presence of the respective target agent.

Figures 50A, 50B:
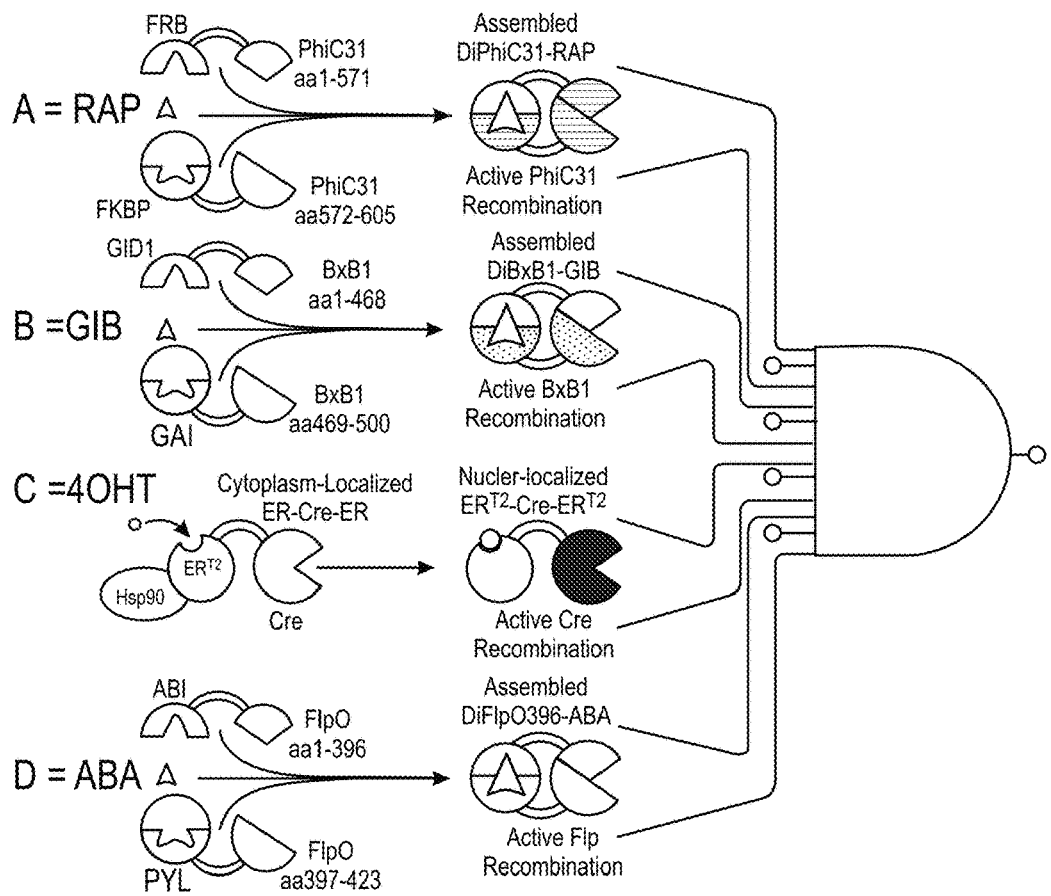

FIG. 50A-50B show an embodiment of a 4-input AND gate. FIG. 50A show examples of four different split recombinases a 4-input AND gate. The split recombinases are A) PhiC31$^1$ (aa 1-571) conjugated to FRB and PhiC31$^2$ (aa572-605) conjugated to FKBP which come together in the presence of RAP, B) BxB$^1$ (aa 1-468) conjugated to GID1 and BxB$^2$ (aa572-605) conjugated to GAI which come together in the presence of 4-hydroxytamoxifen (4OHT); D) Flp$^1$ (aa 1-396) conjugated to ABI and Flp$^2$ (aa 397-423) conjugated to PYL which come together in the presence of ABA. FIG. 50B shows the logic truth table for the 4-input AND gate, where GFP expression is only detected in the presence of RAP, GOB, 4OHT and ABA, due to the rejoinder of all 4 split-recombinases with their respective split fragments as shown in FIG. 50A. Error bars represent standard error of the mean.

Figure 51A:
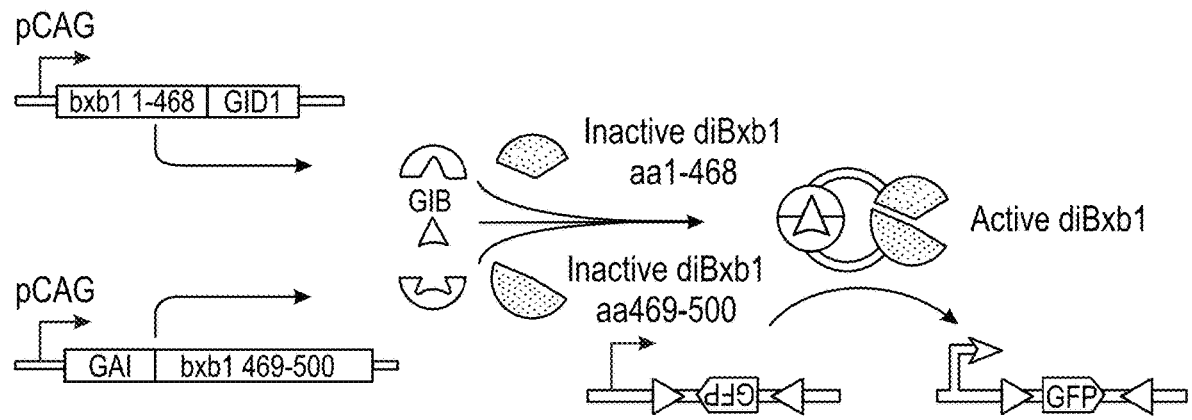
Figure 51B:
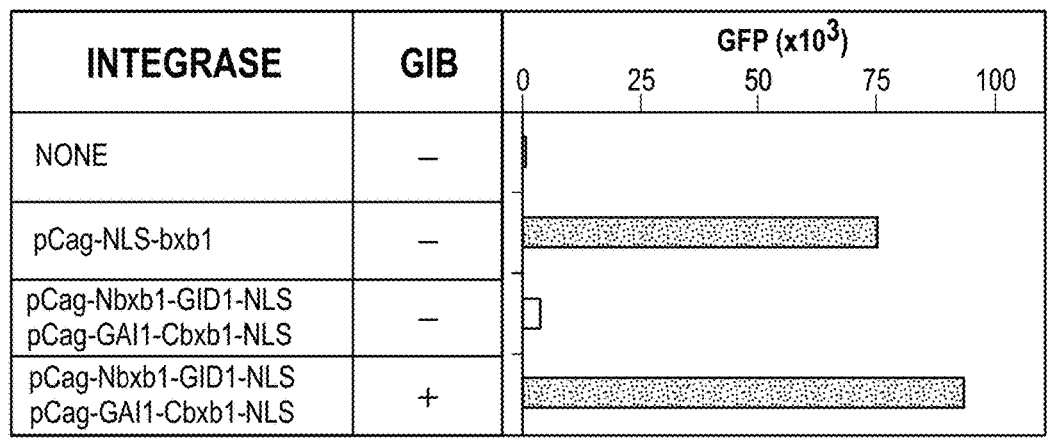

FIG. 51A-51B show an embodiment of BxB1 split into two fragments and resulting GFP expression. FIG. 51A shows an embodiment of BxB1 split into two fragments, BxB1$^1$ (aa 1-468) and BxB1$^2$ (aa 469-500), where BxB1$^1$ is conjugated to GID1 (i.e., CIDD$^A$), and BxB1$^2$ is conjugated to GAI (CIDD$^B$), and in the presence of target agent GIB, GID1 (CIDD$^A$) and GAI (CIDD$^B$) come together to reconstitute BxB1$^1$ and BxB1$^2$ fragments into the active BxB1 recombinase protein, thereby inverting GFP gene which is flanked by two BxB1 recognition sequences resulting in expression being turned ON. FIG. 51B shows that the GFP expression only occurs in the presence of GIB, due to the rejoinder of BxB1$^1$ (aa 1-468) and BxB1$^2$ (aa 469-500) split-recombinase fragments.

DETAILED DESCRIPTION OF THE INVENTION

The technology described herein relates to split-recombinases for use in genetic circuits which come together by drug-mediated protein-complementation. Stated in a different way, the split-recombinases (i.e., two or three or more fragments of a recombinase enzyme) come together by protein-complementation, where the protein complementation is triggered in the presence of a specific drug or inducer agent (herein referred to as an "inducer"). That is, the technology described herein relates to controlled, inducible rejoinder of split-recombinase proteins. Thus, the split-recombinases can be rejoined in a controlled, inducible manner for a variety of uses, e.g., including but not limited to gene therapy, synthetic biology, plant management, environmental clean-up, bacterial and microbial management and synthetic genetic circuits. The split recombinases become active on drug-induced reconstitution, enabling gene therapy, genetic circuits etc. to be independent on expression of the recombinase expression and increasing both activation time and decreasing leaky recombinase expression from their promoters.

Therefore, as the recombinases become active on protein complementation in the presence of an inducer agent or drug, the technology described herein is a system for controlled inducible rejoinder of the recombinase protein fragments, providing an additional level of control of expression of the recombinasaes in genetic circuits. For example, a recombinase protein that is split into at least two inactivated polypeptide fragments, each fragment associated with a complementary protein pair, also referred to herein as "chemical-induced dimerization domains" (or CIDDs). The CIDDs, when brought together by the presence of an inducer agent or drug, form a fully active recombinant protein, and can immediately be used to control gene expression of the gene of interest in the genetic circuit, e.g., BLADE platform. Stated another way, a recombinant protein can be split into at least two inactive fragments, i.e., R' (or $R^1$) and R" ($R^2$), where R' ($R^1$) and R"($R^2$) are each conjugated to complementary chemically-induced dimerization domain (CIDD) protein pairs C' ($CIDD^A$) and C" ($CIDD^B$). In the presence of a specific inducer agent or drug, the CIDDs, C' ($CIDD^A$) and C" ($CIDD^B$) come together, and as a result of being conjugated to C' and C", R' (or $R^1$) and R" ($R^2$) come together by protein complementation to form a fully functional recombinase protein that can control gene expression in a genetic circuit.

Accordingly, in some embodiments, such a controlled inducer rejoinder system, where the recombinase is split into 2 fragments and is controlled by one inducer agent, can comprise the following components:

R'-CIDD1' (which can also be referred to as: $R^1$—$CIDD1^A$)

R"-CIDD1" (which can also be referred to as: $R^2$—$CIDD1^B$)

In the presence of a specific inducer agent or drug of CIDD1, $CIDD1^A$ and its complementary pair $CIDD1^B$ come together, bringing together recombinase fragments $R^1$ and $R^2$, allowing protein complementation to occur and form a fully functional recombinase protein that can control gene expression in a genetic circuit.

In some embodiments, a recombinase protein can be split into three or more fragments. An exemplary embodiment is shown, for example, in FIG. 41A, where the recombinase is split into, for example 3 fragments; R', R" and R'". The first recombinase fragment R' (or $R^1$) is conjugated to a first CIDD1 (i.e., CIDD1' or $CIDD1^A$) and to a second CIDD2 (i.e., CIDD2' or $CIDD2^A$), the second recombinase fragment, R" (or $R^2$) is conjugated to the complementary pair of CIDD1 (i.e., CIDD1" or $CIDD1^B$), a third recombinase fragment R'" ($R^3$) is conjugated to the complementary pair of CIDD2 (i.e., CIDD2" or $CIDD2^B$). In the presence of the inducer of CIDD1, CIDD1'($CIDD1^A$) and CIDD1" ($CIDD1^B$) come together, resulting in the rejoinder of R' ($R^1$) and R" ($R^2$) fragment of the recombinase. In the presence of the inducer of CIDD2, CIDD2'($CIDD2^A$) and CIDD2" ($CIDD2^B$) come together, resulting in the rejoinder of R" (R2) and R'" (R3). As such, when the recombinase is split into three fragments, the rejoinder for the fully active recombinase protein is an AND system, requiring the inducer agent to CIDD1 and the inducer agent to CIDD2.

Accordingly, in some embodiments, such a controlled 2-inducer rejoinder system can comprise the following components:

CIDD1'-R'-CIDD2' (which can also be referred to as: $CIDD1^A$-$R^1$-$CIDD2^A$)

R"-CIDD1" (which can also be referred to as: $R^2$—$CIDD1^B$)

CIDD2' (which can also be referred to as: $R^3$—$CIDD2^B$)

Therefore, in the presence of the inducer to CIDD1, $CIDD1^A$ and $CIDD1^B$ bind to the inducer and dimerize, bringing together $R^1$ and $R^2$, and in the presence of the inducer to CIDD2, $CIDD2^A$ and $CIDD2^B$ bind to the inducer and dimerize, bringing together $R^1$ and $R^3$. Therefore, only in the presence of inducer to CIDD1 and the inducer to CIDD2, does full reconstitution of the recombinase occur.

The inventors herein demonstrate a drug inducible split Flp, PhiC31, VCre, and B3 system that permits regulatable control of their activity, which will allow them control gene expression in genetic circuits, such as but not exclusively genetic circuits disclosed in WO 2015/188191. In particular, the inventors demonstrate reconstituting two halves of the Flp, PhiC31, VCre, and B3 recombinases and their protein recombination can be used to in combination for use in genetic logic gates. These recombinases are large proteins, and it is not clear that a split of these recombinases can be successfully reconstituted by protein complementation.

In some embodiments, the recombinase split-proteins are reconstituted by coming together of attached proteins, such as, e.g., FKBP/FRB proteins, which come together in the presence of Rapalog. In other embodiments, the recombinase split-proteins are reconstituted by coming together of attached proteins, such as, e.g., PYL/ABI proteins, which come together in the presence of Abscisic acid (ABA). In other embodiments, the recombinase split-proteins are reconstituted by coming together of attached proteins, such as, e.g., GAI/GID1 proteins, which come together in the presence of Gibberellin Ester. Other forms of recruiting the two split recombinases can also be used to reconstitute the recombinase, such as through inteins and leucine zippers. In addition, the multiple split proteins can be expressed under different conditional promoters, thus forming an AND gate.

Herein, the inventors demonstrate several split sites on the Flp, PhiC31, B3, VCre recombinases proteins, where their activity can be reconstituted with chemical inducible dimerization system. In particular, the inventors have demonstrated herein, that reconstitution of split recombinases, and therefore recombinase activity induced with Rapalog, abscisic acid, and/or Gibberellins in mammalian cells.

Recombinases in General:

Recombinases, herein, also referred to as "site-specific recombinases" (or "SSR") have been engineered to be very active in a wide range of organisms, including bacteria, mammals, insects, plants and fish. Cre, Flp and PhiC, in particular, have been used widely in animal model development, with Cre being widely used in generation of animal models. However, Cre has demonstrated cytotoxicity, whereas Flp recombinase is very active in mammalian cells and has less toxicity than Cre.

The split-recombinase fragments of the detector protein can be any recombinase polypeptide which associate when brought in to close proximity to generate an active recombinase protein. For example, the two split recombinase proteins can re-associate to generate an active protein. Furthermore, the split-recombinase proteins are designed so that they are in the active state and primed (i.e. in a ready-state) for reconstitution of the active protein in order to minimize any lag time that is traditionally seen with protein complementation in vitro and in vivo.

Split Recombinases

In some embodiments, a recombinase protein is split into at least two, or at least 3 or more split-recombinase polypeptide fragments. As an exemplary embodiment, a recombinase protein is split into an N-terminal fragment (typically referred to herein a a "first recombinase polypeptide fragment") and a C-terminal fragment (typically referred to herein as a "second recombinase polypeptide fragment"). Each of the recombinase fragments are conjugated or attached, either directly (e.g., peptide bonds, covalent bonds or cross-linkers), or indirectly (e.g., with peptide linkers and the like) to a chemical-induced dimerization domains (CIDDs, also sometimes referred to herein as a "binding motif") that can bind to a particular target inducer or drug. When both CIDDs that are conjugated to the N- and C-terminal recombinase polypeptide fragments respectively, binds to the inducer agent or drug, the N- and C-terminal recombinase polypeptide fragments are brought into close proximity with each other allowing protein complementation to occur and the generation of the active recombinase protein.

Stated a different way, a recombinase protein is split into two or more polypeptide fragments, each fragment conjugated with a chemical-induced dimerization domain (CIDDs or binding motif). The polypeptide fragments, when brought together by binding of the conjugated CIDDs to an inducer agent or drug, reconstitute the fully active recombinase protein, and recombinase action can be immediately commenced. Therefore the present technology is advantageous over existing methods to control recombinase activity, in that it can be inducible by a drug or inducer agent, and does not rely on gene expression, and therefore, works in a variety of different types of cells (prokaryotes, eukaryotes), as well as a cell-free system.

Split-recombinase polypeptide fragments as disclosed herein can be any polypeptide fragments of a recombinase protein which associate when brought in to close proximity to generate the active recombinase protein. That is, the split-recombinase polypeptide fragments by themselves are not active, it is only when they come together by protein complementation, to generate the active recombinase enzyme. In one embodiment of the technology described herein, the methods and compostions encompass the design of split-recombinase polypeptide fragments so that they are active immediately upon their reconstitution. In some embodiments, Furthermore, the split-recombinase polypeptide fragments are designed so that they are in the active state and primed (i.e. in a ready-state) for reconstitution of the active protein in order to minimize any lag time that is traditionally seen with protein complementation in vitro and in vivo.

In some embodiments, the recombinase polypeptide fragments are self-complementing fragments of the recombinant protein. Separately, the recombinase polypeptide fragments do not display the recombinase biological activity, but when physically proximate by coming together of the attached CIDDs (or binding motif) which bind to the inducer agent, the fragments spontaneously complement, thereby reconstituting the recombinase protein from which they were derived, restoring the recombinase phenotype. Complementary sets of such fragments are termed "split-recombinase" protein systems. These systems may be generated from any recombinase protein, e.g., PhiC31, Vcre and B3 recombinases, and variants thereof. The split-recombinase system can be used for genetic circuits, such as those disclosed in WO 2015/188191, as well as other uses are envisioned. Also encompassed in the present invention is a split recombinase polypeptides, also referred to as a biomolecular conjugate, produced by the methods described herein.

Recombinase proteins are split at location S where the N-terminal fragment of the protein is from amino acid 1 to amino acid S (inclusive) and the C-terminal fragment of the protein is from S+1 to the end of the protein.

Site Specific Recombinases (SSR) and Recombination Recognition Sequences

The technology disclosed herein relates to splitting recombinase proteins into fragments, which are inactive by themselves, but when in close proximity recombine by protein complementation to result in an active recombinase protein. Recombinases are frequently used to impart stable, DNA-base memory to the logic and memory systems in genetic logic circuits. A "recombinase," as used herein, is a site-specific enzyme that recognizes short DNA sequence(s), which sequence(s) are typically between about 30 base pairs (bp) and 40 bp, and that mediates the recombination between these recombinase recognition sequences, which results in the excision, integration, inversion, or exchange of DNA fragments between the recombinase recognition sequences. A "genetic element," as used herein, refers to a sequence of DNA that has a role in gene expression. For example, a promoter, a transcriptional terminator, and a nucleic acid encoding a product (e.g., a protein product) is each considered to be a genetic element.

Recombinases can be classified into two distinct families: serine recombinases (e.g., resolvases and invertases) and tyrosine recombinases (e.g., integrases), based on distinct biochemical properties. Serine recombinases and tyrosine recombinases are further divided into bidirectional recombinases and unidirectional recombinases. Examples of bidirectional serine recombinases include, without limitation, β-six, CinH, ParA and γδ; and examples of unidirectional serine recombinases include, without limitation, Bxb1, φC31 (phiC31), TP901, TG1, φBTI, R4, cpRV1, cpFCl, MRU, A118, U153 and gp29. Examples of bidirectional tyrosine recombinases include, without limitation, Cre, FLP, and R; and unidirectional tyrosine recombinases include, without limitation, Lambda, HKlO1, HK022 and pSAM2. The serine and tyrosine recombinase names stem from the conserved nucleophilic amino acid residue that the recombinase uses to attack the DNA and which becomes covalently linked to the DNA during strand exchange. Recombinases have been used for numerous standard biological applications, including the creation of gene knockouts and the solving of sorting problems.

Exemplary recombinases for use in the methods and compositions as described herein, and which can be split into two or more protein fragments according to the technology as disclosed herein, include, but are not limited to, Flp, Dre, SCre, VCre, Vika, B2, B3, KD, ΦC31, Bxb1, λ, HK022, HP1, γδ, ParA, Tn3, Gin, R4, TP901-1, TG1, PhiRv1, PhiBT1, SprA, XisF, TnpX, R, BxB1, A118, spoIVCA, PhiMR11, SCCmec, TndX, XerC, XerD, XisA, Hin, Cin, mrpA, beta, PhiFC1, Fre, Clp, sTre, FimE, and HbiF.

The outcome of recombination reaction mediated by coming together of split-recombinase polypeptide fragment depends, in part, on the location and orientation of two short repeated DNA sequences (e.g., RRS) that are to be recombined, typically less than 30 bp long. Recombinases bind to these repeated sequences, which are specific to each recombinase, and are herein referred to as "recombinase recognition sequences" or "recombinase recognition sites" or "RRS". Thus, as used herein, a recombinase is "specific for" a recombinase recognition site when the recombinase can mediate inversion or excision between the repeat DNA sequences. As used herein, a recombinase may also be said to recognize its "cognate recombinase recognition sites," which flank an intervening genetic element (e.g., promoter, terminator, or target gene). A genetic element is said to be "flanked" by recombinase recognition sites when the element is located between and immediately adjacent to two repeated DNA sequences. In some embodiments, the recombinase recognition sites do not overlap each other. However, in other embodiments, recombinase recognition sites do overlap each other, such as described herein below, which permits greatly increased combinatorial complexity.

Exemplary RRS include, but are not limited to, loxP, loxN, lox 511, lox 5171, lox 2272, M2, M3, M7, M11, lox71, lox66, FRT, rox, SloxM1, VloxP, vox, B3RT, KDRT, F3, F14, attB/P, F5, F13, Vlox2272, Slox2272, SloxP, RSRT, and B2RT.

In some embodiments, a recombinase which can be split into two or more protein fragments according to the technology as disclosed herein, can results in an inversion reaction. Inversion recombination happens between two short, inverted, repeated DNA sequences. Without wishing to be bound by theory, a DNA loop formation, assisted by DNA bending proteins, brings the two repeat sequences together, at which point DNA cleavage and ligation occur. This reaction is ATP independent and requires supercoiled DNA. The end result of such an inversion recombination event is that the stretch of DNA between the repeated site inverts (i.e., the stretch of DNA reverses orientation) such that what was the coding strand is now the non-coding strand and vice versa. In such reactions, the DNA is conserved with no net gain or no loss of DNA.

In some embodiments, a recombinase which can be split into two or more protein fragments according to the technology as disclosed herein, can results in an excision reaction. Conversely, excision (integration) recombination occurs between two short, repeated DNA sequences that are oriented in the same direction. In this case, the intervening DNA is excised/removed. For example, an AND gate can be assembled by placing a terminator between each of two different sets of recombinase sites oriented for excision, flanked by a promoter and an output such as a GFP-encoding sequence. In this example, both terminators must be excised by input-dependent action of the recombinase(s) to permit readthrough from the promoter to the GFP-encoding sequence. Thus two inputs are needed to excise both terminators to generate output.

In some embodiments, a recombinase for splitting and use in the present invention is an orthogonal recombinase. In a genetic circuit when a first recombinase is orthogonal to the second recombinase, it means that the second recombinase does not recognize the RRS specific for the first recombinase, neither does the first recombinase recognize the RRS specific for the second recombinase.

In some embodiments, a recombinase which can be split into two or more protein fragments according to the technology as disclosed herein, can also be a irreversible or reversible recombinase. As used herein, an "irreversible recombinase" refers to a recombinase that can catalyze recombination between two complementary recombination sites, but cannot catalyze recombination between the hybrid sites that are formed by this recombination without the assistance of an additional factor. Thus, an "irreversible recognition site" refers to a recombinase recognition site that can serve as the first of two DNA recognition sequences for an irreversible recombinase and that is modified to a hybrid recognition site following recombination at that site. A "complementary irreversible recognition site" refers to a recombinase recognition site that can serve as the second of two DNA recognition sequences for an irreversible recombinase and that is modified to a hybrid recombination site following homologous recombination at that site. For example, attB and attP, described below, are the irreversible recombination sites for Bxb1 and phiC31 recombinases—attB is the complementary irreversible recombination site of attP, and vice versa. Recently, it was shown that the attB/attP sites can be mutated to create orthogonal B/P pairs that only interact with each other but not the other mutants [72]. This allows a single recombinase to control the excision or integration or inversion of multiple orthogonal B/P pairs.

In some embodiments, a recombinase which can be split into two or more recombinase polypeptide fragments according to the technology as disclosed herein is the phiC31 (φC31) integrase. The phiC31 integrase, for example, catalyzes only the attB×attP reaction in the absence of an additional factor not found in eukaryotic cells. The recombinase cannot mediate recombination between the attL and attR hybrid recombination sites that are formed upon recombination between attB and attP. Because recombinases such as the phiC31 integrase cannot alone catalyze the reverse reaction, the phiC31 attB×attP recombination is stable.

Irreversible recombinases, and nucleic acids that encode the irreversible recombinases, are described in the art and can be obtained using routine methods. Examples of irreversible recombinases include, without limitation, phiC31 (φC31) recombinase, coliphage P4 recombinase, coliphage lambda integrase, Listeria A118 phage recombinase, and actinophage R4 Sre recombinase, HK101, HK022, pSAM2, Bxb1, TP901, TG1, φBT1, cpRV1, cpFC1, MRU, U153 and gp29. Conversely, a "reversible recombinase" refers to a recombinase that can catalyze recombination between two complementary recombinase recognition sites and, without the assistance of an additional factor, can catalyze recombination between the sites that are formed by the initial recombination event, thereby reversing it. The product-sites generated by recombination are themselves substrates for subsequent recombination. Examples of reversible recombinase systems include, without limitation, the Cre-lox and the Flp-frt systems, R, β-six, CinH, ParA and γδ.

The recombinases provided herein for splitting into two or more recombinase polypeptide fragments are not meant to be exclusive examples of recombinases that can be used in embodiments of the invention. Other examples of recombinases that can be split into two or more recombinase polypeptide fragments that are useful in the technology as described herein are known to those of skill in the art, and any new recombinase that is discovered or generated is expected to be able to be used in the different embodiments of the invention.

In some embodiments, a recombinase which can be split into two or more recombinase polypeptide fragments according to the technology as disclosed herein is a serine recombinase. Thus, in some embodiments, the recombinase is considered to be irreversible. For some serine recombinases, an initial recombination event can be reversed when a recombinase directionality factor (RDF) is present. RDFs are a diverse group of proteins involved in controlling the directionality of integrase-mediated site-specific recombination reactions. Typically, RDFs are small DNA-binding proteins acting as accessory factors to influence the choice of substrates that are recombined by their cognate recombinase. See Lewis and Hatfull, Nucleic Acids Res. 2001 Jun. 1; 29(11): 2205-2216. For example, when the recombination sites, attB and attP are placed in the antiparallel orientation, the presence of recombinases will stably invert the DNA sequence between the two sites and generate an attL and attR site ("BP reaction"). This inversion remains stable unless a RDF is also expressed along with bxb1 or phiC, which will invert the sequence between attL and attR and regenerate attB and attP site ("LR reaction"). Examples of RDF include, but are not limited to, gp47 for bxb1, gp3 for phiC31, gp3 for PhiBT1, ORF7 for TP901-1, gp25 for TG1, and gp3 for PhiRv1.

In some embodiments, a recombinase which can be split into two or more recombinase polypeptide fragments according to the technology as disclosed herein is a tyrosine recombinase. Thus, in some embodiments, the recombinase is considered to be reversible.

In some embodiments, a recombinase which can be split into two or more recombinase polypeptide fragments according to the technology as disclosed herein is Flp and the corresponding recombinase recognition sequences comprise FRT.

In some embodiments, a recombinase which can be split into two or more recombinase polypeptide fragments according to the technology as disclosed herein is phiC31 (φC31) recombinase and the corresponding recombinase recognition sequences comprise phiC3 lattB and phiC31 attP, to yield product sites attL and attR, respectively.

In some embodiments, a recombinase which can be split into two or more recombinase polypeptide fragments according to the technology as disclosed herein is VCre and the corresponding recombinase recognition sequences comprise VloxP.

In some embodiments, a recombinase which can be split into two or more recombinase polypeptide fragments according to the technology as disclosed herein is B3 and the corresponding recombinase recognition sequences comprise B3RT.

In some embodiments, a recombinase which can be split into two or more recombinase polypeptide fragments according to the technology as disclosed herein is BxB1 recombinase, and the corresponding recombinase recognition sequences are Bxb1 attB and Bxb1 attP to yield product sites attL and attR, respectively.

In some embodiments, a recombinase which can be split into two or more recombinase polypeptide fragments according to the technology as disclosed herein is Dre and the corresponding recombinase recognition sequences comprise rox.

In some embodiments, a recombinase which can be split into two or more recombinase polypeptide fragments according to the technology as disclosed herein is SCre and the corresponding recombinase recognition sequences comprise SloxM1.

In some embodiments, a recombinase which can be split into two or more recombinase polypeptide fragments according to the technology as disclosed herein is Vika and the corresponding recombinase recognition sequences comprise vox.

In some embodiments, a recombinase which can be split into two or more recombinase polypeptide fragments according to the technology as disclosed herein is KD and the corresponding recombinase recognition sequences comprise KDRT.

Flp Recombinase

In some embodiments, the split-recombinase is a Flp or FlpO recombinase. In some embodiments, a split-recombinase protein comprises at least two, or at least three, or at least 4 recombinase polypeptide fragments from the FlpO protein of SEQ ID NO: 1, where when the fragments can complement and reconstitute to generate a active Flp recombinase protein. In the avoidance of any doubt, SEQ ID NO: 1 is as follows:

(SEQ ID NO: 1)
MSQFDILCKTPPKVLVRQFVERFERPSGEKIASCAAELTYLCWMITHNG

TAIKRATFMSYNTIISNSLSFDIVNKSLQFKYKTQKATILEASLKKLIP

AWEFTIIPYNGQKHQSDITDIVSSLQLQFESSEEADKGNSHSKKMLKAL

LSEGESIWEITEKILNSFEYTSRFTKTKTLYQFLFLATFINCGRFSDIK

NVDPKSFKLVQNKYLGVIIQCLVTETKTSVSRHIYFFSARGRIDPLVYL

DEFLRNSEPVLKRVNRTGNSSSNKQEYQLLKDNLVRSYNKALKKNAPYP

-continued

IFAIKNGPKSHIGRHLMTSFLSMKGLTELTNVVGNWSDKRASAVARTTY

THQITAIPDHYFALVSRYYAYDPISKEMIALKDETNPIEEWQHIEQLKG

SAEGSIRYPAWNGIISQEVLDYLSSYINRRI

In some embodiments, a split-recombinase protein comprises at least two, or at least three, or at least 4 recombinase polypeptide fragments from an amino acid sequence that is at least 75%, or at least 80%, or at least 85%, or at least 90% or at least 95%, or at least about 97%, or at least about 98%, or at least about 99% identical to SEQ ID NO: 1, where when the recombinase polypeptide fragments can complement and reconstitute to generate a active Flp recombinase protein.

An active reconstituted Flp protein from the protein complementation of 2 or more recombinase polypeptide fragments can recognize flippase recognition target (FRT) sites, and results in site-specific recombination of a nucleic acid sequence between two such FRT sites.

Accordingly, in some embodiments, a recombinase which can be split into two or more recombinase polypeptide fragments according to the technology as disclosed herein is Flp, and when the two recombinase polypeptide fragments come together, they generate the active Flp recombinase protein which can recognize recombinase recognition sequences comprise FRT. A FRT sequence can comprise nucleic acids GAAGTTCCTATTCTCTAGAAAGTATAG-GAACTTC (SEQ ID NO: 10)

In some embodiments, Flp can be split into at least two, or at least 3 or more split-recombinase polypeptide fragments. As an exemplary embodiment, Flp recombinase protein is split into an N-terminal fragment and a C-terminal fragment, where the N-terminal and C-terminal fragments are conjugated or attached, either directly (e.g., peptide bonds, covalent bonds or cross-linkers), or indirectly (e.g., with peptide linkers and the like) to a chemically-induced dimerization domain (CIDDs, also referred to as "binding motifs") that can bind to a particular inducer agent or drug. When both CIDDs (that are conjugated to the N- and C-terminal Flp recombinase polypeptide fragments respectively), binds to the inducer agent or drug, the N- and C-terminal Flp recombinase polypeptide fragments are brought into close proximity with each other allowing protein complementation to occur and the generation of the active Flp recombinase protein, which can bind to FRT sequence of SEQ ID NO: 10.

Flp recombinase can be split at location S where the N-terminal Flp polypeptide fragment is from amino acid 1 to amino acid S (inclusive) and the C-terminal Flp polypeptide fragment of the protein is from S+1 to the end of the protein. In some embodiments, a N-terminal Flp recombinase polypeptide fragment comprises a continuous stretch of amino acids of a fragment of the N-terminal of SEQ ID NO: 1, where the C-terminus of such a N-terminal Flp fragment ends at amino acid of 27, 49, 74, 81, 160, 112, 132, 150, 168, 234, 249, 257, 264, 275, 290, 301, 349, 374, 392, 396 of SEQ ID NO: 1, or the equivalent amino acid of a protein of at least 70% sequence homology to SEQ ID NO: 1. In some embodiments, a C-terminal Flpe recombinase polypeptide fragment comprises a continuous stretch of amino acids of a fragment of the C-terminal of SEQ ID NO: 1, where the N-terminus of such a C-terminal Flp fragment begins at amino acid of 28, 40, 75, 82, 161, 113, 133, 151, 169, 235, 250, 258, 265, 276, 291, 302, 350, 375, 393, 397 of SEQ ID NO: 1, or the equivalent amino acid of a protein of at least 70% sequence homology to SEQ ID NO: 1. In some embodiments, exemplary N-terminal Flp recombinase polypeptide fragments and exemplary C-terminal Flp recomibase polypeptides are disclosed in Table 1A.

TABLE 1A

Examplary Flp recombinase polypeptide fragments

| Split-Flp recombinase | Split-Flp recombinase fragments (N- and C-terminal fragments) | | | |
|---|---|---|---|---|
| | N-terminal fragment (aa of SEQ ID NO: 1) | SEQ ID NO: | C-terminal fragment (aa of SEQ ID NO: 1) | SEQ ID NO: |
| Flp1 | 1-27 (Flp1-N) | 2 | 28-423 (Flp1-C) | 3 |
| Flp2 | 1-168 (Flp2-N) | 4 | 169-423 (Flp2-C) | 5 |
| Flp3 | 1-374 (Flp3-N) | 6 | 375-423 (Flp3-C) | 7 |
| Flp4 | 1-396 (Flp4-N) | 8 | 397-423 (Flp4-C) | 9 |

Flp1-N:

In some embodiments, a N-terminal Flp recombinase polypeptide fragment comprises a continuous stretch of amino acids of a fragment of the N-terminal of SEQ ID NO: 1, where the C-terminus of such a N-terminal Flp fragment ends at amino acid 27 of SEQ ID NO: 1 (such a Flp polypeptide fragment is herein referred to "Flp1-N"). In some embodiments, a N-terminal Flp recombinase polypeptide fragment comprise amino acids of SEQ ID NO: 2 (i.e., amino acids 1-27 of SEQ ID NO: 1) or a polypeptide of at least 70%, or 80% or 85% or 90%, or 95% or 97% or 98% or 99% identity to SEQ ID NO: 2. In some embodiments, a N-terminal Flp recombinase polypeptide fragment comprises a C-terminal fragment of SEQ ID NO: 2 (i.e., amino acids 1-27 of SEQ ID NO: 1), for example, but by no way a limitation, where at least 1, 2, 3, 4, 5, 6, 7, 8, 9, 10, or more than 10 amino acids are missing from the N-terminal of SEQ ID NO: 2.

Flp2-N:

In some embodiments, a N-terminal Flp recombinase polypeptide fragment comprises a continuous stretch of amino acids of a fragment of the N-terminal of SEQ ID NO: 1, where the C-terminus of such a N-terminal Flp fragment ends at amino acid 168 of SEQ ID NO: 1 (such a Flp polypeptide fragment is herein referred to "Flp2-N"). In some embodiments, a N-terminal Flp recombinase polypeptide fragment comprise amino acids of SEQ ID NO: 4 (i.e., amino acids 1-168 of SEQ ID NO: 1) or a polypeptide of at least 70%, or 80% or 85% or 90%, or 95% or 97% or 98% or 99% identity to SEQ ID NO: 4. In some embodiments, a N-terminal Flp recombinase polypeptide fragment comprises a C-terminal fragment of SEQ ID NO: 4 (i.e., amino acids 1-168 of SEQ ID NO: 1), for example, but by no way a limitation, where at least 1, 2, 3, 4, 5, 6, 7, 8, 9, 10, between 10-20, between 20-30, between 10-50, or more than 50 amino acids are missing from the N-terminal of SEQ ID NO: 4.

Flp3-N

In some embodiments, a N-terminal Flp recombinase polypeptide fragment comprises a continuous stretch of amino acids of a fragment of the N-terminal of SEQ ID NO: 1, where the C-terminus of such a N-terminal Flp fragment ends at amino acid 374 of SEQ ID NO: 1 (such a Flp polypeptide fragment is herein referred to "Flp3-N"). In some embodiments, a N-terminal Flp recombinase polypeptide fragment comprise amino acids of SEQ ID NO: 6 (i.e., amino acids 1-374 of SEQ ID NO: 1) or a polypeptide of at least 70%, or 80% or 85% or 90%, or 95% or 97% or 98% or 99% identity to SEQ ID NO: 6. In some embodiments, a N-terminal Flp recombinase polypeptide fragment comprises a C-terminal fragment of SEQ ID NO: 6 (i.e., amino acids 1-374 of SEQ ID NO: 1), for example, but by no way a limitation, where at least 1, 2, 3, 4, 5, 6, 7, 8, 9, 10, between 10-20, between 20-30, between 10-50, or more than 50 amino acids are missing from the N-terminal of SEQ ID NO: 6.

Flp4-N

In some embodiments, a N-terminal Flp recombinase polypeptide fragment comprises a continuous stretch of amino acids of a fragment of the N-terminal of SEQ ID NO: 1, where the C-terminus of such a N-terminal Flp fragment ends at amino acid 396 of SEQ ID NO: 1 (such a Flp polypeptide fragment is herein referred to "Flp4-N"). In some embodiments, a N-terminal Flp recombinase polypeptide fragment comprise amino acids of SEQ ID NO: 8 (i.e., amino acids 1-396 of SEQ ID NO: 1) or a polypeptide of at least 70%, or 80% or 85% or 90%, or 95% or 97% or 98% or 99% identity to SEQ ID NO: 8. In some embodiments, a N-terminal Flp recombinase polypeptide fragment comprises a C-terminal fragment of SEQ ID NO: 8 (i.e., amino acids 1-396 of SEQ ID NO: 1), for example, but by no way a limitation, where at least 1, 2, 3, 4, 5, 6, 7, 8, 9, 10, between 10-20, between 20-30, between 10-50, or more than 50 amino acids are missing from the N-terminal of SEQ ID NO: 8.

In some embodiments, a cysteine may be added to the C-terminal of a N-terminal Flp polypeptide fragment of any of SEQ ID NO: 2, 4, 6, or 8, or polypeptides of at least 70% identity thereto, or C-terminal fragments thereof, in order to aid its conjugation to a chemically-induced dimerization domains (CIDD or binding motif).

Flp1-C:

In some embodiments, a C-terminal Flp recombinase polypeptide fragment comprises a continuous stretch of amino acids of a fragment of the C-terminal of SEQ ID NO: 1, where the N-terminus of such a C-terminal Flp fragment begins at amino acid 28 of SEQ ID NO: 1 (such a Flp polypeptide fragment is herein referred to "Flp1-C"). In some embodiments, a C-terminal Flp recombinase polypeptide fragment comprise amino acids of SEQ ID NO: 3 (i.e., amino acids 28-423 of SEQ ID NO: 1) or a polypeptide of at least 70%, or 80% or 85% or 90%, or 95% or 97% or 98% or 99% identity to SEQ ID NO: 3. In some embodiments, a C-terminal Flp recombinase polypeptide fragment comprises a N-terminal fragment of SEQ ID NO: 3 (i.e., amino acids 28-423 of SEQ ID NO: 1), for example, but by no way a limitation, where at least 1, 2, 3, 4, 5, 6, 7, 8, 9, 10, between 10-20, between 20-30, between 10-50, or more than 50 amino acids are missing from the C-terminal of SEQ ID NO: 3.

Flp2-C:

In some embodiments, a C-terminal Flp recombinase polypeptide fragment comprises a continuous stretch of amino acids of a fragment of the C-terminal of SEQ ID NO: 1, where the N-terminus of such a C-terminal Flp fragment begins at amino acid 169 of SEQ ID NO: 1 (such a Flp polypeptide fragment is herein referred to "Flp2-C"). In some embodiments, a C-terminal Flp recombinase polypeptide fragment comprise amino acids of SEQ ID NO: 5 (i.e., amino acids 169-423 of SEQ ID NO: 1) or a polypeptide of at least 70%, or 80% or 85% or 90%, or 95% or 97% or 98% or 99% identity to SEQ ID NO: 5. In some embodiments, a C-terminal Flp recombinase polypeptide fragment comprises a N-terminal fragment of SEQ ID NO: 5 (i.e., amino acids 169-423 of SEQ ID NO: 1), for example, but by no way a limitation, where at least 1, 2, 3, 4, 5, 6, 7, 8, 9, 10, between 10-20, between 20-30, between 10-50, or more than 50 amino acids are missing from the C-terminal of SEQ ID NO: 5.

Flp3-C:

In some embodiments, a C-terminal Flp recombinase polypeptide fragment comprises a continuous stretch of amino acids of a fragment of the C-terminal of SEQ ID NO: 1, where the N-terminus of such a C-terminal Flp fragment begins at amino acid 375 of SEQ ID NO: 1 (such a Flp polypeptide fragment is herein referred to "Flp3-C"). In some embodiments, a C-terminal Flp recombinase polypeptide fragment comprise amino acids of SEQ ID NO: 7 (i.e., amino acids 375-423 of SEQ ID NO: 1) or a polypeptide of at least 70%, or 80% or 85% or 90%, or 95% or 97% or 98% or 99% identity to SEQ ID NO: 7. In some embodiments, a C-terminal Flp recombinase polypeptide fragment comprises a N-terminal fragment of SEQ ID NO: 7 (i.e., amino acids 375-423 of SEQ ID NO: 1), for example, but by no way a limitation, where at least 1, 2, 3, 4, 5, 6, 7, 8, 9, 10, between 10-20, between 20-30, or more than 30 amino acids are missing from the C-terminal of SEQ ID NO: 7.

Flp4-C:

In some embodiments, a C-terminal Flp recombinase polypeptide fragment comprises a continuous stretch of amino acids of a fragment of the C-terminal of SEQ ID NO: 1, where the N-terminus of such a C-terminal Flp fragment begins at amino acid 397 of SEQ ID NO: 1 (such a Flp polypeptide fragment is herein referred to "Flp4-C"). In some embodiments, a C-terminal Flp recombinase polypeptide fragment comprise amino acids of SEQ ID NO: 9 (i.e., amino acids 397-423 of SEQ ID NO: 1) or a polypeptide of at least 70%, or 80% or 85% or 90%, or 95% or 97% or 98% or 99% identity to SEQ ID NO: 9. In some embodiments, a C-terminal Flp recombinase polypeptide fragment comprises a N-terminal fragment of SEQ ID NO: 9 (i.e., amino acids 397-423 of SEQ ID NO: 1), for example, but by no way a limitation, where at least 1, 2, 3, 4, 5, 6, 7, 8, 9, 10, 15, or more than 15 amino acids are missing from the C-terminal of SEQ ID NO: 9.

In some embodiments, a cysteine may be added to the N-terminal of a C-terminal Flp polypeptide fragment of any of SEQ ID NO: 3, 5, 7, 9, or polypeptides of at least 70% identity thereto, or N-terminal fragments thereof, in order to aid conjugation to a chemically-induced dimerization domains (CIDD or binding motif).

In some embodiments, a N-terminal Flp polypeptide fragment is inactive by itself and cannot recognize or bind to FRT, but results in an active Flp recombinase protein which can recognize FRT of SEQ ID NO: 10 when it is in close proximity to, and reconstitutes (or protein complements) with its cognate C-terminal Flp polypeptide fragment. That is—a N-terminal Flp polypeptide fragment of SEQ ID NO: 2 (Flp1-N), or homologue or fragment thereof is inactive, but generates the active Flp recombinase protein on protein complementation with its cognate pair of C-terminal Flp polypeptide of SEQ ID NO: 3 (Flp1-C), or a homologue or fragment thereof. Similarly, N-terminal Flp polypeptide fragment of SEQ ID NO: 4 (Flp2-N), or homologue or fragment thereof can protein complement with its cognate pair of C-terminal Flp polypeptide of SEQ ID NO: 5 (Flp2-C), or a homologue or fragment thereof, to reconstitute the active Flp recombinase protein that can bind and recognize FRT of SEQ ID NO: 10. In some embodiments, N-terminal Flp polypeptide fragment of SEQ ID NO: 6 (Flp3-N), or homologue or fragment thereof, can protein complement with its cognate pair of C-terminal Flp polypeptide of SEQ ID NO: 7 (Flp3-C), or a homologue or fragment thereof, to reconstitute the active Flp recombinase protein that can bind and recognize FRT of SEQ ID NO: 10.

The N-terminal and C-terminal Flp polypeptide fragments as disclosed herein, such as of SEQ ID NO: 2-8 and homologues and fragments thereof can be expressed from fragments of the nucleic acid sequence of SEQ ID NO: 11 by one of ordinary skill in the art. SEQ ID NO: 11 is a nucleic acid sequence which encodes the active Flp protein of SEQ ID NO: 1.

As disclosed herein, a recombinase can be split into three or more fragments, therefore requiring two inducer agents for full recombinase rejoinder and reconstitution. Using Flp as an exemplary embodiment, Flp can be split into three fragments, i.e., $Flp^A$, $Flp^B$ and $Flp^C$, where $Flp^A$ can be, for example, Flp1-N (i.e., amino acids 1-27 of Flp, or SEQ ID NO: 2), $Flp^B$ can be, for example, amino acids 28-396 of Flp, and $Flp^C$ can be, for example, amino acids 397-423 of Flp (i.e., Flp4-C or SEQ ID NO: 9).

In some embodiments, in a three-Flp split system, requiring 2 inducers for reconstitution of the active Flp recombinase protein, exemplary N-terminal Flp recombinase polypeptide fragments, exemplary middle Flp fragments and exemplary C-terminal Flp recomibase polypeptides are disclosed in Table 1B. In some embodiments, the split Flp can be split into the following fragments; aa 1-27/aa 28-168/aa 169-423; aa 1-27/aa 28-374/aa 375-423; aa 1-27/aa 28-396/aa 397-423; aa 1-168/aa 169-374/aa 375-423; aa 1-168/aa 169-396/aa 397-423; and aa 1-374/aa 375-396/aa 397-423 of SEQ ID NO: 1, or fragments of at least 75%, or 80% or 85%, or 90%, or 95% or 98% identity to aa 1-27/aa 28-168/aa 169-423; aa 1-27/aa 28-374/aa 375-423; aa 1-27/aa 28-396/aa 397-423; aa 1-168/aa 169-374/aa 375-423; aa 1-168/aa 169-396/aa 397-423; and aa 1-374/aa 375-396/aa 397-423 of SEQ ID NO: 1.

TABLE 1B

Examplary 3-split Flp recombinase polypeptide fragments.

| 3-part split Flp recombinase | $Flp^A$ (N-terminal fragment) | $Flp^B$ (Middle fragment) | $Flp^C$ (C-terminal fragment) |
| --- | --- | --- | --- |
| Flp(1-28-169) | aa 1-27 | aa 28-168 | aa 169-423 |
| Flp(1-28-375) | aa 1-27 | aa 28-374 | aa 375-423 |
| Flp(1-28-397) | aa 1-27 (SEQ ID NO: 2) | aa 28-396 | aa 397-423 (SEQ ID NO: 9) |
| Flp(1-169-375) | aa 1-168 | aa 169-374 | aa 375-423 (SEQ ID NO: 7) |
| Flp(1-169-397) | aa 1-168 | aa 169-396 | aa 397-423 (SEQ ID NO: 9) |
| Flp(1-375-397) | aa 1-374 (SEQ ID NO: 6) | aa 375-396 | aa 397-423 (SEQ ID NO: 9) |

PhiC31 Recombinase

In some embodiments, the split-recombinase is a PhiC31 recombinase. In some embodiments, a split-recombinase protein comprises at least two, or at least three, or at least 4 recombinase polypeptide fragments from the PhiC31 protein of SEQ ID NO: 12, where when the fragments can complement and reconstitute to generate an active PhiC31 recombinase protein. In the avoidance of any doubt, SEQ ID NO: 12 is as follows:

(SEQ ID NO: 12)
MDTYAGAYDRQSRERENSSAASPATQRSANEDKAADLQREVERDGGRFRF

VGHFSEAPGTSAFGTAERPEFERILNECRAGRLNMIIVYDVSRFSRLKVM

DAIPIVSELLALGVTIVSTQEGVFRQGNVMDLIHLIMRLDASHKESSLKS

AKILDTKNLQRELGGYVGGKAPYGFELVSETKEITRNGRMVNVVINKLAH

STTPLTGPFEFEPDVIRWWWREIKTHKHLPFKPGSQAAIHPGSITGLCKR

MDADAVPTRGETIGKKTASSAWDPATVMRILRDPRIAGFAAEVIYKKKPD

GTPTTKIEGYRIQRDPITLRPVELDCGPIIEPAEWYELQAWLDGRGRGKG

LSRGQAILSAMDKLYCECGAVMTSKRGEESIKDSYRCRRRKVVDPSAPGQ

HEGTCNVSMAALDKFVAERIFNKIRHAEGDEETLALLWEAARRFGKLTEA

PEKSGERANLVAERADALNALEELYEDRAAGAYDGPVGRKHFRKQQAALT

LRQQGAEERLAELEAAEAPKLPLDQWFPEDADADPTGPKSWWGRASVDDK

RVFVGLFVDKIVVTKSTTGRGQGTPIEKRASITWAKPPTDDDEDDAQDGT

EDVAA

In some embodiments, a split-recombinase protein comprises at least two, or at least three, or at least 4 recombinase polypeptide fragments from an amino acid sequence that is at least 75%, or at least 80%, or at least 85%, or at least 90% or at least 95%, or at least about 97%, or at least about 98%, or at least about 99% identical to SEQ ID NO: 12, where when the recombinase polypeptide fragments can complement and reconstitute to generate an active PhiC31 (φC31) integrase protein.

The phiC31 integrase, for example, catalyzes only the attB×attP reaction in the absence of an additional factor that is not found in eukaryotic cells. However, once recombination of attB×attP has occurred, the recombinase cannot mediate recombination between the resulting attL and attR hybrid recombination sites (the recombination sites that are formed upon recombination between attB and attP). As such, because phiC31 integrase cannot alone catalyze the reverse reaction, the phiC31 attB×attP recombination is stable (i.e., irreversible).

In some embodiments, a recombinase which can be split into two or more recombinase polypeptide fragments according to the technology as disclosed herein is phiC31 (φC31) recombinase and the corresponding recombinase recognition sequences comprise phiC31 attB and phiC31 attP. Accordingly, in some embodiments, an active reconstituted PhiC31 protein from the protein complementation of 2 or more recombinase polypeptide fragments can recognize attB or attP sites, and results in site-specific recombination of a nucleic acid sequence between two such attB and attP sites.

Accordingly, in some embodiments, a recombinase which can be split into two or more recombinase polypeptide fragments according to the technology as disclosed herein is PhiC31, and when the two recombinase polypeptide fragments come together, they generate the active PhiC31 recombinase protein which can recognize RRS comprising attB and attP. A PhiC31 attB sequence can comprise nucleic acids TGCGGGTGCCAGGGCGTGCCCTTGGGCTCCCCGGGCGCGTACTCC (SEQ ID NO: 13), and a PhiC31 attP sequence can comprise nucleic acids GTGCCCCAACTGGGGTAACCTTT-GAGTTCTCTCAGTTGGGGG (SEQ ID NO: 14)

In some embodiments, PhiC31 can be split into at least two, or at least 3 or more split-recombinase polypeptide fragments. As an exemplary embodiment, PhiC31 recombinase protein is split into an N-terminal fragment and a C-terminal fragment, where the N-terminal and C-terminal fragments are conjugated or attached, either directly (e.g., peptide bonds, covalent bonds or cross-linkers), or indirectly (e.g., with peptide linkers and the like) to a chemically-induced dimerization domains (CIDD or binding motif) that can bind to a particular inducer agent or drug. When both CIDDs (that are conjugated to the N- and C-terminal PhiC31 recombinase polypeptide fragments respectively), binds to the inducer agent or drug, the N- and C-terminal PhiC31 recombinase polypeptide fragments are brought into close proximity with each other allowing protein complementation to occur and the generation of the active PhiC31 recombinase protein, which can bind to attB and attP sequences of SEQ ID NO: 13 and 14.

PhiC31 recombinase can be split at location S where the N-terminal PhiC31 polypeptide fragment is from amino acid 1 to amino acid S (inclusive) and the C-terminal PhiC31 polypeptide fragment of the protein is from S+1 to the end of the protein. In some embodiments, a N-terminal PhiC31 recombinase polypeptide fragment comprises a continuous stretch of amino acids of a fragment of the N-terminal of SEQ ID NO: 12, where the C-terminus of such a N-terminal PhiC31 fragment ends at amino acid of 233, 300, 314, 349, 379, 396, 428, 571 of SEQ ID NO: 12, or the equivalent amino acid of a protein of at least 70% sequence homology to SEQ ID NO: 12. In some embodiments, a C-terminal PhiC31 recombinase polypeptide fragment comprises a continuous stretch of amino acids of a fragment of the C-terminal of SEQ ID NO: 12, where the N-terminus of such a C-terminal PhiC31 fragment begins at amino acid of 234, 301, 315, 350, 380, 397, 429, 572 of SEQ ID NO: 12, or the equivalent amino acid of a protein of at least 70% sequence homology to SEQ ID NO: 12.

In some embodiments, exemplary N-terminal PhiC31 recombinase polypeptide fragments and exemplary C-terminal PhiC31 recomibase polypeptides are disclosed in Table 2. In some embodiments, the N-terminal PhiC31

TABLE 2A

Examplary PhiC31 recombinase polypeptide fragments in a two-split PhiC31 system

| Split-PhiC31 recombinase | N-terminal fragment (aa of SEQ ID NO: 12) | C-terminal fragment (aa of SEQ ID NO: 12) |
|---|---|---|
| PhiC31-1 | 1-233 (PhiC31-1-N) | 234-605 (PhiC31-1-C) |
| PhiC31-2 | 1-396 (PhiC31-2-N) | 397-605 (PhiC31-2-C) |
| PhiC31-3 | 1-428 (PhiC31-3-N) | 429-605 (PhiC31-3-C) |
| PhiC31-4 | 1-571 (PhiC31-4-N) | 572-605 (PhiC31-4-C) |

As discussed above, recombinases can be split into three or more fragments. For example, in some embodiments, exemplary 3-split recombinase systems of PhiC31 are shown in Table 2B:

TABLE 2B

Examplary 3-split PhiC31 recombinase polypeptide fragments.

| | Split-PhiC31 recombinase fragments (shown as aa of SEQ ID NO: 12) | | |
|---|---|---|---|
| 3-part split PhiC31 recombinase | PhiC31$^A$ (N-terminal fragment) | PhiC31$^B$ (Middle fragment) | PhiC31$^C$ (C-terminal fragment) |
| PhiC31(1-234-397) | aa 1-233 | aa 234-396 | aa 397-605 |
| PhiC31(1-234-429) | aa 1-233 | aa 234-428 | aa 429-605 |
| PhiC31(1-234-572) | aa 1-233 | aa 234-571 | aa 572-605 |

TABLE 2B-continued

Examplary 3-split PhiC31 recombinase polypeptide fragments.

| 3-part split PhiC31 recombinase | PhiC31$^A$ (N-terminal fragment) | PhiC31$^B$ (Middle fragment) | PhiC31$^C$ (C-terminal fragment) |
|---|---|---|---|
| PhiC31(1-396-429) | aa 1-396 | aa 397-428 | aa 429-605 |
| PhiC31(1-396-572) | aa 1-396 | aa 397-571 | aa 572-605 |
| PhiC31(1-429-572) | aa 1-428 | aa 429-571 | aa 572-605 |

Split-PhiC31 recombinase fragments (shown as aa of SEQ ID NO: 12)

In some embodiments, a N-terminal PhiC31 recombinase polypeptide fragment comprises a continuous stretch of amino acids of a fragment of the N-terminal of SEQ ID NO: 12, where the C-terminus of such a N-terminal PhiC31 fragment ends at aa 233, or 396, or 428 or 571 of SEQ ID NO: 12, or a polypeptide of at least 70%, or 80% or 85% or 90%, or 95% or 97% or 98% or 99% identity to SEQ ID NO: 12. In such embodiments, a C-terminal PhiC31 recombinase polypeptide fragment comprises a continuous stretch of amino acids of a fragment of the C-terminal of SEQ ID NO: 12, where the N-terminus of such a C-terminal PhiC31 fragment begins at amino acids 234, or 397, or 429 or 572 of of SEQ ID NO: 12, or a polypeptide of at least 70%, or 80% or 85% or 90%, or 95% or 97% or 98% or 99% identity to SEQ ID NO: 12.

In some embodiments, a N-terminal PhiC31 recombinase polypeptide fragment comprises a continuous stretch of amino acids of a fragment of the N-terminal of SEQ ID NO: 12, where the C-terminus of such a N-terminal PhiC31 fragment ends anywhere between amino acids 20-30, or 31-40, or 41-50, or 51-60, or 61-70, or 71-80, or 81-90, or 91-100 of SEQ ID NO: 12, or a polypeptide of at least 70%, or 80% or 85% or 90%, or 95% or 97% or 98% or 99% identity to SEQ ID NO: 12. In such embodiments, a C-terminal PhiC31 recombinase polypeptide fragment comprises a continuous stretch of amino acids of a fragment of the C-terminal of SEQ ID NO: 12, where the N-terminus of such a C-terminal PhiC31 fragment begins anywhere between amino acids 21-31, or 32-41, or 42-51, or 52-61, or 62-72, or 72-81, or 82-91, or 91-101 of SEQ ID NO: 12, or a polypeptide of at least 70%, or 80% or 85% or 90%, or 95% or 97% or 98% or 99% identity to SEQ ID NO: 12.

In some embodiments, a N-terminal PhiC31 recombinase polypeptide fragment comprises a continuous stretch of amino acids of a fragment of the N-terminal of SEQ ID NO: 12, where the C-terminus of such a N-terminal PhiC31 fragment ends anywhere between amino acids 101-150, or 151-200, or 201-250, or 251-300, or 301-350, or 351-400, or 451-500 of SEQ ID NO: 12, or a polypeptide of at least 70%, or 80% or 85% or 90%, or 95% or 97% or 98% or 99% identity to SEQ ID NO: 12. In such embodiments, a C-terminal PhiC31 recombinase polypeptide fragment comprises a continuous stretch of amino acids of a fragment of the C-terminal of SEQ ID NO: 12, where the N-terminus of such a C-terminal PhiC31 fragment begins anywhere between amino acids 102-151, or 152-201, or 202-251, or 252-301, or 302-351, or 352-401, or 452-501 of SEQ ID NO: 12, or a polypeptide of at least 70%, or 80% or 85% or 90%, or 95% or 97% or 98% or 99% identity to SEQ ID NO: 12.

In some embodiments, a N-terminal PhiC31 recombinase polypeptide fragment comprises a continuous stretch of amino acids of a fragment of the N-terminal of SEQ ID NO: 12, where the C-terminus of such a N-terminal PhiC31 fragment ends anywhere between amino acids 501-510, or 511-520, or 521-530, or 531-540, or 541-550, or 551-560, or 561-570, or 571-580, or 581-590, or 591-600, or 601-603 of SEQ ID NO: 12, or a polypeptide of at least 70%, or 80% or 85% or 90%, or 95% or 97% or 98% or 99% identity to SEQ ID NO: 12. In such embodiments, a C-terminal PhiC31 recombinase polypeptide fragment comprises a continuous stretch of amino acids of a fragment of the C-terminal of SEQ ID NO: 12, where the N-terminus of such a C-terminal PhiC31 fragment begins anywhere between amino acids 502-511, or 512-521, or 522-531, or 532-541, or 542-551, or 552-561, or 562-571, or 572-581, or 582-591, or 592-601, or 602-604 of SEQ ID NO: 12, or a polypeptide of at least 70%, or 80% or 85% or 90%, or 95% or 97% or 98% or 99% identity to SEQ ID NO: 12.

The N-terminal and C-terminal PhiC31 polypeptide fragments as disclosed herein, and homologues and fragments thereof can be expressed from fragments of the nucleic acid sequence of SEQ ID NO: 15 by one of ordinary skill in the art. SEQ ID NO: 15 is a nucleic acid sequence which encodes the active PhiC31 protein of SEQ ID NO: 12.

VCre

In some embodiments, the split-recombinase is a VCre recombinase. In some embodiments, a split-recombinase protein comprises at least two, or at least three, or at least 4 recombinase polypeptide fragments from the VCre protein of SEQ ID NO: 16, where when the fragments can complement and reconstitute to generate an active VCre recombinase protein. In the avoidance of any doubt, SEQ ID NO: 16 is as follows:

```
                                          (SEQ ID NO: 16)
MIENQLSLLGDFSGVRPDDVKTAIQAAQKKGINVAENEQFKAAFEHLLNE

FKKREERYSPNTLRRLESAWTCFVDWCLANHRHSLPATPDTVEAFFIERA

EELHRNTLSVYRWAISRVHRVAGCPDPCLDIYVEDRLKAIARKKVREGEA

VKQASPFNEQHLLKLTSLWYRSDKLLLRRNLALLAVAYESMLRASELANI

RVSDMELAGDGTAILTIPITKTNHSGEPDTCILSQDVVSLLMDYTEAGKL

DMSSDGFLFVGVSKHNTCIKPKKDKQTGEVLHKPITTKTVEGVFYSAWET

LDLGRQGVKPFTAHSARVGAAQDLLKKGYNTLQIQQSGRWSSGAMVARYG

RAILARDGAMAHSRVKTRSAPMQWGKDEKD
```

In some embodiments, a split-recombinase protein comprises at least two, or at least three, or at least 4 recombinase polypeptide fragments from an amino acid sequence that is at least 75%, or at least 80%, or at least 85%, or at least 90% or at least 95%, or at least about 97%, or at least about 98%, or at least about 99% identical to SEQ ID NO: 16, where when the recombinase polypeptide fragments can complement and reconstitute to generate an active VCre recombinase protein.

In some embodiments, a recombinase which can be split into two or more recombinase polypeptide fragments according to the technology as disclosed herein is VCre recombinase, which, when reconstituted from its inactive polypeptide fragments, recognizes the VloxP recombinase recognition sequences. Accordingly, in some embodiments, an active reconstituted VCre protein from the protein complementation of 2 or more recombinase polypeptide fragments can recognize VloxP sites, and results in site-specific recombination of a nucleic acid sequence between two such VloxP sites.

Accordingly, in some embodiments, a recombinase which can be split into two or more recombinase polypeptide fragments according to the technology as disclosed herein is VCre, and when the two recombinase polypeptide fragments come together, they generate the active VCre recombinase protein which can recognize RRS comprising VLoxP. A VLoxP sequence can comprise nucleic acids TCAATTTCT-GAGAactgtcatTCTCGGAAATTGA (SEQ ID NO: 17)

In some embodiments, VCre can be split into at least two, or at least 3 or more split-recombinase polypeptide fragments. As an exemplary embodiment, VCre recombinase protein is split into an N-terminal fragment and a C-terminal fragment, where the N-terminal and C-terminal fragments are conjugated or attached, either directly (e.g., peptide bonds, covalent bonds or cross-linkers), or indirectly (e.g., with peptide linkers and the like) to a chemically-induced dimerization domain (CIDD or binding motif) that can bind to a particular inducer agent or drug. When both CIDDs (that are conjugated to the N- and C-terminal VCre recombinase polypeptide fragments respectively), binds to the inducer agent or drug, the N- and C-terminal VCre recombinase polypeptide fragments are brought into close proximity with each other allowing protein complementation to occur and the generation of the active VCre recombinase protein, which can bind to VLoxP sequence of SEQ ID NO: 17.

VCre recombinase can be split at location S where the N-terminal VCre polypeptide fragment is from amino acid 1 to amino acid S (inclusive) and the C-terminal VCre polypeptide fragment of the protein is from S+1 to the end of the protein. In some embodiments, a N-terminal VCre recombinase polypeptide fragment comprises a continuous stretch of amino acids of a fragment of the N-terminal of SEQ ID NO: 16, where the C-terminus of such a N-terminal VCre fragment ends at amino acid of 58, 82, 103, 125, 154, 172, 192, 210, 220, 227, 245, 257, 269, 277, 285, 303, 312, 330 and 366 of SEQ ID NO: 16, or the equivalent amino acid of a protein of at least 70% sequence homology to SEQ ID NO: 16. In some embodiments, a C-terminal VCre recombinase polypeptide fragment comprises a continuous stretch of amino acids of a fragment of the C-terminal of SEQ ID NO: 16, where the N-terminus of such a C-terminal VCre fragment begins at amino acid of 59, 83, 104, 126, 155, 173, 193, 211, 221, 228, 246, 258, 270, 278, 286, 304, 313, 331 and 367 of SEQ ID NO: 16, or the equivalent amino acid of a protein of at least 70% sequence homology to SEQ ID NO: 16.

In some embodiments, exemplary N-terminal VCre recombinase polypeptide fragments and exemplary C-terminal VCre recomibase polypeptides are disclosed in Table 3A. In some embodiments, the N-terminal Vcre.

TABLE 3A

Examplary VCre recombinase polypeptide fragments

| Split-VCre recombinase | N-terminal fragment (aa of SEQ ID NO: 16) | C-terminal fragment (aa of SEQ ID NO: 16) |
|---|---|---|
| VCre-1 | 1-82 (VCre-1-N) | 83-380 (VCre-1-C) |
| VCre-2 | 1-172 (VCre-2-N) | 173-380 (VCre-2-C) |
| VCre-3 | 1-269 (VCre-3-N) | 270-380 (VCre-3-C) |
| VCre-4 | 1-277 (VCre-4-N) | 278-380 (VCre-4-C) |

As discussed above, recombinases can be split into three or more fragments. For example, in some embodiments, exemplary 3-split recombinase systems of VCre are shown in Table 3B. In some embodiments, the split VCre can be split into the following fragments; aa 1-82/83-172/173-380; 1-82/83-269/270-380; 1-82/83-277/278-380; 1-172/173-269/270-380; 1-172/173-277/278-380; and 1-269/270-277/278-380 of SEQ ID NO: 16, or fragments of at least 75%, or 80% or 85%, or 90%, or 95% or 98% identity to aa 11-82/83-172/173-380; 1-82/83-269/270-380; 1-82/83-277/278-380; 1-172/173-269/270-380; 1-172/173-277/278-380; and 1-269/270-277/278-380 of SEQ ID NO: 16.

TABLE 3B

Examplary 3-split VCre recombinase polypeptide fragments.

| 3-part split VCre recombinase | Split-VCre recombinase fragments (shown as aa of SEQ ID NO: 16) | | |
|---|---|---|---|
| | $VCre^A$ (N-terminal fragment) | $VCre^B$ (Middle fragment) | $VCre^C$ (C-terminal fragment) |
| VCre (1-83-173) | aa 1-82 | aa 83-172 | aa 173-380 |
| VCre (1-83-270) | aa 1-82 | aa 83-269 | aa 270-380 |
| VCre (1-83-278) | aa 1-82 | aa 83-277 | aa 278-380 |
| VCre (1-173-270) | aa 1-172 | aa 173-269 | aa 270-380 |
| VCre (1-173-278) | aa 1-172 | aa 173-277 | aa 278-380 |
| VCre (1-269-278) | aa 1-269 | aa 270-277 | aa 278-380 |

In some embodiments, a N-terminal VCre recombinase polypeptide fragment comprises a continuous stretch of amino acids of a fragment of the N-terminal of SEQ ID NO: 16, where the C-terminus of such a N-terminal VCre fragment ends anywhere between amino acids 20-30, or 31-40, or 41-50, or 51-60, or 61-70, or 71-80, or 81-90, or 91-100 of SEQ ID NO: 16, or a polypeptide of at least 70%, or 80% or 85% or 90%, or 95% or 97% or 98% or 99% identity to SEQ ID NO: 16. In such embodiments, a C-terminal VCre recombinase polypeptide fragment comprises a continuous stretch of amino acids of a fragment of the C-terminal of SEQ ID NO: 16, where the N-terminus of such a C-terminal VCre fragment begins anywhere between amino acids 21-31, or 32-41, or 42-51, or 52-61, or 62-72, or 72-81, or 82-91, or 91-101 of SEQ ID NO: 16, or a polypeptide of at least 70%, or 80% or 85% or 90%, or 95% or 97% or 98% or 99% identity to SEQ ID NO: 16.

In some embodiments, a N-terminal VCre recombinase polypeptide fragment comprises a continuous stretch of amino acids of a fragment of the N-terminal of SEQ ID NO: 12, where the C-terminus of such a N-terminal VCre fragment ends anywhere between amino acids 101-150, or 151-200, or 201-250 of SEQ ID NO: 12, or a polypeptide of at least 70%, or 80% or 85% or 90%, or 95% or 97% or 98% or 99% identity to SEQ ID NO: 12. In such embodiments, a C-terminal VCre recombinase polypeptide fragment comprises a continuous stretch of amino acids of a fragment of the C-terminal of SEQ ID NO: 12, where the N-terminus of such a C-terminal VCre fragment begins anywhere between amino acids 102-151, or 152-201, or 202-251 of SEQ ID NO: 12, or a polypeptide of at least 70%, or 80% or 85% or 90%, or 95% or 97% or 98% or 99% identity to SEQ ID NO: 16.

In some embodiments, a N-terminal VCre recombinase polypeptide fragment comprises a continuous stretch of amino acids of a fragment of the N-terminal of SEQ ID NO: 16, where the C-terminus of such a N-terminal VCre fragment ends anywhere between amino acids 251-280, or 281-300, or 301-320, or 321-340, or 341-360 of SEQ ID NO: 16, or a polypeptide of at least 70%, or 80% or 85% or 90%, or 95% or 97% or 98% or 99% identity to SEQ ID NO: 16. In such embodiments, a C-terminal VCre recombinase polypeptide fragment comprises a continuous stretch of amino acids of a fragment of the C-terminal of SEQ ID NO: 16, where the N-terminus of such a C-terminal VCre fragment begins anywhere between amino acids 252-281, or 282-301, or 302-321, or 322-341, or 342-361 of SEQ ID NO: 16, or a polypeptide of at least 70%, or 80% or 85% or 90%, or 95% or 97% or 98% or 99% identity to SEQ6ID NO: 16.

The N-terminal and C-terminal VCre polypeptide fragments as disclosed herein, and homologues and fragments thereof can be expressed from fragments of the nucleic acid sequence of SEQ ID NO: 18 by one of ordinary skill in the art. SEQ ID NO: 18 is a nucleic acid sequence which encodes the active VCre protein of SEQ ID NO: 16.

B3

In some embodiments, the split-recombinase is a B3 recombinase. In some embodiments, a split-recombinase protein comprises at least two, or at least three, or at least 4 recombinase polypeptide fragments from the B3 protein of SEQ ID NO: 19, where when the fragments can complement and reconstitute to generate an active B3 recombinase protein. In the avoidance of any doubt, SEQ ID NO: 19 is as follows:

(SEQ ID NO: 19)
MSSYMDLVDDEPATLYHKFVECLKAGENFCGDKLSGIITMAILKAIKALT

EVKKTTFNKYKTTIKQGLQYDVGSSTISFVYHLKDCDELSRGLSDAFEPY

KFKIKSNKEATSFKTLFRGPSFGSQKNWRKKEVDREVDNLFHSTETDESI

FKFILNTLDSIETQTNTDRQKTVLTFILLMTFFNCCRNNDLMNVDPSTFK

IVKNKFVGYLLQAEVKQTKTRKSRNIFFFPIRENRFDLFLALHDFFRTCQ

PTPKSRLSDQVSEQKWQLFRDSMVIDYNRFFRKFPASPIFAIKHGPKSHL

GRHLMNSFLHKNELDSWANSLGNWSSSQNQRESGARLGYTHGGRDLPQPL

FGFLAGYCVRNEEGHIVGLGLEKDINDLFDGIMDPLNEKEDTEICESYGE

WAKIVSKDVLIFLKRYHSKNACRRYQNSTLYARTFLKTESVTLSGSKGSE

EPSSPVRIPILSMGKASPSEGRKLRASEHANDDNEIEKIDSDSSQSEEIP

IEMSDSEDETTASNISGIYLDMSKANSNVVYSPPSQTGRAAGAGRKRGVG

GRRTVESKRRRVLAPINR

In some embodiments, a split-recombinase protein comprises at least two, or at least three, or at least 4 recombinase polypeptide fragments from an amino acid sequence that is at least 75%, or at least 80%, or at least 85%, or at least 90% or at least 95%, or at least about 97%, or at least about 98%, or at least about 99% identical to SEQ ID NO: 19, where when the recombinase polypeptide fragments can complement and reconstitute to generate an active B3 recombinase protein.

In some embodiments, a recombinase which can be split into two or more recombinase polypeptide fragments according to the technology as disclosed herein is B3 recombinase, where the active reconstituted protein recognizes RRS of B3RT. Accordingly, in some embodiments, an active reconstituted B3 protein from the protein complementation of 2 or more recombinase polypeptide fragments can recognize attB or attP sites, and results in site-specific recombination of a nucleic acid sequence between two such attB and attP sites.

Accordingly, in some embodiments, a recombinase which can be split into two or more recombinase polypeptide fragments according to the technology as disclosed herein is B3, and when the two recombinase polypeptide fragments come together, they generate the active B3 recombinase protein which can recognize RRS comprising B3RT. A B3 B3RT sequence can comprise nucleic acids GGTTGCT-TAAGAATAAGTAATTCTTAAGCAACC (SEQ ID NO: 20).

In some embodiments, B3 can be split into at least two, or at least 3 or more split-recombinase polypeptide fragments. As an exemplary embodiment, B3 recombinase protein is split into an N-terminal fragment and a C-terminal fragment, where the N-terminal and C-terminal fragments are conjugated or attached, either directly (e.g., peptide bonds, covalent bonds or cross-linkers), or indirectly (e.g., with peptide linkers and the like) to a chemically-induced dimerization domain (CIDD or binding motif) that can bind to a particular target agent or drug (i.e., inducer). When both CIDDs (that are conjugated to the N- and C-terminal B3 recombinase polypeptide fragments respectively), binds to the inducer or drug, the N- and C-terminal B3 recombinase polypeptide fragments are brought into close proximity with each other allowing protein complementation to occur and the generation of the active B3 recombinase protein, which can bind to a B3RT sequences of SEQ ID NO: 20.

B3 recombinase can be split at location S where the N-terminal B3 polypeptide fragment is from amino acid 1 to amino acid S (inclusive) and the C-terminal B3 polypeptide fragment of the protein is from S+1 to the end of the protein. In some embodiments, a N-terminal B3 recombinase polypeptide fragment comprises a continuous stretch of amino acids of a fragment of the N-terminal of SEQ ID NO: 19, where the C-terminus of such a N-terminal B3 fragment ends at amino acid of 27, 49, 74, 84, 106, 122, 146, 164, 206, 220, 230, 234, 250, 254, 259, 285, 345, 378, 394, 403, 428, 439, 504, 512, 527, 539 and 549 of SEQ ID NO: 19, or the equivalent amino acid of a protein of at least 70% sequence homology to SEQ ID NO: 19. In some embodiments, a C-terminal B3 recombinase polypeptide fragment comprises a continuous stretch of amino acids of a fragment of the C-terminal of SEQ ID NO: 19, where the N-terminus of such a C-terminal B3 fragment begins at amino acid of 28, 50, 75, 85, 107, 123, 147, 165, 207, 221, 231, 235, 251, 255, 260, 286, 346, 379, 395, 404, 429, 440, 505, 513, 528, 540 and 550 of SEQ ID NO: 19, or the equivalent amino acid of a protein of at least 70% sequence homology to SEQ ID NO: 19.

In some embodiments, exemplary N-terminal B3 recombinase polypeptide fragments and exemplary C-terminal B3 recomibase polypeptides are disclosed in Table 4. In some embodiments, the N-terminal B3

TABLE 4

Examplary B3 recombinase polypeptide fragments

| Split-B3 recombinase | N-terminal fragment (aa of SEQ ID NO: 19) | C-terminal fragment (aa of SEQ ID NO: 19) |
| --- | --- | --- |
| B3-A | 1-539 (B3-A-N) | 540-568 |
| B3-1 | 1 and aa 20-100 | 21-101 to 568 |
| B3-2 | 1 and aa 100-300 | 101-301 to 568 |
| B3-3 | 1 and aa 300-400 | 301-401 to 568 |
| B3-4 | 1 and aa 400-550 | 401-551 to 568 |

In some embodiments, a N-terminal B3 recombinase polypeptide fragment comprises a continuous stretch of amino acids of a fragment of the N-terminal of SEQ ID NO: 19, where the C-terminus of such a N-terminal B3 fragment ends anywhere between amino acids 20-30, or 31-40, or 41-50, or 51-60, or 61-70, or 71-80, or 81-90, or 91-100 of SEQ ID NO: 19, or a polypeptide of at least 70%, or 80% or 85% or 90%, or 95% or 97% or 98% or 99% identity to SEQ ID NO: 19. In such embodiments, a cognate C-terminal B3 recombinase polypeptide fragment comprises a continuous stretch of amino acids of a fragment of the C-terminal of SEQ ID NO: 19, where the N-terminus of such a C-terminal B3 fragment begins anywhere between amino acids 21-31, or 32-41, or 42-51, or 52-61, or 62-72, or 72-81, or 82-91, or 91-101 of SEQ ID NO: 19, or a polypeptide of at least 70%, or 80% or 85% or 90%, or 95% or 97% or 98% or 99% identity to SEQ ID NO: 19.

In some embodiments, a N-terminal B3 recombinase polypeptide fragment comprises a continuous stretch of amino acids of a fragment of the N-terminal of SEQ ID NO: 19, where the C-terminus of such a N-terminal B3 fragment ends anywhere between amino acids 101-150, or 151-200, or 201-250, or 251-300, or 301-350, or 351-400 of SEQ ID NO: 19, or a polypeptide of at least 70%, or 80% or 85% or 90%, or 95% or 97% or 98% or 99% identity to SEQ ID NO: 19. In such embodiments, a C-terminal B3 recombinase polypeptide fragment comprises a continuous stretch of amino acids of a fragment of the C-terminal of SEQ ID NO: 19, where the N-terminus of such a C-terminal B3 fragment begins anywhere between amino acids 102-151, or 152-201, or 202-251, or 252-301, or 302-351, or 352-401 of SEQ ID NO: 19, or a polypeptide of at least 70%, or 80% or 85% or 90%, or 95% or 97% or 98% or 99% identity to SEQ ID NO: 19.

In some embodiments, a N-terminal B3 recombinase polypeptide fragment comprises a continuous stretch of amino acids of a fragment of the N-terminal of SEQ ID NO: 19, where the C-terminus of such a N-terminal B3 fragment ends anywhere between amino acids 401-420-, or 421-440, or 441-460, or 461-480, or 481-500, or 501-510, or 511-520, or 521-530, or 531-540, or 541-550, or 551-560 of SEQ ID NO: 19, or a polypeptide of at least 70%, or 80% or 85% or 90%, or 95% or 97% or 98% or 99% identity to SEQ ID NO: 19. In such embodiments, a cognate C-terminal B3 recombinase polypeptide fragment comprises a continuous stretch of amino acids of a fragment of the C-terminal of SEQ ID NO: 19, where the N-terminus of such a C-terminal B3 fragment begins anywhere between amino acids 402-421, or 422-441, or 442-461, or 462-481, or 482-501, or 502-511, or 512-521, or 522-531, or 532-541, or 542-551, or 552-561 of SEQ ID NO: 19, or a polypeptide of at least 70%, or 80% or 85% or 90%, or 95% or 97% or 98% or 99% identity to SEQ ID NO: 19.

The N-terminal and C-terminal B3 polypeptide fragments as disclosed herein, and homologues and fragments thereof can be expressed from fragments of the nucleic acid sequence of SEQ ID NO: 21 by one of ordinary skill in the art. SEQ ID NO: 21 is a nucleic acid sequence which encodes the active B3 protein of SEQ ID NO: 19.

Bxb1 Recombinase

In some embodiments, the split-recombinase is a BxB1 (also known as "Bxb1") recombinase. In some embodiments, a split-recombinase protein comprises at least two, or at least three, or at least 4 recombinase polypeptide fragments from the Bxb1 protein of SEQ ID NO: 41, where when the fragments can complement and reconstitute to generate an active Bxb1 recombinase protein. In the avoidance of any doubt, SEQ ID NO: 41 is as follows:

(SEQ ID NO: 41)
MRALVVIRLSRVTDATTSPERQLESCQQLCAQRGWDVVGVAEDLDVSGA

VDPFDRKRRPNLARWLAFEEQPFDVIVAYRVDRLTRSIRHLQQLVHWAE

-continued
DHKKLVVSATEAHFDTTTPFAAVVIALMGTVAQMELEAIKERNRSAAHF

NIRAGKYRGSLPPWGYLPTRVDGEWRLVPDPVQRERILEVYHRVVDNHE

PLHLVAHDLNRRGVLSPKDYFAQLQGREPQGREWSATALKRSMISEAML

GYATLNGKTVRDDDGAPLVRAEPILTREQLEALRAELVKTSRAKPAVST

PSLLLRVLFCAVCGEPAYKFAGGGRKHPRYRCRSMGFPKHCGNGTVAMA

EWDAFCEEQVLDLLGDAERLEKVWVAGSDSAVELAEVNAELVDLTSLIG

SPAYRAGSPQREALDARIAALAARQEELEGLEARPSGWEWRETGQRFGD

WWREQDTAAKNTWLRSMNVRLTFDVRGGLTRTIDFGDLQEYEQHLRLGS

VVERLHTGMS.

In some embodiments, a split-recombinase protein comprises at least two, or at least three, or at least 4 recombinase polypeptide fragments from an amino acid sequence that is at least 75%, or at least 80%, or at least 85%, or at least 90% or at least 95%, or at least about 97%, or at least about 98%, or at least about 99% identical to SEQ ID NO: 41, where when the recombinase polypeptide fragments can complement and reconstitute to generate an active Bxb1 integrase protein.

The Bxb1 integrase, for example, catalyzes only the attB×attP reaction in the absence of an additional factor that is not found in eukaryotic cells. However, once recombination of attB×attP has occurred, the recombinase cannot mediate recombination between the resulting attL and attR hybrid recombination sites (the recombination sites that are formed upon recombination between attB and attP). As such, because Bxb1 integrase cannot alone catalyze the reverse reaction, the Bxb1 attB×attP recombination is stable (i.e., irreversible).

In some embodiments, a recombinase which can be split into two or more recombinase polypeptide fragments according to the technology as disclosed herein is Bxb1 recombinase and the corresponding recombinase recognition sequences comprise Bxb1 attB and phiC31 attP. Accordingly, in some embodiments, an active reconstituted Bxb1 protein from the protein complementation of 2 or more recombinase polypeptide fragments can recognize attB or attP sites, and results in site-specific recombination of a nucleic acid sequence between two such attB and attP sites.

Accordingly, in some embodiments, a recombinase which can be split into two or more recombinase polypeptide fragments according to the technology as disclosed herein is Bxb1, and when the two recombinase polypeptide fragments come together, they generate the active Bxb1 recombinase protein which can recognize RRS comprising attB and attP. Exemplary Bxb1 attB sequence can comprise nucleic acids TCGGCCGGCTTGTCGACGACGGCGGTCTCCGT-CGTCAGGATCATCCGGGC (SEQ ID NO: 42), or a sequence with at least 85% identity to SEQ ID NO: 42 and an exemplary bxb1 attP sequence can comprise nucleic acids GTCGTGGTTTGTCTGGTCAAC-CACCGCGGTCTCAGTGGTGTACGGTA-CAAACCCCGAC (SEQ ID NO: 43), or a sequence of at least 85% identity to SEQ ID NO: 43.

In some embodiments, Bxb1 can be split into at least two, or at least 3 or more split-recombinase polypeptide fragments. As an exemplary embodiment, Bxb1 recombinase protein is split into an N-terminal fragment and a C-terminal fragment, where the N-terminal and C-terminal fragments are conjugated or attached, either directly (e.g., peptide bonds, covalent bonds or cross-linkers), or indirectly (e.g., with peptide linkers and the like) to a chemically-induced dimerization domains (CIDD or binding motif) that can bind to a particular inducer agent or drug. When both CIDDs (that are conjugated to the N- and C-terminal Bxb1 recombinase polypeptide fragments respectively), binds to the inducer agent or drug, the N- and C-terminal Bxb1 recombinase polypeptide fragments are brought into close proximity with each other allowing protein complementation to occur and the generation of the active Bxb1 recombinase protein, which can bind to attB and attP sequences of SEQ ID NO: 42 and 43.

Bxb1 recombinase can be split at location S where the N-terminal Bxb1 polypeptide fragment is from amino acid 1 to amino acid S (inclusive) and the C-terminal Bxb1 polypeptide fragment of the protein is from S+1 to the end of the protein (amino acid 500 of SEQ ID NO: 41). In some embodiments, a N-terminal Bxb1 recombinase polypeptide fragment comprises a continuous stretch of amino acids of a fragment of the N-terminal of SEQ ID NO: 41, where the C-terminus of such a N-terminal Bxb1 fragment ends at amino acid 468 of SEQ ID NO: 41, or the equivalent amino acid of a protein of at least 70% sequence homology to SEQ ID NO: 41. In some embodiments, a N-terminal fragment of SEQ ID NO: 41 comprises a N-terminal signal sequence on, which is as follows: MDPKKKRKV (SEQ ID NO: 46).

In some embodiments, a C-terminal Bxb1 recombinase polypeptide fragment comprises a continuous stretch of amino acids of a fragment of the C-terminal of SEQ ID NO: 41, where the N-terminus of such a C-terminal Bxb1 fragment begins at amino acid of 469 of SEQ ID NO: 41, or the equivalent amino acid of a protein of at least 70% sequence homology to SEQ ID NO: 41.

In some embodiments, exemplary N-terminal Bxb1 recombinase polypeptide fragments and exemplary C-terminal Bxb1 recomibase polypeptides are disclosed in Table 8. In some embodiments, the N-terminal Bxb1

TABLE 8

Examplary Bxb1 recombinase polypeptide fragments in a two-split Bxb1 system

| Split-Bxb1 recombinase | N-terminal fragment (aa of SEQ ID NO: 41) | C-terminal fragment (aa of SEQ ID NO: 41) |
|---|---|---|
| Bxb1-1 | 1-468 (Bxb1-1-N) | 469-500 (Bxb1-1-C) |
| Bxb1-2 | 1 and aa 20-100 (Bxb1-2-N) | 21-101 and 500 (Bxb1-2-C) |
| Bxb1-3 | 1 and aa 100-200 (Bxb1-3-N) | 101-201 and 500 (Bxb1-3-C) |
| Bxb1-4 | 1 and aa 200-300 (Bxb1-4-N) | 201-301 and 500 (Bxb1-4-C) |
| Bxb1-5 | 1 and aa 300-400 (Bxb1-5-N) | 301-401 and 500 (Bxb1-4-C) |
| Bxb1-6 | 1 and aa 400-497 (Bxb1-5-N) | 401- and 498 (Bxb1-5-C) |

As discussed above, Bxb1 recombinase can be split into three or more fragments.

In some embodiments, a N-terminal Bxb1 recombinase polypeptide fragment comprises a continuous stretch of amino acids of a fragment of the N-terminal of SEQ ID NO: 41, where the C-terminus of such a N-terminal Bxb1 fragment ends anywhere between amino acids 20-30, or 31-40, or 41-50, or 51-60, or 61-70, or 71-80, or 81-90, or 91-100 of SEQ ID NO: 41, or a polypeptide of at least 70%, or 80% or 85% or 90%, or 95% or 97% or 98% or 99% identity to SEQ ID NO: 41. In such embodiments, a cognate C-terminal Bxb1 recombinase polypeptide fragment comprises a continuous stretch of amino acids of a fragment of the C-terminal of SEQ ID NO: 40, where the N-terminus of such a C-terminal Bxb1 fragment begins anywhere between amino acids 21-31, or 32-41, or 42-51, or 52-61, or 62-72, or 72-81, or 82-91, or 91-101 of SEQ ID NO: 41, or a polypeptide of at least 70%, or 80% or 85% or 90%, or 95% or 97% or 98% or 99% identity to SEQ ID NO: 41.

In some embodiments, a N-terminal Bxb1 recombinase polypeptide fragment comprises a continuous stretch of amino acids of a fragment of the N-terminal of SEQ ID NO: 41, where the C-terminus of such a N-terminal Bxb1 fragment ends anywhere between amino acids 101-150, or 151-200, or 201-250, or 251-300, or 301-350, or 351-400 of SEQ ID NO: 41, or a polypeptide of at least 70%, or 80% or 85% or 90%, or 95% or 97% or 98% or 99% identity to SEQ ID NO: 41. In such embodiments, a C-terminal Bxb1 recombinase polypeptide fragment comprises a continuous stretch of amino acids of a fragment of the C-terminal of SEQ ID NO: 41, where the N-terminus of such a C-terminal Bxb1 fragment begins anywhere between amino acids 102-151, or 152-201, or 202-251, or 252-301, or 302-351, or 352-401 of SEQ ID NO: 41, or a polypeptide of at least 70%, or 80% or 85% or 90%, or 95% or 97% or 98% or 99% identity to SEQ ID NO: 41.

In some embodiments, a N-terminal Bxb1 recombinase polypeptide fragment comprises a continuous stretch of amino acids of a fragment of the N-terminal of SEQ ID NO: 41, where the C-terminus of such a N-terminal Bxb1 fragment ends anywhere between amino acids 401-420-, or 421-440, or 441-460, or 461-480, or 481-497, of SEQ ID NO: 41, or a polypeptide of at least 70%, or 80% or 85% or 90%, or 95% or 97% or 98% or 99% identity to SEQ ID NO: 41. In such embodiments, a cognate C-terminal Bxb1 recombinase polypeptide fragment comprises a continuous stretch of amino acids of a fragment of the C-terminal of SEQ ID NO: 41, where the N-terminus of such a C-terminal Bxb1 fragment begins anywhere between amino acids 402-421, or 422-441, or 442-461, or 462-481, or 482-498 of SEQ ID NO: 41, or a polypeptide of at least 70%, or 80% or 85% or 90%, or 95% or 97% or 98% or 99% identity to SEQ ID NO: 41.

The N-terminal and C-terminal Bxb1 polypeptide fragments as disclosed herein, and homologues and fragments thereof can be expressed from fragments of the nucleic acid sequence of SEQ ID NO: 44 by one of ordinary skill in the art. SEQ ID NO: 44 is a nucleic acid sequence which encodes the active Bxb1 protein of SEQ ID NO: 41. SEQ ID NO: 45 is a nucleic acid sequence which encodes the active Bxb1 protein of SEQ ID NO: 41 that comprises a N-terminal signal sequence of SEQ ID NO: 46 at the N-terminus.

Chemically-Induced Dimerization Domains (CIDDs)

As discussed above, a recombinase protein can be split into two or more fragments, e.g., at least an N-terminal fragment (typically referred to herein a "first recombinase polypeptide fragment") and at least a C-terminal fragment (typically referred to herein as a "second recombinase polypeptide fragment"). Each of theses recombinase polypeptide fragments are conjugated or attached, either directly (e.g., peptide bonds, covalent bonds or cross-linkers), or indirectly (e.g., with peptide linkers and the like) to a chemically-induced dimerization domains (CIDD or binding motif) that can bind to a particular inducer agent or drug. When both CIDDs or binding motifs, that are conjugated to the N- and C-terminal recombinase polypeptide fragments respectively, binds to the inducer agent or drug, the N- and C-terminal recombinase polypeptide fragments are brought into close proximity with each other allowing protein complementation to occur and the reconstitution of the active recombinase protein.

In some embodiments, the binding of the conjugated CIDD or binding motif to a inducer results in in the dimerization of the CIDDS and brings together the recombinase polypeptide fragments ro reconstitute the recombinase protein to produce a fully active protein, and recombinase action can be immediately commenced (i.e., recognition of the RRS and subsequent recombinase action).

In some embodiments, the chemical-induced dimerization domain pair are FKBP/FRB proteins, which come together in the presence of Rapalog. In other embodiments, the chemical-induced dimerization domain pair are PYL/ABI proteins, which come together in the presence of Abscisic acid. In other embodiments, the chemical-induced dimerization domain pair are GAI/GID1 proteins, which come together in the presence of Gibberellin Ester. Other forms of recruiting the two split recombinases can also be used to reconstitute the recombinase, such as through inteins and leucine zippers and other systems known to an ordinary skilled artisan. In some embodiments, the chemical-induced dimerization domain pair can be nucleic acids, and can be engineered to provide a feed-back loop from the result of the active recombinase function after the recombinase has reconstituted from its polypeptide fragments.

FKBP/FBP:

In some embodiments, the chemical-induced dimerization domain pair are FKBP/FRB proteins, which come together and dimerize in the presence of Rapalog. The amino acid sequence of FKBP binding motif corresponds to SEQ ID NO: 22 and is as follows:

(SEQ ID NO: 22)
SRGVQVETISPGDGRTFPKRGQTCVVHYTGMLEDGKKFDSSRDRNKPFKF

MLGKQEVIRGWEEGVAQMSVGQRAKLTISPDYAYGATGHPGIIPPHATLV

FDVELLKLE

The amino acid sequence of FRB binding motif corresponds to SEQ ID NO: 23 is as follows:

(SEQ ID NO: 23)
ILWHEMWHEGLEEASRLYFGERNVKGMFEVLEPLHAMMERGPQTLKETSF

NQAYGRDLMEAQEWCRKYMKSGNVKDLLQAWDLYYHVFRRIS.

Accordingly, in some embodiments, a first recombinase polypeptide can be attached or conjugated to a FKBP binding motif of SEQ ID NO: 22, or a FKBP protein that has an amino acid sequence that is at least 75%, or at least 80%, or at least 85%, or at least 90% or at least 95%, or at least about 97%, or at least about 98%, or at least about 99% identical to SEQ ID NO: 22. In such embodiments, a second recombinase polypeptide can be attached or conjugated to a FRB binding motif of SEQ ID NO: 23, or a FRB protein that has an amino acid sequence that is at least 75%, or at least 80%, or at least 85%, or at least 90% or at least 95%, or at least about 97%, or at least about 98%, or at least about 99% identical to SEQ ID NO: 23. In alternative embodiments, a first recombinase polypeptide (e.g., a N-terminal recombinase fragment) can be conjugated to a FKBP protein or homologue thereof, and the second recombinase polypeptide fragment (e.g., C-terminal recombinsae fragment) can conjugated to a FRB protein or homologue thereof; or vice versa, a C-terminal recombinsae fragment can be conjugated to a FKBP protein or a homologue of at least 75% identity thereto, and the N-terminal recombinase fragment is conjugated to a FRB protein or a homologue of at least 75% identity thereto. As such, in the presence of Rapalog, or an analogue thereof, the FKBP and FRB binding motifs dimerize, resulting in the first and second recombinase polypeptide fragments coming into close proximity and reconstituting to result in the active recombinase protein.

The nucleic acid sequence encoding the FKBP binding motif of SEQ ID NO: 22 is SEQ ID NO: 24. The nucleic acid sequence encoding the FRP binding motif of SEQ ID NO: 23 is SEQ ID NO: 25.

PYL/ABI:

In some embodiments, the chemical-induced dimerization domain pair are PYL/ABI proteins, which come together and dimerize in the presence of Abscisic acid (ABA). The amino acid sequence of PYL binding motif corresponds to SEQ ID NO: 26 and is as follows:

(SEQ ID NO: 26)
APTQDEFTQLSQSIAEFHTYQLGNGRCSSLLAQRIHAPPETVWSVVRRFD

RPQIYKHFIKSCNVSEDFEMRVGCTRDVNVISGLPANTSRERLDLLDDDR

RVTGFSITGGEHRLRNYKSVTTVHRFEKEEEEERIWTVVLESYVVDVPEG

NSEEDTRLFADTVIRLNLQKLASITEAMNYPYDVPDYA

The amino acid sequence of ABI binding motif corresponds to SEQ ID NO: 27 is as follows:

(SEQ ID NO: 27)
PLYGFTSICGRRPEMEDAVSTIPRFLQSSSGSMLDGRFDPQSAAHFFGVY

DGHGGSQVANYCRERMHLALAEEIAKEKPMLCDGDTWLEKWKKALFNSFL

RVDSEIGSVAPETVGSTSVVAVVFPSHIFVANCGDSRAVLCRGKTALPLS

VDHKPDREDEAARIEAAGGKVIQWNGARVFGVLAMSRSIGDRYLKPSIIP

DPEVTAVKRVKEDDCLILASDGVWDVMTDEEACEMARKRILLWHKKNAVA

GDASLLADERRKEGKDPAAMSAAEYLSKLAIQRGSKDNISVVVVDLKDYK

DDDDK

Accordingly, in some embodiments, a first recombinase polypeptide can be attached or conjugated to a PYL binding motif of SEQ ID NO: 26, or a PYL protein that has an amino acid sequence that is at least 75%, or at least 80%, or at least 85%, or at least 90% or at least 95%, or at least about 97%, or at least about 98%, or at least about 99% identical to SEQ ID NO: 26. In such embodiments, a second recombinase polypeptide can be attached or conjugated to a ABI binding motif of SEQ ID NO: 27, or a ABI protein that has an amino acid sequence that is at least 75%, or at least 80%, or at least 85%, or at least 90% or at least 95%, or at least about 97%, or at least about 98%, or at least about 99% identical to SEQ ID NO: 27. In alternative embodiments, a first recombinase polypeptide (e.g., a N-terminal recombinase fragment) can be conjugated to a PYL protein or homologue thereof, and the second recombinase polypeptide fragment (e.g., C-terminal recombinsae fragment) can conjugated to a ABI protein or homologue thereof; or vice versa, a C-terminal recombinsae fragment can be conjugated to a PYL protein or a homologue of at least 75% identity thereto, and the N-terminal recombinase fragment is conjugated to a ABI protein or a homologue of at least 75% identity thereto. As such, in the presence of Abscisic acid (ABA), or an analogue thereof, the PYL and ABI CIDDs or binding motifs dimerize, resulting in the first and second recombinase polypeptide fragments coming into close proximity and reconstituting to result in the active recombinase protein.

The nucleic acid sequence encoding the PYL binding motif of SEQ ID NO: 26 is SEQ ID NO: 28. The nucleic acid sequence encoding the ABI binding motif of SEQ ID NO: 27 is SEQ ID NO: 29.

GAI/GID1:

In other embodiments, the chemical-induced dimerization domain pair are GAI/GID1 proteins, which come together in the presence of Gibberellin Ester (GE). The amino acid sequence of GAI binding motif corresponds to SEQ ID NO: 30 and is as follows:

(SEQ ID NO: 30)
MKRDHHHHHHQDKKTMMMNEEDDGNGMDELLAVLGYKVRSSEMADVAQKL

EQLEVMMSNVQEDDLSQLATETVHYNPAELYTWLDSMLTDLN

The amino acid sequence of GID1 binding motif corresponds to SEQ ID NO: 31 is as follows:

(SEQ ID NO: 31)
MAASDEVNLIESRTVVPLNTWVLISNFKVAYNILRRPDGTFNRHLAEYLD

RKVTANANPVDGVFSFDVLIDRRINLLSRVYRPAYADQEQPPSILDLEKP

VDGDIVPVILFFHGGSFAHSSANSAIYDTLCRRLVGLCKCVVVSVNYRRA

PENPYPCAYDDGWIALNWVNSRSWLKSKKDSKVHIFLAGDSSGGNIAHNV

ALRAGESGIDVLGNILLNPMFGGNERTESEKSLDGKYFVTVRDRDWYWKA

FLPEGEDREHPACNPFSPRGKSLEGVSFPKSLVVVAGLDLIRDWQLAYAE

GLKKAGQEVKLMHLEKATVGFYLLPNNNHFHNVMDEISAFVNAEC.

Accordingly, in some embodiments, a first recombinase polypeptide can be attached or conjugated to a GAI binding motif of SEQ ID NO: 30, or a GAI protein that has an amino acid sequence that is at least 75%, or at least 80%, or at least 85%, or at least 90% or at least 95%, or at least about 97%, or at least about 98%, or at least about 99% identical to SEQ ID NO: 30. In such embodiments, a second recombinase polypeptide can be attached or conjugated to a GID1 binding motif of SEQ ID NO: 31, or a GID1 protein that has an amino acid sequence that is at least 75%, or at least 80%, or at least 85%, or at least 90% or at least 95%, or at least about 97%, or at least about 98%, or at least about 99% identical to SEQ ID NO: 31. In alternative embodiments, a first recombinase polypeptide (e.g., a N-terminal recombinase fragment) can be conjugated to a GAI protein or homologue thereof, and the second recombinasae polypeptide fragment (e.g., C-terminal recombinsae fragment) can conjugated to a GID1 protein or homologue thereof; or vice versa, a C-terminal recombinsae fragment can be conjugated to a GAI protein or a homologue of at least 75% identity thereto, and the N-terminal recombinase fragment is conjugated to a GID1 protein or a homologue of at least 75% identity thereto. As such, in the presence of Gibberellin Ester, or an analogue thereof, the GAI and GID1 binding motifs dimerize, resulting in the first and second recombinase polypeptide fragments coming into close proximity and reconstituting to result in the active recombinase protein.

The nucleic acid sequence encoding the GAI binding motif of SEQ ID NO: 30 is SEQ ID NO: 32. The nucleic acid sequence encoding the GID1 binding motif of SEQ ID NO: 31 is SEQ ID NO: 33.

Light-Inducing Dimerization Domains (LIDD)

In some embodiments, as shown in FIGS. 46 and 47, a recombinase protein can be split into two or more fragments, e.g., at least an N-terminal fragment (typically referred to herein a "first recombinase polypeptide fragment") and at least a C-terminal fragment (typically referred to herein as a "second recombinase polypeptide fragment"). In some embodiments, each of theses recombinase polypeptide fragments are conjugated or attached, either directly (e.g., peptide bonds, covalent bonds or cross-linkers), or indirectly (e.g., with peptide linkers and the like) to a light-inducible dimerization domains (CIDD or binding motif) that, in the presence of a particular light signal, or light pulse exposure, the domains dimerize. When the LIDD pair, that are conjugated to the N- and C-terminal recombinase polypeptide fragments respectively, dimerize in the presence of the light signal or light pulse exposure, the N- and C-terminal recombinase polypeptide fragments are brought into close proximity with each other allowing protein complementation to occur and the reconstitution of the active recombinase protein.

In some embodiments, the dimerization of the conjugated LIDDs or binding motifs due to the light signal brings together the recombinase polypeptide fragments ro reconstitute the recombinase protein to produce a fully active protein, and recombinase action can be immediately commenced (i.e., recognition of the RRS and subsequent recombinase action).

In some embodiments, the light-inducible dimerization domain (LIDD) pair can be nMag/pMag proteins, which come together in the presence of Blue light. In other embodiments, the light-inducible dimerization domain (LIDD) pair are CRY2/CIBN proteins, which come together in the presence of blue light. Other forms of recruiting the two split recombinases can also be used to reconstitute the recombinase, such as through inteins and leucine zippers and other systems known to an ordinary skilled artisan. In some embodiments, the chemical-induced dimerization domain pair can be nucleic acids, and can be engineered to provide a feed-back loop from the result of the active recombinase function after the recombinase has reconstituted from its polypeptide fragments.

nMag/pMag:

In some embodiments, the light-inducible dimerization domain (LIDD) pair are nMag/pMag proteins, which come together and dimerize in on blue light signal. The amino acid sequence of nMag binding motif corresponds to SEQ ID NO: 51 and is as follows:

(SEQ ID NO: 51)
HTLYAPGGYDIMGYLDQIGNRPNPQVELGPVDTSCALILCDLKQKDTPIV

YASEAFLYMTGYSNAEVLGRNCRFLQSPDGMVKPKSTRKYVDSNTINTMR

KAIDRNAEVQVEVVNFKKNGQRFVNFLTMIPVRDETGEYRYSMGFQCETE

The amino acid sequence of pMag binding motif corresponds to SEQ ID NO: 52 is as follows:

(SEQ ID NO: 52)
HTLYAPGGYDIMGYLRQIRNRPNPQVELGPVDTSCALILCDLKQKDTP

IVYASEAFLYMTGYSNAEVLGRNCRFLQSPDGMVKPKSTRKYVDSNTI

NTMRKAIDRNAEVQVEVVNFKKNGQRFVNFLTMIPVRDETGEYRYSMG

FQCETE.

Accordingly, in some embodiments, a first recombinase polypeptide can be attached or conjugated to a nMag LIDD (or binding motif) of SEQ ID NO: 51, or a nMag protein that has an amino acid sequence that is at least 75%, or at least 80%, or at least 85%, or at least 90% or at least 95%, or at least about 97%, or at least about 98%, or at least about 99% identical to SEQ ID NO: 51. In such embodiments, a second recombinase polypeptide can be attached or conjugated to a pMag LIDD (or binding motif) of SEQ ID NO: 52, or a pMag protein that has an amino acid sequence that is at least 75%, or at least 80%, or at least 85%, or at least 90% or at least 95%, or at least about 97%, or at least about 98%, or at least about 99% identical to SEQ ID NO: 52.

In alternative embodiments, a first recombinase polypeptide (e.g., a N-terminal recombinase fragment) can be conjugated to a nMag protein or homologue thereof, and the second recombinase polypeptide fragment (e.g., C-terminal recombinsae fragment) can conjugated to a pMag protein or homologue thereof; or vice versa, a C-terminal recombinase fragment can be conjugated to a nMag protein or a homologue of at least 75% identity thereto, and the N-terminal recombinase fragment is conjugated to a pMag LIDD protein or a homologue of at least 75% identity thereto. As such, in the presence of a blue light, e.g., after a blue light pulse signal, or pulse of a light of an appropriate wavelength, the pMag and nMag LIDDs (or binding motifs) dimerize, resulting in the first and second recombinase polypeptide fragments coming into close proximity and reconstituting to result in the active recombinase protein.

The nucleic acid sequence encoding the nMag LIDD of SEQ ID NO: 51 is SEQ ID NO: 53. The nucleic acid sequence encoding the pMag LIDD of SEQ ID NO: 52 is SEQ ID NO: 54.

CIBN/CRY2:

In some embodiments, the the light-inducible dimerization domain (LIDD) pair are CIBN/CRY2 proteins, which come together and dimerize in on blue light signal. The amino acid sequence of CIBN LIDD corresponds to SEQ ID NO: 55 and is as follows:

(SEQ ID NO: 55)
MNGAIGGDLLLNFPDMSVLERQRAHLKYLNPTFDSPLAGFFADSSMITGG

EMDSYLSTAGLNLPMMYGETTVEGDSRLSISPETTLGTGNFKKRKFDTET

KDCNEKKKKMTMNRDDLVEEGEEEKSKITEQNNGSTKSIKKMKHKAKKEE

NNFSNDSSKVTKELEKTDYIH

The amino acid sequence of CRY2 LIDD corresponds to SEQ ID NO: 56 is as follows:

(SEQ ID NO: 56)
MKMDKKTIVWFRRDLRIEDNPALAAAAHEGSVFPVFIWCPEEEGQFYPGR

ASRWWMKQSLAHLSQSLKALGSDLTLIKTHNTISAILDCIRVTGATKVVF

NHLYDPVSLVRDHTVKEKLVERGISVQSYNGDLLYEPWEIYCEKGKPFTS

FNSYWKKCLDMSIESVMLPPPWRLMPITAAAEAIWACSIEELGLENEAEK

PSNALLTRAWSPGWSNADKLLNEFIEKQLIDYAKNSKKVVGNSTSLLSPY

LHFGEISVRHVFQCARMKQIIWARDKNSEGEESADLFLRGIGLREYSRYI

-continued

CFNFPFTHEQSLLSHLRFFPWDADVDKFKAWRQGRTGYPLVDAGMRELWA

TGWMHNRIRVIVSSFAVKFLLLPWKWGMKYFWDTLLDADLECDILGWQYI

SGSIPDGHELDRLDNPALQGAKYDPEGEYIRQWLPELARLPTEWIHHPWD

APLTVLKASGVELGTNYAKPIVDIDTARELLAKAISRTREAQIMIGAAPD

EIVADSFEALGANTIKEPGLCPSVSSNDQQVPSAVRYNGSKRVKPEEEEE

RDMKKSRGFDERELFSTAESSSSSSVFFVSQSCSLASEGKNLEGIQDSSD

QITTSLGKNGCK.

Accordingly, in some embodiments, a first recombinase polypeptide can be attached or conjugated to a CIBN (or binding motif) of SEQ ID NO: 55, or a CIBN protein that has an amino acid sequence that is at least 75%, or at least 80%, or at least 85%, or at least 90% or at least 95%, or at least about 97%, or at least about 98%, or at least about 99% identical to SEQ ID NO: 55. In such embodiments, a second recombinase polypeptide can be attached or conjugated to a CRY2 LIDD (or binding motif) of SEQ ID NO: 56, or a CRY2 protein that has an amino acid sequence that is at least 75%, or at least 80%, or at least 85%, or at least 90% or at least 95%, or at least about 97%, or at least about 98%, or at least about 99% identical to SEQ ID NO: 52.

In alternative embodiments, a first recombinase polypeptide (e.g., a N-terminal recombinase fragment) can be conjugated to a CIBN protein or homologue thereof, and the second recombinase polypeptide fragment (e.g., C-terminal recombinsae fragment) can conjugated to a CRY2 protein or homologue thereof; or vice versa, a C-terminal recombinase fragment can be conjugated to a CIBN protein or a homologue of at least 75% identity thereto, and the N-terminal recombinase fragment is conjugated to a CRY2 LIDD protein or a homologue of at least 75% identity thereto. As such, in the presence of a blue light, e.g., after a blue light pulse signal, or pulse of a light of an appropriate wavelength, the CIBN and CRY2 LIDDs (or binding motifs) dimerize, resulting in the first and second recombinase polypeptide fragments coming into close proximity and reconstituting to result in the active recombinase protein.

The nucleic acid sequence encoding the CIBN LIDD of SEQ ID NO: 55 is SEQ ID NO: 57. The nucleic acid sequence encoding the CRY2 LIDD of SEQ ID NO: 56 is SEQ ID NO: 58.

Conjugates and Fusion Proteins:

As discussed above, recombinase proteins are split at location S where the N-terminal portion of the protein is from amino acid 1 to amino acid S (inclusive) and the C-terminal portion of the protein is from S+1 to the end of the protein. The N-terminal recombinase fragment is attached to one CIDD, and the C-terminal recombinase fragment is attached to the complementary CIDD. Any combination of recombinase and CIDD is envisioned. Exemplary conjugates are shown in Table 5:

TABLE 5

Exemplary recombinase-CIDD conjugates and their cognate pairs.

| recombinase | FKBP/FRB CIDD pair | PYL/ABI CIDD pair | GAI/GID1 CIDD pair |
| --- | --- | --- | --- |
| Flp | (Flp-N)-FKBP and (Flp-C)-FRB or (Flp-N)-FRB and (Flp-C)-FKBP | (Flp-N)-PYL and (Flp-C)-ABI or (Flp-N)-ABI and (Flp-C)-PYL | (Flp-N)-GAI and (Flp-C)-GID1 or (Flp-N)-GID1 and (Flp-C)-GAI |

TABLE 5-continued

Exemplary recombinase-CIDD conjugates and their cognate pairs.

| recombinase | FKBP/FRB CIDD pair | PYL/ABI CIDD pair | GAI/GID1 CIDD pair |
|---|---|---|---|
| PhiC31 | (PhiC31-N)-FKBP and (PhiC31-C)-FRB or (PhiC31-N)-FRB and (PhiC31-C)-FKBP | (PhiC31-N)-PYL and (PhiC31-C)-ABI or (PhiC31-N)-ABI and (PhiC31-C)-PYL | (PhiC31-N)-GAI and (PhiC31-C)-GID1 or (PhiC31-N)-GID1 and (PhiC31-C)-GAI |
| VCre | (VCre-N)-FKBP and (VCre-C)-FRB or (VCre-N)-FRB and (VCre-C)-FKBP | (VCre-N)-PYL and (VCre-C)-ABI or (VCre-N)-ABI and (VCre-C)-PYL | (VCre-N)-GAI and (VCre-C)-GID1 or (VCre-N)-GID1 and (VCre-C)-GAI |
| B3 | (B3-N)-FKBP and (B3-C)-FRB or (B3-N)-FRB and (B3-C)-FKBP | (B3-N)-PYL and (B3-C)-ABI or (B3-N)-ABI and (B3-C)-PYL | (B3-N)-GAI and (B3-C)-GID1 or (B3-N)-GID1 and (B3-C)-GAI |
| Bxb1 | (Bxb1-N)-FKBP and (Bxb1-C)-FRB or (Bxb1-N)-FRB and (Bxb1-C)-FKBP | (Bxb1-N)-PYL and (Bxb1-C)-ABI or (Bxb1-N)-ABI and (Bxb1-C)-PYL | (Bxb1-N)-GAI and (Bxb1-C)-GID1 or (Bxb1-N)-GID1 and (Bxb1-C)-GAI |

It is noted that the CIDD can be attached to either the C-terminus or N-terminus of the recombinsae fragment. In some embodiments, a CIDD is attached to the N-terminal recombinsae fragment at the C-terminus (e.g., N-terminus recombinase fragment-CIDD). In contrast, in some embodiments, the CIDD is attached to the C-terminal recombinase fragment at the N-terminus (e.g., CIDD-C-terminus recombinase fragment). However, the opposite can occur, e.g., CIDD-N-terminal fragment and C-terminal recombinase fragment-CIDD).

In some embodiments, a nuclear localization signal (NLS) is at the C terminus of any recombinase polypeptide fragment-CIDD fusion protein. An exemplary NLS is a SV40 NLS of PKKKRKV (SEQ ID NO: 34), which is encoded by nucleic acids CCCAAGAAAAAGCGGAAGGTG (SEQ ID NO: 35). NLS are well known to one of ordinary skill in the art and are envisioned for use in the methods, compositions and fusion proteins herein.

In some embodiments, a linker peptide is located between the recombinase polypeptide fragment and a CIDD. An exemplary linker is L1 of SGGSGSGSSGGSGT (SEQ ID NO: 36) which is encoded by nucleic acids tccggagggtctggctccggatcaagtggtggcagcggtacc (SEQ ID NO: 37). Linkers are well known to one of ordinary skill in the art and are envisioned for use in the methods, compositions and fusion proteins herein.

In some embodiments, to produce a fusion protein comprising a N-terminal recombinase fragment attached to a CID or binding motif, an exemplary nucleic acid construct (construct 1) is as follows:

startcodon-Recombinase(N-terminus-to-S)-Linker-CIDD#1-NLS, where CIDD#1 is selected from any of the CIDDs of: FRB, ABI, GID1 and S is the last amino acid before the split location.

In some embodiments, an example of a nucleic acid construct (construct) that encodes the cognate protein to the above construct 1 is as follows:

startcodon-CIDD#2-linker-Recombinase(S+1-to-C-terminus)-NLS, where where CIDD#2 is selected from any of FKBP, PYL, GAI, and and S is the last amino acid before the split location.

One of ordinary skill in the art can generate nucleic acid construct encoding the recombinase-CIDD conjugate proteins. As an exemplary example, a nucleic acid construct for a split-Flp recombinase that is reconstituted by the CIDD pair ABI/PYL show in Table 6.

TABLE 6

Exemplary production of nucleic acid constructs.

| Flp-CIDD conjugate | Protein sequence | Nucleic acid constuct |
|---|---|---|
| FlpO(1-396)-L1-ABI-NLS (N-terminal Flp fragment) | SEQ ID NO: 38 | SEQ ID NO: 40 |
| PYL-L1-FlpO(397-423)-NLS (C-terminal Flp fragment) | SEQ ID NO: 39 | SEQ ID NO: 50 |

In some embodiments, the split-recombinase polypeptide fragment can be conjugated to the CIDD protein via a peptide bond to form a fusion protein. In some embodiments, the split-recombinase polypeptide fragment can be conjugated to the CIDD protein via a cross-linker, e.g., a cross-linking reagent, for example, a cross-linking reagent selected from CDAP(1-cyano-4-dimethylaminopyridinium tetrafluoroborate), EDC (1-Ethyl-3-[3-dimethylaminopropyl]carbodiimide hydrochloride), sodium cyanoborohydride; cyanogen bromide; or ammonium bicarbonate/iodoacetic acid. In some embodiments, the split-recombinase polypeptide fragment is cross-linked to carboxyl, hydroxyl, amino, phenoxyl, hemiacetal, and mecapto functional groups of the CIDD or other moiety. In some embodiments, the split-recombinase polypeptide fragment is covalently bonded to a CIDD or other moiety.

Cross-Linking Reagents:

Many bivalent or polyvalent linking agents are useful in coupling protein molecules to other molecules. For example, representative coupling agents can include organic compounds such as thioesters, carbodiimides, succinimide esters, disocyanates, glutaraldehydes, diazobenzenes and hexamethylene diamines. This listing is not intended to be exhaustive of the various classes of coupling agents known in the art but, rather, is exemplary of the more common coupling agents. See Killen & Lindstrom, 133 J. Immunol. 1335 (1984); Jansen et al., 62 Imm. Rev. 185 (1982); Vitetta et al.

In some embodiments, cross-linking reagents agents described in the literature are encompassed for use in the methods, immunogenic compositions and kits as disclosed herein. See, e.g., Ramakrishnan, et al., 44 Cancer Res. 201 (1984) (describing the use of MBS (M-maleimidobenzoyl-N-hydroxysuccinimide ester)); Umemoto et al., U.S. Pat. No. 5,030,719 (describing the use of a halogenated acetyl hydrazide derivative coupled to an antibody by way of an oligopeptide linker). Particular linkers include: (a) EDC (1-ethyl-3-(3-dimethylamino-propyl) carbodiimide hydrochloride; (b) SMPT (4-succinimidyloxycarbonyl-alpha-methyl-alpha-(2-pyridyl-dithio)-toluene (Pierce Chem. Co., Cat. (21558G); (c) SPDP (succinimidyl-6 [3-(2-pyridyldithio) propionamido] hexanoate (Pierce Chem. Co., Cat #21651G); (d) Sulfo-LC-SPDP (sulfosuccinimidyl 6 [3-(2-pyridyldithio)-propianamide] hexanoate (Pierce Chem. Co. Cat. #2165-G); and (f) sulfo-NHS (N-hydroxysulfo-succinimide: Pierce Chem. Co., Cat. #24510) conjugated to EDC.

The linkages or linking agents described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage can be cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

Exemplary cross-linking molecules for use in the methods and immunogenic compostions as disclosed herein include, but are not limited to those listed in Tables 7A and 7B.

TABLE 7A

Exemplary homobifunctional crosslinkers*.

| Crosslinking Target | Crosslinker Reactive Groups, Features | Example Products |
| --- | --- | --- |
| Amine-to-Amine | NHS esters | DSG; DSS; BS3; TSAT (trifunctional); Bioconjugate Toolkit Reagent Pairs |
| | NHS esters, PEG spacer | BS(PEG)5; BS(PEG)9 |
| | NHS esters, thiol-cleavable | DSP; DTSSP |
| | NHS esters, misc-cleavable | DST; BSOCOES; EGS; Sulfo-EGS |
| | Imidoesters | DMA; DMP; DMS |
| | Imidoesters, thiol-cleavable | DTBP |
| | Other | DFDNB; THPP (trifunctional); Aldehyde-Activated Dextran Kit |
| Sulfhydryl-to-Sulfhydryl | Maleimides | BMOE; BMB; BMH; TMEA (trifunctional) |
| | Maleimides, PEG spacer | BM(PEG)2; BM(PEG)3 |
| | Maleimides, cleavable | BMDB; DTME |
| | Pyridyldithiols (cleavable) | DPDPB |
| | Other | HBVS (vinylsulfone) |
| Nonselective | Aryl azides | BASED (thiol-cleavable) |

*crosslinking reagents that have the same type of reactive group at either end. Reagents are classified by what chemical groups they cross link (left column) and their chemical composition (middle column).
Products are listed in order of increasing length within each cell.

TABLE 7B

Exemplary heterobifunctional crosslinkers*

| Crosslinking Targets | Crosslinker Reactive Groups, Features | Example Products |
| --- | --- | --- |
| Amine-to-Sulfhydryl | NHS ester/Maleimide | AMAS; BMPS; GMBS and Sulfo-GMBS; MBS and Sulfo-MBS; SMCC and Sulfo-SMCC; EMCS and Sulfo-EMCS; SMPB and Sulfo-SMPB; SMPH; LC-SMCC; Sulfo-KMUS |
| | NHS ester/Maleimide, PEG spacer | SM(PEG)2; SM(PEG)4; SM(PEG)6; SM(PEG)8; SM(PEG)12; SM(PEG)24 |
| | NHS ester/Pyridyldithiol, cleavable | SPDP; LC-SPDP and Sulfo-LC-SPDP; SMPT; Sulfo-LC-SMPT |
| | NHS esters/Haloacetyl | SIA; SBAP; SIAB; Sulfo-SIAB |
| Amine-to-Nonselective | NHS ester/Aryl Azide | NHS-ASA<br>ANB-NOS<br>Sulfo-HSAB<br>Sulfo-NHS-LC-ASA<br>SANPAH and Sulfo-SANPAH |
| | NHS ester/Aryl Azide, cleavable | Sulfo-SFAD; Sulfo-SAND; Sulfo-SAED |
| | NHS ester/Diazirine | SDA and Sulfo-SDA; LC-SDA and Sulfo-LC-SDA |
| | NHS ester/Diazirine, cleavable | SDAD and Sulfo-SDAD |

TABLE 7B-continued

Exemplary heterobifunctional crosslinkers*

| Crosslinking Targets | Crosslinker Reactive Groups, Features | Example Products |
|---|---|---|
| Amine-to-Carboxyl | Carbodiimide | DCC; EDC |
| Sulfhydryl-to-Nonselective | Pyridyldithiol/Aryl Azide | APDP |
| Sulfhydryl-to-Carbohydrate | Maleimide/Hydrazide | BMPH; EMCH; MPBH; KMUH |
|  | Pyridyldithiol/Hydrazide | BMPH; EMCH; MPBH; KMUH |
| Carbohydrate-to-Nonselective | Hydrazide/Aryl Azide | ABH |
| Hydroxyl-to-Sulfhydryl | Isocyanate/Maleimide | PMPI |
| Amine-to-DNA | NHS ester/Psoralen | SPB |

*crosslinking reagents that have the different reactive groups at either end. Reagents are classified by what chemical groups they cross link (left column) and their chemical composition (middle column). Products are listed in order of increasing length within each cell.

Uses of the Chemically-Induced Rejoinder of Split-Recombinases

In some embodiments, the chemically-induced rejoinder of the split recombinases can be used in a wide range of areas, including but not limited to gene therapy, synthetic biology, plant management, environmental clean-up, bacterial and microbial management and synthetic genetic circuits. In some embodiments, the can be used in platforms of nucleic acid logic cassettes on single transcriptional units. Such nucleic acid logic cassettes can perform simple or complex logic functions, e.g., in mammalian cells, including, but not limited to, A, N, NOT A, NOT B, NOR, OR, AND, NAND, A IMPLY B, B IMPLY A, A NIMPLY B, B NIMPLY A, XOR, XNOR, decoder, half adder, half subtractor, half adder-subtractor, full adder, full subtractor, Feynman gate, logic selector, memory, Ripple carry adder, array multiplier, arithmetic logic unit, and any combinations thereof. To perform a logic function, a nucleic acid logic cassette can receive at least one input, preferably at least two inputs (e.g., 2, 3, 4, 5, 6, 7, or more), and produce at least one output (e.g., 1, 2, 3, 4, 5, 6, or more) as a function of the input(s).

Examples of such logic circuits are disclosed in WO2015/188191, which is incorporated herein in its reference. For example, a split-recombinase can be reconstituted and become active and can work on a nucleic acid sequence (e.g., a target gene) is flanked by a pair of recombinase recognition sequences (RRS) in the same orientation, the nucleic acid sequence can be excised upon the recognition of the RRS by the proper recombinase; when a nucleic acid sequence is flanked by a pair of recombinase recognition sequences (RRS) in an inverse orientation, the nucleic acid sequence can be inverted upon the recognition of the RRS by the proper recombinase. The inversion and/or excision reactions by the reconstituted recombinase will place the nucleic acid sequence (e.g., a target gene) in a new location and/or orientation to make it operatively linked to a promoter, thereby driving expression of the nucleic acid sequence. Based on these operation principles, depending on the combination of excision and inversion of 1, 2, or more nucleic acid sequence(s), in the presence of the inducers the reconstituted recombinase can recognize their corresponding RRS to construct nucleic acid logic cassettes for a specific logic function.

The reconstituted recombinase can function on modular nucleic acid logic cassettes. Each module can be a nucleic acid sequence flanked by a pair of RRS. Depending on the specific logic functions, the modules can be connected in series, or there can be overlapping nucleic acid regions between the modules. A truth table for a desired logic function can be used to guide the placement of each module. Generally, a truth table is composed of one column for each input variable (for example, A and B), and one final column for all of the possible results of the logical operation that the table is meant to represent (for example, A XOR B).

It has been reported in US2014/0315310, which is incorporated herein by reference, the creation of recombinase-based logic gates in bacterial cells only. US2014/0315310 describes simple recombinase-based logic gates, i.e., logic gates that require no more than two inputs and produce no more than one output. In contrast, the present invention relates to recombinase-based expression vectors or gene circuits in mammalian cells. For example, the inventors have used recombinases and their corresponding heterospecific DNA binding sites to create all sixteen Boolean logic gates in the human embryonic kidney cell line. Additionally, the inventors have created expression vectors that can perform complex logic functions with more than two inputs (e.g., 3, 4, 5, 6, 7, 8, or more) and/or more than one output (e.g., 2, 3, 4, or more) in a single transcription unit. This is a significant advantage, as the present invention provides methods and cassettes for complex logic functions in mammalian cells using a series arrangement of simple modules in a single cassette.

The nucleic acid logic cassettes described herein can be used in vitro or in vivo. An example of in vitro use is the study of cell culture, in which cells contain the nucleic acid logic cassettes described herein. An example of in vivo use is the use of the nucleic acid logic cassettes described herein to regulate or control gene expression in a subject such as a human.

Genetic Circuit Platforms

The use of split-recombinases, and their corresponding heterospecific DNA binding sites (e.g., recombinase recognition sequences (RRS)), can be used in mammalian cells, to control a suite of multi-input-multi-output (MIMO) circuits, such as a Half Adder, Half Subtractor, 2-Input Decoder, Full Adder, Full Subtractor, and Half Adder-Subtractor. Moreover, the split-recombinases, and their corresponding RRS binding sites can be used in a Programmable Read Only Memory (PROM) device that can select between 16 2-Input logic gates based on 4 inputs. Furthermore, the chemically induced rejoinder of the split recombinases as disclosed herein can be used to create all of the computation circuits in a single transcription unit (e.g., cassette)—no linkages between different transcription units are required to achieve the desired circuits.

In some embodiments, the chemically induced rejoinder of the split recombinases as disclosed herein can be used in a platform of logic gates called Boolean Logic and Arithmetic through DNA Excision (BLADE). All logic computation for BLADE circuits is done on a single transcriptional layer and circuit construction is based on a BLADE template. N-input BLADE templates feature $2^N$ distinct regions of DNA termed addresses (Z).

In some embodiments, the chemically induced rejoinder of the split recombinases as disclosed herein can be used in a platform which is the foundation for generating logic gates with arbitrary number of inputs and outputs.

The following are examples of the use of the chemically induced rejoinder of the split recombinases as disclosed herein:

1. As powerful genetic tools for investigating and manipulating genetic functions
   Cell-type expression of exogenous genes.
      Expression of optogenetic proteins for optical control and study of specific cell types in the brain
      Delivery of proteins/peptides/RNAs for therapeutic purposes
   Cell-type overexpression, knockdown, knockout or mutation of endogenous genes (via genome modifying proteins such as TAL, Zinc finger and Cas9 effectors and nucleases)
      Generation of animal models for study of diseases (e.g. cancer, neurological diseases, and other genetic pathologies)
      Therapeutic correction of a pathogenic gene (e.g. repression of a cancer-causing oncogene or reactivation of a mutated tumor suppressing gene)
2. As advanced implantable cellular computers for seek-and-destroy or diagnostic purposes
   a. Cell-based therapeutics
      i. Cancer cell and pathogen seek-and-destroy engineered immune cells
   b. Cell-based diagnostics
      i. Disease biomarker sensing (e.g. detection of overexpression of an oncogene)
      ii. Metabolite sensing and regulation (e.g. blood sugar regulation)
      iii. Pathogen detection (e.g. HIV, pathogenic bacteria)

The chemically induced rejoinder of the split recombinases as disclosed herein can be used as biological devices and in circuits as disclosed in WO2015/188191 for wide-reaching applications and commercial interest. As a research tool, this technology can allow a scientist to genetically target specific cell-types in the body for studying and manipulating physiological functions. Moreover, cell-based gene therapies have shown tremendous clinical success and investor interest. The technology described herein can vastly enhance such strategies by integrating advanced cellular computations. For instance, one can create implantable cellular computers that could act as early-warning systems for diseases, attack cancerous cells, or monitor and regulate blood-glucose levels. Current technologies can't integrate the large numbers and logical nature of biological and environmental signals that these applications would require.

Many commercial applications would also benefit by the chemically induced rejoinder of the split recombinases as disclosed herein in genetic logic gates as disclosed herein. For example, adoptive T cell therapy is a type of gene therapy that has had tremendous clinical success and gained significant investor interest. The therapy involves the replacement of a cancer patient's immune cells with genetically engineered ones that are programmed with a chimeric antigen receptor (CAR) that targets proteins overexpressed on cancer cells. However, most other cancers are not as easily targeted since markers are not exclusively expressed on the surface of the cells. The use of the chemically induced rejoinder of the split recombinases as disclosed herein, can offer a novel solution for these difficulties to target cancers and controlling gene expression by inducers that result in the controlled recombinase rejoinder.

With the genetic logic gate systems disclosed herein, one is not limited to just targeting proteins that are overexpressed on the surface of cancer cells, it can be used to also induce or repress activation of the genetically engineered T cells with the abundance or absence of cellular and environmental signals. For instance, it can be used to limit off-target effects by limiting activation of the engineered T cells to the location of the cancer. This can be done via logical integration of multiple signals, such as the presence/absence of metabolites and cytokines found in the cancer, oxygen levels (i.e. tumor hypoxia) and spatial release of a chemical inducer.

Others have utilized other strategies for programming digital logic in living organisms. Most utilize transcription-factor based methods in both bacteria and in mammalian cells. DNA-binding proteins are expressed that either promote or repress gene expression on the transcriptional level. Although this method can be highly modular, a plurality levels of cascading components is required to achieve complex logical tasks. A plurality of plasmids is often necessary, which makes implementation into organisms more difficult, as all of the elements need to be expressed in single cells and at the correct ratio for these systems to function properly.

In contrast, the genetic logic gates as disclosed herein are advantageous in that they rely on the use of SSR and their corresponding RRS. Accordingly, one can create a single nucleic acid cassette capable of performing complicated logical tasks by utilizing heterospecific recombination sites. For instance, one of the genetic circuits, the full adder, is a three-input, two-output logic circuit that can digitally add up to three. It requires only one plasmid, far fewer than transcription-factor-based strategies would necessitate, thus making incorporation of all of the components into the genome of a single cell much easier. Therefore, the platform as disclosed herein using site-specific recombinases is well suited for the wide variety of commercial applications involving the need for cell-type specification and sensing of environmental signals.

In one aspect, the invention relates to a mammalian cell containing a nucleic acid logic cassette or logic system described herein. The logic cassette or system can be introduced into a cell using any method known to one of skill in the art. The term "transformation" as used herein refers to the introduction of genetic material into a cell, tissue or organism. Transformation of a cell can be stable or transient. The term "transient transformation" or "transiently transformed" refers to the introduction of one or more transgenes into a cell in the absence of integration of the transgene into the host cell's genome. Transient transformation can be detected by, for example, enzyme linked immunosorbent assay (ELISA), which detects the presence of a polypeptide encoded by one or more of the transgenes. For example, a molecular circuit can further comprise a promoter operatively linked to an output product, such as a reporter protein. Expression of that reporter protein indicates that a cell has been transformed or transfected with the molecular circuit, and is hence implementing the circuit. Alternatively, transient transformation can be detected by detecting the activity of the protein encoded by the transgene. The term "transient transformant" refers to a cell which has transiently incorporated one or more transgenes.

In contrast, the term "stable transformation" or "stably transformed" refers to the introduction and integration of one or more transgenes into the genome of a cell or cellular system, preferably resulting in chromosomal integration and stable heritability through meiosis. Stable transformation of a cell can be detected by Southern blot hybridization of genomic DNA of the cell with nucleic acid sequences, which are capable of binding to one or more of the transgenes. Alternatively, stable transformation of a cell can also be detected by the polymerase chain reaction of genomic DNA of the cell to amplify transgene sequences. The term "stable transformant" refers to a cell or cellular, which has stably integrated one or more transgenes into the genomic DNA. Thus, a stable transformant is distinguished from a transient transformant in that, whereas genomic DNA from the stable transformant contains one or more transgenes, genomic DNA from the transient transformant does not contain a transgene. Transformation also includes introduction of genetic material into plant cells in the form of plant viral vectors involving epichromosomal replication and gene expression, which can exhibit variable properties with respect to meiotic stability. Transformed cells, tissues, or plants are understood to encompass not only the end product of a transformation process, but also transgenic progeny thereof.

Switches for Adoptive T-Cell Therapy

One aspect of the invention relates to use of the controlled induced rejoinder of the split recombinases as disclosed herein as switches and their use in adoptive T-cell therapy. These nucleic acid-based switches are based on the DNA recombinase systems. Chimeric antigen receptors (CARs) direct T-cell activity towards cancer cells. CARs are a fusion of the single chain variable fragment (scFv) of an antibody fused to the signaling domain from the T-cell receptor (TCR).

In one aspect, the invention relates to a switch operable in a mammalian immune cell, comprising: (i) a nucleic acid sequence encoding a mammalian promoter; (ii) a first pair of recombinase recognition sequences (RRS1) for a first recombinase (R1), wherein each of the RRS1 flanks each side of a first nucleic acid sequence, and wherein the RRS1 are in an inverse orientation with respect to each other, and wherein at least one of the RRS1 is positioned downstream of the promoter; (iii) a second pair of recombinase recognition sequences (RRS2) for a second recombinase (R2), wherein each of the RRS2 flanks each side of a second nucleic acid sequence, and wherein the RRS2 are in an inverse orientation with respect to each other, and wherein at least one of the RRS2 is positioned downstream of at least one of the RRS1; and (iv) a target gene positioned downstream of at least one of the RRS1, whereby expression of the target gene is controlled by the presence or absence of at least one of the R1 and R2.

Figures 25, 26:
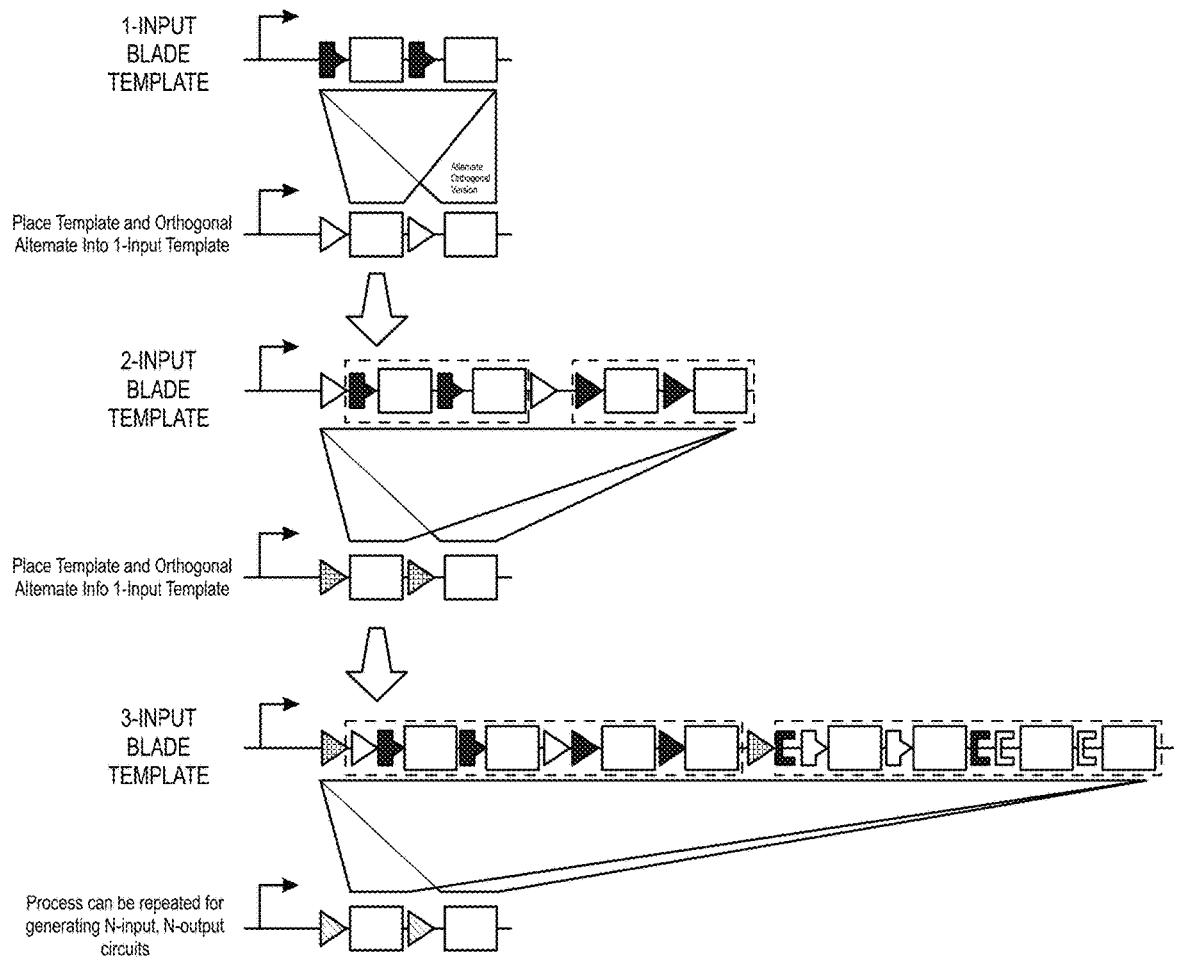

The working mechanism of the switches described herein is a two-step process. In the first step, the presence of the R2 inverts a second nucleic acid sequence. This inversion is not stable as the switch keep switching uncontrollably. In the second step, the presence of the R1 excises a portion of the switch, thus making the inversion permanent. In some embodiments, the switching mechanism is shown in FIG. 25.

In some embodiments, the R1 and R2 are each a tyrosine recombinase. Without wishing to be bound by theory, one pair of tyrosine recombinase sites would lead to bidirectional inversion, i.e. the switch would keep switching uncontrollably.

In some embodiments, the R1 and R2 are each a serine recombinase.

Figures 18A, 18B:
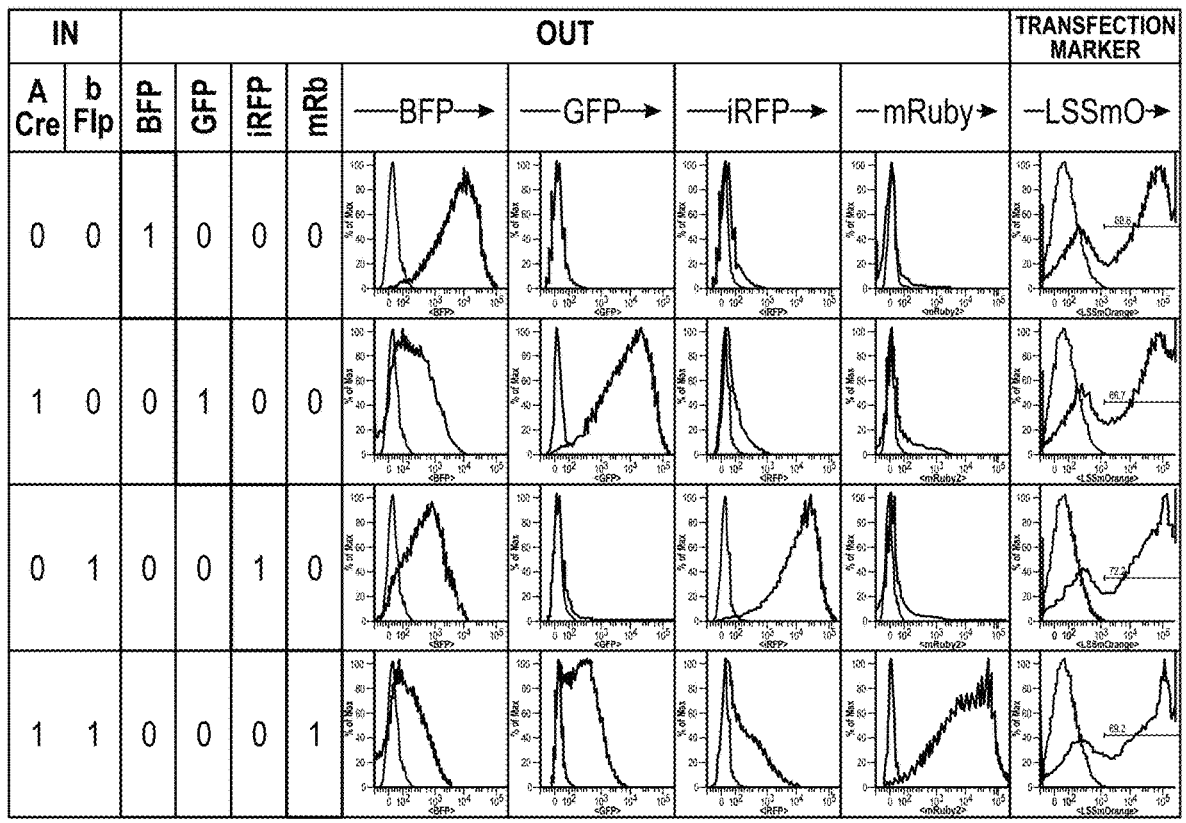

The switches described herein can control the response of the T-cell to a target antigen. FIG. 18 illustrates some embodiments of these switches. In some embodiments, the switch is a temporal switch. The temporal switch can be an On switch, which allows the cell to stay in an "off" state where no CAR is expressed until the drug is added, at which point the CAR is expressed and the T-cell is "on." This design allows for a doctor to turn the CAR on only when they feel it is necessary. The temporal switch can also be an OFF switch, which begins with the T-cell in the "on" state, and upon drug addition, will turn the T-cell "off." This switch can be used to turn the therapy off upon remission to minimize the possibility of cytotoxic effects.

In some embodiments of the On switch, there is an overlap between the first nucleic acid sequence and the second nucleic acid sequence. Specifically, the first nucleic acid sequence comprises one of the RRS2 and the target gene in an inverted orientation with respect to the promoter, and the second nucleic acid sequence comprises the target gene and one of the RRS1. The target gene is not expressed in the absence of the correct input. In the presence of the R2 and then R1, the target gene is inverted, thereby turning on the expression of the target gene.

In some embodiments of the Off switch, there is an overlap between the first nucleic acid sequence and the second nucleic acid sequence. Specifically, the first nucleic acid sequence comprises one of the RRS2 and the target gene in the same orientation as the promoter, and the second nucleic acid sequence comprises the target gene and one of the RRS1. The target gene is expressed in the absence of the correct input. In the presence of the R2 and then R1, the target gene is inverted, thereby turning off the expression of the target gene.

In some embodiments, the switch is a target switch. Different targets for CARs can provoke different responses in the T-cell due to the variability in antigen expression level and activation levels. As cancers can have multiple targets, this switch will allow for tuning of the therapy by changing the target. This switch can be adapted for different targets.

In some embodiments of the target switch, there is an overlap between the first nucleic acid sequence and the second nucleic acid sequence. Specifically, the first nucleic acid sequence comprises a first target gene in the same orientation as the promoter, one of the RRS2, and a second target gene in an inverted orientation. The second nucleic acid sequence comprises the second target gene and one of the RRS1. The first target gene is expressed in the absence of the correct input. In the presence of the R1 and R2, the second target gene is operatively linked to the promoter, thereby turning on the expression of the second target gene and turning off the expression of the first target gene.

In some embodiments, the switch is an affinity switch. T-cell activation using CARs is dependent in part on the affinity of the scFv for the target antigen. Anti-Her2 CARs have varying affinities and can be used to construct a switch that can change the affinity of the T-cell for the antigen. Her2 is an EGFR family receptor that is overexpressed in a number of cancers, including breast, colon, and ovarian cancer. Existing versions of Her2-CAR have affinities that span four orders of magnitude. In some embodiments, this switch will start with expression of a low-affinity CAR. While using a low-affinity CAR may reduce the probability of binding to a cancer cell, it will also reduce the probability of binding to a healthy cell that expresses Her2. In the case that the patient does not respond to a low-affinity Her2-CAR, they will then be switched to a high-affinity Her2-CAR.

In some embodiments, the genetic architecture of the affinity switch is the same as that of the target switch. In these embodiments, the first target gene is a low-affinity CAR, and the second target gene is a high-affinity CAR. In some embodiments, the high-affinity CAR has an affinity to a target at least 20% (e.g., at least 50%, at least 60%, at least 70%, at least 80%, at least 90%, at least 100%, at least 2 fold, at least 3 fold) higher than that of the low affinity CAR to the same target.

In some embodiments, the switch is an expression level switch. Another method to impact T-cell activation is to alter the level of expression of CARs. One strategy to affect expression level is to change the promoter under which the CAR is expressed. In the expression level switch, the T-cell will start with the CAR transcribed under a low-expressing promoter. To increase the strength of the treatment, the circuit will then drive the expression of CAR under a different, high-expressing promoter.

In some embodiments of the expression level switch, the promoter is in an inverted orientation. There is an overlap between the first nucleic acid sequence and the second nucleic acid sequence. Specifically, the first nucleic acid sequence comprises the promoter and one of the RRS2. The second nucleic acid sequence comprises the promoter and one of the RRS1. The target gene is positioned downstream of the RRS1 and RRS2, whereby in the presence of the R1 and R2, the promoter is inverted, thereby turning on the expression of the target gene. In the absence of the correct input, the target gene is not expressed.

The switches described herein can be used in adoptive T-cell therapy. Adoptive T-cell therapy uses a patient's own immune cells to target and kill cancer cells. One of the primary challenges are potential autoimmune effects of the therapy, as many of the target antigens that are overexpressed on cancer cells can also be found at lower levels on healthy cells. While the use of CARs in some patients allows for targeted killing of cancer cells, other patients who express high amounts of the antigen on normal cells have experienced fatal autoimmune effects upon targeting of healthy tissue. By implementing the switches in the adoptive T-cell therapy, the autoimmune effects can be reduced.

Accordingly, in one aspect, a method is provided herein to treat cancer in a subject, the method comprising incorporating a switch described herein into T cells and administering the T cells to the subject. In some embodiments, the method further comprises administering a lymphodepletion procedure to the subject prior to the administration of the T cells. In a lymphodepletion procedure, drugs such as fludarabine and cytoxan can be used to significantly reduce the number of normal lymphocytes circulating in the patient's body.

In some embodiments, the method further comprises culturing and/or expanding the T cells containing the switch prior to their administration. Methods of culturing and/or expanding cells are known in the art. For switches that comprise an inducible promoter, the method further comprises administering a compound to activate the switch. The compound can be selected from the group consisting of doxycycline, tamoxifen, rapamycin, and abscisic acid, depending on the inducible promoter.

Logic Gates

Previously, the inventors have constructed a plurality of nucleic acid logic cassettes capable of performing different logic functions. The controlled induced rejoinder of the split recombinases as disclosed herein can be used to in such logic gates, providing another level of control of the logic gate function. For example, in an exemplary 6-input-one output genetic device which receives two data inputs, a split-recombinase protein enables at least one or two inducers, in addition to the four select inputs $S_1$-$S_4$ to control the output of the GFP expression, where A and B are inputs. This circuit has two data inputs, A and B, and four select inputs, $S_1$, $S_2$, $S_3$, and $S_4$. Each select input can control which buffer gates are GFP ON or OFF. Thus, each combination of select inputs configures the device to a specific Boolean logic gate with up to two inputs and one output. For example, where the input A is from Cre, B is input from Flp, $S_1$ is input from φC31 (phiC31), $S_2$ is input from Vika, $S_3$ is input from B3 and $S_4$ is input from bxb1 recombinases, each of these recombinases can be split into two or more functions, allowing an additional level of control by the presence of the inducers. It should be understood that these are exemplary recombinases for splitting for the inputs for the logic gates described herein. The invention contemplates the use of other inputs, which may be chosen by the end-user and used interchangeably with or in place of Cre, or Flp as A and B inputs, or φC31 (phiC31), Vika, B3 and bxb1 as S1-S4 recombinases respectively.

As such, the controlled induced rejoinder of the split recombinases as disclosed herein can be used in sixteen different logic gates (e.g., AND, OR, NOT A, NOT B, NOR, NAND, XOR, XNOR, A IMPLY B, B IMPLY A, A NIMPLY B, B NIMPLY A, A, B, FALSE and TRUE), as well as other logic gates which are described in 2015/188191, which is incorporated herein in its reference.

Herein, a promoter is considered to be "operatively linked" when it is in a functional location and orientation in relation to a nucleic acid sequence it regulates to control ("drive") transcriptional initiation and/or expression of that sequence. A promoter is said to be "conditionally operatively linked" when, upon a genetic recombination event, it is placed in a functional location and orientation in relation to a nucleic acid sequence it regulates.

An "inverted" genetic element (e.g., inverted promoter, inverted terminator, inverted target gene) is one that is in the reverse orientation, such that what was the coding (sense) strand is now the non-coding (antisense) strand. In its inverted, reverse orientation, a genetic element is non-functional (e.g., not operatively linked to another genetic element such as a target gene). Function of the genetic element can be restored upon recombination of flanking complementary recognition sites and subsequent inversion of the genetic element back to its correct orientation. Thus, an inverted promoter flanked by recombination recognition sites may be considered to be "conditionally operatively linked" to a downstream target gene if, upon recombination of the flanking complementary recognition sites, the promoter is oriented such that what was the non-coding strand is now the coding strand, and the promoter is able to control transcriptional initiation and/or expression of the target gene. Likewise, an inverted target gene flanked by recombination recognition sites may be "conditionally operatively linked" to an upstream promoter if, upon recombination of the flanking recognition sites, the target gene is oriented such that what was the non-coding strand is now the coding strand, and the upstream promoter is able to control transcriptional initiation and/or expression of the output nucleic acid.

Illustrative examples of a promoter operatively linked to a target gene are shown in the NOR, NAND, TRUE, NOT A, NOT B and XNOR logic gates of FIGS. 4, 7 and 8A-8B of WO2015/188191. Illustrative examples of a promoter conditionally operatively linked to a target gene are shown in the AND, OR, A, B, A NIMPLY B, B NIMPLY A and XOR logic gates of FIGS. 4 and 7, 8A-8B of WO2015/

188191. Logic gates A IMPLY B and B IMPLY A contain both a promoter that is operatively linked to a target gene and a promoter that is conditionally operatively linked to a target gene.

Herein, a target gene is considered to be downstream of a genetic element if the target gene is located toward the 3' end and the genetic element is located toward the 5' end of the coding (sense) strand. One genetic element is considered to be "immediately downstream" of another genetic element the two are proximal to each other (e.g., no other genetic element is located between the two).

Target Genes and Output Products

A variety of target genes and output products are provided for use in accordance with the invention. As used herein, "output products" refer to gene products that may be used as markers of specific states of the logic gates and systems described herein. A target gene of the invention can encode for a protein or RNA that is used to track or mark the state of the cell upon receiving a particular input. Such output products can be used to distinguish between various states (e.g., "ON" or "OFF") of a cell. Representative output products for the logic cassettes and systems of the invention include, without limitation, reporter proteins, transcriptional repressors, transcriptional activators, selection markers, enzymes, receptor proteins, ligand proteins, RNAs, riboswitches, short-hairpin RNAs and recombinases. Aspects of the invention relate to logic cassettes and systems that include a plurality of logic gates {e.g., at least two logic gates). It should be understood that in such systems, each logic gate may include one or more different output nucleic acid (e.g., that encode(s) different, or unique, output product(s)). Thus, a single cell or system may include at least 2, 3, 4, 5, 6, 7, 8, 9, 10 or more different output nucleic acids.

In some embodiments, the target gene of the invention may encode a "reporter" or "reporter molecule." Such target gene is also called the reporter gene. As used herein, a reporter refers to a protein that can be used to measure gene expression and generally produce a measurable signal such as fluorescence, luminescence or color. The presence of a reporter in a cell or organism is readily observed. For example, fluorescent proteins (e.g., GFP, red fluorescent protein such as mCherry) cause a cell to fluoresce when excited with light of a particular wavelength, luciferases cause a cell to catalyze a reaction that produces light, and enzymes such as β-galactosidase convert a substrate to a colored product. In some embodiments, reporters may be used to quantify the strength or activity of the input received by the systems of the invention. In some embodiments, reporters can be fused in-frame to other protein coding sequences to identify where a protein is located in a cell or organism. Reporters for use in accordance with the invention include any reporter described herein or known to one of ordinary skill in the art.

There are several different ways to measure or quantify a reporter depending on the particular reporter and what kind of characterization data is desired. In some embodiments, microscopy can be a useful technique for obtaining both spatial and temporal information on reporter activity, particularly at the single cell level. In some embodiments, flow cytometers can be used for measuring the distribution in reporter activity across a large population of cells. In some embodiments, plate readers may be used for taking population average measurements of many different samples over time. In some embodiments, instruments that combine such various functions, may be used, such as multiplex plate readers designed for flow cytometers, and combination microscopy and flow cytometric instruments.

Fluorescent proteins may be used for visualizing or quantifying the output of logic gates/systems. Fluorescence can be readily quantified using a microscope, plate reader or flow cytometer equipped to excite the fluorescent protein with the appropriate wavelength of light. Several different fluorescent proteins are available, thus multiple gene expression measurements can be made in parallel. Examples of genes encoding fluorescent proteins that may be used in accordance with the invention include, without limitation, those proteins provided in U.S. Patent Application No. 2012/0003630 (see Table 59), incorporated herein by reference.

Examples of UV fluorescent proteins include, but are not limited to, Sirius. Examples of blue fluorescent proteins include, but are not limited to, Azurite, EBFP2, mKalama1, mTagBFP2, and tagBFP. Examples of cyan fluorescent proteins include, but are not limited to, ECFP, Cerulean, mCerulean3, SCFP3A, CyPet, mTurquoise, mTurquoise2, TagCFP, Mtfp1, monomeric Midoriishi-Cyan, and Aquamarine. Examples of green fluorescent proteins include, but are not limited to, TurboGFP, TagGFP2, mUKG, Superfolder GFP, Emerald, EGFP, Monomeric Azami Green, mWasabi, Clover, and mNeonGreen. Examples of yellow fluorescent proteins include, but are not limited to, TagYFP, EYFP, Topaz, Venus, SYFP2, Citrine, Ypet, IanRFP-ΔS83, and mPapayal. Examples of orange fluorescent proteins include, but are not limited to, Monomeric Kusabira-Orange, mOrange, mOrange2, mKOκ, and Mko2. Examples of red fluorescent proteins include, but are not limited to, TagRFP, TagRFP-T, mRuby, mRuby2, mTangerine, mApple, mStrawberry, FusionRed, mCherry, and mNectarine. Examples of far red fluorescent proteins include, but are not limited to, mKate2, HcRed-Tandem, mPlum, mRaspberry, mNeptune, NirFP, TagRFP657, TagRFP675, and mCardinal. Examples of near IR fluorescent proteins include, but are not limited to, iFP1.4, iRFP713 (iRFP), iRFP670, iRFP682, iRFP702, iRFP720, and iFP2.0. Examples of sapphire-type fluorescent proteins include, but are not limited to, Sapphire, T-Sapphire, and mAmetrine. Examples of long Stokes shift fluorescent proteins include, but are not limited to, mKeima Red, mBeRFP, LSS-mKate2, LSS-mKate1, and LSSmOrange.

Luciferases may also be used for visualizing or quantifying the output of logic gates/systems, particularly for measuring low levels of gene expression, as cells tend to have little to no background luminescence in the absence of a luciferase. Luminescence can be readily quantified using a plate reader or luminescence counter. Examples of genes encoding luciferases for that may be used in accordance with the invention include, without limitation, dmMyD88-linker-Rluc, dmMyD88-linker-Rluc-linker-PEST191, Renilla luciferase, and firefly luciferase (from *Photinus pyralis*).

Enzymes that produce colored substrates ("colorimetric enzymes") may also be used for visualizing or quantifying the output of logic gates/systems. Enzymatic products may be quantified using spectrophotometers or other instruments that can take absorbance measurements including plate readers. Like luciferases, enzymes such as β-galactosidase can be used for measuring low levels of gene expression because they tend to amplify low signals. Examples of genes encoding colorimetric enzymes that may be used in accordance with the invention include, without limitation, lacZ alpha fragment, lacZ (encoding beta-galactosidase, full-length), and xylE.

In some embodiments, the reporter molecule is chloramphenicol acetyltransferase. In some embodiments, the reporter molecule is neomycin phosphotransferase. In some embodiments, the reporter molecule is Secreted Placental Alkaline Phosphatase (SEAP). In some embodiments, the reporter molecule is secreted α-amylase (SAMY).

Transcriptional Outputs

In some embodiments, the target gene of the invention may encode a transcriptional activator or repressor, the production of which by an output gene can result in a further change in state of the cell, and provide additional input signals to subsequent or additional logic gates. Transcriptional regulators either activate or repress transcription from cognate promoters. Transcriptional activators typically bind nearby to transcriptional promoters and recruit RNA polymerase to directly initiate transcription. Repressors bind to transcriptional promoters and sterically hinder transcriptional initiation by RNA polymerase. Other transcriptional regulators serve as either an activator or a repressor depending on where it binds and cellular conditions. Transcriptional regulators for use in accordance with the invention include any transcriptional regulator described herein or known to one of ordinary skill in the art. Examples of genes encoding transcriptional regulators that may be used in accordance with the invention include, without limitation, those regulators provided in U.S. Patent Application No. 2012/0003630, incorporated herein by reference.

Selection Marker Outputs

In some embodiments, the target gene of the invention may encode a selection marker. As used herein, a "selection marker" refers to protein coding sequence that confers a selective advantage or disadvantage to a biological unit, such as a cell. For example, a common type of prokaryotic selection marker is one that confers resistance to a particular antibiotic. Thus, cells that carry the selection marker can grow in media despite the presence of antibiotic. For example, most plasmids contain antibiotic selection markers so that it is ensured that the plasmid is maintained during cell replication and division, as cells that lose a copy of the plasmid will soon either die or fail to grow in media supplemented with antibiotic. A second common type of selection marker, often termed a positive selection marker, is toxic to the cell. Positive selection markers are frequently used during cloning to select against cells transformed with the cloning vector and ensure that only cells transformed with a plasmid containing the insert. Selection markers for use in accordance with the invention include any selection marker described herein or known to one of ordinary skill in the art. Examples of genes encoding selection markers that may be used in accordance with the invention include, without limitation, those markers provided in U.S. Patent Application No. 2012/0003630, incorporated herein in its entirety by reference.

Enzyme Outputs

In some embodiments, the target gene of the invention may encode an enzyme. In some embodiments, an enzyme is used as a response to a particular input. For example, in response to a particular input received by a logic and memory system of the invention, such as a certain range of toxin concentration present in the environment, the system may turn "ON" a logic gate containing a target gene that encodes an enzyme that can degrade or otherwise destroy the toxin.

In some embodiments, output products may be "biosynthetic enzymes" that catalyze the conversion of substrates to products. For example, such biosynthetic enzymes can be used in accordance with the invention to assemble pathways that produce or degrade useful chemicals and materials, in response to specific signals. These combinations of enzymes can reconstitute either natural or synthetic biosynthetic pathways. These enzymes have applications in specialty chemicals, biofuels and bioremediation. Enzymes for use in accordance with the invention include any enzyme described herein or known to one of ordinary skill in the art. Examples of genes encoding enzymes that may be used in accordance with the invention include, without limitation, those provided in U.S. Patent Application No. 2012/0003630, incorporated herein by reference.

Receptors, Ligands and Lytic Proteins

In some embodiments, the target gene of the invention may encode a receptor, ligand or lytic protein. Receptors tend to have three domains: an extracellular domain for binding ligands such as proteins, peptides or small molecules, a transmembrane domain and an intracellular or cytoplasmic domain, which frequently can participate in some sort of signal transduction event such as phosphorylation. In some embodiments, transporters, channels or pumps are used as output products. Transporters are membrane proteins responsible for transport of substances across the cell membrane Channels are made up of proteins that form transmembrane pores through which selected ions can diffuse.

Pumps are membrane proteins that can move substances against their gradients in an energy-dependent process known as active transport. In some embodiments, nucleic acid sequences encoding proteins and protein domains whose primary purpose is to bind other proteins, ions, small molecules, and other ligands may be used in accordance with the invention. Receptors, ligands and lytic proteins for use in accordance with the invention include any receptor, ligand and lytic protein, described herein or known to one of ordinary skill in the art.

Examples of genes encoding receptors, ligands and lytic proteins that may be used in accordance with the invention include, without limitation, those provided in U.S. Patent Application No. 2012/0003630, incorporated herein by reference.

A target gene can be any gene of interest, e.g., a gene that encodes a therapeutic protein or peptide of interest, a therapeutic protein inhibitor, miRNA, siRNA, etc., nucleic acid inhibitor (e.g., RNAi) etc., antibody or fragment thereof. Exemplary therapeutic proteins include, but are not limited to, antibodies or fragments thereof, CAR for cancer therapy as disclosed herein.

In some embodiments, the target gene of the invention may encode a RNA molecule of interest. For example, the RNA molecule of interest can be an sgRNA from the CRISPR/Cas9 system.

Genetic Engineering of Logic Gates and Systems

A cell to be engineered for use with the logic cassettes, switches, and systems of the invention may be any cell or host cell. As defined herein, a "cell" or "cellular system" is the basic structural and functional unit of all known independently living organisms. It is the smallest unit of life that is classified as a living thing. Some organisms, such as most bacteria, are unicellular (consist of a single cell). Other organisms, such as humans, are multicellular. The logic cassettes, switches, and systems described herein can be used in a cell of a variety of organisms. Preferably, the host cell is a mammalian cell. More preferably, the host cell is a human cell. The logic cassettes, switches, and systems described herein can be used in a variety of cell types. Exemplary cell types include, but are not limited to, liver cells, gastrointestinal cells, epithelial cells, endothelial cells, kidney cells, cancer cells, blood cells, stem cells, bone cells, smooth muscle cells, striated muscle cells, cardiac muscle cells, immune cells and nerve cells. Blood cells include, e.g., leukocytes, such as neutrophils, lymphocytes, monocytes, eosinophils, basophils, macrophages. Immune cells include, but are not limited to, monocytes, Natural Killer (NK) cells, dendritic cells (which could be immature or mature), subsets of dendritic cells including myeloid, plasmacytoid (also called lymphoid) or Langerhans; macrophages such as histiocytes, Kupffer's cells, alveolar macrophages or peritoneal macrophages; neutrophils, eosinophils, mast cells, basophils; B cells including plasma B cells, memory B cells, B-1 cells, B-2 cells; CD45RO (naive T), CD45RA (memory T); CD4 Helper T Cells including Th1, Th2 and Tr1/Th3; CD8 Cytotoxic T Cells, Regulatory T Cells and Gamma Delta T Cells.

In some embodiments, a cell for use in accordance with the invention is an eukaryotic cell, which comprises membrane-bound compartments in which specific metabolic activities take place, such as a nucleus. Examples of eukaryotic cells for use in accordance with the invention include, without limitation, mammalian cells, insect cells, yeast cells {e.g., *Saccharomyces cerevisiae*) and plant cells. In some embodiments, the eukaryotic cells are from a vertebrate animal. Examples of vertebrate cells for use in accordance with the invention include, without limitation, reproductive cells including sperm, ova and embryonic cells, and non-reproductive cells, including kidney, lung, spleen, lymphoid, cardiac, gastric, intestinal, pancreatic, muscle, bone, neural, brain and epithelial cells. Stem cells, including embryonic stem cells, can also be used.

In some embodiments, a cell for use in accordance with the invention is a prokaryotic cell, which may comprise a cell envelope and a cytoplasmic region that contains the cell genome (DNA) and ribosomes and various sorts of inclusions. In some embodiments, the cells are bacterial cells. As used herein, the term "bacteria" encompasses all variants of bacteria, for example, prokaryotic organisms and cyanobacteria. Bacteria are small (typical linear dimensions of around 1 micron), non-compartmentalized, with circular DNA and ribosomes of 70S. The term "bacteria" also includes bacterial subdivisions of Eubacteria and Archaebacteria. Eubacteria can be further subdivided into gram-positive and gram-negative Eubacteria, which depend upon a difference in cell wall structure. Also included herein are those classified based on gross morphology alone (e.g., cocci, bacilli). In some embodiments, the bacterial cells are gram-negative cells, and in some embodiments, the bacterial cells are gram-positive cells. Examples of bacterial cells that may be used in accordance with the invention include, without limitation, cells from *Yersinia* spp., *Escherichia* spp., *Klebsiella* spp., *Bordetella* spp., *Neisseria* spp., *Aeromonas* spp., *Franciesella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Salmonella* spp., *Vibrio* spp., *Bacillus* spp., *Erysipelothrix* spp., *Salmonella* spp., *Stremtomyces* spp. In some embodiments, the bacterial cells are from *Staphylococcus aureus, Bacillus subtilis, Clostridium butyricum, Brevibacterium lactofermentum, Streptococcus agalactiae, Lactococcus lactis, Leuconostoc lactis, Streptomyces, Actinobacillus actinobycetemcomitans, Bacteroides, cyanobacteria, Escherichia coli, Helobacter pylori, Selnomonas ruminatium, Shigella sonnei, Zymomonas mobilis, Mycoplasma mycoides, Treponema denticola, Bacillus thuringiensis, Staphylococcus lugdunensis, Leuconostoc oenos, Corynebacterium xerosis, Lactobacillus planta rum, Streptococcus faecalis, Bacillus coagulans, Bacillus ceretus, Bacillus popillae, Synechocystis* strain PCC6803, *Bacillus liquefaciens, Pyrococcus abyssi, Selenomonas nominantium, Lactobacillus hilgardii, Streptococcus ferus, Lactobacillus pentosus, Bacteroides fragilis, Staphylococcus epidermidis, Zymomonas mobilis, Streptomyces phaechromo* genes, *Streptomyces ghanaenis, Halobacterium* strain GRB, or *Halobaferax* sp. strain Aa2.2.

In some embodiments, a non-cellular system such as a virus or phage may be used in accordance with the invention. For examples, any one or more component(s) of the synthetic logic and memory systems may be introduced, by direct integration of logic system nucleic acids, for example, into a viral genome. A virus for use as described herein may be a double-stranded DNA (dsDNA) virus (e.g., Adenoviruses, Herpesviruses, Poxviruses), a single-stranded DNA (ssDNA) viruses ((+)sense DNA) (e.g. Parvoviruses); a double-stranded RNA (dsRNA) virus (e.g., Reoviruses); a (+)ssRNA viruses ((+)sense RNA) (e.g. Picornaviruses, Togaviruses); (−)ssRNA virus ((−)sense RNA) (e.g., Orthomyxoviruses, Rhabdo viruses); a single-stranded RNA (ssRNA)-Reverse Transcriptase viruses ((+)sense RNA with DNA intermediate in life-cycle) (e.g., Retroviruses); or a dsDNA-Reverse Transcriptase virus (e.g., Hepadnaviruses).

Viruses may also include plant viruses and bacteriophages or phages. Examples of phage families that may be used in accordance with the invention include, without limitation, Myoviridae (T4-like viruses; Pl-like viruses; P2-like viruses; Mu-like viruses; SPOl-like viruses; phiH-like viruses); Siphoviridae γ-like viruses (Tl-like viruses; T5-like viruses; c2-like viruses; L5-like viruses; .psi.Ml-like viruses; phiC31-like viruses; N15-like viruses); Podoviridae (T7-like viruses; phi29-like viruses; P22-like viruses; N4-like viruses); Tectiviridae (Tecti virus); Corticoviridae (Corticovirus); Lipothrixviridae (Alphalipothrixvirus, Betalipothrixvirus, Gammalipothrixvirus, Deltalipothrixvirus); Plasmaviridae (Plasmavirus); Rudiviridae (Rudi virus); Fuselloviridae (Fusellovirus); Inoviridae (Inovirus, Plectro virus); Microviridae (Micro virus, Spiromicro virus, Bdellomicro virus, Chlamydiamicro virus); Leviviridae (Levi virus, Allolevivirus) and Cystoviridae (Cysto virus). Such phages may be naturally occurring or engineered phages.

In some embodiments, the cell or cellular system is a "natural cell" (e.g., found in nature; not artificial or synthetic). In some embodiments, the cell or cellular system is an artificial cell or synthetic cell. As used herein, an "artificial cell" or a "synthetic cell" is a minimal cell formed from artificial parts that can function in ways that a natural cell can function (e.g., transcribe and translate proteins and generate ATP).

A host cell in accordance with the invention includes any host cell that, upon transformation or transfection with one or more component(s) of the synthetic logic system (e.g., logic gates) is capable of supporting the activation and expression of the synthetic logic and memory system component(s).

In some embodiments, one or more component(s) of the synthetic logic and memory systems of the invention may be introduced into a cellular or non-cellular system using a vector or plasmid. As used herein, a "vector" is used interchangeably with "plasmid" to refer to a nucleic acid molecule capable of transporting another nucleic acid to which it has been linked. Vectors capable of directing the expression of genes and/or nucleic acid sequence to which they are operatively linked are referred to herein as "expression vectors." In general, expression vectors described herein are often in the form of plasmids, which are circular double-stranded DNA loops not bound to chromosome. Expression vectors may be vectors for stable or transient expression of the DNA. A vector may be either a selfreplicating extrachromosomal vector or a vector which integrates into a host genome. Other expression vectors may be used in accordance with the invention including, without limitation, episomes, bacteriophages and viral vectors, and such vectors can integrate into the host's genome or replicate autonomously in the particular cellular system used. Other forms of expression vectors known by those skilled in the art which serve the equivalent functions may also be used.

Vectors comprising nucleic acid sequences of the invention (e.g., those encoding logic gates) may be "introduced" into cells as polynucleotides by techniques well-known in the art for introducing DNA and RNA into cells. As used herein, "transfection" refers to the introduction of genetic material (e.g., a vector comprising nucleic acid sequences) into a cell, tissue or organism. Transfection of a cell may be stable or transient. A host cell is considered to be transiently transfected when nucleic acid is introduced into the cell and does not integrate into the host cell's genome. Transient transfection may be detected by, for example, enzyme linked immunosorbent assay (ELISA), which detects the presence of a polypeptide encoded by the nucleic acid, or it may be detected by detecting the activity of a protein encoded by the nucleic acid. By contrast, a host cell is considered to be stably transfected when nucleic acid is introduced into the cell and does integrate into the host cell's genome. Stably transfected cells pass the introduced nucleic acid to their progeny (i.e., stable heritability through meiosis). Stable transfection of a cell may be detected by Southern blot hybridization of genomic DNA of the cell with nucleic acid sequences, which are capable of binding to one or more of the transgenes, or by polymerase chain reaction of genomic DNA of the cell to amplify transgene sequences.

In some embodiments, a synthetic RNA-processing platform may be used to process mRNAs to separate the 5' untranslated region (UTR) from the downstream gene. For example, a sequence encoding a recombinase as disclosed herein may be inserted upstream (e.g., directly upstream) of the output nucleic acid to improve expression of the gene. In some embodiments, the bacterial clustered regularly interspaced short palindromic repeat (CRISPR) pathway may be used to process mRNAs to separate the 5' UTR from the downstream gene. In some embodiments, a coupled translational system with an upstream "throwaway" open reading frame (ORF) and downstream ORF may be used to generate mRNAs with more reliable and programmable translation of the downstream. Other synthetic RNA-processing platforms are also contemplated herein.

Uses of Synthetic Cassettes, Switches, and Systems

The components of the nucleic acid logic cassettes or switches shown are exemplary. One skilled in the art can readily substitute the different genetic elements such as promoters and RRS in the cassettes or switches. For example, one can readily substitute the recombinases and integrases depending on the RRS and/or the cell into which the cassette is to be inserted. The different examples of genetic elements such as promoters, RRS, and recombinases as discussed can be used in any combinations to construct a cassette or switch capable of a desirable logic function. The target genes used can readily be selected based upon the cell and desired use. For example, the target gene used in the cassettes or switches can be a regulatory gene, a marker gene, or a therapeutic gene.

The nucleic acid logic cassettes and switches of the invention can be constructed using methods known in the art. In some embodiments, a Gibson isothermal assembly method can be used.

The nucleic acid logic cassettes, switches, and systems of the invention are useful for, inter alia, engineering complex behavioral phenotypes in cellular systems, such as prokaryotic, eukaryotic and synthetic cells, or in non-cellular systems, including cell-free systems, test tubes, viruses and phages. The logic cassettes and systems described herein combine the power of nucleic acid-based engineering methods with computational and systems biology approaches for programming cellular, or biological, state machines, behaviors and pathways for therapeutic, diagnostic and basic science applications. As used herein, a "state machine" refers to any tool that stores the status (or state) of something at a given time and can operate on input(s) to change the status and/or cause an action(s) or output(s) to take place for any given change. Typically, a state machine includes a set of input events, a set of output events, a set of states, a function that maps states and input(s) to output(s), a function that maps states and inputs to new states (which is referred to as a state transition function), and a description of the initial state.

The synthetic logic cassettes, switches, systems of the invention may be used for a variety of applications and in many different types of methods, including, but not limited to, bioremediation, biosensing and biomedical therapeutics. In some embodiments, the logic and memory systems may be used to build multiplexed cellular switches for gene expression or synthetic differentiation cascades. Cellular signals can be integrated as inputs to the logic and memory systems by linking the signals to recombinase expression. Multicellular systems endowed with the synthetic logic cassettes, switches, systems of the invention may also implement distributed computation or synthetic cellular consortia.

The nucleic acid logic cassettes, switches, and systems of the invention are useful to control gene expression for cell-based immunotherapy (e.g., adoptive T-cell therapy). Exemplary target genes of interest include, but are not limited to, chimeric antigen receptor, T cell receptor, cytokines (e.g., IL-2, IL-12, IL-15), and suicide genes (e.g., HSV-TK, iCasp9).

In some embodiments, the synthetic logic cassettes, switches, and systems of the invention may also be used to build "digital-to-analog converters," which translate digital representations back into analog outputs. Such systems may be used to reliably set internal system states. For example, instead of fine-tuning transcriptional activity with varying amounts of chemical inducers, a digital-to-analog converter, composed of a bank of genetic switches (different recombinases and logic gates), each of which is sensitive to a different inducer, provides better control. By enabling, through each activated switch, transcription from promoters of varying strengths (e.g., P output,3>P output,2>P output, 1), digital combinations of inducers may be used to program defined levels of transcriptional activities. Such a circuit may be used in biotechnology applications, where reliable expression of different pathways is needed for programming different modes of operation in engineered cells. In addition, digital-to-analog converters are useful for providing a multiplexed method for probing synthetic circuits. For example, because each analog level is associated with a distinct digital state, a single analog output can allow one to infer the internal digital state of a synthetic gene network.

Further, in some embodiments, the synthetic logic cassettes, switches, and systems of the invention may be used for detection of arsenic in drinking water and/or a range of toxins and/or heavy metals. The systems may be coupled to genetically engineered bacteria, which are capable of digesting and neutralizing toxins and heavy metals. This may be achieved, for example, by the bacteria sensing a specific toxin or heavy metal, and the sensor being directly linked as input for an inducible promoter that controls recombinase expression, which in turn activates the logic/memory system by flipping (e.g., activating or de-activating) the gene, promoter or terminator. As a result, the pathway that controls digesting and neutralizing toxins and heavy metals is turned on.

The methods and uses of the synthetic logic cassettes, switches, and systems of the invention may involve in vivo, ex vivo, or in vitro systems. The term "in vivo" refers to assays or processes that occur in or within an organism, such as a multicellular animal. In some embodiments, a method or use can be said to occur in vivo when a unicellular organism, such as a bacteria, is used. The term "ex vivo" refers to methods and uses that are performed using a living cell with an intact membrane that is outside of the body of a multicellular animal or plant (e.g., explants, cultured cells, including primary cells and cell lines, transformed cell lines, and extracted tissue or cells, including blood cells, among others). The term "in vitro" refers to assays and methods that do not require the presence of a cell with an intact membrane, such as cellular extracts, and may refer to introducing an engineered genetic counter in a non-cellular system, such as a media not comprising cells or cellular systems, such as cellular extracts.

It should be understood that this invention is not limited to the particular methodology, protocols, and reagents, etc., disclosed herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

Although any known methods, devices, and materials may be used in the practice or testing of the invention, the methods, devices, and materials in this regard are disclosed herein.

In some embodiments, the present application may be defined in any of the following paragraphs:

1. A split-recombinase polypeptide, comprising:
   i. a recombinase protein split into at least two recombinase polypeptide fragments, wherein each recombinase polypeptide fragment is conjugated to a chemically-induced dimerization domain (CIDD), and wherein each recombinase polypeptide fragment is not active by itself, but can rapidly complement with the one or more recombinase polypeptide fragments to reconstitute the active recombinase protein;
   ii. at least one chemically-induced dimerization domain pair (CIDD pair), comprising a first chemically-induced dimerization domain (CIDD$^A$) and at least a second complementary CIDD (CIDD$^B$) wherein the first CIDD (CIDD$^A$) and the second complementary CIDD (CIDD$^B$) come together in the presence of a target agent or target signal, resulting in protein complementation of the at least two recombinase polypeptide fragments to form the active recombinase protein in the presence of the target agent.
2. The split-recombinase polypeptide of paragraph 1, comprising:
   a. at least a first recombinase polypeptide fragment ($R^1$) and at least a second recombinase polypeptide fragment ($R^2$), where the first and second recombinase polypeptide fragments are not active by themselves and rapidly complement to reconstitute the active recombinase protein; and
   b. at least a first chemically-induced dimerization domain (CIDD) (CIDD$^A$) and at least a second complementary CIDD (CIDD$^B$) wherein the first CIDD (CIDD$^A$) and the second complementary CIDD (CIDD$^B$) can bind to a target agent, or come together in the presence of a target signal, wherein the first CIDD (CIDD$^A$) is conjugated to the first recombinase polypeptide fragment ($R^1$), and the second complementary CIDD (CIDD$^B$) is conjugated to the second recombinase polypeptide fragment ($R^2$), resulting in protein complementation of the first recombinase polypeptide fragment with the second polypeptide recombinase fragment to form the active recombinase protein in the presence of the target agent or target signal.
3. The split-recombinase polypeptide of paragraph 1, comprising:
   a. a first recombinase polypeptide fragment ($R^1$), a second recombinase polypeptide fragment ($R^2$), and a third recombinase polypeptide fragment ($R^3$), wherein $R^1$, $R^2$ and $R^3$ recombinase polypeptide fragments are not active by themselves and rapidly complement to reconstitute the active recombinase protein; and
   b. at least two CIDD pairs comprising:
      i. at least a first chemically-induced dimerization domain pair (CIDD1 pair) comprising a first CIDD1 (CIDD1$^A$) and the second complementary CIDD1 (CIDD1$^B$) which can dimerize on binding to first target agent,
      ii. a second CIDD pair (CIDD2 pair) comprising a second CIDD2 (CIDD2$^A$) and the second complementary CIDD2 (CIDD2$^B$) which can dimerize on binding to a second target agent,
   wherein:
      $R^1$ is conjugated to the CIDD1$^A$ and the CIDD2$^A$,
      $R^2$ is conjugated to the CIDD1$^B$, and
      $R^3$ is conjugated to the CIDD2$^B$,
      and protein complementation of $R^1$ with $R^2$ occurs in the presence of the first inducer, and protein complementation of $R^2$ with $R^3$ occurs in the presence of the second inducer to form the active recombinase protein in the presence of both the first and second target agent.
4. The split-recombinase polypeptide of any of paragraphs 1 to 3, wherein the recombinase protein is selected from the group consisting of: Flp, PhiC31, VCre, Bxb1 and B3 recombinases.
5. The split-recombinase polypeptide of any of paragraphs 1 to 4, wherein the first ($R^1$) and second ($R^2$) recombinase polypeptide fragments are Flp recombinase polypeptide fragments, wherein R1 and R2 are selected from any of:
   a. $R^1$ comprises a N-terminal polypeptide fragment of SEQ ID NO: 1 with the C-terminus ending at amino acid 27 of SEQ ID NO:1 or a polypeptide that is 85% identity thereof, and $R^2$ comprises a C-terminal polypeptide fragment of SEQ ID NO: 1 with the N-terminus beginning at amino acid 28 of SEQ ID NO:1 or a polypeptide that is 85% identity thereof;

b. R¹ comprises a N-terminal polypeptide fragment of SEQ ID NO: 1 with the C-terminus ending at amino acid 167 of SEQ ID NO:1 or a polypeptide that is 85% identity thereof, and R² comprises a C-terminal polypeptide fragment of SEQ ID NO: 1 with the N-terminus beginning at amino acid 168 of SEQ ID NO:1 or a polypeptide that is 85% identity thereof;

c. R¹ comprises a N-terminal polypeptide fragment of SEQ ID NO: 1 with the C-terminus ending at amino acid 374 of SEQ ID NO:1 or a polypeptide that is 85% identity thereof, and R² comprises a C-terminal polypeptide fragment of SEQ ID NO: 1 with the N-terminus beginning at amino acid 375 of SEQ ID NO:1 or a polypeptide that is 85% identity thereof; and d. R¹ comprises a N-terminal polypeptide fragment of SEQ ID NO: 1 with the C-terminus ending at amino acid 396 of SEQ ID NO:1 or a polypeptide that is 85% identity thereof, and R² comprises a C-terminal polypeptide fragment of SEQ ID NO: 1 with the N-terminus beginning at amino acid 397 of SEQ ID NO:1 or a polypeptide that is 85% identity thereof 6. The split-recombinase polypeptide of any of paragraphs 1 to 5, wherein the first (R¹), second (R²) and third (R³) recombinase polypeptide fragments are Flp recombinase polypeptide fragments, wherein R¹, R² and R³ are selected from any of:

a. R¹ comprises amino acids 1-27 of SEQ ID NO: 1 or a polypeptide that is 85% identity thereof, and R² comprises amino acids 28-168 of SEQ ID NO: 1 or a polypeptide that is 85% identity thereof; and R³ comprises amino acids 169-423 of SEQ ID NO: 1 or a polypeptide of 85% sequence identity thereof;

b. R¹ comprises amino acids 1-27 of SEQ ID NO: 1 or a polypeptide that is 85% identity thereof, and R² comprises amino acids 28-374 of SEQ ID NO: 1 or a polypeptide that is 85% identity thereof; and R³ comprises amino acids 375-423 of SEQ ID NO: 1 or a polypeptide of 85% sequence identity thereof;

c. R¹ comprises amino acids 1-27 of SEQ ID NO: 1 or a polypeptide that is 85% identity thereof, and R² comprises amino acids 28-396 of SEQ ID NO: 1 or a polypeptide that is 85% identity thereof; and R³ comprises amino acids 397-423 of SEQ ID NO: 1 or a polypeptide of 85% sequence identity thereof;

d. R¹ comprises amino acids 1-168 of SEQ ID NO: 1 or a polypeptide that is 85% identity thereof, and R² comprises amino acids 169-374 of SEQ ID NO: 1 or a polypeptide that is 85% identity thereof; and R³ comprises amino acids 375-423 of SEQ ID NO: 1 or a polypeptide of 85% sequence identity thereof;

e. R¹ comprises amino acids 1-168 of SEQ ID NO: 1 or a polypeptide that is 85% identity thereof, and R² comprises amino acids 169-396 of SEQ ID NO: 1 or a polypeptide that is 85% identity thereof; and R³ comprises amino acids 397-423 of SEQ ID NO: 1 or a polypeptide of 85% sequence identity thereof; and f. R¹ comprises amino acids 1-374 of SEQ ID NO: 1 or a polypeptide that is 85% identity thereof, and R² comprises amino acids 375-396 of SEQ ID NO: 1 or a polypeptide that is 85% identity thereof; and R³ comprises amino acids 397-423 of SEQ ID NO: 1 or a polypeptide of 85% sequence identity thereof 7. The split-recombinase polypeptide of any of paragraphs 1 to 4, wherein the first (R¹) and second (R²) recombinase polypeptide fragments are PhiC31 recombinase polypeptide fragments, wherein R¹ and R² are selected from any of:

a. R¹ comprises a N-terminal polypeptide fragment of SEQ ID NO: 12 with the C-terminus ending at amino acid 233 of SEQ ID NO:12 or a polypeptide that is 85% identity thereof, and R² comprises a C-terminal polypeptide fragment of SEQ ID NO: 12 with the N-terminus beginning at amino acid 234 of SEQ ID NO:12 or a polypeptide that is 85% identity thereof;

b. R¹ comprises a N-terminal polypeptide fragment of SEQ ID NO: 12 with the C-terminus ending at amino acid 396 of SEQ ID NO:12 or a polypeptide that is 85% identity thereof, and R² comprises a C-terminal polypeptide fragment of SEQ ID NO: 12 with the N-terminus beginning at amino acid 397 of SEQ ID NO:12 or a polypeptide that is 85% identity thereof;

c. R¹ comprises a N-terminal polypeptide fragment of SEQ ID NO: 12 with the C-terminus ending at amino acid 428 of SEQ ID NO:12 or a polypeptide that is 85% identity thereof, and R² comprises a C-terminal polypeptide fragment of SEQ ID NO: 12 with the N-terminus beginning at amino acid 459 of SEQ ID NO:12 or a polypeptide that is 85% identity thereof; and d. R¹ comprises a N-terminal polypeptide fragment of SEQ ID NO: 12 with the C-terminus ending at amino acid 571 of SEQ ID NO:12 or a polypeptide that is 85% identity thereof, and R² comprises a C-terminal polypeptide fragment of SEQ ID NO: 12 with the N-terminus beginning at amino acid 572 of SEQ ID NO:12 or a polypeptide that is 85% identity thereof;

8. The split-recombinase polypeptide of any of paragraphs 1 to 4, wherein the first (R¹), second (R²) and third (R³) recombinase polypeptide fragments are PhiC31 recombinase polypeptide fragments, wherein R¹, R² and R³ are selected from any of:

a. R¹ comprises amino acids 1-233 of SEQ ID NO: 12 or a polypeptide that is 85% identity thereof, and R² comprises amino acids 234-369 of SEQ ID NO: 12 or a polypeptide that is 85% identity thereof; and R³ comprises amino acids 397-605 of SEQ ID NO: 12 or a polypeptide of 85% sequence identity thereof;

b. R¹ comprises amino acids 1-233 of SEQ ID NO: 12 or a polypeptide that is 85% identity thereof, and R² comprises amino acids 234-428 of SEQ ID NO: 12 or a polypeptide that is 85% identity thereof; and R³ comprises amino acids 429-605 of SEQ ID NO: 12 or a polypeptide of 85% sequence identity thereof;

c. R¹ comprises amino acids 1-233 of SEQ ID NO: 12 or a polypeptide that is 85% identity thereof, and R² comprises amino acids 234-571 of SEQ ID NO: 12 or a polypeptide that is 85% identity thereof; and R³ comprises amino acids 572-605-of SEQ ID NO: 12 or a polypeptide of 85% sequence identity thereof;

d. R¹ comprises amino acids 1-396 of SEQ ID NO: 12 or a polypeptide that is 85% identity thereof, and R² comprises amino acids 2397-428 of SEQ ID NO: 12 or a polypeptide that is 85% identity thereof; and R³ comprises amino acids 429-605 of SEQ ID NO: 12 or a polypeptide of 85% sequence identity thereof;

e. R¹ comprises amino acids 1-396 of SEQ ID NO: 12 or a polypeptide that is 85% identity thereof, and R² comprises amino acids 397-571 of SEQ ID NO: 12 or a polypeptide that is 85% identity thereof; and R³ comprises amino acids 572-605 of SEQ ID NO: 12 or a polypeptide of 85% sequence identity thereof; and f. $R^1$ comprises amino acids 1-428 of SEQ ID NO: 12 or a polypeptide that is 85% identity thereof, and $R^2$ comprises amino acids 429-571 of SEQ ID NO: 12 or a polypeptide that is 85% identity thereof; and $R^3$ comprises amino acids 572-605 of SEQ ID NO: 12 or a polypeptide of 85% sequence identity thereof;

9. The split-recombinase polypeptide of any of paragraphs 1 to 4, wherein the first ($R^1$) and second ($R^2$) recombinase polypeptide fragments are VCre recombinase polypeptide fragments, wherein $R^1$ and $R^2$ are selected from any of:

a. $R^1$ comprises a N-terminal polypeptide fragment of SEQ ID NO: 16 with the C-terminus ending at amino acid 82 of SEQ ID NO:16 or a polypeptide that is 85% identity thereof, and $R^2$ comprises a C-terminal polypeptide fragment of SEQ ID NO: 16 with the N-terminus beginning at amino acid 83 of SEQ ID NO:16 or a polypeptide that is 85% identity thereof;

b. $R^1$ comprises a N-terminal polypeptide fragment of SEQ ID NO: 16 with the C-terminus ending at amino acid 172 of SEQ ID NO:16 or a polypeptide that is 85% identity thereof, and $R^2$ comprises a C-terminal polypeptide fragment of SEQ ID NO: 16 with the N-terminus beginning at amino acid 173 of SEQ ID NO:16 or a polypeptide that is 85% identity thereof;

c. $R^1$ comprises a N-terminal polypeptide fragment of SEQ ID NO: 16 with the C-terminus ending at amino acid 269 of SEQ ID NO:16 or a polypeptide that is 85% identity thereof, and $R^2$ comprises a C-terminal polypeptide fragment of SEQ ID NO: 16 with the N-terminus beginning at amino acid 270 of SEQ ID NO:16 or a polypeptide that is 85% identity thereof; and d. $R^1$ comprises a N-terminal polypeptide fragment of SEQ ID NO: 16 with the C-terminus ending at amino acid 277 of SEQ ID NO:16 or a polypeptide that is 85% identity thereof, and $R^2$ comprises a C-terminal polypeptide fragment of SEQ ID NO: 16 with the N-terminus beginning at amino acid 278 of SEQ ID NO:16 or a polypeptide that is 85% identity thereof;

10. The split-recombinase polypeptide of any of paragraphs 1 to 4, wherein the first ($R^1$), second ($R^2$) and third ($R^3$) recombinase polypeptide fragments are VCre recombinase polypeptide fragments, wherein $R^1$, $R^2$ and $R^3$ are selected from any of:

a. $R^1$ comprises amino acids 1-82 of SEQ ID NO: 16 or a polypeptide that is 85% identity thereof, and $R^2$ comprises amino acids 83-172 of SEQ ID NO: 16 or a polypeptide that is 85% identity thereof; and $R^3$ comprises amino acids 173-380 of SEQ ID NO: 16 or a polypeptide of 85% sequence identity thereof;

b. $R^1$ comprises amino acids 1-82 of SEQ ID NO: 16 or a polypeptide that is 85% identity thereof, and $R^2$ comprises amino acids 83-269 of SEQ ID NO: 16 or a polypeptide that is 85% identity thereof; and $R^3$ comprises amino acids 270-380 of SEQ ID NO: 16 or a polypeptide of 85% sequence identity thereof;

c. $R^1$ comprises amino acids 1-82 of SEQ ID NO: 16 or a polypeptide that is 85% identity thereof, and $R^2$ comprises amino acids 83-277 of SEQ ID NO: 16 or a polypeptide that is 85% identity thereof; and $R^3$ comprises amino acids 278-380 of SEQ ID NO: 16 or a polypeptide of 85% sequence identity thereof;

d. $R^1$ comprises amino acids 1-172 of SEQ ID NO: 16 or a polypeptide that is 85% identity thereof, and $R^2$ comprises amino acids 173-269 of SEQ ID NO: 16 or a polypeptide that is 85% identity thereof; and $R^3$ comprises amino acids 270-380 of SEQ ID NO: 16 or a polypeptide of 85% sequence identity thereof;

e. $R^1$ comprises amino acids 1-172 of SEQ ID NO: 16 or a polypeptide that is 85% identity thereof, and $R^2$ comprises amino acids 173-277 of SEQ ID NO: 16 or a polypeptide that is 85% identity thereof; and $R^3$ comprises amino acids 278-380 of SEQ ID NO: 16 or a polypeptide of 85% sequence identity thereof; and f. $R^1$ comprises amino acids 1-269 of SEQ ID NO: 16 or a polypeptide that is 85% identity thereof, and $R^2$ comprises amino acids 270-277 of SEQ ID NO: 16 or a polypeptide that is 85% identity thereof; and $R^3$ comprises amino acids 278-380 of SEQ ID NO: 16 or a polypeptide of 85% sequence identity thereof;

11. The split-recombinase polypeptide of any of paragraphs 1 to 4, wherein the first ($R^1$) and second ($R^2$) recombinase polypeptide fragments are B3 recombinase polypeptide fragments, wherein $R^1$ and $R^2$ are selected from any of:

a. $R^1$ comprises a N-terminal polypeptide fragment of SEQ ID NO: 19 with the C-terminus ending at amino acid 539 of SEQ ID NO:19 or a polypeptide that is 85% identity thereof, and $R^2$ comprises a C-terminal polypeptide fragment of SEQ ID NO: 19 with the N-terminus beginning at amino acid 540 of SEQ ID NO:19 or a polypeptide that is 85% identity thereof;

b. $R^1$ comprises a N-terminal polypeptide fragment of SEQ ID NO: 19 with the C-terminus ending between amino acids 20-100 of SEQ ID NO:19 or a polypeptide that is 85% identity thereof, and $R^2$ comprises a C-terminal polypeptide fragment of SEQ ID NO: 19 with the N-terminus beginning between amino acids 21-101 of SEQ ID NO:19 or a polypeptide that is 85% identity thereof;

c. $R^1$ comprises a N-terminal polypeptide fragment of SEQ ID NO: 19 with the C-terminus ending between amino acids 100-300 of SEQ ID NO:19 or a polypeptide that is 85% identity thereof, and $R^2$ comprises a C-terminal polypeptide fragment of SEQ ID NO: 19 with the N-terminus beginning between amino acids 101-301 of SEQ ID NO:19 or a polypeptide that is 85% identity thereof;

d. $R^1$ comprises a N-terminal polypeptide fragment of SEQ ID NO: 19 with the C-terminus ending between amino acids 300-400 of SEQ ID NO:19 or a polypeptide that is 85% identity thereof, and $R^2$ comprises a C-terminal polypeptide fragment of SEQ ID NO: 19 with the N-terminus beginning between amino acids 301-401 of SEQ ID NO:19 or a polypeptide that is 85% identity thereof; and e. $R^1$ comprises a N-terminal polypeptide fragment of SEQ ID NO: 19 with the C-terminus ending between amino acids 400-500 of SEQ ID NO:19 or a polypeptide that is 85% identity thereof, and $R^2$ comprises a C-terminal polypeptide fragment of SEQ ID NO: 19 with the N-terminus beginning between amino acids 401-501 of SEQ ID NO:19 or a polypeptide that is 85% identity thereof;

12. The split-recombinase polypeptide of any of paragraphs 1 to 4, wherein the first ($R^1$) and second ($R^2$)

recombinase polypeptide fragments are Bxb1 recombinase polypeptide fragments, wherein $R^1$ and $R^2$ are selected from any of:

a. $R^1$ comprises a N-terminal polypeptide fragment of SEQ ID NO: 41 with the C-terminus ending at amino acid 468 of SEQ ID NO:19 or a polypeptide that is 85% identity thereof, and $R^2$ comprises a C-terminal polypeptide fragment of SEQ ID NO: 41 with the N-terminus beginning at amino acid 469 of SEQ ID NO:41 or a polypeptide that is 85% identity thereof;

b. $R^1$ comprises a N-terminal polypeptide fragment of SEQ ID NO: 41 with the C-terminus ending between amino acids 20-100 of SEQ ID NO:41 or a polypeptide that is 85% identity thereof, and $R^2$ comprises a C-terminal polypeptide fragment of SEQ ID NO: 41 with the N-terminus beginning between amino acids 21-101 of SEQ ID NO:41 or a polypeptide that is 85% identity thereof;

c. $R^1$ comprises a N-terminal polypeptide fragment of SEQ ID NO: 41 with the C-terminus ending between amino acids 100-200 of SEQ ID NO:41 or a polypeptide that is 85% identity thereof, and $R^2$ comprises a C-terminal polypeptide fragment of SEQ ID NO: 41 with the N-terminus beginning between amino acids 101-201 of SEQ ID NO:41 or a polypeptide that is 85% identity thereof;

d. $R^1$ comprises a N-terminal polypeptide fragment of SEQ ID NO: 41 with the C-terminus ending between amino acids 200-300 of SEQ ID NO:41 or a polypeptide that is 85% identity thereof, and $R^2$ comprises a C-terminal polypeptide fragment of SEQ ID NO: 41 with the N-terminus beginning between amino acids 201-301 of SEQ ID NO:41 or a polypeptide that is 85% identity thereof;

e. $R^1$ comprises a N-terminal polypeptide fragment of SEQ ID NO: 41 with the C-terminus ending between amino acids 300-400 of SEQ ID NO:41 or a polypeptide that is 85% identity thereof, and $R^2$ comprises a C-terminal polypeptide fragment of SEQ ID NO: 41 with the N-terminus beginning between amino acids 301-401 of SEQ ID NO:41 or a polypeptide that is 85% identity thereof; and f. $R^1$ comprises a N-terminal polypeptide fragment of SEQ ID NO: 41 with the C-terminus ending between amino acids 400-497 of SEQ ID NO:41 or a polypeptide that is 85% identity thereof, and $R^2$ comprises a C-terminal polypeptide fragment of SEQ ID NO: 41 with the N-terminus beginning between amino acids 401-498 of SEQ ID NO:41 or a polypeptide that is 85% identity thereof;

13. The split-recombinase polypeptide of any of paragraphs 1 to 12, wherein the chemically-induced dimerization domain pair (CIDD pair) comprises a $CIDD^A$ and $CIDD^B$ selected from any one or more of:

a. a $CIDD^A$ comprising a GID1 domain or a fragment thereof, and a $CIDD^B$ comprising a GAI domain, wherein the GID1 domain and GAI domain bind to the target agent Gibberlin Ester (GIB);

b. a $CIDD^A$ comprising a FKBP domain or a fragment thereof, and a $CIDD^B$ comprising a FRB domain, wherein the FKBP domain and FRB domain bind to the target agent Rapalog (RAP);

c. a $CIDD^A$ comprising a PYL domain or a fragment thereof, and a $CIDD^B$ comprising a ABI domain, wherein the PLY domain and ABI domain bind to the target agent Absorbic acid (ABA);

d. a $CIDD^A$ comprising a Light-inducible dimerization domain (LIDD), wherein a LIDD dimerizes with a complementary LIDD ($CIDD^B$) upon exposure to a light signal of an appropriate wavelength.

14. The split-recombinase polypeptide of any of paragraphs 1 to 13, wherein the LIDD is nMag or CIBN, wherein nMag can dimerize with the complementary LIDD pMag upon exposure to a blue light signal, and wherein CIBN can dimerize with the complementary CRY2 upon exposure to a blue light signal.

15. The split-recombinase polypeptide of any of paragraphs 1 to 14, wherein the light signal is a pulse light signal.

16. The split-recombinase of any of paragraphs 1 to 15, wherein the active recombinase protein can recognize the recombinant recognition sequence (RRS) of the recombinase protein.

17. A fusion protein comprising a Flp recombinase polypeptide fragment fused to at least one chemically-inducible dimerization domain (CIDD), wherein the Flp recombinase polypeptide fragment is selected from any of:

a N-terminal polypeptide comprising a fragment of SEQ ID NO: 1 with the C-terminus ending at any one of amino acids 27, 168, 374 or 396 of SEQ ID NO:1, or a C-terminal polypeptide comprising a fragment of SEQ ID NO: 1 with the N-terminus beginning at any one of amino acids selected from any of: 28, 169, 375 or 397 of SEQ ID NO:1 and wherein the CIDD is selected from any of:

a. a GID1 domain or GAI domain;

b. a FKBP domain or a FRB domain; or c. a PYL domain or a ABI domain.

18. A fusion protein comprising a PhiC31 recombinase polypeptide fragment fused to at least one chemically-inducible dimerization domain (CIDD), wherein the PhiC31 recombinase polypeptide fragment is selected from any of:

a N-terminal polypeptide comprising a fragment of SEQ ID NO: 12 with the C-terminus ending at any one of amino acids 223, 396, 428, 571, 605 of SEQ ID NO:12, or a C-terminal polypeptide comprising a fragment of SEQ ID NO: 12 with the N-terminus beginning at any one of amino acids selected from any of: 224, 397, 429, 572 of SEQ ID NO:12 and wherein the CIDD is selected from any of:

a. a GID1 domain or GAI domain;

b. a FKBP domain or a FRB domain; or c. a PYL domain or a ABI domain.

19. A fusion protein comprising a VCre recombinase polypeptide fragment fused to at least one chemically-inducible dimerization domain (CIDD), wherein the VCre recombinase polypeptide fragment is selected from any of:

a N-terminal polypeptide comprising a fragment of SEQ ID NO: 16 with the C-terminus ending at any one of amino acids 82, 172, 269, 277 of SEQ ID NO:16, or a C-terminal polypeptide comprising a fragment of SEQ ID NO: 16 with the N-terminus beginning at any one of amino acids selected from any of: 83, 173, 270, 278 of SEQ ID NO:16 and wherein the CIDD is selected from any of:
a. a GID1 domain or GAI domain;
b. a FKBP domain or a FRB domain; or
c. a PYL domain or a ABI domain.

20. A fusion protein comprising a B3 recombinase polypeptide fragment fused to at least one chemically-inducible dimerization domain (CIDD), wherein the B3 recombinase polypeptide fragment is selected from any of:
a N-terminal polypeptide comprising a fragment of SEQ ID NO: 19 with the C-terminus ending at amino acid 539 of SEQ ID NO:19, or an protein with 85% sequence identity thereto; or
a C-terminal polypeptide comprising a fragment of SEQ ID NO: 19 with the N-terminus beginning at amino acid 540 of SEQ ID NO:19, or an protein with 85% sequence identity thereto;
and wherein the CIDD is selected from any of:
a. a GID1 domain or GAI domain;
b. a FKBP domain or a FRB domain; or
c. a PYL domain or a ABI domain.

21. A fusion protein comprising a Bxb1 recombinase polypeptide fragment fused to at least one chemically-inducible dimerization domain (CIDD), wherein the Bxb1 recombinase polypeptide fragment is selected from any of:
a N-terminal polypeptide comprising a fragment of SEQ ID NO: 41 with the C-terminus ending at amino acid 468 of SEQ ID NO:41, or an protein with 85% sequence identity thereto; or
a C-terminal polypeptide comprising a fragment of SEQ ID NO: 41 with the N-terminus beginning at amino acid 469 of SEQ ID NO:41, or an protein with 85% sequence identity thereto;
and wherein the CIDD is selected from any of:
a. a GID1 domain or GAI domain;
b. a FKBP domain or a FRB domain; or
c. a PYL domain or a ABI domain.

22. A nucleic acid molecule encoding the fusion protein of any of paragraphs 17-21.

23. A cell comprising the nucleic acid of paragraph 22.

24. A kit comprising a split-recombinase polypeptide according to any of paragraphs 1-16.

25. A kit comprising fusion protein of any of paragraphs 17-21.

Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

As used herein, the term "comprising" or "comprises" is used in reference to compositions, methods, and respective component(s) thereof, that are useful to an embodiment, yet open to the inclusion of unspecified elements, whether useful or not.

As used herein, the term "consisting essentially of" refers to those elements required for a given embodiment. The term permits the presence of elements that do not materially affect the basic and novel or functional characteristic(s) of that embodiment of the invention.

The term "refolding" refers to the folding of the dissociated protein molecules produced in the solubilizing process into their native three-dimensional conformation. This procedure is affected by the amino acid sequence of the protein. It is well-known that the disulfide bonds are formed in correct positions when the refolding precedes the formation of disulfide bonds in a protein, thereby causing the formation of an active protein of native conformation.

The term "conjugate" or "conjugated" refer to the joining or attachment of two or more entities. The joining can be fusion of the two or more polypeptides, i.e., by a peptide bond (to form a fusion protein), or other covalent, ionic, or hydrophobic interactions whereby the moieties of a molecule are held together and preserved in proximity. In some embodiments, the conjugation is via cross-linkers. In some embodiments, the attachment of the entities (i.e., the split-recombinase fragment and a CIDD or other moiety) can be a direct linkage, or can be together by linkers, chemical modification, peptide linkers, chemical linkers, covalent or non-covalent bonds, or protein fusion or by any means known to one skilled in the art. The joining may be permanent or reversible. In some embodiments, the conjugation is irreverable. In some embodiments, several linkers, such as for example, peptide linkers, may be included between the split-recombinase fragment and CIDD or other moiety, in order to take advantage of desired properties of each linker and each protein in the conjugate. Flexible linkers and linkers that increase the solubility of the conjugates are contemplated for use alone or with other linkers are incorporated herein. Peptide linkers may be linked by expressing DNA encoding the linker to one or more proteins in the conjugate. Linkers may be acid cleavable, photocleavable and heat sensitive linkers.

The term "moieties" or "motif" used interchangeably herein, refers to a molecule; nucleic acid or protein or otherwise, capable of performing a particular function. "Nucleic acid binding moieties" or "nucleic acid binding motif" refers to a molecule capable of binding to the nucleic acid in specific manner.

The term "analyte" as used in the context of non-nucleic acid analyte herein, is intended to refer to any chemical, biological or structural entity that is not a nucleic acid or nucleotide or nucleic acid analogue. Such an analyte includes, but is not limited to organic molecules, inorganic molecules, biomolecules, metabolites etc.

As used herein, the term "cassette" refers to a nucleic acid molecule, or a fragment thereof, that can be introduced to a host cell and incorporated into the host cell's genome. A cassette can comprise a target gene. A cassette can be an isolated nucleotide fragment, e.g. a dsDNA or can be comprised by a vector, e.g. a plasmid, cosmid, and/or viral vector. In some embodiments, a cassette is a single nucleic acid construct, e.g., an engineered nucleic acid sequence.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of lupus nephritis. A subject can be male or female.

As used herein, the term "administering," refers to the placement of a compound or a cell into a subject by a method or route which results in at least partial delivery of the agent at a desired site. Any appropriate route which results in an effective treatment in the subject can be used.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intrahepatic, intraperitoneal, transtracheal, subcutaneous, subcuticular, intraarticular, sub capsular, subarachnoid, intraspinal, intracerebro spinal, and intrasternal injection and infusion. The administration can be systemic or local.

A cell for use with the cassettes and switches described herein can be any cell or host cell. As defined herein, a "cell" or "cellular system" is the basic structural and functional unit of all known independently living organisms. It is the smallest unit of life that is classified as a living thing, and is often called the building block of life. Some organisms, such as most bacteria, are unicellular (consist of a single cell). Other organisms, such as humans, are multicellular. A "natural cell," as defined herein, refers to any prokaryotic or eukaryotic cell found naturally. A "prokaryotic cell" can comprise a cell envelope and a cytoplasmic region that contains the cell genome (DNA) and ribosomes and various sorts of inclusions.

In some embodiments, the cell is a eukaryotic cell, preferably a mammalian cell. A eukaryotic cell comprises membrane-bound compartments in which specific metabolic activities take place, such as a nucleus. In other embodiments, the cell or cellular system is an artificial or synthetic cell. As defined herein, an "artificial cell" or a "synthetic cell" is a minimal cell formed from artificial parts that can do many things a natural cell can do, such as transcribe and translate proteins and generate ATP.

Cells of use in the various aspects described herein upon transformation or transfection with the cassettes or switches described herein include any cell that is capable of supporting the activation and expression of the molecular circuits. In some embodiments of the aspects described herein, a cell can be from any organism or multi-cell organism. Examples of eukaryotic cells that can be useful in aspects described herein include eukaryotic cells selected from, e.g., mammalian, insect, yeast, or plant cells. The molecular circuits described herein can be introduced into a variety of cells including, e.g., fungal, plant, or animal (nematode, insect, plant, bird, reptile, or mammal (e.g., a mouse, rat, rabbit, hamster, gerbil, dog, cat, goat, pig, cow, horse, whale, monkey, or human)). The cells can be primary cells, immortalized cells, stem cells, or transformed cells. In some preferred embodiments, the cells comprise stem cells. Expression vectors for the components of the molecular circuit will generally have a promoter and/or an enhancer suitable for expression in a particular host cell of interest. The present invention contemplates the use of any such vertebrate cells for the molecular circuits, including, but not limited to, reproductive cells including sperm, ova and embryonic cells, and non-reproductive cells, such as kidney, lung, spleen, lymphoid, cardiac, gastric, intestinal, pancreatic, muscle, bone, neural, brain, and epithelial cells.

As used herein, the term "gene" refers to a nucleic acid sequence comprising an open reading frame encoding a polypeptide, including both exon and (optionally) intron sequences. A "gene" refers to coding sequence of a gene product, as well as non-coding regions of the gene product, including 5'UTR and 3'UTR regions, introns and the promoter of the gene product. These definitions generally refer to a single-stranded molecule, but in specific embodiments will also encompass an additional strand that is partially, substantially or fully complementary to the single-stranded molecule. Thus, a nucleic acid sequence can encompass a double-stranded molecule or a double-stranded molecule that comprises one or more complementary strand(s) or "complement(s)" of a particular sequence comprising a molecule. As used herein, a single stranded nucleic acid can be denoted by the prefix "ss", a double stranded nucleic acid by the prefix "ds", and a triple stranded nucleic acid by the prefix "ts."

The term "expression" as used herein refers to the biosynthesis of a gene product, preferably to the transcription and/or translation of a nucleotide sequence, for example an endogenous gene or a heterologous gene, in a cell. For example, in the case of a heterologous nucleic acid sequence, expression involves transcription of the heterologous nucleic acid sequence into mRNA and, optionally, the subsequent translation of mRNA into one or more polypeptides. Expression also refers to biosynthesis of a microRNA or RNAi molecule, which refers to expression and transcription of an RNAi agent such as siRNA, shRNA, and antisense DNA but does not require translation to polypeptide sequences. The term "expression construct" and "nucleic acid construct" as used herein are synonyms and refer to a nucleic acid sequence capable of directing the expression of a particular nucleotide sequence, such as the heterologous target gene sequence in an appropriate host cell (e.g., a prokaryotic cell, eukaryotic cell, or mammalian cell). If translation of the desired heterologous target gene is required, it also typically comprises sequences required for proper translation of the nucleotide sequence. The coding region can code for a protein of interest but can also code for a functional RNA of interest, for example, microRNA, microRNA target sequence, antisense RNA, dsRNA, or a nontranslated RNA, in the sense or antisense direction. The nucleic acid construct as disclosed herein can be chimeric, meaning that at least one of its components is heterologous with respect to at least one of its other components.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 19th Edition, published by Merck Sharp & Dohme Corp., 2011 (ISBN 978-O-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

Other than in the operating examples, or where otherwise indicated, all numbers expressing quantities of ingredients or reaction conditions used herein should be understood as modified in all instances by the term "about." The term "about" when used in connection with percentages may mean ±1% of the value being referred to. For example, about 100 means from 99 to 101.

Although methods and materials similar or equivalent to those disclosed herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology disclosed herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are disclosed herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments disclosed herein can be combined to provide further embodiments. Aspects of the disclosure can be modified, if necessary, to employ the compositions, functions and concepts of the above references and application to provide yet further embodiments of the disclosure.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The technology disclosed herein is further illustrated by the following examples which in no way should be construed as being further limiting.

Materials and Methods

DNA Assembly

Figure 13A:
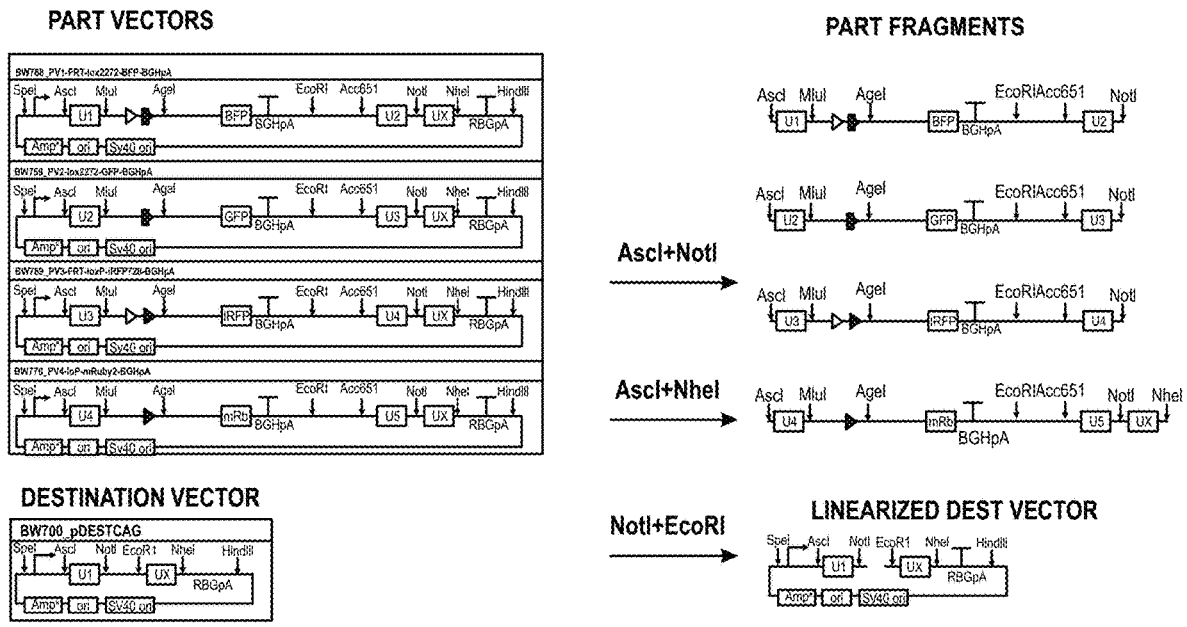
Figure 13B:
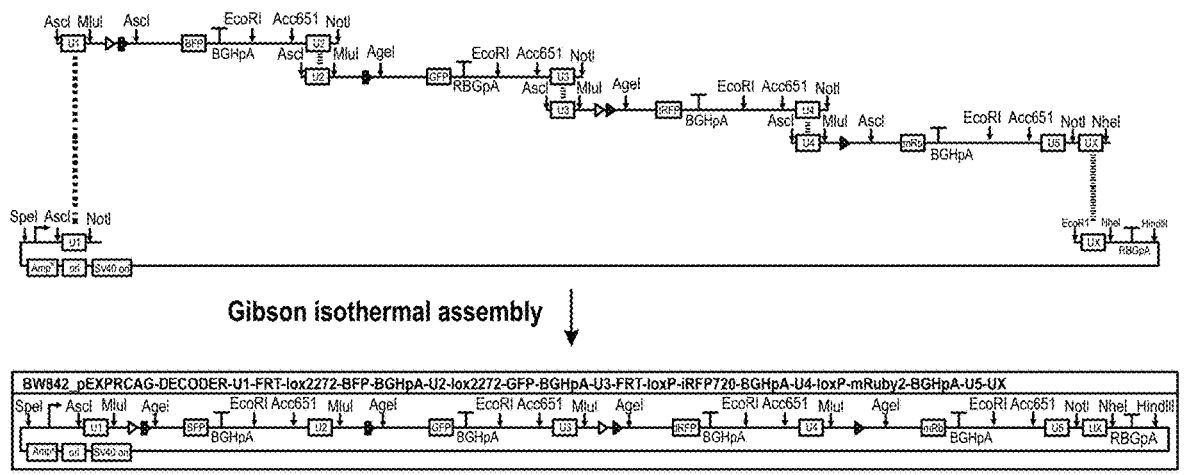
Figure 14:
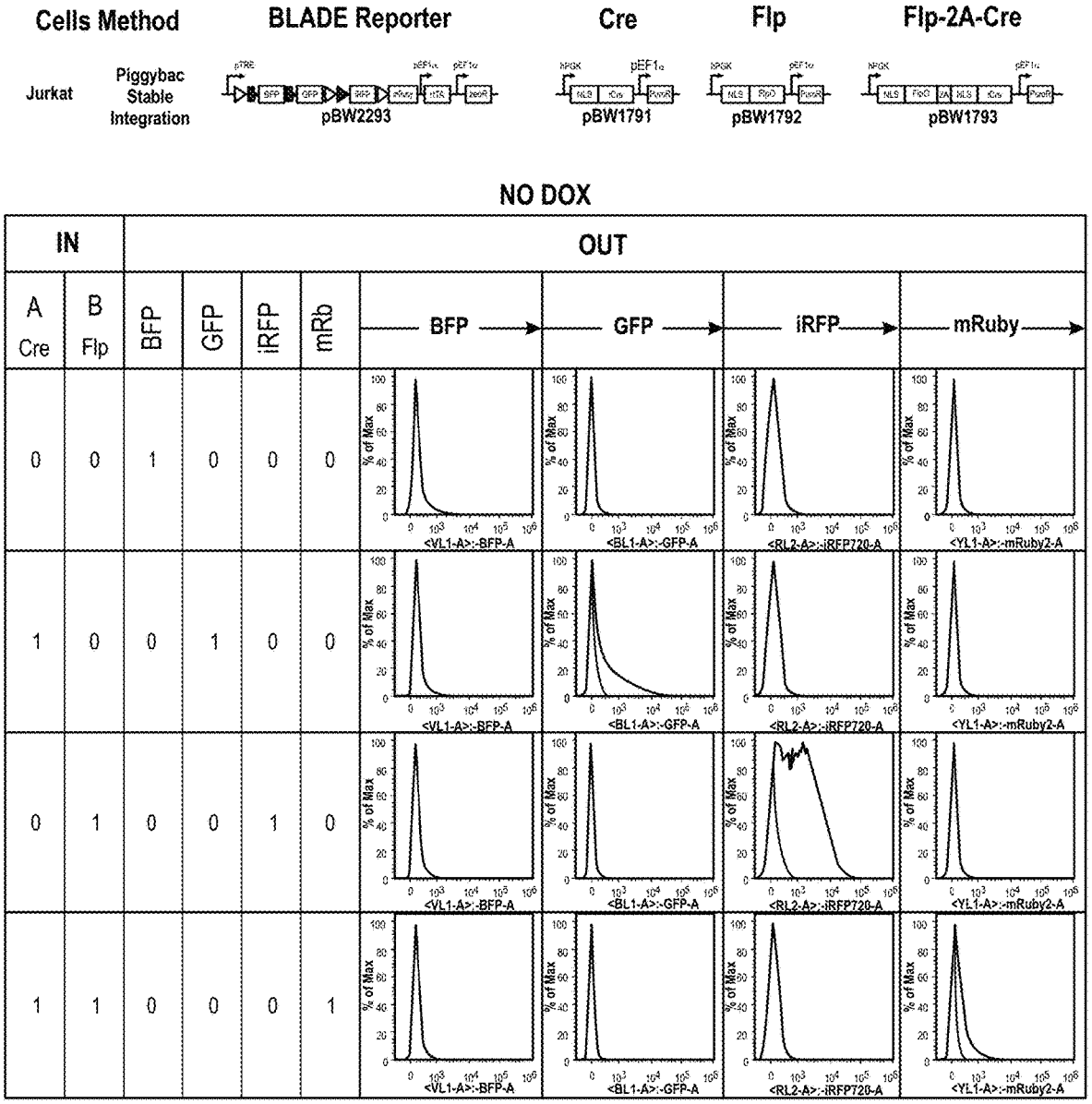
Figure 15:
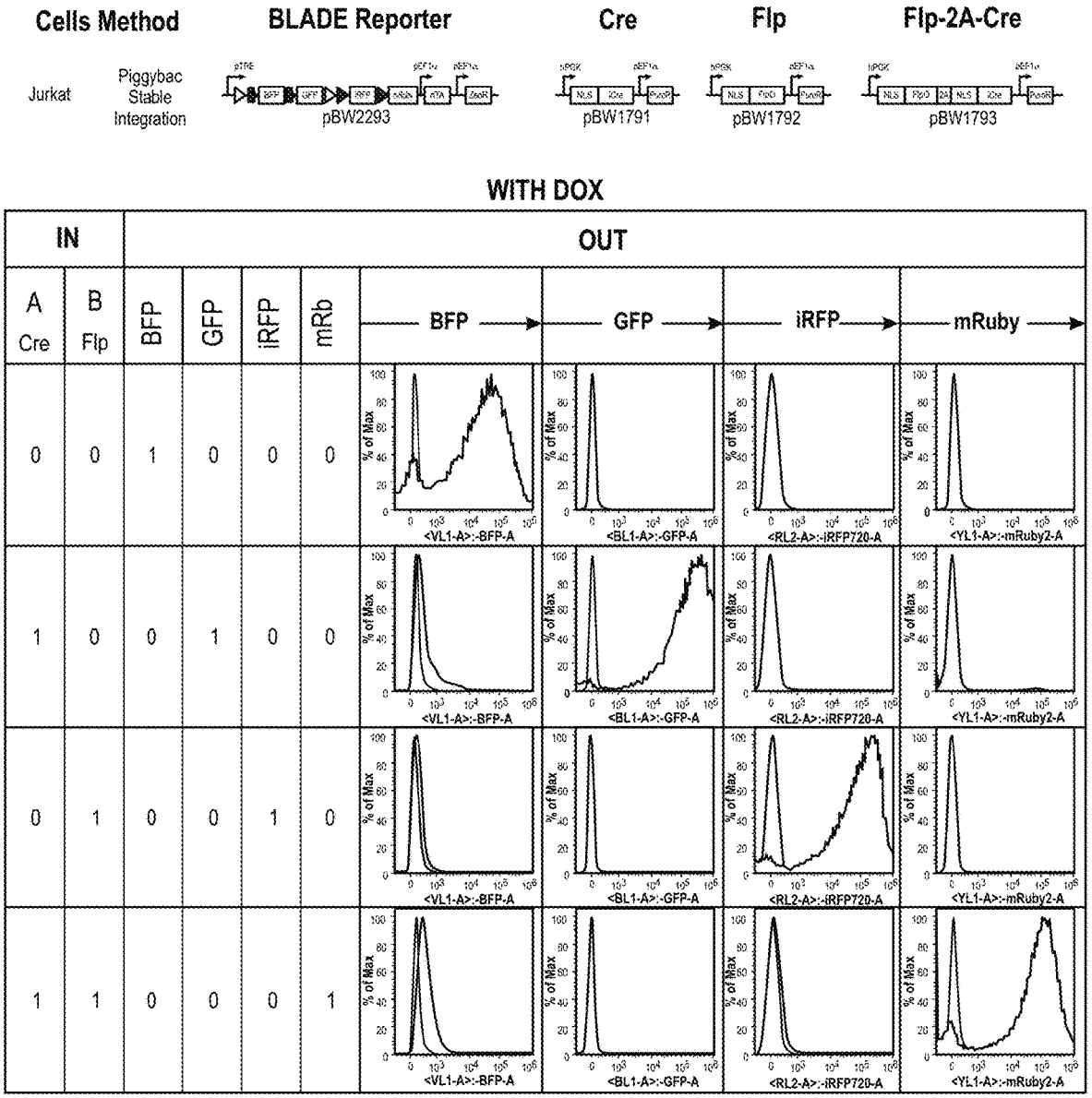

All constructs were transformed and maintained in Top10 *Escherichia coli* competent cells (Life Technologies) at 37° C. or 30° C. prior to miniprep (Epoch Life Sciences) or midiprep (Macherey Nagel). All plasmids were created using standard molecular biology practices of ligation, digestion and transformation, in addition to Gibson isothermal assembly and Unique Nucleotide Sequence Guided assembly (a modular extension of Gibson assembly), where DNA fragments that are to be connected to each other are flanked by short homology sequences and are then fused together by a one-pot isothermal digestion, polymerization, and ligation reaction. This latter strategy permits a modular, easy, efficient and fast framework for construction of DNA. In UNS-guided assembly, the homology sequences have been standardized (e.g. U1, U2, U3 . . . UX) and have been computationally optimized for proper assembly (reduction of hairpins, sequence homology, and GC tracts) and ease of use (no start codons or useful restriction sites). Genetic cassettes that are to be connected are cloned into part vectors, which contain the UNSes that surround the insert. Part vectors are then sequenced-verified using Sanger sequencing (Quintara Biosciences). Restriction digests and gel purifications are then performed to isolate the cassettes flanked with the UNSes. Finally, these products are joined to a linearized destination vector via Gibson isothermal assembly. For the 113 circuits displayed in FIG. 3, analytical PCRs were performed to verify inserts were assembled correctly through amplifications across the UNS sequences. Construction details are elaborated in FIGS. 11, 13 and 24.

Maintenance and Transient DNA Transfection of HEK293FT Cells

DNA was transfected into the human embryonic kidney cell line (HEK293FT) using a polyethylenimine (PEI) protocol. Cells were plated onto 48-(2504) or 96-well (1004) plates the day prior to transfection (200,000 cells/mL), such that the cells were 50-70% confluent the day of transfection. Cells were kept in a humidified incubator at 37° C. and 5% $CO_2$ and maintained in DMEM medium (Corning) with 10% Heat Inactivated Fetal Bovine Serum (Life Technologies), 50 U.I./mL penicillin/50 µg/mL streptomycin (Corning), 2 mM glutamine (Corning) and 1 mM sodium pyruvate (Lonza). PEI stocks were made from linear polyethylenimine (Polysciences 23966-2) and were dissolved at a concentration of 0.323 g/L in deionized water with the assistance of concentrated hydrochloric acid and sodium hydroxide and then filtered sterilized (0.24 µm). PEI stocks were stored at −80° C. until use and warmed to room temperature prior to usage. For 48-well plate transfections, DNA (1000 ng, 50 ng/4) was dissolved and brought up to a volume of 50 µL using 0.15 M sodium chloride (NaCl, Fisher Scientific). DNA-NaCl solutions were then mixed with 50 µL of a PEI-NaCl mixture (8 uL PEI: 42 uL NaCl). These solutions were then incubated at room temperature for ten minutes and 25 µL was carefully dropped into individual wells of HEK293FT cells (250 ng DNA/well). Similarly, for 96-well plate transfections, DNA (500 ng, 50 ng/4) was dissolved and brought up to a volume of 25 µL using 0.15 M sodium chloride (NaCl). DNA-NaCl solutions were then mixed with 25 µL of a PEI-NaCl (4 uL PEI: 21 uL NaCl) mixture. These solutions were then incubated at room temperature for ten minutes and 10 µL was carefully dropped into individual wells of HEK293FT cells (100 ng DNA/well). Electronic space-adjustable multichannel pipettors (Integra Biosciences) were utilized throughout the process for rapid aspiration and dispensing of molecular and cellular reagents. A Countess II image-based cell counter (Life Technologies) was used for measuring human cell population densities.

Small Molecule Chemical Induction

1000× stock small molecules abscisic acid (100 mM, Sigma Aldrich), doxycycline (200 µg/mL, Fisher Scientific), and 4-hydroxytamoxifen (1 mM, Sigma Aldrich) were dissolved in 100% ethanol and stored at recommended temperatures. For transient transfection induction experiments, two hours post-transfection, small molecules were mixed with mammalian cell medium such the concentrations were 25×; then, proper volumes were dispensed into wells such that the final concentration was 1×.

Rapamycin analog (Clontech A/C heterodimerizer AP21967, 0.5 mM) was used as a 1000× stock for chemical induction experiments. All other 1000× stock small molecules abscisic acid (100 mg/mL, Sigma Aldrich), doxycycline (200 µg/mL, Fisher Scientific), esterified gibberellin (10 mg/mL, Toronto Research Chemicals), 4-hydroxytamoxifen (1 mM, Sigma Aldrich) were dissolved in 100% ethanol and stored at recommended temperatures. For transient transfection induction experiments, two hours post-transfection, small molecules were mixed into mammalian cell medium such the concentrations were 25×; then, proper volumes were dispensed into wells such that the final concentration was 1×.

Flow Cytometry.

Two days post-transfection and after trypsinization (0.05% Trypsin/0.53 mM EDTA, Corning) and resuspension, all HEK293FT cell populations were analyzed using a Becton Dickinson (BD) LSRFortessa SORP flow cytometer with HTS. The LSRFortessa was equipped for detection of EGFP (488 nm laser, 530/30 emission filter, 505 longpass dichroic mirror), tagBFP (405 nm laser, 450/50 emission filter), mCherry or mRuby2 (561 nm, 610/20 emission filter, 595 longpass dichroic mirror), iRFP-720 (637 nm laser, 730/45 emission filter, 685 longpass dichroic mirror) and LSS-mOrange (405 nm, 610/20 emission filter, 535 longpass dichroic mirror).

A gate was applied on FSC-A and SSC-A to remove debris from cell populations in FlowJo (Tree Star). pCAG-tagBFP or pCAG-LSS-mOrange plasmids were used as HEK293FT transient transfection markers and were gated for by applying a gate on the top 0.1% wildtype cells in those channels. Figure plots represent at least 5000 events in the transfected cell subset. Compensation was applied for five-color experiments.

Maintenance and Generation of Stable Jurkat T Lymphocytes Through Electroporation, piggyBac-Mediated Integration, Eukaryotic Selection, and Doxycycline Induction Wild type Jurkat T lymphocyte cells were kept in a humidified incubator at 37° C. and 5% $CO_2$ and maintained in RPMI medium (Corning) with 5% Heat Inactivated Fetal Bovine Serum (HI-FBS, Life Technologies), 50 U.I./mL penicillin/50 µg/mL streptomycin (Corning), and 2 mM glutamine (Corning). Prior to electroporation, cells were changed with medium containing 10% HI-FBS and without antibiotics. On days of transfection, cells were checked to be within $5-8 \times 10^5$ cells/mL and $2 \times 10^7$ cells were spun down at 300×g and resuspended in 300 µL medium per transfection. Cell solutions were mixed with 20 µg transposon vector and 4 µg of transposase (pCAG-SuperPBase, pBW900). After fifteen minutes of room temperature incubation, DNA/cell mixtures were transferred to a 4 mm electroporation cuvette and electroporated in a Harvard Apparatus BTX instrument using a single pulse 300V square wave for ten milliseconds. Cells were then transferred to 10% HI-FBS medium without antibiotics and placed into the incubator. One to two days later, cells were spun down and resuspended in medium with 5% HI-FBS with antibiotic and antieukaryotic chemicals. Puromycin (Thermo Scientific) was used at a final concentration of 2 µg/mL and zeocin (Invivogen) at 400 µg/mL. Antieukaryotic selections were performed for at least ten days before removing antieukaryotic compounds.

Figures 2A, 2B:
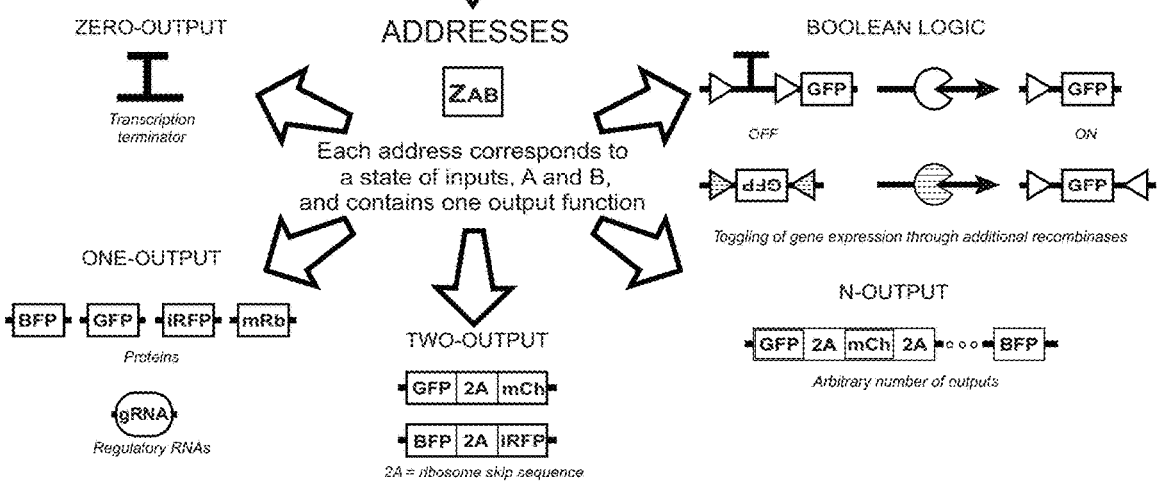
Figure 3A:
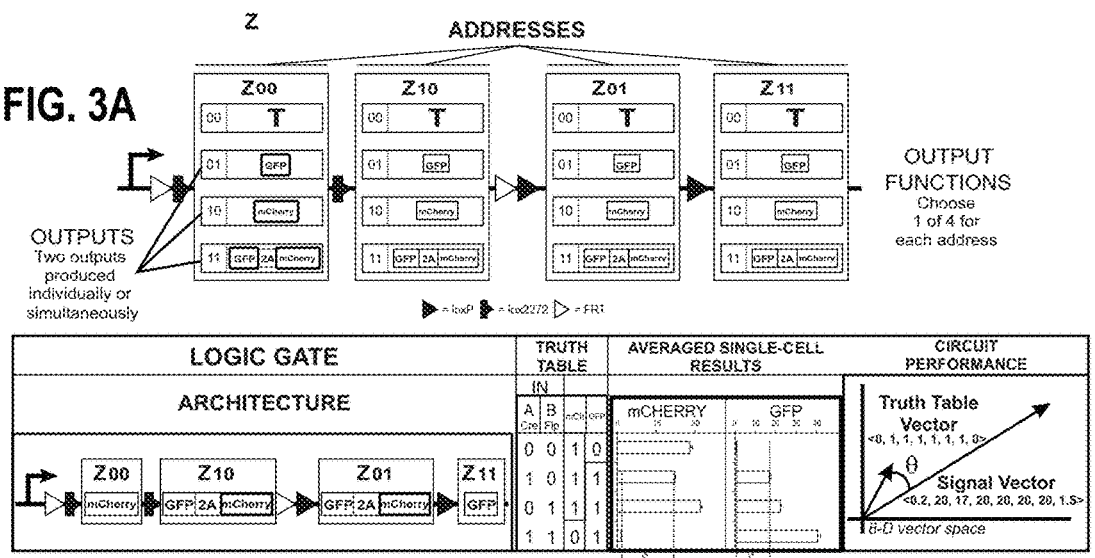
Figure 3B:
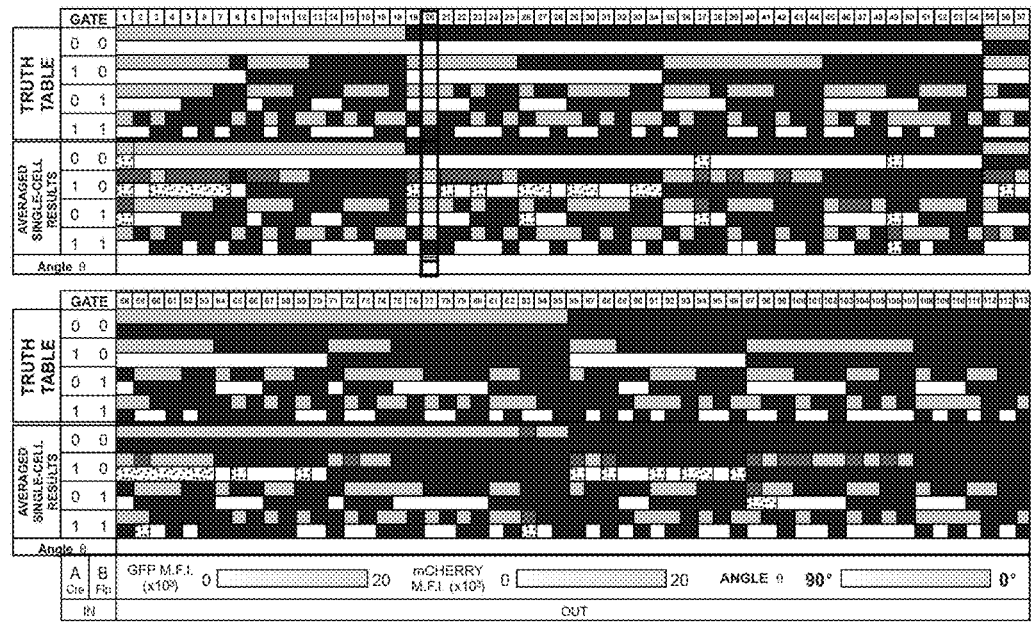
Figure 3C:
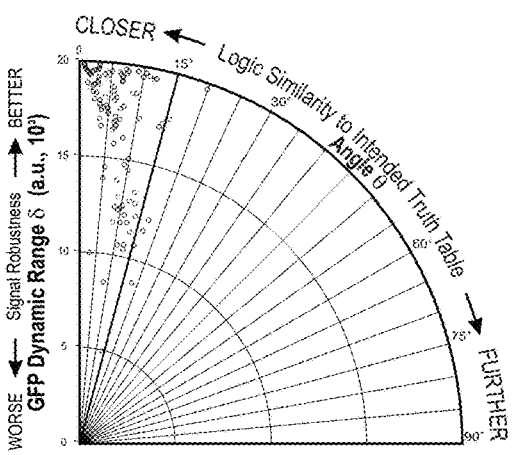
Figure 3C:
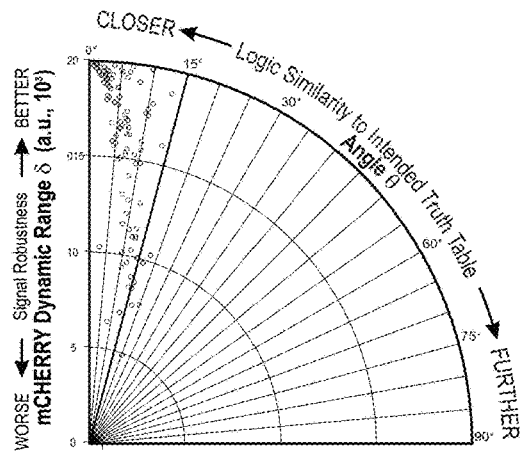

For experiment in FIG. 2B, the decoder recombinase reporter (pBW2293) was first integrated and selected with zeocin; then, recombinase expression vectors (hPGK-iCre, hPGK-FlpO, hPGK-FlpO-2A-iCre) were integrated and selected for with puromycin in duplicate (n=2). After final stable line generation, 300,000 Jurkat cells of each line were spun down and resuspended in doxycycline or ethanol-containing medium. Cells were maintained in respective media for given number of time (fourteen days in ethanol and then with or without doxycycline for three days in FIG. 2B, square points in FIG. 17) and then run for cytometric readings.

Flow Cytometry

Two days post-transfection and after trypsinization (0.05% Trypsin/0.53 mM EDTA, Corning) and resuspension, all HEK293FT cell populations were analyzed using a Becton Dickinson (BD) LSRFortessa SORP flow cytometer with HTS, except for data in FIG. 5, which were recorded on a BD LSRII. Time-course data was achieved through trypsinization and fixation of cells at particular time points (BD Cytofix) and kept at 4° C. until analyzed through flow cytometry. The LSRFortessa was equipped for detection of EGFP (488 nm laser, 530/30 emission filter, 505 longpass dichroic mirror), tagBFP (405 nm laser, 450/50 emission filter), mCherry or mRuby2 (561 nm, 610/20 emission filter, 595 longpass dichroic mirror), iRFP-720 (637 nm laser, 730/45 emission filter, 685 longpass dichroic mirror) and LSS-mOrange (405 nm, 610/20 emission filter, 535 longpass dichroic mirror). The LSRII was similarly equipped for detection of EGFP, tagBFP, mCherry and mRuby2, but with additional channels for iRFP-720 (633 nm laser, 720/40 emission filter, 710 longpass dichroic mirror) and LSS-mOrange (405 nm, 590/35 emission filter, 505 longpass dichroic mirror). All Jurkat T lymphocyte experiments were run using a Life Technologies Attune Nxt 4-laser acoustic focusing flow cytometer. The Attune Nxt was equipped for detection of EGFP (488 nm laser, 510/10 emission filter), tagBFP (405 nm laser, 440/50 emission filter), mRuby2 (561 nm, 585/16 emission filter), iRFP-720 (638 nm laser, 720/30 emission filter) and LSS-mOrange (405 nm, 603/48 emission filter).

Figure 27:
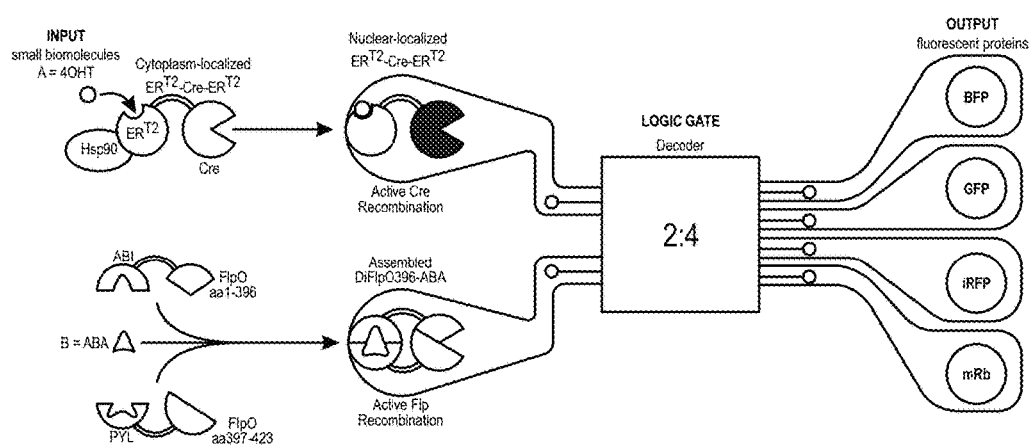
Figure 28:
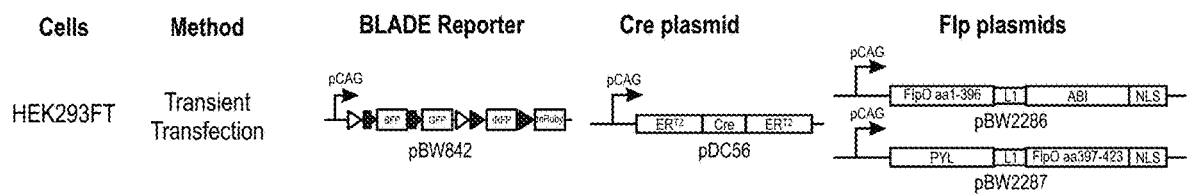
FIG. 28 shows the mean fluorescence intensity values for 2-Input 4-hydroxytamoxifen and abscisic acid-inducible decoder in HEK293FT cells over two days represented with histograms. 2-Input decoder produces a particular fluorescent protein for each row of the truth table. Error bars indicate standard error of the mean of three replicates.
Figure 28:
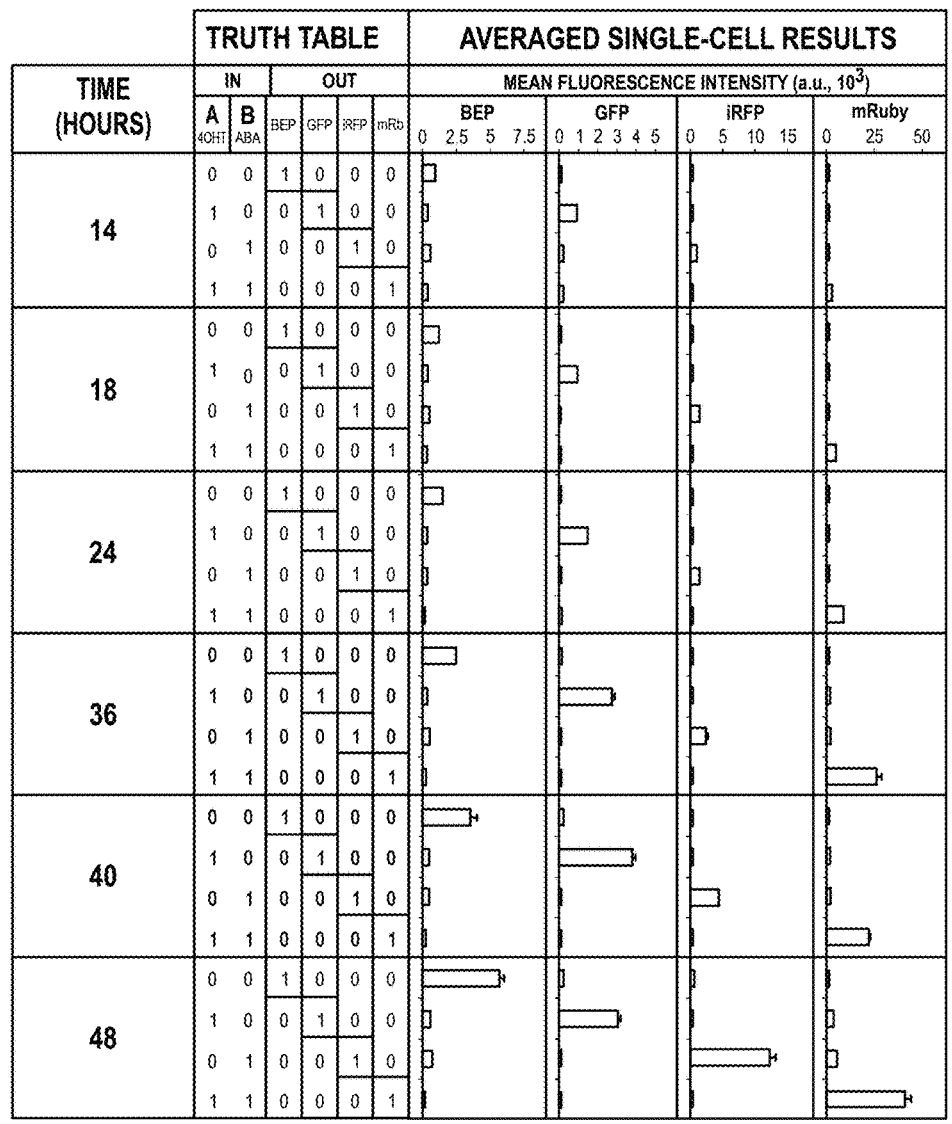
Figure 29:
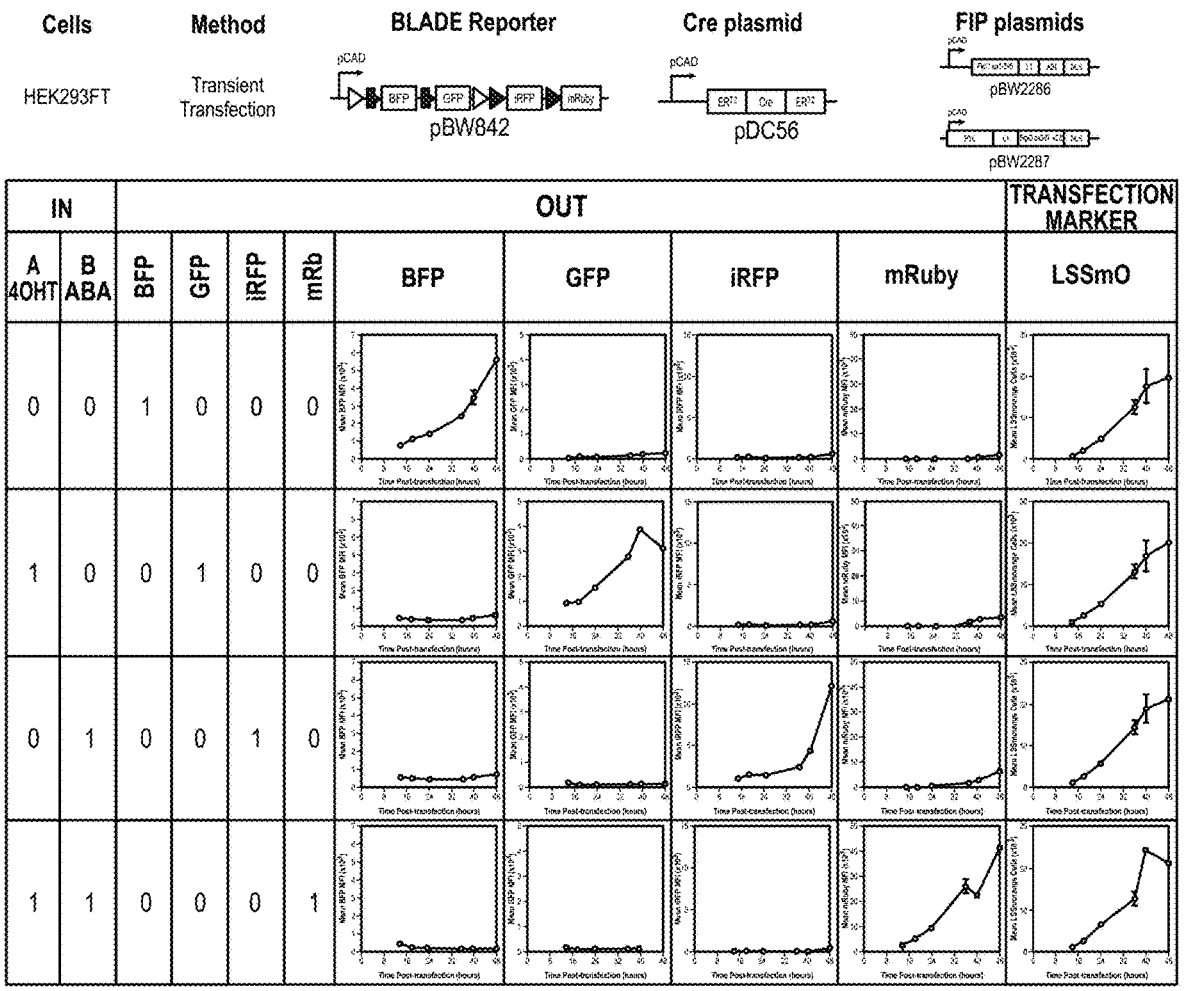
FIG. 29 shows the mean fluorescence intensity values for 2-Input 4-hydroxytamoxifen and abscisic acid-inducible decoder in HEK293FT cells over two days represented as a line plot. 2-Input decoder produces a particular fluorescent protein for each row of the truth table. Error bars indicate standard error of the mean of three replicates.

A gate was applied on FSC-A and SSC-A to remove debris from cell populations in FlowJo (Tree Star) (FIG. 32). pCAG-tagBFP or pCAG-LSS-mOrange plasmids were used as HEK293FT transient transfection markers and were gated for by applying a gate on the top 0-0.1% wildtype cells in those channels. Figure plots represent at least 5000 events in the transfected cell subset. Compensation was applied for four and five-color experiments (FIGS. 27, 28, and 29). No gates other than a viable cell FSC/SSC were applied for Jurkat T lymphocyte stable line experiments. To demonstrate the digital ON/OFF behavior of the genetic devices, main text plots have additionally been expressed as percentage of cells in an ON state through application of gates in fluorescent protein channels. Gates were chosen per experiment in an arbitrarily-defined manner, but applied uniformly for all samples in each experiment (FIGS. 7, 12, 19, 21, 25, and 27).

Quantitative Real-Time Polymerase Chain Reaction Analysis

RNA was extracted from HEK293FT cells using the Qiagen RNeasy Plus Mini kit. 500 ng of RNA was reverse-transcribed into cDNA using qScript cDNA SuperMix 20 uL reaction kit (Quanta BioSciences). cDNA samples were diluted to 100 μL using DEPC-treated water. Next, 5 μL of diluted cDNA was amplified using primers (Table 9) through the use of the LightCycler 480 SYBR Green I Master polymerase kit (Roche) and a LightCycler 480 Instrument II (Roche). Relative fold-changes were determined using the ΔΔCt method.

TABLE 9

Guide RNA target sequences and quantitative real-time PCR primers. Human guide RNAs and qPCR primers were adapted from [2].

| NAME: | SEQUENCE (5' to 3'): | SEQ ID NO: |
|---|---|---|
| gTRE | ATCGTTCTCTATCACTGATA | 59 |
| gNGN2 | GGCGGTGGCGGGGAGGAGG | 60 |
| gMIAT | GCGCCCATGAAATTTTAATG | 61 |
| gACTC1 | TGGCGCCCTGCCCTCTGCTG | 62 |
| gTTN | CCTTGGTGAAGTCTCCTTTG | 63 |
| β-actin Forward | CATGTACGTTGCTATCCAGGC | 64 |
| β-actin Reverse | CTCCTTAATGTCACGCACGAT | 65 |
| NGN2 Forward | TGGGTCTGGTACACGATTGC | 66 |
| NGN2 Reverse | GGGTCTCGATCTTGGTGAGC | 67 |
| MIAT Forward | TGGCTGGGGTTTGAACCTTT | 68 |
| MIAT Reverse | AGGAAGCTGTTCCAGACTGC | 69 |
| ACTC1 Forward | ATGTGTGACGACGAGGAGAC | 70 |
| ACTC1 Reverse | CACGATGGACGGGAAGAC | 71 |
| TTN Forward | TGTTGCCACTGGTGCTAAAG | 72 |
| TTN Reverse | ACAGCAGTCTTCTCCGCTTC | 73 |

Vector Proximity Computational Analysis

Each desired 2-input 2-output Boolean function corresponded to a truth table with four rows and two output columns. The two output columns in each desired Boolean function $f$ were mapped to an 8-dimensional binary vector t, which we call the Truth Table Vector. The fluorescent reporter signals measured from each of the two outputs, for each of the four input conditions from every genetic circuit implementation were also mapped to an 8-dimensional real vector s, which we call the Signal Vector. An Ideal Implementation of t is a circuit whose signal vector satisfies the equation s=c·t, for some positive real number c. We quantified the correctness of a genetic circuit implementing Boolean function $f$ by computing the angle θ between the vectors t and s using the formula $$\theta = \cos^{-1}\left(\frac{x}{y}\right), \text{ where } x = \sum_{i=1}^{8} t_i \cdot \hat{s}_i, \, y = \sqrt{\sum_{i=1}^{8} t_i^2} \cdot \sqrt{\sum_{i=1}^{8} \hat{s}_i^2},$$

and $t_i$ and $s_i$ are the i-th components of the vectors t and s. In computing θ, we capped the signal values $s_i$ to a maximum of $2 \times 10^4$ a.u., denoted by $\hat{s}_i$ in the formulae above. The angular difference ranges from 0° (best) to 90° (worst). We quantified the strength of the signal vector by computing its Dynamic Range (δ) of a genetic circuit implementation as $$\delta = \min_{\{i:t_i=1\}} (s_i) - \max_{\{i:t_i=0\}} (s_i).$$

The Dynamic Range was calculated separately for the two outputs of each circuit and omitted the computation for circuits where the magnitude differences were not defined. Consequently, the inventors had to omit two circuits (always ON GFP/always OFF mCherry, and always ON GFP and mCherry) from the 8 computation and 16 GFP or mCherry outputs of circuits (but not both) from the 8 computation.

Example 1

Recombinases and Binding Site Characterization

Figure 1A:
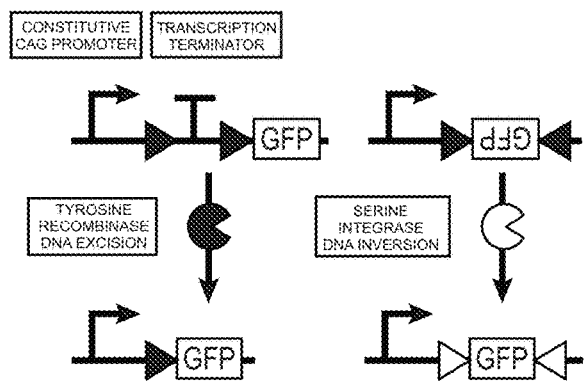
Figure 1B:
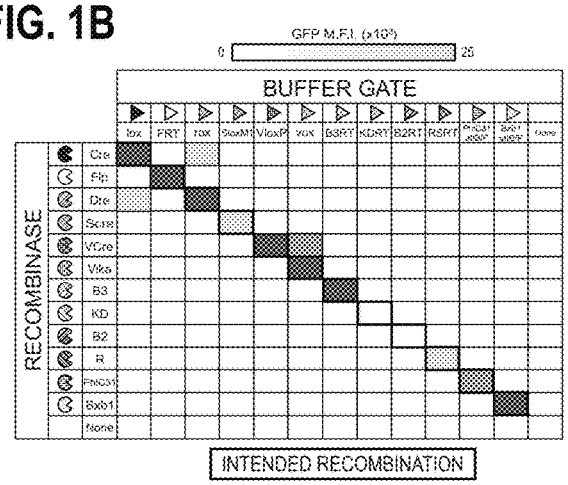
Figure 7A:
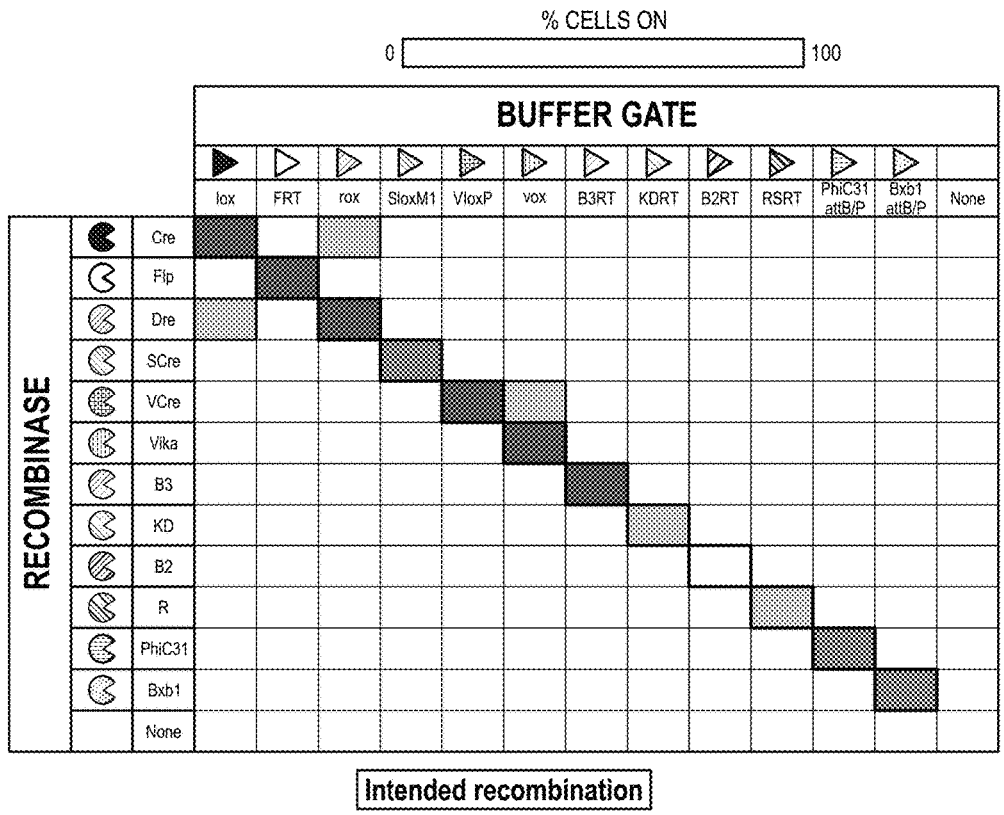

Multi-input recombinase-based biological computational devices require robust and orthogonal genetic components. Here, twelve recombinases, including both tyrosine recombinase and serine integrase families were tested for activity and orthogonality in a human embryonic kidney cell line (HEK293FT). Through transient transfection of recombinases and their reporters (deletion-based BUF gates for tyrosine recombinases and inversion-based for serine integrases), ten of the enzymes were found to be highly active and sufficiently orthogonal to each other for our circuit design effort (FIG. 1B, FIG. 7A, Table 10A, 10B).

Table 10A and Table 10B: Setup of buffer gates and recombinase expression plasmids for recombinase cross-reactivity table as detailed in FIG. 1b, in addition to co-transfection with 62.5 ng pCAG-tagBFP (pBW462) and 62.5 ng pCAG-FALSE (pBW363).

Figure 1C:
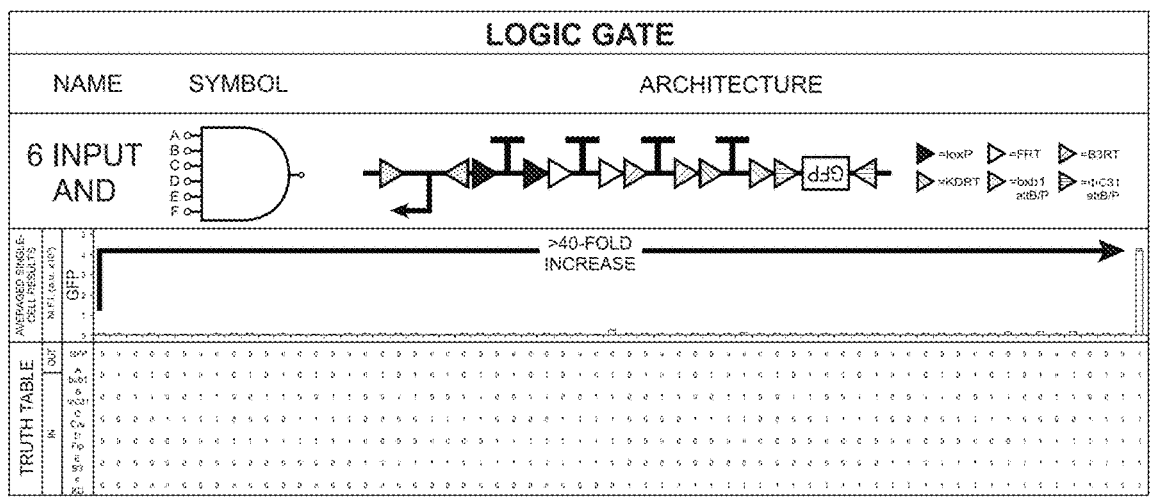
Figure 7B:
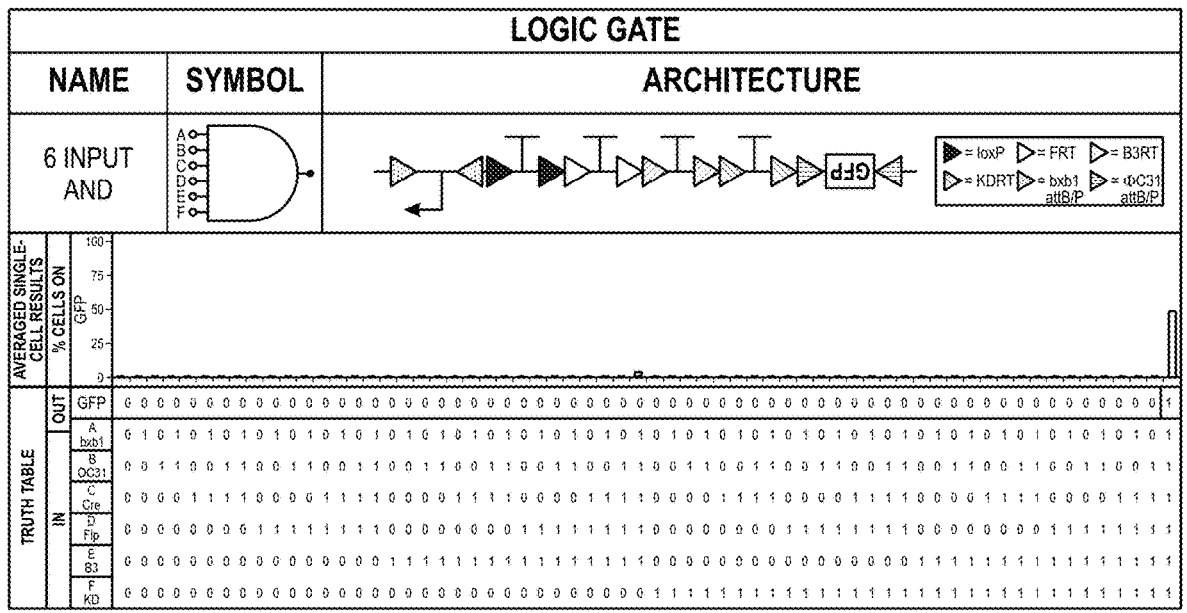
Figure 8A:
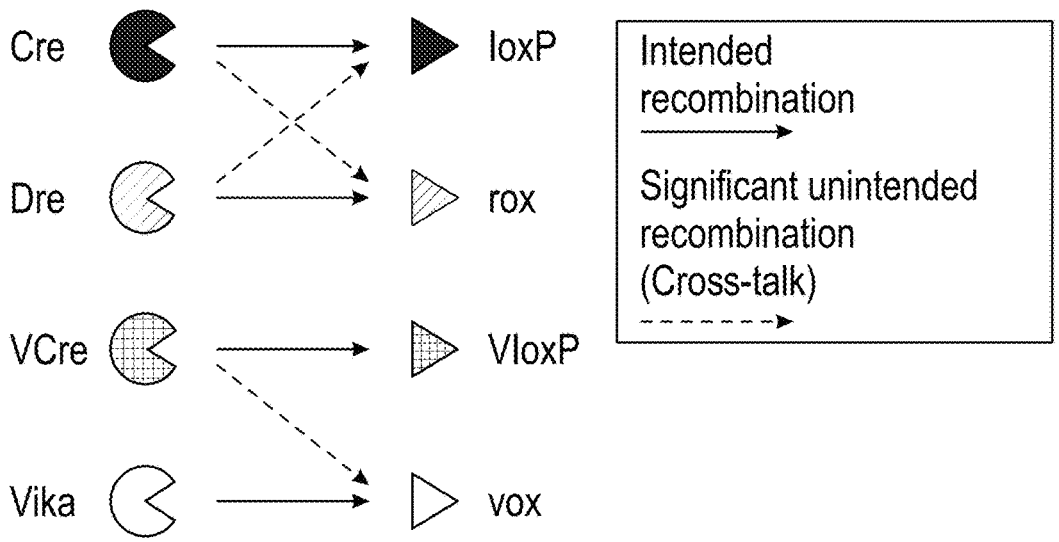
Figure 8B:
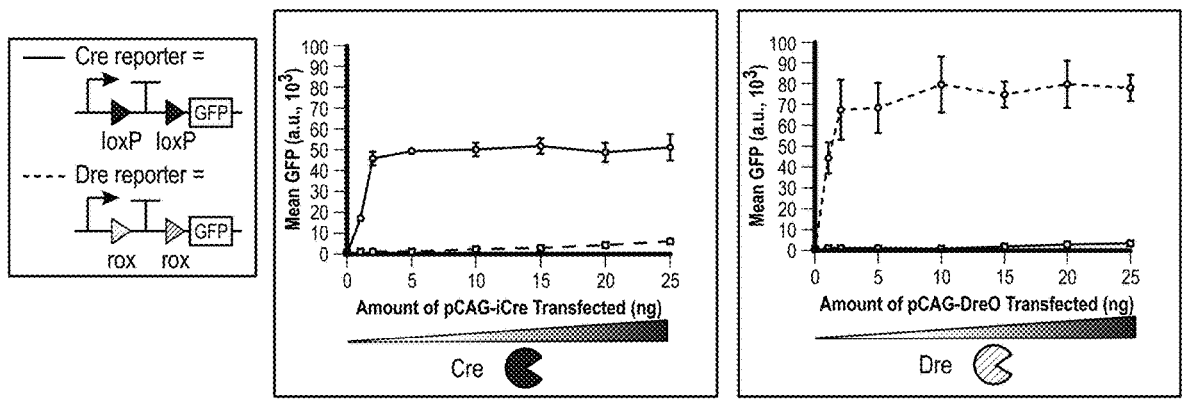
Figure 8C:
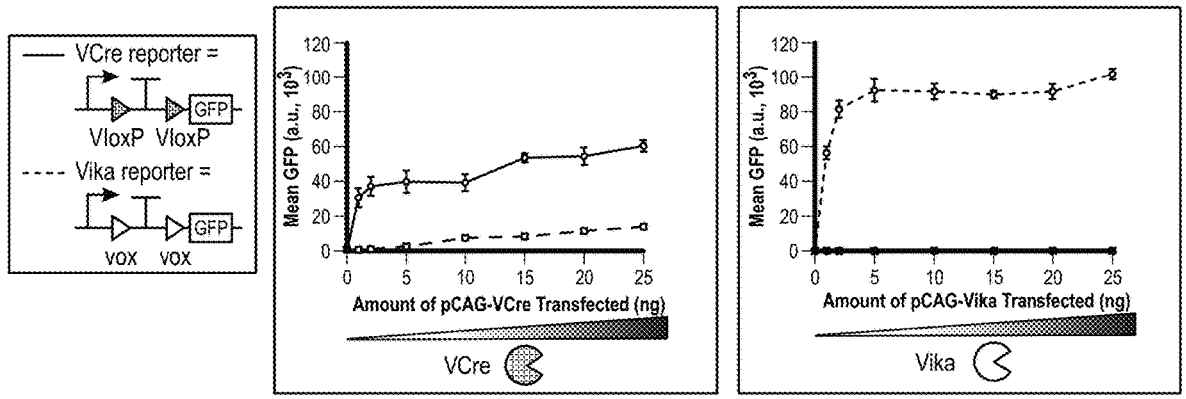

Surprisingly, some of the reportedly orthogonal recombinases, such as Dre, Cre, Vika, and VCre[35-38] showed cross-reactivity in a dose-dependent manner (FIG. 8). Therefore, when using these recombinases for circuit design, a lower dose was required to minimize crosstalk. By applying these properties to Cre and Flp, the two most commonly used recombinases in mammalian genetics literature, we created all sixteen possible two-input Boolean logic gates (FIG. 9, Table 11). Note that the 2-input AND is created by placing two transcription termination sequences in tandem. Due to the orthogonality of recombinases, it becomes possible to generate multi-input AND gates simply by placing more termination sequences in tandem between a promoter and GFP. Indeed, we created a 6-input AND gate that expresses GFP upon the excision of four termination sequences by tyrosine recombinases and the inversion of the EF1α promoter and GFP by two serine integrases (FIG. 1C, FIG. 7B, Table 12). In contrast to earlier multi-layer 4-input AND gate work in $E.\ coli^{13}$, this multi-input AND gate was on a single layer, which could facilitate implementation in mammalian genetic systems.

TABLE 10A

|  | Plasmid ID | LoxP pBW338 | FRT pBW339 | rox pBW364 | SloxM1 pBW271 | VloxP pBW273 | vox pBW275 |
|---|---|---|---|---|---|---|---|
| iCre | pBW390 | 62.5 ng each | 62.5 ng each | 62.5 ng each | 62.5 ng each | 62.5 ng each | 62.5 ng each |
| FlpO | pBW391 | 62.5 ng each | 62.5 ng each | 62.5 ng each | 62.5 ng each | 62.5 ng each | 62.5 ng each |
| DreO | pBW431 | 62.5 ng each | 62.5 ng each | 62.5 ng each | 62.5 ng each | 62.5 ng each | 62.5 ng each |
| SCre | pBW432 | 62.5 ng each | 62.5 ng each | 62.5 ng each | 62.5 ng each | 62.5 ng each | 62.5 ng each |
| VCre | pBW433 | 62.5 ng each | 62.5 ng each | 62.5 ng each | 62.5 ng each | 62.5 ng each | 62.5 ng each |
| Vika | pBW434 | 62.5 ng each | 62.5 ng each | 62.5 ng each | 62.5 ng each | 62.5 ng each | 62.5 ng each |
| B3 | pBW435 | 62.5 ng each | 62.5 ng each | 62.5 ng each | 62.5 ng each | 62.5 ng each | 62.5 ng each |
| KD | pBW436 | 62.5 ng each | 62.5 ng each | 62.5 ng each | 62.5 ng each | 62.5 ng each | 62.5 ng each |
| B2 | pBW437 | 62.5 ng each | 62.5 ng each | 62.5 ng each | 62.5 ng each | 62.5 ng each | 62.5 ng each |
| R | pBW438 | 62.5 ng each | 62.5 ng each | 62.5 ng each | 62.5 ng each | 62.5 ng each | 62.5 ng each |
| PhiC31 | pBW440 | 62.5 ng each | 62.5 ng each | 62.5 ng each | 62.5 ng each | 62.5 ng each | 62.5 ng each |
| Bxb1 | pBW439 | 62.5 ng each | 62.5 ng each | 62.5 ng each | 62.5 ng each | 62.5 ng each | 62.5 ng each |
| None | pBW363 | 62.5 ng each | 62.5 ng each | 62.5 ng each | 62.5 ng each | 62.5 ng each | 62.5 ng each |

TABLE 10B

|  | Plasmid ID | B3RT pBW276 | KDRT pBW277 | B2RT pBW278 | RSRT pBW279 | PhiC31 attB/P pBW409 | Bxb1 attB/P pBW406 | None pBW363 |
|---|---|---|---|---|---|---|---|---|
| iCre | pBW390 | 62.5 ng each | 62.5 ng each | 62.5 ng each | 62.5 ng each | 62.5 ng each | 62.5 ng each | 62.5 ng each |
| FlpO | pBW391 | 62.5 ng each | 62.5 ng each | 62.5 ng each | 62.5 ng each | 62.5 ng each | 62.5 ng each | 62.5 ng each |
| DreO | pBW431 | 62.5 ng each | 62.5 ng each | 62.5 ng each | 62.5 ng each | 62.5 ng each | 62.5 ng each | 62.5 ng each |
| SCre | pBW432 | 62.5 ng each | 62.5 ng each | 62.5 ng each | 62.5 ng each | 62.5 ng each | 62.5 ng each | 62.5 ng each |
| VCre | pBW433 | 62.5 ng each | 62.5 ng each | 62.5 ng each | 62.5 ng each | 62.5 ng each | 62.5 ng each | 62.5 ng each |
| Vika | pBW434 | 62.5 ng each | 62.5 ng each | 62.5 ng each | 62.5 ng each | 62.5 ng each | 62.5 ng each | 62.5 ng each |
| B3 | pBW435 | 62.5 ng each | 62.5 ng each | 62.5 ng each | 62.5 ng each | 62.5 ng each | 62.5 ng each | 62.5 ng each |
| KD | pBW436 | 62.5 ng each | 62.5 ng each | 62.5 ng each | 62.5 ng each | 62.5 ng each | 62.5 ng each | 62.5 ng each |
| B2 | pBW437 | 62.5 ng each | 62.5 ng each | 62.5 ng each | 62.5 ng each | 62.5 ng each | 62.5 ng each | 62.5 ng each |
| R | pBW438 | 62.5 ng each | 62.5 ng each | 62.5 ng each | 62.5 ng each | 62.5 ng each | 62.5 ng each | 62.5 ng each |
| PhiC31 | pBW440 | 62.5 ng each | 62.5 ng each | 62.5 ng each | 62.5 ng each | 62.5 ng each | 62.5 ng each | 62.5 ng each |
| Bxb1 | pBW439 | 62.5 ng each | 62.5 ng each | 62.5 ng each | 62.5 ng each | 62.5 ng each | 62.5 ng each | 62.5 ng each |
| None | pBW363 | 62.5 ng each | 62.5 ng each | 62.5 ng each | 62.5 ng each | 62.5 ng each | 62.5 ng each | 62.5 ng each |

TABLE 11

Transient transfection setup for 2-input, 1-output logic gates detailed in FIG. 9.

| Reporter, ng | Input State A B | Enzyme 1, ng pCAG-iCre (pBW390) | Enzyme 2, ng pCAG-FlpO (pBW391) | Blank, ng pCAG-FALSE (pBW363) | Marker, ng pCAG-tagBFP (pBW462) |
|---|---|---|---|---|---|
| Values shown below | 0 0 | 0 | 0 | 50 | 25 |
|  | 1 0 | 25 | 0 | 25 | 25 |
|  | 0 1 | 0 | 25 | 25 | 25 |
|  | 1 1 | 25 | 25 | 0 | 25 |

Logic gate

| Gate | Plasmid ID | ng |
|---|---|---|
| NOR | pBW334 | 25 |
| OR | pBW335 | 25 |
| AND | pBW336 | 25 |
| NAND | pBW337 | 25 |
| A | pBW338 | 25 |
| B | pBW339 | 25 |
| NOTA | pBW340 | 25 |
| NOTB | pBW341 | 25 |
| A IMPLY B | pBW342 | 25 |
| B IMPLY A | pBW343 | 25 |
| A NIMPLY B | pBW344 | 25 |
| B NIMPLY A | pBW345 | 25 |
| XOR | pBW344 | 12.5 |
|  | pBW345 | 12.5 |
| XNOR | pBW334 | 12.5 |
|  | pBW336 | 12.5 |
| TRUE | pBW361 | 25 |
| FALSE | pBW363 | 25 |
| XOR | pBW448 | 25 |
| XNOR | pBW450 | 25 |

TABLE 12

Transient transfection setup of six-input AND gate as detailed in FIG. 1C.

| AND GATE, ng pCAG-6AND (pBW479) | Enzyme 1, ng pCAG-PhiC31 (pBW440) | Enzyme 2, ng pCAG-bxb1 (pBW439) | Enzyme 3, ng pCAG-iCre (pBW390) | Enzyme 4, ng pCAG-FlpO (pBW391) | Enzyme 5, ng pCAG-B3 (pBW435) | Enzyme 6, ng pCAG-KD (pBW436) | Blank, ng pCAG-FALSE (pBW363) | Marker, ng pCAG-tagBFP (pBW462) |
|---|---|---|---|---|---|---|---|---|
| 150 | 0 or 12.5 | 0 or 12.5 | 0 or 12.5 | 0 or 12.5 | 0 or 12.5 | 0 or 12.5 | Fill to total DNA amount = 250 ng | 25 |

TABLE 13

Setup of buffer gates and recombinase expression plasmids for recombinase heterospecificity table as detailed in FIG. 10, in addition to co-transfection with 62.5 ng pCAG-tagBFP (pBW462), 62.5 ng pCAG-FALSE (pBW363), and 62.5 ng corresponding recombinase expression plasmid.

Buffer Gate

| Buffer Gate | pBW | ng |
|---|---|---|
| pCAG-loxP-STOP-loxP-GFP | 338 | 25 |
| pCAG-lox2272-STOP-lox2272-GFP | 427 | 25 |
| pCAG-loxN-STOP-loxN-GFP | 428 | 25 |
| pCAG-loxP-STOP-lox2272-GFP | 451 | 25 |
| pCAG-loxP-STOP-loxN-GFP | 452 | 25 |
| pCAG-lox2272-STOP-loxN-GFP | 453 | 25 |
| pCAG-FRT-STOP-FRT-GFP | 339 | 25 |
| pCAG-F3-STOP-F3-GFP | 429 | 25 |
| pCAG-F14-STOP-F14-GFP | 430 | 25 |
| pCAG-FRT-STOP-F3-GFP | 454 | 25 |
| pCAG-FRT-STOP-F14-GFP | 455 | 25 |
| pCAG-F3-STOP-F14-GFP | 456 | 25 |
| pCAG-VloxP-STOP-VloxP-GFP | 273 | 25 |
| pCAG-Vlox2272-STOP-Vlox2272-GFP | 274 | 25 |
| pCAG-VloxP-STOP-Vlox2272-GFP | 331 | 25 |

Single-Layer Multi-Input Recombinase-Based Digital Logic Platform

While the ad hoc design approach employed earlier and elsewhere[7, 8, 31, 32, 40] is successful in creating some recombinase-based circuits with small truth tables, a universal strategy for generating any N-input-M-output logic behavior has never been demonstrated before and will be more reliable and convenient for genetic circuit design. The inventors exploited the characteristics of site-specific recombinases to establish a platform for N-input-M-output combinatorial computation in mammalian cells called Boolean Logic and Arithmetic through DNA Excision (BLADE), A key element that allows complex computation on a single transcriptional unit is the usage of heterospecific recombination sites. Heterospecific sites, such as loxP and lox2272, differ from one another by only a few base pairs[39], but they retain DNA excision capabilities in the presence of Cre, as long as two of the same sites are present, i.e. loxP with loxP. This feature allows the excision of more than one non-connected region of DNA simultaneously. We validated three sets of lox sites (loxP, lox2272, loxN), three sets of FRT (FRT, F3, F14) and Vlox (VloxP, Vlox2272), which demonstrated heterospecificity using Cre, Flp, and VCre enzymes, respectively (FIG. 10, Table 13). Beyond the orthogonality of the recombinases and heterospecific sites, no further characterization of individual components is needed to design the BLADE platform.

where N and M can be any non-negative integer. Each BLADE circuit is organized as a single transcriptional layer comprising a single promoter upstream of up to $2^N$ regions of DNA sequences called addresses (Z), which are surrounded by recombination sites. Each BLADE device is designed such that when it is presented with recombinase inputs, addresses become transcriptionally active via excision of intervening regions between recombination sites downstream of the promoter. For example, a two-input (N=2) BLADE circuit, which responds to inputs A and B, can accommodate up to $2^2=4$ addresses with possible addresses being $Z=Z_{AB}=Z_{00}$, $Z_{10}$, $Z_{01}$, and $Z_{11}$, enumerating all combinatorial states of inputs A and B (FIG. 2A). The BLADE design is flexible in and agnostic to what outputs may be generated; these can range from no transcriptional outputs (transcription terminator) at all, an arbitrary combination of outputs separated by ribosomal skip sequences (2A), Boolean functions like BUF that can toggle transcriptional responses ON or OFF through use of additional site-specific recombinases, or even other BLADE devices. A BLADE design that utilizes $2^N$ addresses permits creation of all possible N-input-M-output combinatorial circuits and thus is necessary for implementing the most complex multi-input-multi-output truth tables[41].

Figures 11, 12:
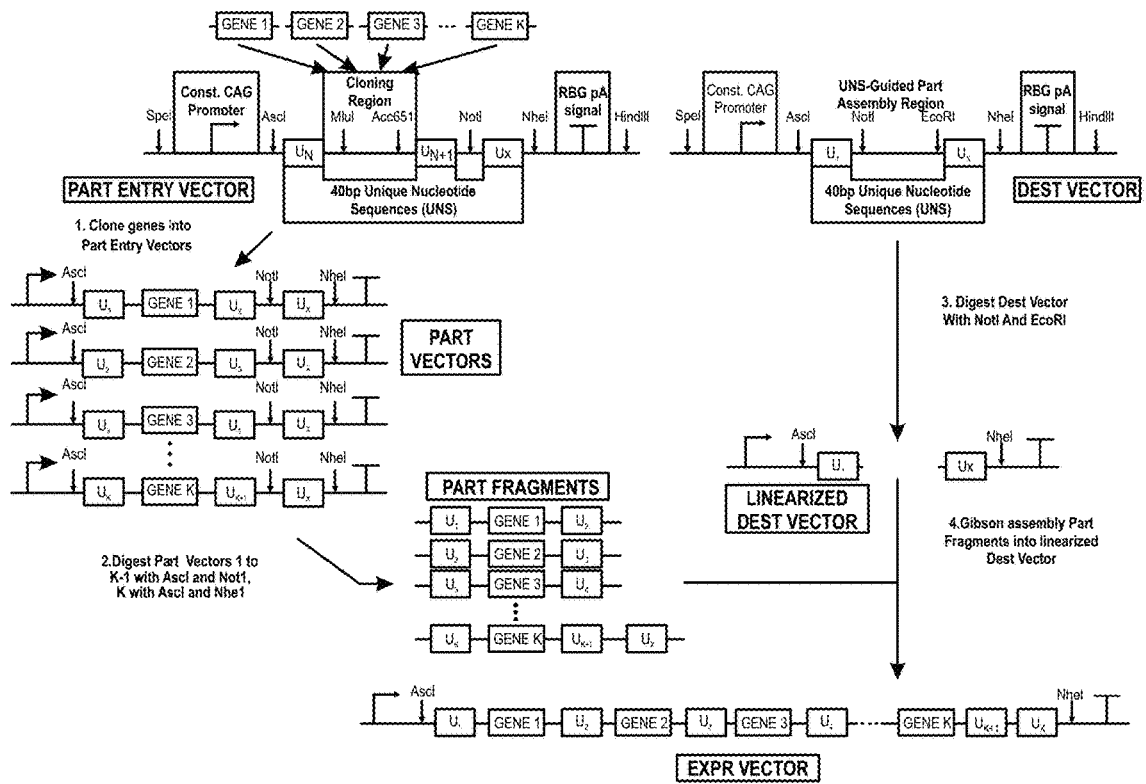

Since BLADE circuits have broad applicability and utility in a host of different biological contexts, we have made measures to make BLADE circuits rapidly implementable. Relevant plasmids and sequences will be available on non-profit DNA repository Addgene for sharing of molecular reagents around the world. Once BLADE components are received, they can be easily fashioned and customized using a modular assembly strategy known as Unique Nucleotide Sequence-Guided Assembly, based on Gibson isothermal assembly[42,43] (FIG. 11). Additional restriction sites are included so that cloning of recombinase sites is unnecessary, which often fail double-stranded DNA synthesis services due to their hairpin structures and can increase the price and shipment time of single-stranded oligonucleotide synthesis when many sequences need to be coupled together.

A Two-Input, Four-Output Circuit Using the Two-Input BLADE Platform

Figure 16:
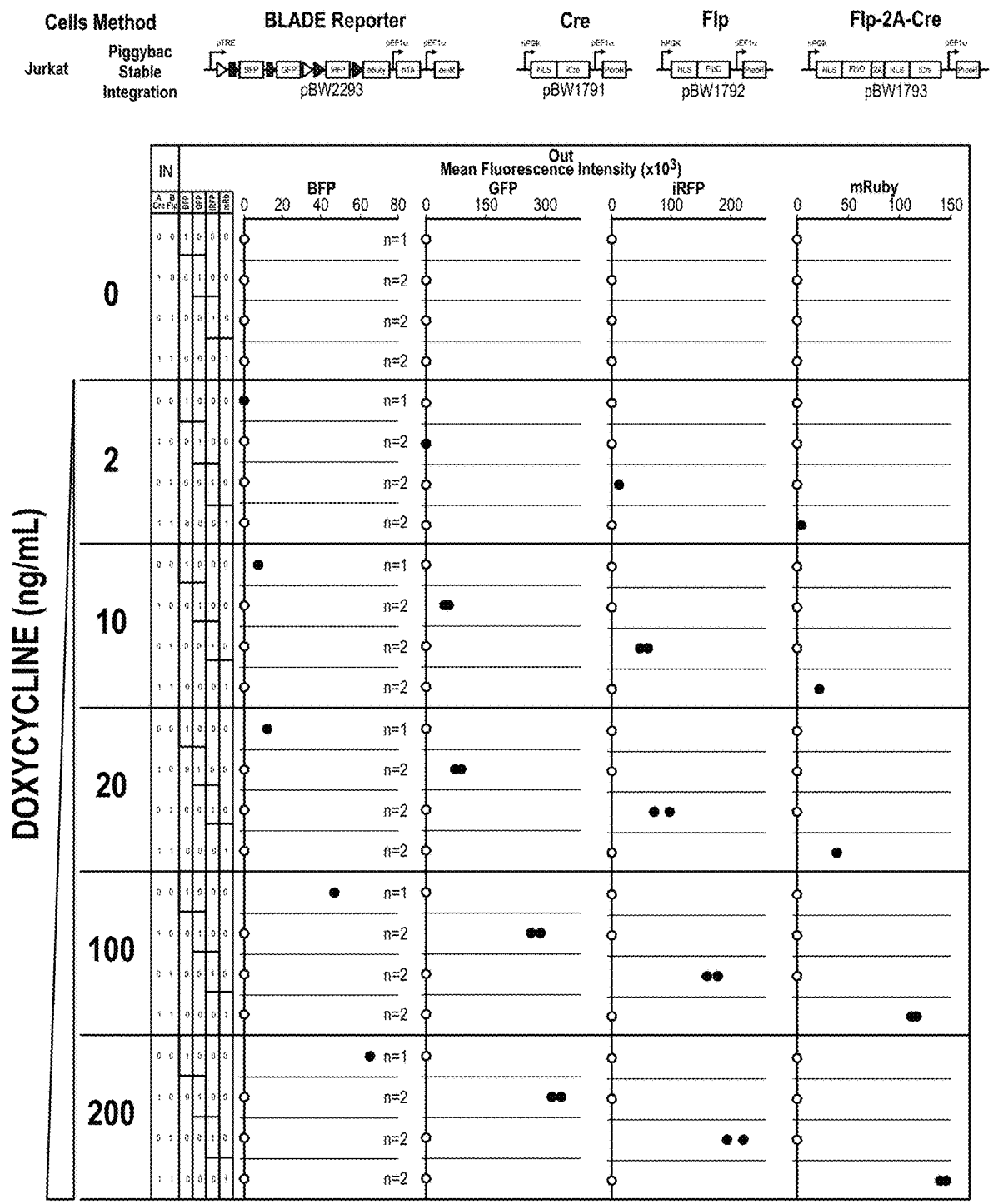
Figure 17:
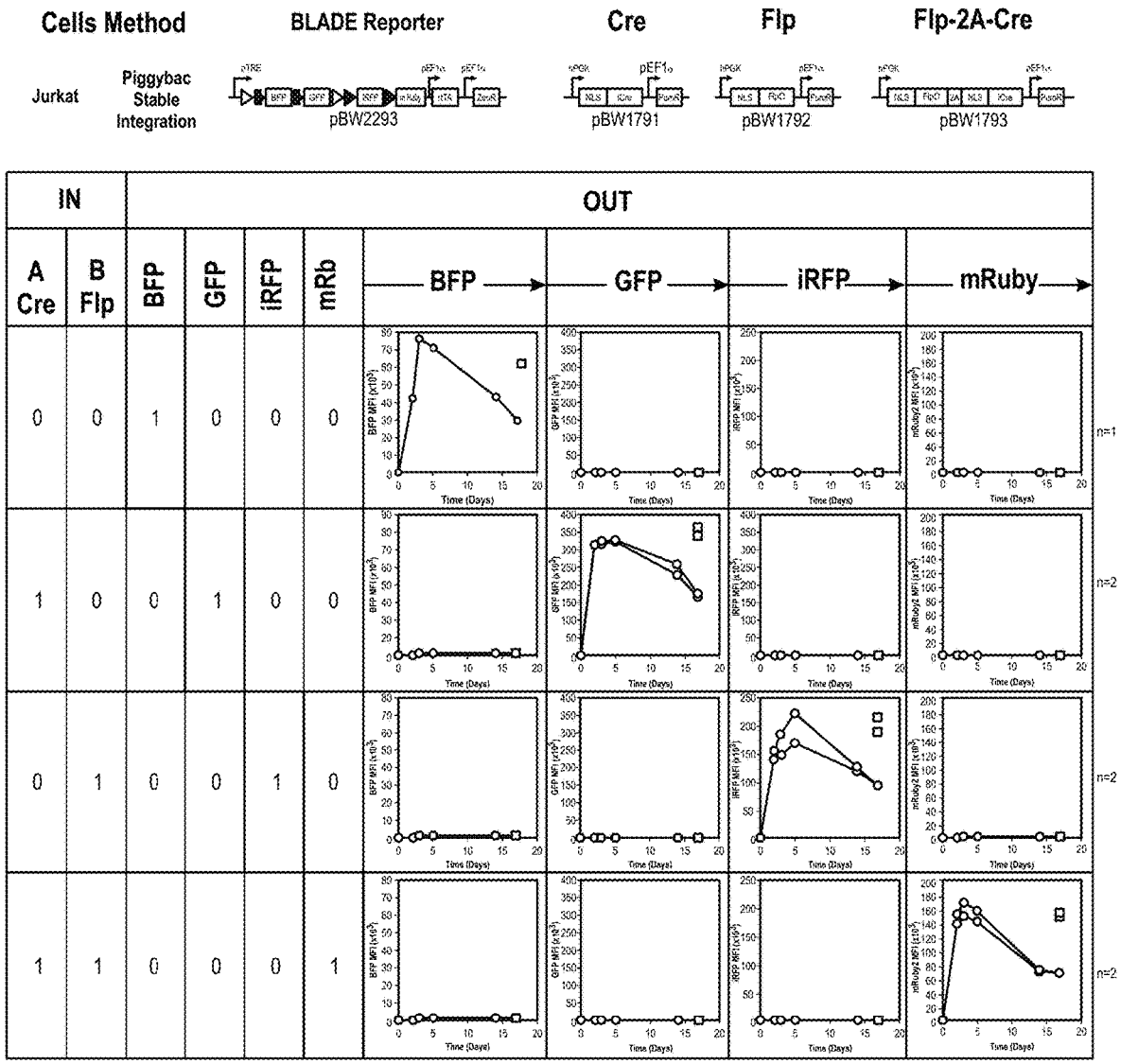

For initial characterization of the 2-input BLADE platform, single transcriptional output functions were tested. The inventors constructed a 2-input, 4-output decoder circuit, which necessitates four addresses where each coincides with a distinct output: blue, green, infrared and red fluorescent proteins (tagBFP, EGFP, iRFP720, and mRuby2, respectively) (FIG. 2B, FIGS. 12, 13, 14 and 15). Moreover, one advantage that is unique to the BLADE platform over other gene circuit devices is that expression of outputs is driven by only a single promoter, thereby permitting additional control of the response through use of a drug-regulated promoter or encoding of further transcriptional logic. The inventors demonstrated this principle through stable integration of a doxycycline-controlled decoder circuit into Jurkat T lymphocytes through piggyBac-mediated transposition. Jurkat T cells were chosen because they are an important suspension cell line for understanding T cell signaling and easy to maintain during long-term passages. Constitutively-expressing recombinases were then integrated into the genome. Following stable integration of the recombinases driven by constitutive promoters, doxycycline was used to regulate final output expression in a dose-dependent manner (FIG. 16). This strategy provides a facile way of scaling the circuit response while maintaining the logical functionality of the circuit. Furthermore, long term studies demonstrate that BLADE circuit functionality can be maintained for at least two weeks under varying doxycycline conditions (FIG. 17). Furthermore, the decoder circuit performed as predicted through transient transfection in HEK293FT cells with strong fluorescent protein expression for each state of inputs (FIG. 18, Table 14). HEK293FT was chosen here (and for subsequent experiments) because its high transfection efficiency enables high-throughput experimentation.

TABLE 14

Transient transfection setup for 2-input, 4-output decoder circuit detailed in FIG. 18.

| Reporter pEXPRCAG-DECODER (pBW842) | Input State A B | Enzyme 1, ng pCAG-iCre (pBW390) | Enzyme 2, ng pCAG-FlpO (pBW391) | Blank, ng pCAG-FALSE (pBW363) | Marker, ng pCAG-LSS-mOrange (pBW474) |
|---|---|---|---|---|---|
| 35.7 | 0 0 | 0 | 0 | 178.5 | 35.7 |
|  | 1 0 | 35.7 | 0 | 142.8 | 35.7 |
|  | 0 1 | 0 | 35.7 | 142.8 | 35.7 |
|  | 1 1 | 35.7 | 35.7 | 107.1 | 35.7 |

Over One-Hundred Characterized Logically Distinct 2-Input BLADE Devices

To test the robustness of the BLADE platform on a large scale, the inventors produced the largest collection of functionally unique logic circuits in mammalian cells (a library of 113 circuits with up to two inputs and outputs (FIG. 3, FIG. 19, and data not included)). Of note, are two 2-input devices: the half adder (Gate 104) and half subtractor (Gate 99), which perform 2-input arithmetic and are widely-used and studied in electronics. Whereas all the 113 circuits were qualitatively observed to implement the correct computation, we quantified their functional correctness using a novel Vector Proximity (VP) metric measuring the misalignment between a circuit's biological implementation and its ideal implementation from its intended truth table (See Methods). Truth tables and obtained experimental results were represented as vectors, Truth Table and Signal Vectors, respectively, in an 8-dimensional vector space. The angular error between these two vectors (VP angle metric) was calculated with 0° meaning the data represents the intended truth table perfectly and 90° meaning the data demonstrates completely incorrect output (inverted response to the intended truth table). The VP angle metric shows that 93.8% (106/113) of the circuits had an angle no more than 15°, and none had an angle of more than 25° from their ideal implementation.

Figure 20A:
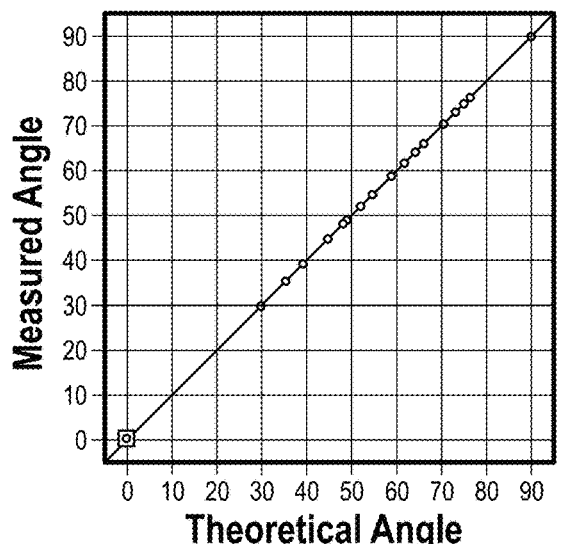
Figure 20B:
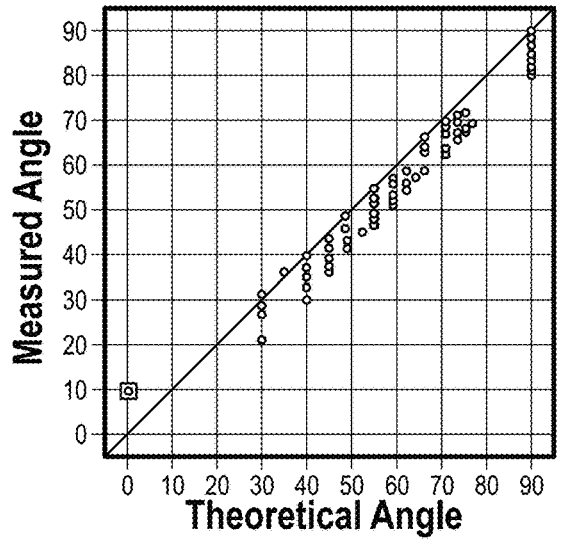
Figure 20C:
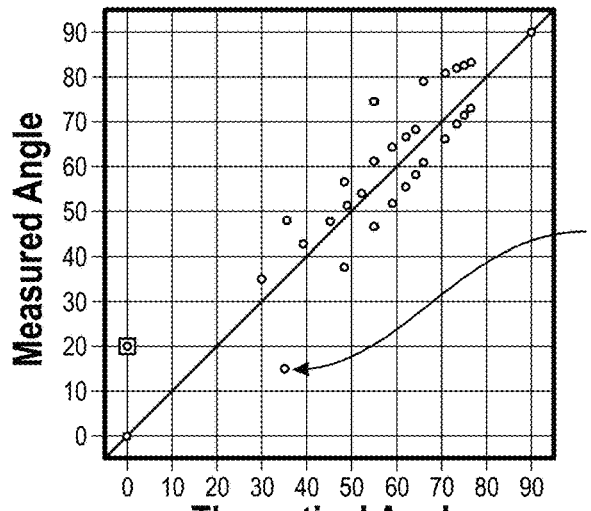

The inventors extended the VP measure of correctness to obtain a quantitative and discrete test of whether an implemented circuit is correct or incorrect. For any implemented circuit we measured its VP angle from all possible truth tables, and sorted the results in ascending order. The inventors defined the rank of the intended truth table in this sorted list as the circuit's VP global rank. The inventors call a circuit as functionally valid under this measure, if it has the best (that is, smallest) VP global rank. For our library of 113 circuits, the VP angle was calculated between each Signal Vector and all 255 (up to 2-input, up to 2-output, excluding the 0-input, 0-output FALSE) Truth Table vectors. Global rank values were determined according to how many Truth Table Vectors had lower VP angles than the Intended Truth Table Vector. We found that 96.5% (109/113) of the tested circuits gave the lowest angle between their Signal Vector (global rank=0/255) and their Intended Truth Table vectors (FIG. 20 and Table 15). This success rate of 96.5% is the highest reported for large scale circuit construction in mammalian cells. Only four circuits had a global rank of 1, meaning there was only one other truth table that yielded a lower VP angle; no circuits had a rank more than 1. To facilitate data sharing and further analysis by other researchers, we have developed an interactive website (datasheets.synbiotools.org) that contains the data all of our 113 circuits summarized in a datasheet format[44].

TABLE 15

Figure 19A:
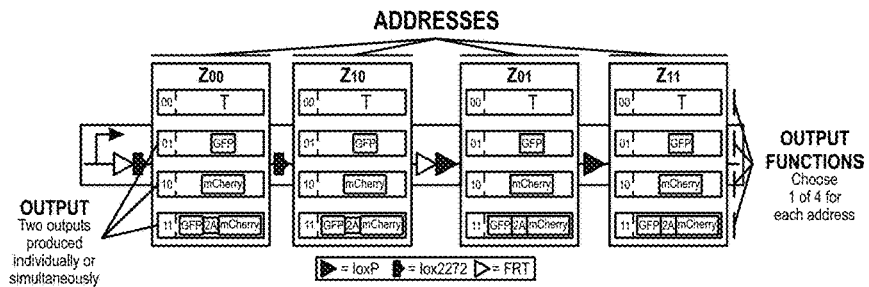
Figure 19B:
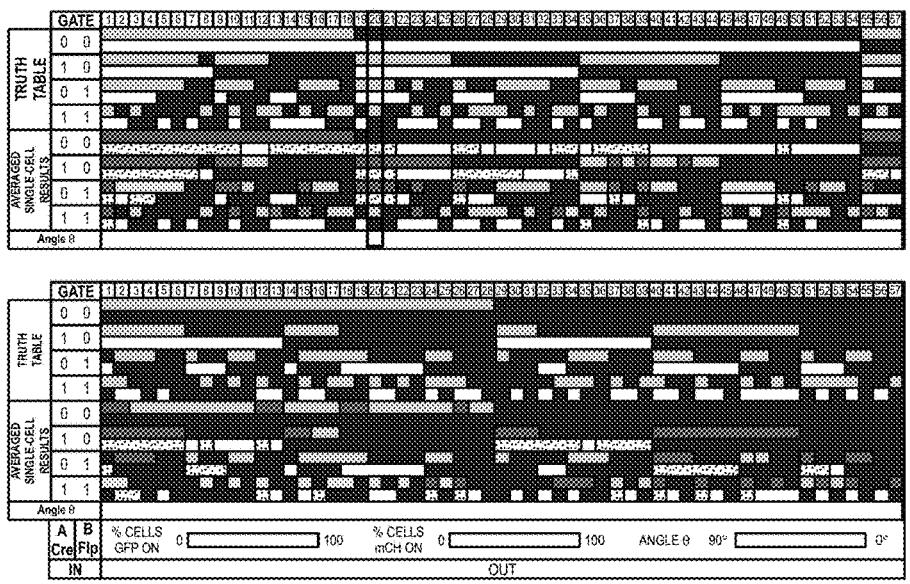
Figure 19C:
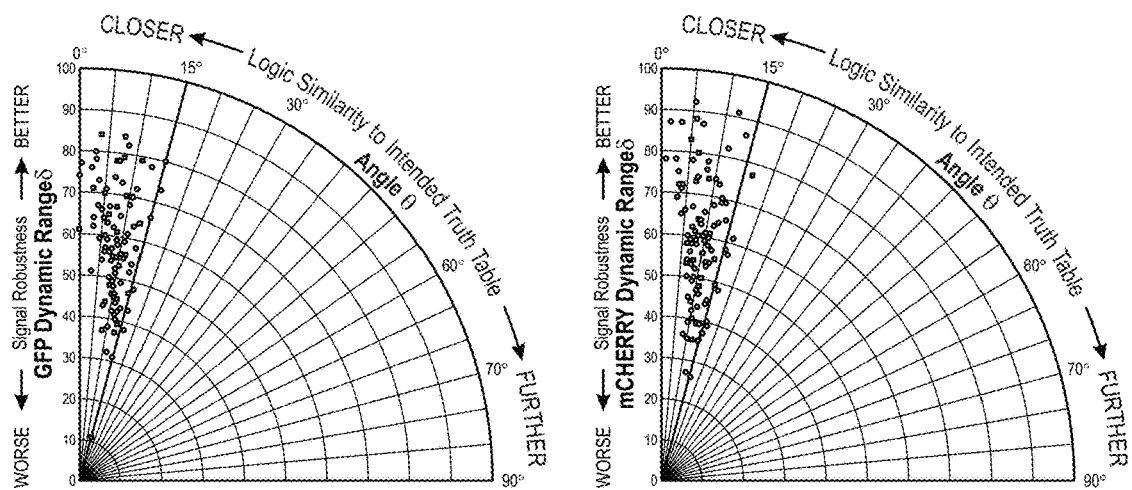

Summary of Vector Proximity (VP) angle and global ranks scores for mean fluorescence intensity (MFI) data of the 2-input-2-output logic gate library in FIG. 3 and % Cell ON data in FIG. 19 in terms of number of circuits (#) and percentage of circuits (%).

| | Analysis: | | | |
|---|---|---|---|---|
| | MFI | | % CELLS ON | |
| | # | % | # | % |
| VP Global Rank | | | | |
| 0 | 109 | 96.46% | 112 | 99.12% |
| 1 | 4 | 3.54% | 1 | 0.88% |
| >1 | 0 | 0.00% | 0 | 0.00% |
| VP Angle | | | | |
| <15° | 106 | 93.81% | 107 | 94.69% |

Re-Programmable Combinatorial Logic

Figure 4:
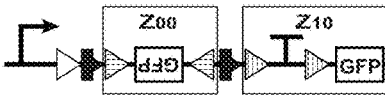
Figure 21:
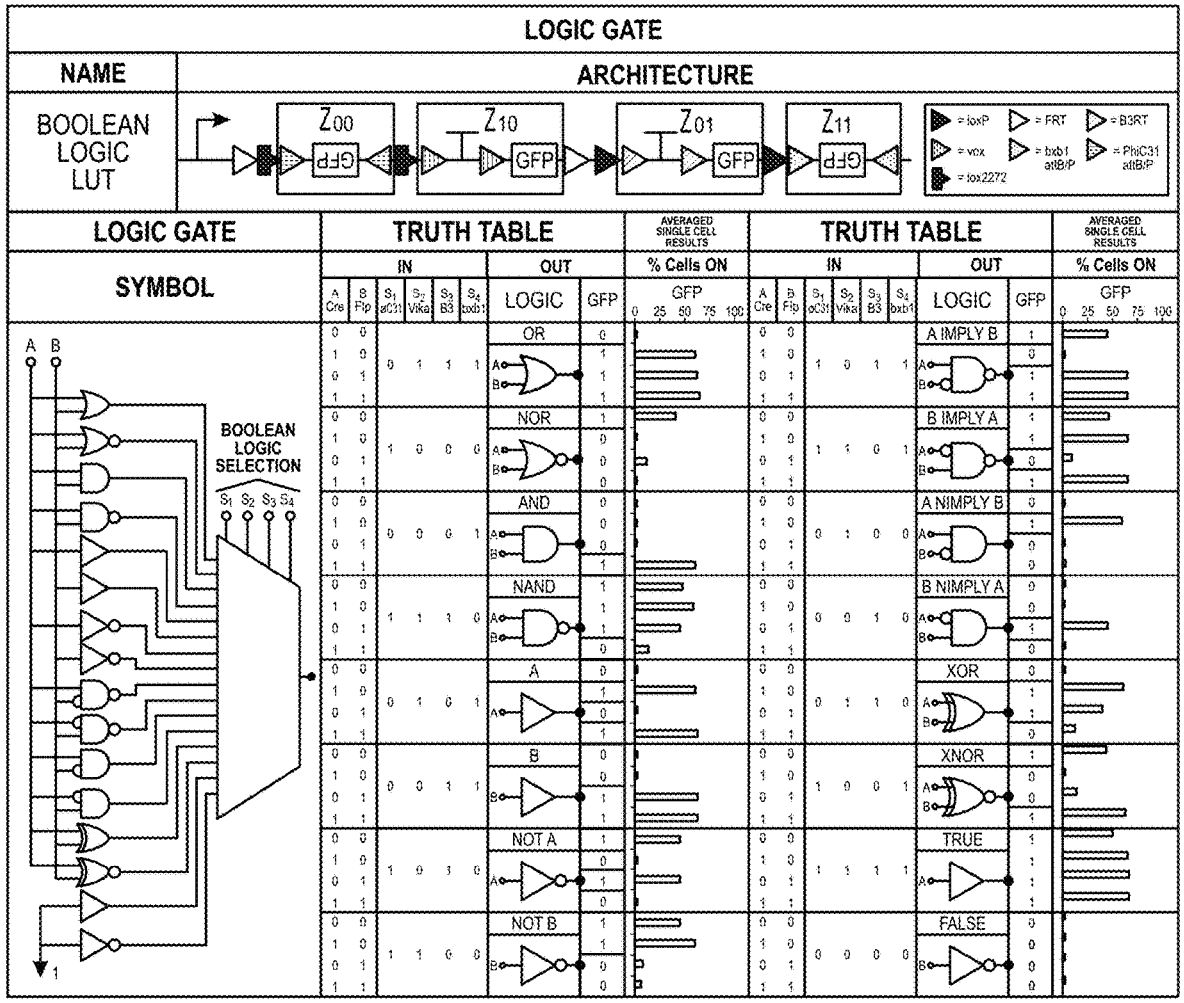
Figures 22A, 22B:
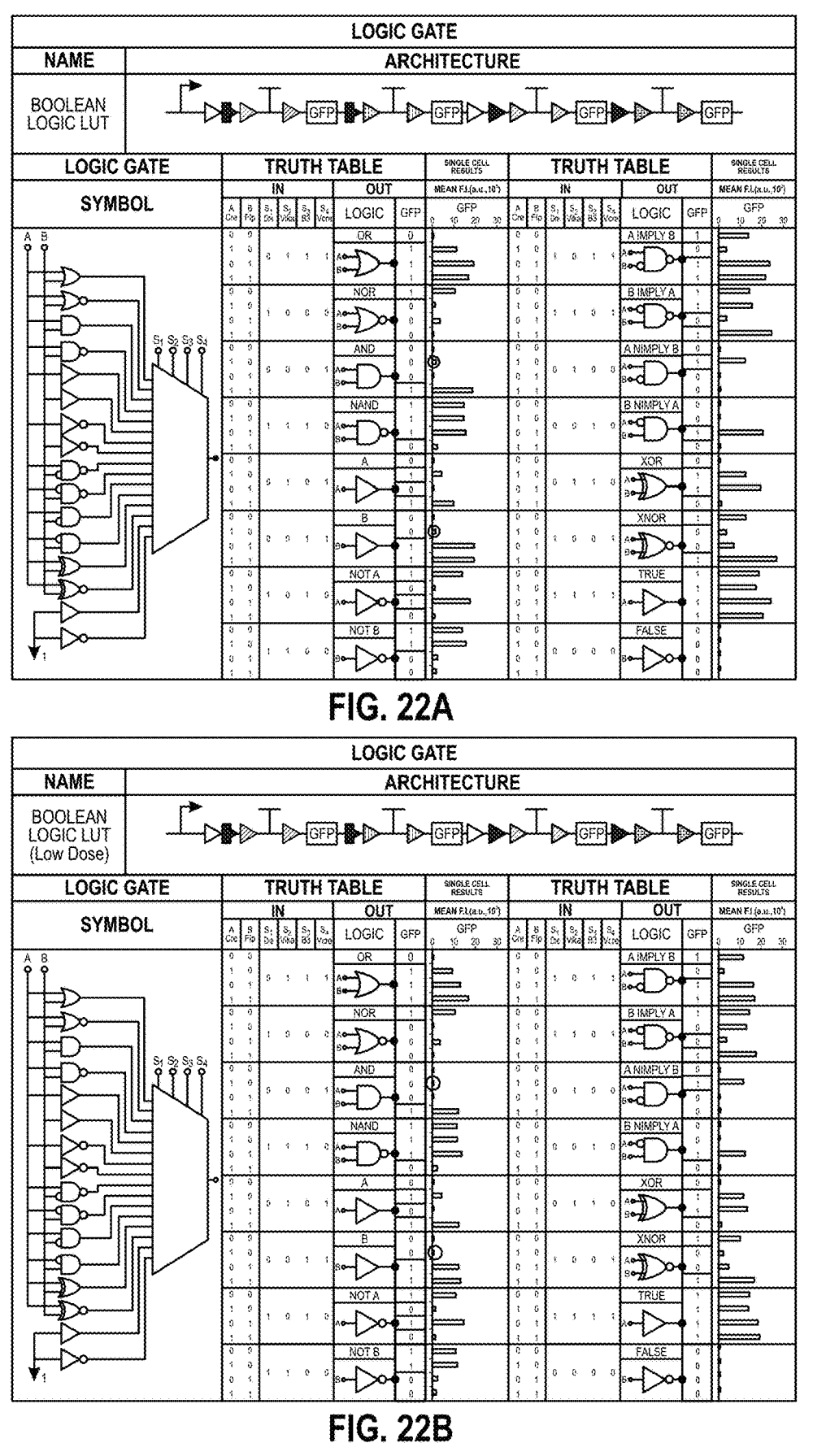

One important class of devices found in electronics is Field-Programmable Read-Only Memory (FPROM). The input-output behavior of these circuits can be configured in the field post-manufacturing, allowing users to program the function computed by the device at a later time. The inventors built the first genetic FPROM device in living cells termed a Boolean Logic Look-Up Table (LUT) that is based on placing BUF gates into the four addresses of the 2-input BLADE template. (FIG. 4, FIG. 21, Table 16). This circuit has two data inputs, A and B, and four select inputs, $S_1$, $S_2$, $S_3$, and $S_4$. Each select input can control which buffer gates are transcriptionally active or not (GFP ON or OFF). Thus, each combination of select inputs configures the device to one of sixteen-possible Boolean logic gates with up to two inputs and one output. For instance, an OR function can be achieved using select inputs S2, S3, and S4, keeping address $Z_{00}$ GFP OFF and setting addresses $Z_{10}$, $Z_{01}$, and $Z_{11}$ GFP ON. Thus, this circuit allows one to reconfigure the computation within living cells without requiring additional DNA assembly. This circuit behaves as expected in HEK293FT cells. To illustrate the flexibility of our platform in terms of recombinase choices, we created an alternative Boolean Logic LUT (FIG. 22).

TABLE 16

Transient transfection setup for six-input Boolean Logic Look-up Table genetic device in FIG. 4.

| BOOLEAN LOGIC LUT, ng pEXPRCA G- LUT (pBW829) | Input State A B | Enzyme 1, ng pCAG- iCre (pBW390) | Enzyme 2, ng pCAG- FlpO (pBW391) | Enzyme 3, ng pCAG- PhiC31 (pBW440) | Enzyme 4, ng pCAG- Vika (pBW434) | Enzyme 5, ng pCAG- B3 (pBW435) | Enzyme 6, ng pCAG- bxb1 (pBW439) | Blank, ng pCAG- FALSE (pBW363) | Marker, ng pCAG- tagBFP (pBW462) |
|---|---|---|---|---|---|---|---|---|---|
| 75 | 0 0 | 0 | 0 | 0 or 25 | 0 or 25 | 0 or 25 | 0 or 25 | Fill to total DNA amount = 250 ng | 25 |
| | 1 0 | 25 | 0 | | | | | | |
| | 0 1 | 0 | 25 | | | | | | |
| | 1 1 | 25 | 25 | | | | | | |

Figure 5A:
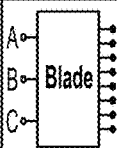
Figure 5B:
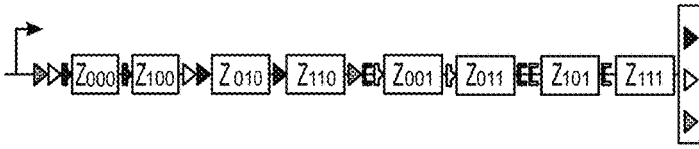
Figure 23:
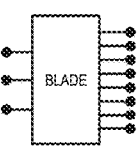
Figure 24A:
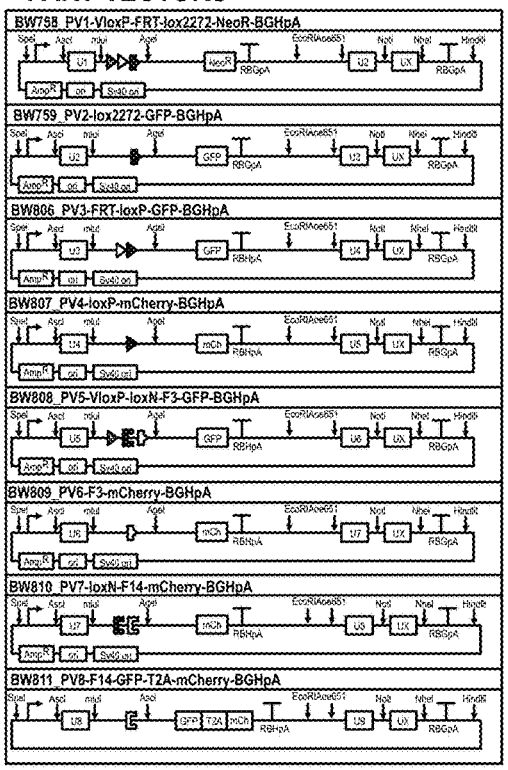
Figure 24A:
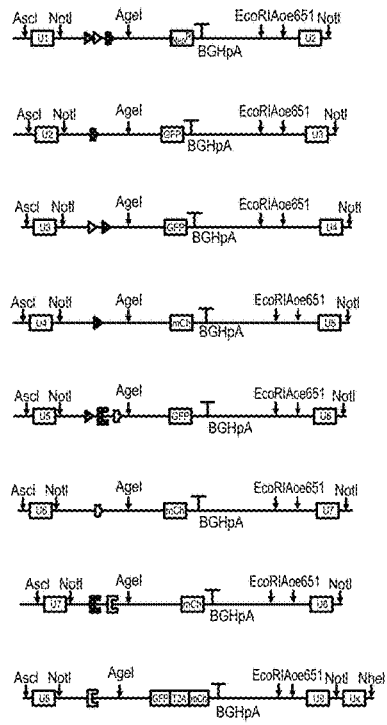
Figure 24A:
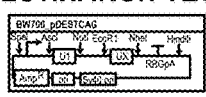
Figure 24A:
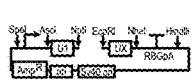
Figure 24B:
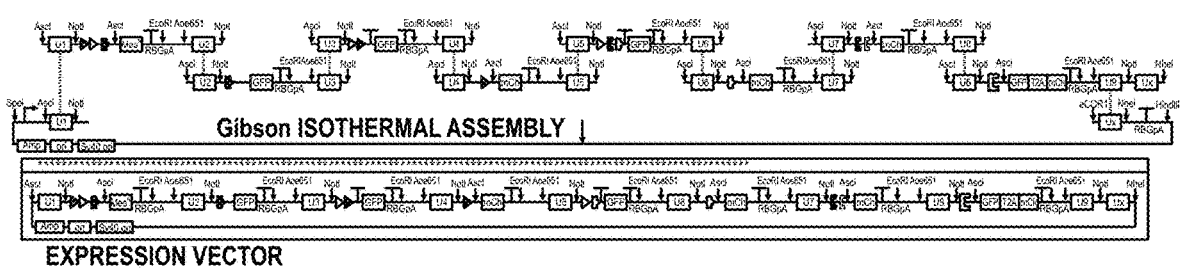

BLADE Platform can be Scaled for More than Two Inputs to Perform Arithmetic Operations Extending the BLADE framework further, the inventors developed a 3-input BLADE template for constructing sophisticated arithmetic functions in human cells (FIG. 5A, FIG. 23 and FIG. 24). This template responds to three inputs (Cre, Flp, and VCre) and contains eight addresses for expression of up to eight distinct transcriptional outputs. This design utilizes three different heterospecific sites for Cre and Flp, but just one site for VCre. Three 3-input-2-output arithmetic computational circuits were made and tested in HEK293FT cells from the 3-input BLADE template (FIG. 5B, FIG. 25, Table 17). The full adder and full subtractor can perform either binary addition or subtraction of three 1-bit inputs, respectively. Furthermore, the half adder-subtractor is an arithmetic FPROM circuit that can compute addition or subtraction on two data inputs, A and B, depending on the presence of one select input C. BLADE templates with more than three inputs can be generated by using additional recombinases and heterospecific recombination sites that follow a simple recursive design algorithm where simple recombinase switches are nested within each other yielding designs for implementing any N-input combinatorial logic function (FIG. 26). This non-intensive computational approach produces designs with the total number of recombination site pairs for N-inputs being $2^N-1$, for $N \geq 0$; this is consistent with the $2^N$ rows needed to specify the truth table of an N-input function.

TABLE 17

Transient transfection setup for 3-input logic gates detailed in FIG. 5b.

| Reporter | Input State A B C | Enzyme 1, ng pCAG-iCre (pBW390) | Enzyme 2, ng pCAG-FlpO (pBW391) | Enzyme 3, ng pCAG-VCre (pBW433) | Blank, ng pCAG-FALSE (pBW363) | Marker, ng pCAG-tagBFP (pBW462) |
|---|---|---|---|---|---|---|
| Values shown below | 0 0 0 | 0 | 0 | 0 | 0 | 62.5 |
| | 1 0 0 | 41.7 | 0 | 0 | 83.3 | 62.5 |
| | 0 1 0 | 0 | 41.7 | 0 | 83.3 | 62.5 |
| | 0 0 1 | 0 | 0 | 41.7 | 83.3 | 62.5 |
| | 1 1 0 | 41.7 | 41.7 | 0 | 41.7 | 62.5 |
| | 1 0 1 | 41.7 | 0 | 41.7 | 41.7 | 62.5 |
| | 0 1 1 | 0 | 41.7 | 41.7 | 41.7 | 62.5 |
| | 1 1 1 | 41.7 | 41.7 | 41.7 | 0 | 62.5 |

| Logic gate | | |
|---|---|---|
| Gate | Plasmid ID | ng |
| FULL ADDER | pBW820 | 62.5 |
| FULL SUBTRACTOR | pBW840 | 62.5 |
| HALF ADDER-SUBTRACTOR | pBW841 | 62.5 |

Example 2

Interfacing BLADE with Small Molecule Inputs

Figure 6A:
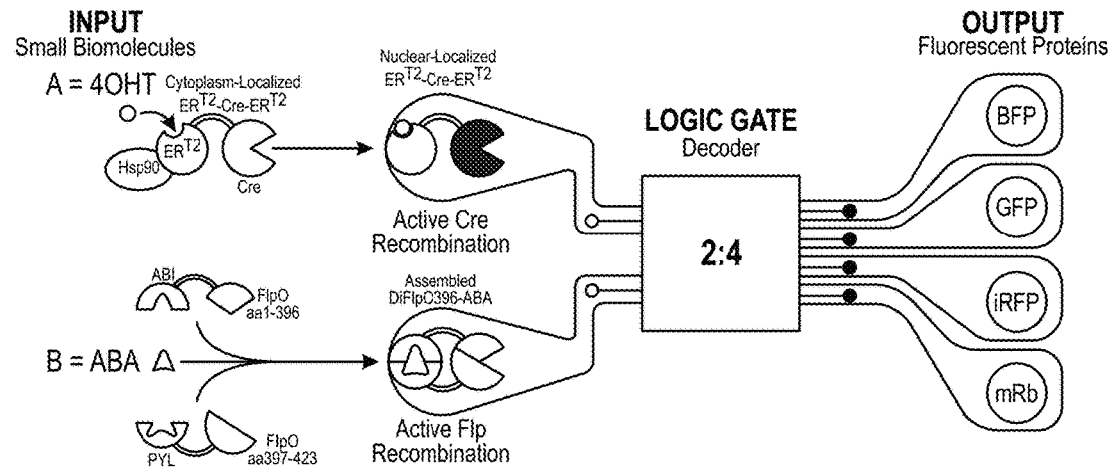

Next, the inventors interfaced the BLADE system with biochemically relevant inputs. To induce Cre recombination, an $ER^{T2}$-Cre-$ER^{T2}$ construct was used whereby a mutated estrogen receptor ($ER^{T2}$) secludes Cre recombinase activity from the nucleus unless a small molecule 4-hydroxytamoxifen (4OHT) is added, which permits translocation of the fusion protein to the nucleus. For Flp induction, a novel split Flp system was developed that induces Flp recombinase activity upon phytohormone abscisic acid (ABA)-induced heterodimerization (FIG. 6A, FIG. 27, Table 18). Logical detection of these two small molecule inputs was successful using the 2-input BLADE decoder with minimal leaky recombinase behavior in HEK293FT cells. Logic induction dynamics were characterized over the course of 48 hours, which revealed early encoding of logic and introduction of leaky recombinase behavior towards the end of the time course (FIGS. 28, 29 and 30). The inventors discovered that most existing inducible Cre and Flp systems were more leaky in the transient transfection setting and had difficulty shutting off gene expression, implying slow onset of recombination (data not shown). A BLADE decoder affords the ability to combinatorially select an exponential number of DNA regions (e.g. eight regions via three inputs), which is advantageous for the limited set of eukaryotic inducible systems.

Example 3

Figure 6B:
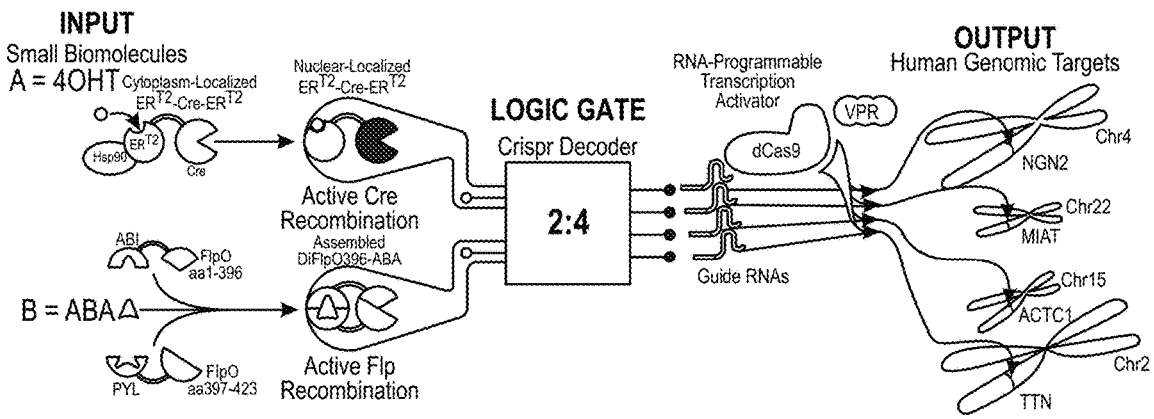

Interfacing BLADE with CRISPR/Cas9 for Logical Regulation of Endogenous Human Genes To test whether the BLADE system could be used for controlling endogenous gene expression, we interfaced it with the CRISPR/Cas9 system through recombinase-based excision of guide RNA (gRNA) sequences. The inventors first tested whether recombination sites or cloning scar DNA sequences would affect the activity of a Cas9 transcription activator (dCas9-VPR), as these sequences would be directly coded into RNA fused to the gRNA. The inventors demonstrated that these sequences (up to 136 bases) added to the 5' end of the gRNA had no detrimental effect on transcription activation of a mCherry reporter plasmid (FIG. 31). Next, the two-input decoder was rebuilt to use an RNA polymerase III human U6 promoter and single guide RNAs (gRNAs) as addresses that target promoters of four human endogenous genes (NGN2, MIAT, ACTC1 and TTN). These targets were chosen because of their documented efficient gRNA activity[45]. This CRISPR-based two-input decoder system was transfected along with a Cas9 transcription activator (dCas9-VPR)[45] and recombinase activities were induced with 4OHT and ABA (FIG. 6B, Tables 19 and 20). At the completion of the HEK293FT transient transfection, mRNA fold changes were determined for each gene using quantitative real-time PCR and corresponded to the two-

TABLE 18

Transient transfection setup for inducible fluorescent protein decoder detailed in FIG. 6a.

| Reporter pEXPRCAG-DECODER (pBW842) | 4OHT (1 μM) | ABA (100 μM) | Recombinase Constructs | Blank, ng pCAG-FALSE (pBW363) | Marker, ng pCAG-LSS-mOrange (pBW474) |
|---|---|---|---|---|---|
| 35.7 | 0 | 0 | 35.7 ng each: pDC56 (pCAG-ERT2-Cre-ERT2), pBW2286 (pCAG-Flp1-396-ABI), pBW2287 (pCAG-PYL-Flp397-423-ABI) | 71.4 | 35.7 |
| | 1 | 0 | | | |
| | 0 | 1 | | | |
| | 1 | 1 | | | | input decoder truth table logic. Due to the easy programmability of the CRISPR/Cas9 system, this system will be very useful for genome-wide transcriptional reprogramming studies, entailing unprecedented control of endogenous human genes and cell states.

metrics. Some circuits did not pass a stringent VP global rank metric evaluation; however, all circuits yielded results that had close alignment with their intended truth table. A potential source of underperformance could arise from interference of recombinase sites sequences on ribosome activities (e.g. hair-pinning hampering translation initiation or cryptic translation initiation sequences). The RNA Pol III/CRISPR-based BLADE system could be an attractive circuit design to explore since gRNA or other regulatory RNA outputs are not subjected to translation-based failure modes. Key attributes of the BLADE platform are summarized in Table 20.

TABLE 19

Transient transfection setup for CRISPR decoder detailed in FIG. 6B.

| Reporter pEXPRCAG-CRISPR-DECODER (pBW842) | 4OHT (1 μM) | ABA (100 μM) | Recombinase Constructs | CMV-dCas9-VPR (Addgene: 63798) | Blank, ng pCAG-FALSE (pBW363) | Marker, ng pCAG-GFP (pBW361) |
|---|---|---|---|---|---|---|
| 35.7 | 0 | 0 | 35.7 ng each: pDC16 (pSFFV-ERT2-Cre-ERT2), pBW2286 (pCAG-Flp1-396-ABI), pBW2287 (pCAG-PYL-Flp397-423-ABI) | 35.7 | 35.7 | 35.7 |
|  | 1 | 0 |  |  |  |  |
|  | 0 | 1 |  |  |  |  |
|  | 1 | 1 |  |  |  |  |

Example 4

The inventors developed a well-defined platform capable of generating a large number of complex genetic circuits. To demonstrate the application of BLADE in genetic circuit design, more than 100 functionally distinct circuits were created, most of which have never been documented before in any living organism. A major fraction of the circuits displayed the intended logic, as quantified by our novel VP

TABLE 20

Comparison between BLADE and recent recombinase-based circuit designs or the large-scale circuit design platform Cello.

| Key Attributes | BLADE | Siuti et al.[3] | Bonnet et al.[4] | Roquet et al.[5] | Hsiao et al.[6] | Nielsen et al.[7] |
|---|---|---|---|---|---|---|
| Host Organism Operation | H. sapiens Segment Excision | E. coli Part Inversion | E. coli Terminator Inversion | E. coli Segment Excision/Inversion | E. coli Part Excision/Inversion | E. coli Promoter Repression |
| Computing Resource | | | Recombinase | | | Transcription Factor |
| Fundamental Building Block | Line decoder circuit | | N/A | | | NOR/NOT gates |
| Device Design Algorithm | Recursive algorithm based on # of inputs[a] | Ad hoc for each circuit[b] | Ad hoc for each circuit | Exhaustive search[c] | Ad hoc for each circuit | Heuristic search[d] |
| Number of functional and distinct circuits shown | >110 | ~20 | ~10 | ~5 | 1 | ~60 |
| Metric (% success) | Yes (>93%)[e] | | | No | | Yes (75%) |
| Maximum # of inputs shown | 6 | 2 | 2 | 3 | 2 | 3 |
| Maximum # of transcriptional outputs from one circuit shown | 4 | 1 | 1 | 3-5[f] | 2 | 1 |
| Types of outputs | ORF, gRNA | ORF | ORF | ORF | ORF | ORF |

Key:
[a]Circuits with more inputs can be designed systematically with a recursive strategy that insert the BLADE circuit into another 1-input recombinase circuit (FIG. 26).
[b]Each circuit has a unique design approach.
[c]All possible circuit permutations are based on available recombination sites are computationally evaluated.
[d]Circuit design is based on characterized parts and prior experimental results.
[e]93.81% of circuits have a VP angle of ≤15°. 96.46% of circuits have a VP global rank equal to 0.
[f]Some of the circuits can display up to 16 states, but only a subset of them can produce transcription outputs.

The BLADE platform is enabled by the unique chemistry of recombinases (DNA rearrangement) in regulating gene expression. The same recombinase can activate and inhibit gene expression simultaneously in the same transcription unit with equal efficiency, a feature that is very difficult to accomplish with transcription factors. This feature allowed us to design the BLADE platform in a single transcription unit to implement any combinatorial Boolean logic provided sufficient numbers of recombinases and heterospecific sites are available. Multiple orthogonal recombinases can be used together as a single input if insufficient heterospecific sites are available. Genome-mining has been performed to uncover and test a large set of serine integrases[34] and many putative recombinases remain to be characterized from structural identification in genome sequence databases. Furthermore, efforts have been made to design and implement recombinases that can be made to recombine different DNA sequences through fusion of recombinase catalytic domains to programmable DNA-binding proteins, such as zinc finger, TAL, and Cas9 sequences[46-50]; generation of chimeric recombinases[51,52]; or alteration of specificity through molecular evolution experiments[53-55]. Therefore, it can be envisioned that an unlimited set of recombinase parts could be available for incorporation with BLADE and thus further push the boundaries of biological circuit engineering in living cells.

The BLADE platform also represents a new direction in biological circuit design that deviates from its electronic counterpart. Composition of simple gates into large hierarchies of modules implementing complex functions has been a successful strategy in electronic circuit design because components are physically separated from each other, allowing reuse of well-characterized and high-performing parts. These facts permitted the electronics community to generate computing devices with extremely predictable behaviors.

The multi-layer design typically found in other circuits can, in principle, allow construction of new circuits by reconnecting smaller circuits in a different way. The performance of the circuits may be predicted from the properties of smaller circuits that comprised them. However, multilayer circuit design also requires more orthogonal biological "wires", which drives effort toward parts development[58-60] at the expense of circuit design. Furthermore, these biological wires often have unpredictable properties. In contrast, the inventors demonstrated herein that a single-layer BLADE platform can use fewer protein components to perform a large set of complex logical operations in mammalian cells. A trade-off for the single layer design is that the performance of circuits cannot be predicted based on the property of its components. In addition, the inventors have illustrated a strategy to nest multiple circuits within a single transcription unit, thus expanding the sophistication of genetic circuit engineering achieved in living cells. The flexibility and efficiency of recombinases in regulating gene expression, coupled with the single layer design, allowed the BLADE platform to be highly robust and digital, as shown by the low deviations from ideal truth tables. It avoids the biophysical and computational challenges of having to tune or match output signal levels of one gate to input signal levels of another.

In addition to regulating messenger RNA expression, the inventors have also demonstrated herein that the BLADE system can also be readily adapted to control guide RNA expression, thus increasing its ability to modulate cell functions. Importantly, when combined with drug-inducible control of recombinase activity, the inventors were able to conditionally regulate gene expression and cell states. With the emergence of adoptive T cell therapy and the need for regulated T cell function to enhance their efficacy and safety, the BLADE system can be used as powerful control circuits for regulating chimeric antigen receptors[61,62] or cytokine expression. While foreign transgenes expression in human cell may elicit immunogenicity, strategies to circumvent immunogenicity, such as through the disruption of the HLA (e.g. HLA knockout)[63], or overexpression of immunosuppressive surface proteins (e.g. HLA-G, HLA-E)[64], are available, especially in the context of adoptive cell therapy where extensive genetic and genome engineering are feasible and becoming routine.

When identifying the most suitable drug inducible system to control Cre and Flp activity, the inventors created the first split Flp protein for which its activity can be reconstituted with chemically inducible dimerization systems. This split Flp configuration could be valuable to many animal geneticists. Furthermore, the inventors have shown that the BLADE system is functional in very different cell types (e.g. embryonic kidney and T cells). Since recombinases and CRISPR/Cas9 have been shown to function in many eukaryotic organisms, our BLADE platform and recombinases should be generalizable to other species.

Transcription factor-based genetic circuits have played a dominant role in synthetic circuit design[11,21,65-67]. This is due to the fact that natural genetic circuits, which commonly serve as the inspiration for synthetic circuits design, are mostly implemented using transcription factors, with only a few documented cases involving recombinases (e.g. fim invertase in *Escherichia coli*)[68,69] Transcription factor-based circuits allow continuous sensing and response, which is important for many natural cellular processes to track periodic or dynamic inputs. However, as the number of inputs and outputs of the circuit increases, the number of transcription units required to generate the circuits often increases significantly, which further complicates design and construction efforts. As such, very few synthetic multi-input-multi-output circuits have been reported.

In contrast to transcription-based circuits, recombinase-based circuits as described here and elsewhere are single-use systems, which prevent them from tracking dynamic input signals. However, recombinases are particularly advantageous for engineering logic behaviors. Furthermore, when integrated into the genome, recombinase-based systems can provide stable memory and have proven to be invaluable in numerous experiments, such as in tissue specific gene expression experiments where memory of tissue or condition specific inputs that lead to sustained gene expression (or knockout) is more desirable. In addition, serine integrases have been used to develop temporal logic state machines in bacteria where the circuits can sense and remember the order at which signal inputs appeared[70, 71]. It is conceivable that their designs can be refactored to function in mammalian cells. It is also possible to modify the BLADE platform to perform temporal logic computations, thus enabling the use of the more widely adopted tyrosine recombinases in single-layer circuit topology. The prevalence of recombinase in different systems and organisms illustrates the fact that single-use systems are often sufficient in biomedical research and biotechnological applications[26,72].

Another important feature of recombinase-based circuits is that they do not require signal integration at the promoter, thus providing a convenient mechanism for adjusting the output gene expression level independent of the logic operation. As demonstrated by the BLADE platform disclosed herein, the expression level in the addressable regions be can be arbitrarily modulated without affecting the intended logic; this is difficult to achieve with solely transcription-factor based circuits. This property can provide even more flexibility for precisely controlling cell states. More importantly, transcription factor- and recombinase-based circuit designs are complementary to each other and can be integrated together if necessary. Furthermore, some large serine integrases, such as PhiC31 and TP901-1 integrases have known recombination directionality factors (RDF) that can reverse the inversion reaction performed by the integrases[73]. Some of the RDFs are active in mammalian cells (data not shown); therefore, encompassed herein is a reversible system equivalent to BLADE except through DNA inversion rather than excision. Together, the inventors envision that the BLADE design principle and platform will enable the programming of sophisticated computations in many eukaryotic organisms.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc. As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of" when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited. All references, patents and patent applications disclosed herein are incorporated by reference with respect to the subject matter for which each is cited, which in some cases may encompass the entirety of the document.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

REFERENCES

The references disclosed herein are incorporated in their entirety by reference.

1. Khalil, A. S. & Collins, J. J. Synthetic biology: applications come of age. *Nature reviews. Genetics* 11, 367-379 (2010).
2. Wei, P. et al. Bacterial virulence proteins as tools to rewire kinase pathways in yeast and immune cells. *Nature* 488, 384-388 (2012).
3. Roybal, K. T. et al. Precision Tumor Recognition by T Cells With Combinatorial Antigen-Sensing Circuits. *Cell* 164, 770-779 (2016).
4. Chakravarti, D. & Wong, W. W. Synthetic biology in cell-based cancer immunotherapy. *Trends in biotechnology* 33, 449-461 (2015).
5. Slomovic, S. & Collins, J. J. DNA sense-and-respond protein modules for mammalian cells. *Nature methods* 12, 1085-1090 (2015).
6. Courbet, A., Endy, D., Renard, E., Molina, F. & Bonnet, J. Detection of pathological biomarkers in human clinical samples via amplifying genetic switches and logic gates. *Sci Transl Med* 7, 289ra283 (2015).
7. Fenno, L. E. et al. Targeting cells with single vectors using multiple-feature Boolean logic. *Nature methods* 11, 763-772 (2014).
8. Madisen, L. et al. Transgenic mice for intersectional targeting of neural sensors and effectors with high specificity and performance. *Neuron* 85, 942-958 (2015).
9. Ro, D. K. et al. Production of the antimalarial drug precursor artemisinic acid in engineered yeast. *Nature* 440, 940-943 (2006).
10. Bogorad, I. W., Lin, T. S. & Liao, J. C. Synthetic non-oxidative glycolysis enables complete carbon conservation. *Nature* 502, 693-697 (2013).
11. Stricker, J. et al. A fast, robust and tunable synthetic gene oscillator. *Nature* 456, 516-519 (2008).
12. Gaber, R. et al. Designable DNA-binding domains enable construction of logic circuits in mammalian cells. *Nature chemical biology* 10, 203-208 (2014).
13. Moon, T. S., Lou, C., Tamsir, A., Stanton, B. C. & Voigt, C. A. Genetic programs constructed from layered logic gates in single cells. *Nature* 491, 249-253 (2012).
14. Leisner, M., Bleris, L., Lohmueller, J., Xie, Z. & Benenson, Y. Rationally designed logic integration of regulatory signals in mammalian cells. *Nature nanotechnology* 5, 666-670 (2010).
15. Xie, Z., Wroblewska, L., Prochazka, L., Weiss, R. & Benenson, Y. Multi-input RNAi-based logic circuit for identification of specific cancer cells. *Science* 333, 1307-1311 (2011).
16. Guinn, M. & Bleris, L. Biological 2-input decoder circuit in human cells. *ACS synthetic biology* 3, 627-633 (2014).
17. Weber, W. et al. A synthetic time-delay circuit in mammalian cells and mice. *Proceedings of the National Academy of Sciences of the United States of America* 104, 2643-2648 (2007).
18. Regot, S. et al. Distributed biological computation with multicellular engineered networks. *Nature* 469, 207-211 (2011).
19. Chen, Y., Kim, J. K., Hirning, A. J., Josic, K. & Bennett, M. R. Emergent genetic oscillations in a synthetic microbial consortium. *Science* 349, 986-989 (2015).
20. Brophy, J. A. & Voigt, C. A. Principles of genetic circuit design. *Nature methods* 11, 508-520 (2014).
21. Nielsen, A. A. et al. Genetic circuit design automation. *Science* 352, aac7341 (2016).
22. Appleton, E., Tao, J., Haddock, T. & Densmore, D. Interactive assembly algorithms for molecular cloning. *Nature methods* 11, 657-662 (2014).
23. Rodrigo, G. & Jaramillo, A. AutoBioCAD: full biodesign automation of genetic circuits. *ACS synthetic biology* 2, 230-236 (2013).
24. Huynh, L., Kececioglu, J., Koppe, M. & Tagkopoulos, I. Automatic design of synthetic gene circuits through mixed integer non-linear programming. *PloS one* 7, e35529 (2012).
25. Stanton, B. C. et al. Genomic mining of prokaryotic repressors for orthogonal logic gates. *Nature chemical biology* 10, 99-105 (2014).
26. Nagy, A. Cre recombinase: the universal reagent for genome tailoring. *Genesis* 26, 99-109 (2000).
27. Ventura, A. et al. Restoration of p53 function leads to tumour regression in vivo. *Nature* 445, 661-665 (2007).
28. Feil, R., Wagner, J., Metzger, D. & Chambon, P. Regulation of Cre recombinase activity by mutated estrogen receptor ligand-binding domains. *Biochemical and biophysical research communications* 237, 752-757 (1997).
29. Ham, T. S., Lee, S. K., Keasling, J. D. & Arkin, A. P. Design and construction of a double inversion recombination switch for heritable sequential genetic memory. *PloS one* 3, e2815 (2008).
30. Friedland, A. E. et al. Synthetic gene networks that count. *Science* 324, 1199-1202 (2009).
31. Siuti, P., Yazbek, J. & Lu, T. K. Synthetic circuits integrating logic and memory in living cells. *Nature biotechnology* 31, 448-452 (2013).
32. Bonnet, J., Yin, P., Ortiz, M. E., Subsoontorn, P. & Endy, D. Amplifying genetic logic gates. *Science* 340, 599-603 (2013).
33. Awatramani, R., Soriano, P., Rodriguez, C., Mai, J. J. & Dymecki, S. M. Cryptic boundaries in roof plate and choroid plexus identified by intersectional gene activation. *Nature genetics* 35, 70-75 (2003).
34. Yang, L. et al. Permanent genetic memory with >1-byte capacity. *Nature methods* (2014).
35. Sauer, B. & McDermott, J. DNA recombination with a heterospecific Cre homolog identified from comparison of the pac-c1 regions of P1-related phages. *Nucleic acids research* 32, 6086-6095 (2004).
36. Sajgo, S. et al. Dre-Cre sequential recombination provides new tools for retinal ganglion cell labeling and manipulation in mice. *PloS one* 9, e91435 (2014).
37. Suzuki, E. & Nakayama, M. VCre/VloxP and SCre/SloxP: new site-specific recombination systems for genome engineering. *Nucleic acids research* 39, e49 (2011).
38. Karimova, M. et al. Vika/vox, a novel efficient and specific Cre/loxP-like site-specific recombination system. *Nucleic acids research* 41, e37 (2013).
39. Lee, G. & Saito, I. Role of nucleotide sequences of loxP spacer region in Cre-mediated recombination. *Gene* 216, 55-65 (1998).
40. Schonhuber, N. et al. A next-generation dual-recombinase system for time- and host-specific targeting of pancreatic cancer. *Nature medicine* 20, 1340-1347 (2014).
41. Shannon, C. E. The Synthesis of Two-Terminal Switching Circuits. *Bell System Technical Journal* 28, 59-98 (1949).
42. Torella, J. P. et al. Rapid construction of insulated genetic circuits via synthetic sequence-guided isothermal assembly. *Nucleic acids research* 42, 681-689 (2014).

43. Torella, J. P. et al. Unique nucleotide sequence-guided assembly of repetitive DNA parts for synthetic biology applications. *Nature protocols* 9, 2075-2089 (2014).
44. Canton, B., Labno, A. & Endy, D. Refinement and standardization of synthetic biological parts and devices. *Nature biotechnology* 26, 787-793 (2008).
45. Chavez, A. et al. Highly efficient Cas9-mediated transcriptional programming. *Nature methods* 12, 326-328 (2015).
46. Mercer, A. C., Gaj, T., Fuller, R. P. & Barbas, C. F., 3rd Chimeric TALE recombinases with programmable DNA sequence specificity. *Nucleic acids research* 40, 11163-11172 (2012).
47. Gordley, R. M., Gersbach, C. A. & Barbas, C. F., 3rd Synthesis of programmable integrases. *Proceedings of the National Academy of Sciences of the United States of America* 106, 5053-5058 (2009).
48. Sirk, S. J., Gaj, T., Jonsson, A., Mercer, A. C. & Barbas, C. F., 3rd Expanding the zinc-finger recombinase repertoire: directed evolution and mutational analysis of serine recombinase specificity determinants. *Nucleic acids research* 42, 4755-4766 (2014).
49. Liu, D. R., Guilinger, J. P. & Thompson, D. B. (Google Patents, 2015).
50. Akopian, A., He, J., Boocock, M. R. & Stark, W. M. Chimeric recombinases with designed DNA sequence recognition. *Proceedings of the National Academy of Sciences of the United States of America* 100, 8688-8691 (2003).
51. Farruggio, A. P. & Calos, M. P. Serine integrase chimeras with activity in *E. coli* and HeLa cells. *Biol Open* 3, 895-903 (2014).
52. Shaikh, A. C. & Sadowski, P. D. Chimeras of the Flp and Cre recombinases: tests of the mode of cleavage by Flp and Cre. *Journal of molecular biology* 302, 27-48 (2000).
53. Karpinski, J. et al. Directed evolution of a recombinase that excises the provirus of most HIV-1 primary isolates with high specificity. *Nature biotechnology* 34, 401-409 (2016).
54. Hauber, I. et al. Highly significant antiviral activity of HIV-1 LTR-specific tre-recombinase in humanized mice. *PLoS pathogens* 9, e1003587 (2013).
55. Sarkar, I., Hauber, I., Hauber, J. & Buchholz, F. HIV-1 proviral DNA excision using an evolved recombinase. *Science* 316, 1912-1915 (2007).
56. Jayanthi, S., Nilgiriwala, K. S. & Del Vecchio, D. Retroactivity controls the temporal dynamics of gene transcription. *ACS synthetic biology* 2, 431-441 (2013).
57. Mutalik, V. K. et al. Quantitative estimation of activity and quality for collections of functional genetic elements. *Nature methods* 10, 347-353 (2013).
58. Khalil, A. S. et al. A synthetic biology framework for programming eukaryotic transcription functions. *Cell* 150, 647-658 (2012).
59. Chen, Y. J. et al. Characterization of 582 natural and synthetic terminators and quantification of their design constraints. *Nature methods* 10, 659-664 (2013).
60. Green, A. A., Silver, P. A., Collins, J. J. & Yin, P. Toehold switches: de-novo-designed regulators of gene expression. *Cell* 159, 925-939 (2014).
61. Grupp, S. A. et al. Chimeric antigen receptor-modified T cells for acute lymphoid leukemia. *N Engl J Med* 368, 1509-1518 (2013).
62. Morgan, R. A. et al. Case report of a serious adverse event following the administration of T cells transduced with a chimeric antigen receptor recognizing ERBB2. *Molecular therapy: the journal of the American Society of Gene Therapy* 18, 843-851 (2010).
63. Torikai, H. et al. Toward eliminating HLA class I expression to generate universal cells from allogeneic donors. *Blood* 122, 1341-1349 (2013).
64. Zhao, L., Teklemariam, T. & Hantash, B. M. Heterelogous expression of mutated HLA-G decreases immunogenicity of human embryonic stem cells and their epidermal derivatives. *Stem cell research* 13, 342-354 (2014).
65. Tamsir, A., Tabor, J. J. & Voigt, C. A. Robust multicellular computing using genetically encoded NOR gates and chemical 'wires'. *Nature* 469, 212-215 (2011).
66. Gardner, T. S., Cantor, C. R. & Collins, J. J. Construction of a genetic toggle switch in *Escherichia coli*. *Nature* 403, 339-342 (2000).
67. Elowitz, M. B. & Leibler, S. A synthetic oscillatory network of transcriptional regulators. *Nature* 403, 335-338 (2000).
68. Johnson, R. C. in Mobile DNA II (American Society of Microbiology, 2002).
69. Blomfield, I. C. The regulation of pap and type 1 fimbriation in *Escherichia coli*. *Advances in microbial physiology* 45, 1-49 (2001).
70. Roquet, N., Soleimany, A. P., Ferris, A. C., Aaronson, S. & Lu, T. K. Synthetic recombinase-based state machines in living cells. *Science* 353, aad8559 (2016).
71. Hsiao, V., Hon, Y., Rothemund, P. W. & Murray, R. M. A population-based temporal logic gate for timing and recording chemical events. *Molecular systems biology* 12, 869 (2016).
72. Branda, C. S. & Dymecki, S. M. Talking about a revolution: The impact of site-specific recombinases on genetic analyses in mice. *Developmental cell* 6, 7-28 (2004).
73. Bonnet, J., Subsoontorn, P. & Endy, D. Rewritable digital data storage in live cells via engineered control of recombination directionality. *Proceedings of the National Academy of Sciences of the United States of America* 109, 8884-8889 (2012).
1 Torella, J. P. et al. Unique nucleotide sequence-guided assembly of repetitive DNA parts for synthetic biology applications. *Nature protocols* 9, 2075-2089, doi:10.1038/nprot.2014.145 (2014).
2 Chavez, A. et al. Highly efficient Cas9-mediated transcriptional programming. *Nature methods* 12, 326-328, doi: 10.1038/nmeth.3312 (2015).
3 Siuti, P., Yazbek, J. & Lu, T. K. Synthetic circuits integrating logic and memory in living cells. *Nature biotechnology* 31, 448-452, doi:10.1038/nbt.2510 (2013).
4 Bonnet, J., Yin, P., Ortiz, M. E., Subsoontorn, P. & Endy, D. Amplifying genetic logic gates. *Science* 340, 599-603, doi:10.1126/science.1232758 (2013).
5 Roquet, N., Soleimany, A. P., Ferris, A. C., Aaronson, S. & Lu, T. K. Synthetic recombinase-based state machines in living cells. *Science* 353, aad8559, doi:10.1126/science.aad8559 (2016).
6 Hsiao, V., Hori, Y., Rothemund, P. W. & Murray, R. M. A population-based temporal logic gate for timing and recording chemical events. *Molecular systems biology* 12, 869, doi:10.15252/msb.20156663 (2016).
7 Nielsen, A. A. et al. Genetic circuit design automation. *Science* 352, aac7341, doi:10.1126/science.aac7341 (2016).
8. Jullien et al., Regulation of Cre recombinase by ligand-induced complementation of inactive fragments. *Nucleic Acids Research* 2003, 31(21); e131).

The invention claimed is:

1. A split-recombinase polypeptide, comprising:
   a. at least two complementary protein pairs (CPP), wherein each CPP comprises a binding motif (CPP$^A$) and a complementary binding motif (CPP$^B$), wherein each CPP$^A$ and CPP$^B$ are a pair of chemically-induced dimerization domains (CIDDs), or wherein each CPP$^A$ and CPP$^B$ are a pair of light-induced dimerization domains (LIDDs), and wherein the at least two CPPs comprise:
      i. at least a first CPP (CPP1) comprising a CPP1 binding motif (CPP1$^A$) and a complementary CPP1 binding motif (CPP1$^B$), wherein CPP1$^A$ and CPP1$^B$ are a pair of CIDDs, and CPP1$^A$ binds to a first target agent, and CPP1$^B$ also binds to the same first target agent, or wherein CPP1$^A$ and CPP1$^B$ are a pair of LIDDs that bind to each other upon exposure to a first light signal of appropriate wavelength, and
      ii. a second CPP (CPP2) comprising a CPP2 binding motif (CPP2$^A$) and a complementary CPP2 binding motif (CPP2$^B$), wherein CPP2$^A$ and CPP2$^B$ are a pair of CIDDs, and CPP2$^A$ binds to a second target agent, and CPP2$^B$ also binds to the same second target agent, or wherein CPP2$^A$ and CPP2$^B$ are a pair of LIDDs that bind to each other upon exposure to a second light signal of appropriate wavelength, and
   b. a recombinase protein, wherein the recombinase protein is split into three fragments; a first recombinase polypeptide fragment ($R^1$), a second recombinase polypeptide fragment ($R^2$), and a third recombinase polypeptide fragment ($R^3$), wherein $R^1$, $R^2$ and $R^3$ recombinase polypeptide fragments are each not active by themselves, and wherein $R^1$, $R^2$ and $R^3$ recombinase fragments can recombine in real-time to form the recombinase protein in an active configuration;

wherein:
R$^1$ is conjugated to the CPP1$^A$,
R$^2$ is conjugated to the CPP1$^B$ and the CPP2$^A$, and
R$^3$ is conjugated to the CPP2$^B$,
wherein in the presence of the first target agent, CPP1$^A$ and CPP1$^B$ both bind to the first target agent resulting in protein complementation of R$^1$ and R$^2$, or upon exposure to the first light signal CPP1$^A$ and CPP1$^B$ bind to each other resulting in protein complementation of R$^1$ and R$^2$, and
wherein in the presence of the second target agent, CPP2$^A$ and CPP2$^B$ both bind to the second target agent resulting in protein complementation of R$^2$ and R$^3$, or upon exposure to the second light signal CPP2 and CPP2$^B$ bind to each other resulting in protein complementation of R$^2$ and R$^3$,
wherein the recombinase protein is formed into the active configuration only in the presence of both (1) the first target agent or the first light signal; and (2) the second target agent or the second light signal,
wherein the recombinase protein is selected from the group consisting of: Flp, PhiC31 (@C31), SEQ ID NO: 16 or a polypeptide that has at least 85% identity to the amino acid sequence of SEQ ID NO: 16, B3, Bxb1, Dre, Vika, and FlpO, and
wherein the binding motif (CPP$^A$) and complementary binding motif (CPP$^B$) of each CPP is selected from any one of:
a. the CPP$^A$ comprises a GID1 domain or a fragment thereof, and the CPP$^B$ comprises a GAI domain, wherein the GID1 domain and GAI domain bind to the target agent Gibberellin Ester (GIB);
b. the CPP$^A$ comprises a FKBP domain or a fragment thereof, and the CPP$^B$ comprises an FRB domain, wherein the FKBP domain and FRB domain bind to the target agent Rapalog (RAP);
c. the CPP$^A$ comprises a PYL domain or a fragment thereof, and the CPP$^B$ comprises an ABI domain, wherein the PLY domain and ABI domain bind to the target agent Ascorbic-acid (ABA); or
d. the CPP$^A$ comprises a LIDD, and the CPP$^B$ comprises a complementary LIDD, wherein the LIDD dimerizes with the complementary LIDD upon exposure to a light signal of an appropriate wavelength.

2. The split-recombinase polypeptide of claim 1, wherein the first (R$^1$), second (R$^2$) and third (R$^3$) recombinase polypeptide fragments are Flp recombinase polypeptide fragments, wherein R$^1$, R$^2$ and R$^3$ are selected from any of:
a. R$^1$ comprises amino acids 1-27 of SEQ ID NO: 1 or a polypeptide that has 85% sequence identity thereto; and R$^2$ comprises amino acids 28-168 of SEQ ID NO: 1 or a polypeptide that has 85% sequence identity thereto; and R$^3$ comprises amino acids 169-423 of SEQ ID NO: 1 or a polypeptide that has 85% sequence identity thereto;
b. R$^1$ comprises amino acids 1-27 of SEQ ID NO: 1 or a polypeptide that has 85% sequence identity thereto; and R$^2$ comprises amino acids 28-374 of SEQ ID NO: 1 or a polypeptide that has 85% sequence identity thereto; and R$^3$ comprises amino acids 375-423 of SEQ ID NO: 1 or a polypeptide that has 85% sequence identity thereto;
c. R$^1$ comprises amino acids 1-27 of SEQ ID NO: 1 or a polypeptide that has 85% sequence identity thereto; and R$^2$ comprises amino acids 28-396 of SEQ ID NO: 1 or a polypeptide that has 85% sequence identity thereto; and R$^3$ comprises amino acids 397-423 of SEQ ID NO: 1 or a polypeptide that has 85% sequence identity thereto;
d. R$^1$ comprises amino acids 1-168 of SEQ ID NO: 1 or a polypeptide that has 85% sequence identity thereto; and R$^2$ comprises amino acids 169-374 of SEQ ID NO: 1 or a polypeptide that has 85% sequence identity thereto; and R$^3$ comprises amino acids 375-423 of SEQ ID NO: 1 or a polypeptide that has 85% sequence identity thereto;
e. R$^1$ comprises amino acids 1-168 of SEQ ID NO: 1 or a polypeptide that has 85% sequence identity thereto; and R$^2$ comprises amino acids 169-396 of SEQ ID NO: 1 or a polypeptide that has 85% sequence identity thereto; and R$^3$ comprises amino acids 397-423 of SEQ ID NO: 1 or a polypeptide that has 85% sequence identity thereto; and
f. R$^1$ comprises amino acids 1-374 of SEQ ID NO: 1 or a polypeptide that has 85% sequence identity thereto; and R$^2$ comprises amino acids 375-396 of SEQ ID NO: 1 or a polypeptide that has 85% sequence identity thereto; and R$^3$ comprises amino acids 397-423 of SEQ ID NO: 1 or a polypeptide that has 85% sequence identity thereto.

3. The split-recombinase polypeptide of claim 1, wherein the first (R$^1$), second (R$^2$) and third (R$^3$) recombinase polypeptide fragments are PhiC31 recombinase polypeptide fragments, wherein R$^1$, R$^2$ and R$^3$ are selected from any of:
a. R$^1$ comprises amino acids 1-233 of SEQ ID NO: 12 or a polypeptide that has 85% sequence identity thereto; and R$^2$ comprises amino acids 234-369 of SEQ ID NO: 12 or a polypeptide that has 85% sequence identity thereto; and R$^3$ comprises amino acids 397-605 of SEQ ID NO: 12 or a polypeptide that has 85% sequence identity thereto;
b. R$^1$ comprises amino acids 1-233 of SEQ ID NO: 12 or a polypeptide that has 85% sequence identity thereto; and R$^2$ comprises amino acids 234-428 of SEQ ID NO: 12 or a polypeptide that has 85% sequence identity thereto; and R$^3$ comprises amino acids 429-605 of SEQ ID NO: 12 or a polypeptide that has 85% sequence identity thereto;
c. R$^1$ comprises amino acids 1-233 of SEQ ID NO: 12 or a polypeptide that has 85% sequence identity thereto; and R$^2$ comprises amino acids 234-571 of SEQ ID NO: 12 or a polypeptide that has 85% sequence identity thereto; and R$^3$ comprises amino acids 572-605 of SEQ ID NO: 12 or a polypeptide that has 85% sequence identity thereto;
d. R$^1$ comprises amino acids 1-396 of SEQ ID NO: 12 or a polypeptide that is has 85% sequence identity thereto; and R$^2$ comprises amino acids 397-428 of SEQ ID NO: 12 or a polypeptide that has 85% sequence identity thereto; and R$^3$ comprises amino acids 429-605 of SEQ ID NO: 12 or a polypeptide that has 85% sequence identity thereto;
e. R$^1$ comprises amino acids 1-396 of SEQ ID NO: 12 or a polypeptide that has 85% sequence identity thereto; and R$^2$ comprises amino acids 397-571 of SEQ ID NO: 12 or a polypeptide that has 85% sequence identity thereto; and R$^3$ comprises amino acids 572-605 of SEQ ID NO: 12 or a polypeptide that has 85% sequence identity thereto; and
f. R$^1$ comprises amino acids 1-428 of SEQ ID NO: 12 or a polypeptide that has 85% sequence identity thereto; and R$^2$ comprises amino acids 429-571 of SEQ ID NO: 12 or a polypeptide that has 85% sequence identity thereto; and R³ comprises amino acids 572-605 of SEQ ID NO: 12 or a polypeptide that has 85% sequence identity thereto.

4. The split-recombinase polypeptide of claim 1, wherein the first (R¹), second (R²) and third (R³) recombinase polypeptide fragments are VCre recombinase polypeptide fragments, wherein R¹, R² and R³ are selected from any of:
   a. R¹ comprises amino acids 1-82 of SEQ ID NO: 16 or a polypeptide that has 85% sequence identity thereto; and R² comprises amino acids 83-172 of SEQ ID NO: 16 or a polypeptide that has 85% sequence identity thereto; and R³ comprises amino acids 173-380 of SEQ ID NO: 16 or a polypeptide that has 85% sequence identity thereto;
   b. R¹ comprises amino acids 1-82 of SEQ ID NO: 16 or a polypeptide that has 85% sequence identity thereto; and R² comprises amino acids 83-269 of SEQ ID NO: 16 or a polypeptide that has 85% sequence identity thereto; and R³ comprises amino acids 270-380 of SEQ ID NO: 16 or a polypeptide that has 85% sequence identity thereto;
   c. R¹ comprises amino acids 1-82 of SEQ ID NO: 16 or a polypeptide that has 85% sequence identity thereto; and R² comprises amino acids 83-277 of SEQ ID NO: 16 or a polypeptide that has 85% sequence identity thereto; and R³ comprises amino acids 278-380 of SEQ ID NO: 16 or a polypeptide that has 85% sequence identity thereto;
   d. R¹ comprises amino acids 1-172 of SEQ ID NO: 16 or a polypeptide that has 85% sequence identity thereto; and R² comprises amino acids 173-269 of SEQ ID NO: 16 or a polypeptide that has 85% sequence identity thereto; and R³ comprises amino acids 270-380 of SEQ ID NO: 16 or a polypeptide that has 85% sequence identity thereto;
   e. R¹ comprises amino acids 1-172 of SEQ ID NO: 16 or a polypeptide that has 85% sequence identity thereto; and R² comprises amino acids 173-277 of SEQ ID NO: 16 or a polypeptide that has 85% sequence identity thereto; and R³ comprises amino acids 278-380 of SEQ ID NO: 16 or a polypeptide that has 85% sequence identity thereto; and
   f. R¹ comprises amino acids 1-269 of SEQ ID NO: 16 or a polypeptide that has 85% sequence identity thereto; and R² comprises amino acids 270-277 of SEQ ID NO: 16 or a polypeptide that has 85% sequence identity thereto; and R³ comprises amino acids 278-380 of SEQ ID NO: 16 or a polypeptide that has 85% sequence identity thereto.

5. The split-recombinase polypeptide of claim 1, wherein the LIDD is nMag or CIBN, wherein nMag dimerizes with the complementary LIDD pMag upon exposure to a blue light signal, and wherein CIBN dimerizes with the complementary CRY2 upon exposure to a blue light signal.

6. The split-recombinase polypeptide of claim 5, wherein the blue light signal is a pulse light signal.

7. The split-recombinase of claim 1, wherein the active recombinase protein can recognize the recombinant recognition sequence (RRS) of the recombinase protein.

8. The split-recombinase polypeptide of claim 1, wherein the GID1 domain comprises an amino acid sequence of SEQ ID NO: 31 or a polypeptide with 85% sequence identity to SEQ ID NO: 31, and the GAI domain comprises an amino acid sequence of SEQ ID NO: 30 or a polypeptide with 85% sequence identity to SEQ ID NO: 30.

9. The split-recombinase polypeptide of claim 1, wherein the FKBP domain comprises an amino acid sequence of SEQ ID NO: 22 or a polypeptide with 85% sequence identity to SEQ ID NO: 22, and the FBP domain comprises an amino acid sequence of SEQ ID NO: 23 or a polypeptide with 85% sequence identity to SEQ ID NO: 23.

10. The split-recombinase polypeptide of claim 1, wherein the PYL domain comprises an amino acid sequence of SEQ ID NO: 26 or a polypeptide with 85% sequence identity to SEQ ID NO: 26, and the ABI domain comprises an amino acid sequence of SEQ ID NO: 27 or a polypeptide with 85% sequence identity to SEQ ID NO: 27.

11. The split-recombinase polypeptide of claim 5, wherein the nMag LIDD comprises an amino acid sequence of SEQ ID NO: 51 or a polypeptide with 85% sequence identity to SEQ ID NO: 51, and the pMag complementary LIDD comprises an amino acid sequence of SEQ ID NO: 52 or a polypeptide with 85% sequence identity to SEQ ID NO: 52.

12. The split-recombinase polypeptide of claim 5, wherein the CIBN LIDD comprises an amino acid sequence of SEQ ID NO: 55 or a polypeptide with 85% sequence identity to SEQ ID NO: 55, and the CRY2 complementary LIDD comprises an amino acid sequence of SEQ ID NO: 56 or a polypeptide with 85% sequence identity to SEQ ID NO: 56.

* * * * *

SEQUENCE LISTING

<160> NUMBER OF SEQ ID NOS: 78

<210> SEQ ID NO 1
<211> LENGTH: 423
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Ser Gln Phe Asp Ile Leu Cys Lys Thr Pro Pro Lys Val Leu Val
1               5                   10                  15

Arg Gln Phe Val Glu Arg Phe Glu Arg Pro Ser Gly Glu Lys Ile Ala
                20                  25                  30

Ser Cys Ala Ala Glu Leu Thr Tyr Leu Cys Trp Met Ile Thr His Asn
            35                  40                  45

Gly Thr Ala Ile Lys Arg Ala Thr Phe Met Ser Tyr Asn Thr Ile Ile
50                  55                  60

Ser Asn Ser Leu Ser Phe Asp Ile Val Asn Lys Ser Leu Gln Phe Lys
65                  70                  75                  80

Tyr Lys Thr Gln Lys Ala Thr Ile Leu Glu Ala Ser Leu Lys Lys Leu
                85                  90                  95

Ile Pro Ala Trp Glu Phe Thr Ile Ile Pro Tyr Asn Gly Gln Lys His
            100                 105                 110

Gln Ser Asp Ile Thr Asp Ile Val Ser Ser Leu Gln Leu Gln Phe Glu
        115                 120                 125

Ser Ser Glu Glu Ala Asp Lys Gly Asn Ser His Ser Lys Lys Met Leu
130                 135                 140

Lys Ala Leu Leu Ser Glu Gly Glu Ser Ile Trp Glu Ile Thr Glu Lys
145                 150                 155                 160

Ile Leu Asn Ser Phe Glu Tyr Thr Ser Arg Phe Thr Lys Thr Lys Thr
                165                 170                 175

Leu Tyr Gln Phe Leu Phe Leu Ala Thr Phe Ile Asn Cys Gly Arg Phe
            180                 185                 190

Ser Asp Ile Lys Asn Val Asp Pro Lys Ser Phe Lys Leu Val Gln Asn
        195                 200                 205

Lys Tyr Leu Gly Val Ile Ile Gln Cys Leu Val Thr Glu Thr Lys Thr
210                 215                 220

Ser Val Ser Arg His Ile Tyr Phe Phe Ser Ala Arg Gly Arg Ile Asp
225                 230                 235                 240

Pro Leu Val Tyr Leu Asp Glu Phe Leu Arg Asn Ser Glu Pro Val Leu
                245                 250                 255

Lys Arg Val Asn Arg Thr Gly Asn Ser Ser Asn Lys Gln Glu Tyr
            260                 265                 270

Gln Leu Leu Lys Asp Asn Leu Val Arg Ser Tyr Asn Lys Ala Leu Lys
        275                 280                 285

Lys Asn Ala Pro Tyr Pro Ile Phe Ala Ile Lys Asn Gly Pro Lys Ser
290                 295                 300

His Ile Gly Arg His Leu Met Thr Ser Phe Leu Ser Met Lys Gly Leu
305                 310                 315                 320

Thr Glu Leu Thr Asn Val Val Gly Asn Trp Ser Asp Lys Arg Ala Ser
                325                 330                 335

Ala Val Ala Arg Thr Thr Tyr Thr His Gln Ile Thr Ala Ile Pro Asp
            340                 345                 350

```
His Tyr Phe Ala Leu Val Ser Arg Tyr Tyr Ala Tyr Asp Pro Ile Ser
            355                 360                 365

Lys Glu Met Ile Ala Leu Lys Asp Glu Thr Asn Pro Ile Glu Glu Trp
        370                 375                 380

Gln His Ile Glu Gln Leu Lys Gly Ser Ala Glu Gly Ser Ile Arg Tyr
385                 390                 395                 400

Pro Ala Trp Asn Gly Ile Ile Ser Gln Glu Val Leu Asp Tyr Leu Ser
                405                 410                 415

Ser Tyr Ile Asn Arg Arg Ile
            420

<210> SEQ ID NO 2
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Met Ser Gln Phe Asp Ile Leu Cys Lys Thr Pro Pro Lys Val Leu Val
1               5                   10                  15

Arg Gln Phe Val Glu Arg Phe Glu Arg Pro Ser
            20                  25

<210> SEQ ID NO 3
<211> LENGTH: 396
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gly Glu Lys Ile Ala Ser Cys Ala Ala Glu Leu Thr Tyr Leu Cys Trp
1               5                   10                  15

Met Ile Thr His Asn Gly Thr Ala Ile Lys Arg Ala Thr Phe Met Ser
            20                  25                  30

Tyr Asn Thr Ile Ile Ser Asn Ser Leu Ser Phe Asp Ile Val Asn Lys
        35                  40                  45

Ser Leu Gln Phe Lys Tyr Lys Thr Gln Lys Ala Thr Ile Leu Glu Ala
    50                  55                  60

Ser Leu Lys Lys Leu Ile Pro Ala Trp Glu Phe Thr Ile Ile Pro Tyr
65                  70                  75                  80

Asn Gly Gln Lys His Gln Ser Asp Ile Thr Asp Ile Val Ser Ser Leu
                85                  90                  95

Gln Leu Gln Phe Glu Ser Ser Glu Glu Ala Asp Lys Gly Asn Ser His
            100                 105                 110

Ser Lys Lys Met Leu Lys Ala Leu Leu Ser Glu Gly Glu Ser Ile Trp
        115                 120                 125

Glu Ile Thr Glu Lys Ile Leu Asn Ser Phe Glu Tyr Thr Ser Arg Phe
    130                 135                 140

Thr Lys Thr Lys Thr Leu Tyr Gln Phe Leu Phe Leu Ala Thr Phe Ile
145                 150                 155                 160

Asn Cys Gly Arg Phe Ser Asp Ile Lys Asn Val Asp Pro Lys Ser Phe
                165                 170                 175

Lys Leu Val Gln Asn Lys Tyr Leu Gly Val Ile Ile Gln Cys Leu Val
            180                 185                 190
```

Thr Glu Thr Lys Thr Ser Val Ser Arg His Ile Tyr Phe Ser Ala
            195                 200                 205

Arg Gly Arg Ile Asp Pro Leu Val Tyr Leu Asp Glu Phe Leu Arg Asn
210                 215                 220

Ser Glu Pro Val Leu Lys Arg Val Asn Arg Thr Gly Asn Ser Ser Ser
225                 230                 235                 240

Asn Lys Gln Glu Tyr Gln Leu Leu Lys Asp Asn Leu Val Arg Ser Tyr
            245                 250                 255

Asn Lys Ala Leu Lys Lys Asn Ala Pro Tyr Pro Ile Phe Ala Ile Lys
            260                 265                 270

Asn Gly Pro Lys Ser His Ile Gly Arg His Leu Met Thr Ser Phe Leu
            275                 280                 285

Ser Met Lys Gly Leu Thr Glu Leu Thr Asn Val Val Gly Asn Trp Ser
290                 295                 300

Asp Lys Arg Ala Ser Ala Val Ala Arg Thr Thr Tyr Thr His Gln Ile
305                 310                 315                 320

Thr Ala Ile Pro Asp His Tyr Phe Ala Leu Val Ser Arg Tyr Tyr Ala
            325                 330                 335

Tyr Asp Pro Ile Ser Lys Glu Met Ile Ala Leu Lys Asp Glu Thr Asn
            340                 345                 350

Pro Ile Glu Glu Trp Gln His Ile Glu Gln Leu Lys Gly Ser Ala Glu
            355                 360                 365

Gly Ser Ile Arg Tyr Pro Ala Trp Asn Gly Ile Ile Ser Gln Glu Val
            370                 375                 380

Leu Asp Tyr Leu Ser Ser Tyr Ile Asn Arg Arg Ile
385                 390                 395

<210> SEQ ID NO 4
<211> LENGTH: 168
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Ser Gln Phe Asp Ile Leu Cys Lys Thr Pro Pro Lys Val Leu Val
1               5                   10                  15

Arg Gln Phe Val Glu Arg Phe Glu Arg Pro Ser Gly Glu Lys Ile Ala
            20                  25                  30

Ser Cys Ala Ala Glu Leu Thr Tyr Leu Cys Trp Met Ile Thr His Asn
        35                  40                  45

Gly Thr Ala Ile Lys Arg Ala Thr Phe Met Ser Tyr Asn Thr Ile Ile
    50                  55                  60

Ser Asn Ser Leu Ser Phe Asp Ile Val Asn Lys Ser Leu Gln Phe Lys
65                  70                  75                  80

Tyr Lys Thr Gln Lys Ala Thr Ile Leu Glu Ala Ser Leu Lys Lys Leu
            85                  90                  95

Ile Pro Ala Trp Glu Phe Thr Ile Ile Pro Tyr Asn Gly Gln Lys His
            100                 105                 110

Gln Ser Asp Ile Thr Asp Ile Val Ser Ser Leu Gln Leu Gln Phe Glu
        115                 120                 125

Ser Ser Glu Glu Ala Asp Lys Gly Asn Ser His Ser Lys Lys Met Leu
130                 135                 140

Lys Ala Leu Leu Ser Glu Gly Glu Ser Ile Trp Glu Ile Thr Glu Lys
145                 150                 155                 160

Ile Leu Asn Ser Phe Glu Tyr Thr
            165

<210> SEQ ID NO 5
<211> LENGTH: 255
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Ser Arg Phe Thr Lys Thr Lys Thr Leu Tyr Gln Phe Leu Phe Leu Ala
1               5                   10                  15

Thr Phe Ile Asn Cys Gly Arg Phe Ser Asp Ile Lys Asn Val Asp Pro
            20                  25                  30

Lys Ser Phe Lys Leu Val Gln Asn Lys Tyr Leu Gly Val Ile Ile Gln
        35                  40                  45

Cys Leu Val Thr Glu Thr Lys Thr Ser Val Ser Arg His Ile Tyr Phe
    50                  55                  60

Phe Ser Ala Arg Gly Arg Ile Asp Pro Leu Val Tyr Leu Asp Glu Phe
65                  70                  75                  80

Leu Arg Asn Ser Glu Pro Val Leu Lys Arg Val Asn Arg Thr Gly Asn
                85                  90                  95

Ser Ser Ser Asn Lys Gln Glu Tyr Gln Leu Leu Lys Asp Asn Leu Val
            100                 105                 110

Arg Ser Tyr Asn Lys Ala Leu Lys Lys Asn Ala Pro Tyr Pro Ile Phe
        115                 120                 125

Ala Ile Lys Asn Gly Pro Lys Ser His Ile Gly Arg His Leu Met Thr
    130                 135                 140

Ser Phe Leu Ser Met Lys Gly Leu Thr Glu Leu Thr Asn Val Val Gly
145                 150                 155                 160

Asn Trp Ser Asp Lys Arg Ala Ser Ala Val Ala Arg Thr Thr Tyr Thr
                165                 170                 175

His Gln Ile Thr Ala Ile Pro Asp His Tyr Phe Ala Leu Val Ser Arg
            180                 185                 190

Tyr Tyr Ala Tyr Asp Pro Ile Ser Lys Glu Met Ile Ala Leu Lys Asp
        195                 200                 205

Glu Thr Asn Pro Ile Glu Glu Trp Gln His Ile Gln Leu Lys Gly
    210                 215                 220

Ser Ala Glu Gly Ser Ile Arg Tyr Pro Ala Trp Asn Gly Ile Ile Ser
225                 230                 235                 240

Gln Glu Val Leu Asp Tyr Leu Ser Ser Tyr Ile Asn Arg Arg Ile
                245                 250                 255

<210> SEQ ID NO 6
<211> LENGTH: 374
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Ser Gln Phe Asp Ile Leu Cys Lys Thr Pro Pro Lys Val Leu Val
1               5                   10                  15

Arg Gln Phe Val Glu Arg Phe Glu Arg Pro Ser Gly Glu Lys Ile Ala
            20                  25                  30

Ser Cys Ala Ala Glu Leu Thr Tyr Leu Cys Trp Met Ile Thr His Asn
        35                  40                  45

Gly Thr Ala Ile Lys Arg Ala Thr Phe Met Ser Tyr Asn Thr Ile Ile
 50                  55                  60

Ser Asn Ser Leu Ser Phe Asp Ile Val Asn Lys Ser Leu Gln Phe Lys
 65                  70                  75                  80

Tyr Lys Thr Gln Lys Ala Thr Ile Leu Glu Ala Ser Leu Lys Lys Leu
                 85                  90                  95

Ile Pro Ala Trp Glu Phe Thr Ile Ile Pro Tyr Asn Gly Gln Lys His
                100                 105                 110

Gln Ser Asp Ile Thr Asp Ile Val Ser Ser Leu Gln Leu Gln Phe Glu
                115                 120                 125

Ser Ser Glu Glu Ala Asp Lys Gly Asn Ser His Ser Lys Lys Met Leu
    130                 135                 140

Lys Ala Leu Leu Ser Glu Gly Glu Ser Ile Trp Glu Ile Thr Glu Lys
145                 150                 155                 160

Ile Leu Asn Ser Phe Glu Tyr Thr Ser Arg Phe Thr Lys Thr Lys Thr
                165                 170                 175

Leu Tyr Gln Phe Leu Phe Leu Ala Thr Phe Ile Asn Cys Gly Arg Phe
                180                 185                 190

Ser Asp Ile Lys Asn Val Asp Pro Lys Ser Phe Lys Leu Val Gln Asn
                195                 200                 205

Lys Tyr Leu Gly Val Ile Ile Gln Cys Leu Val Thr Glu Thr Lys Thr
    210                 215                 220

Ser Val Ser Arg His Ile Tyr Phe Phe Ser Ala Arg Gly Arg Ile Asp
225                 230                 235                 240

Pro Leu Val Tyr Leu Asp Glu Phe Leu Arg Asn Ser Glu Pro Val Leu
                245                 250                 255

Lys Arg Val Asn Arg Thr Gly Asn Ser Ser Ser Asn Lys Gln Glu Tyr
                260                 265                 270

Gln Leu Leu Lys Asp Asn Leu Val Arg Ser Tyr Asn Lys Ala Leu Lys
                275                 280                 285

Lys Asn Ala Pro Tyr Pro Ile Phe Ala Ile Lys Asn Gly Pro Lys Ser
    290                 295                 300

His Ile Gly Arg His Leu Met Thr Ser Phe Leu Ser Met Lys Gly Leu
305                 310                 315                 320

Thr Glu Leu Thr Asn Val Val Gly Asn Trp Ser Asp Lys Arg Ala Ser
                325                 330                 335

Ala Val Ala Arg Thr Thr Tyr Thr His Gln Ile Thr Ala Ile Pro Asp
                340                 345                 350

His Tyr Phe Ala Leu Val Ser Arg Tyr Tyr Ala Tyr Asp Pro Ile Ser
    355                 360                 365

Lys Glu Met Ile Ala Leu
    370

<210> SEQ ID NO 7
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Lys Asp Glu Thr Asn Pro Ile Glu Glu Trp Gln His Ile Glu Gln Leu

```
                1               5                   10                  15
Lys Gly Ser Ala Glu Gly Ser Ile Arg Tyr Pro Ala Trp Asn Gly Ile
                20                  25                  30

Ile Ser Gln Glu Val Leu Asp Tyr Leu Ser Ser Tyr Ile Asn Arg Arg
        35                  40                  45

Ile

<210> SEQ ID NO 8
<211> LENGTH: 396
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Ser Gln Phe Asp Ile Leu Cys Lys Thr Pro Pro Lys Val Leu Val
1               5                   10                  15

Arg Gln Phe Val Glu Arg Phe Glu Arg Pro Ser Gly Glu Lys Ile Ala
                20                  25                  30

Ser Cys Ala Ala Glu Leu Thr Tyr Leu Cys Trp Met Ile Thr His Asn
        35                  40                  45

Gly Thr Ala Ile Lys Arg Ala Thr Phe Met Ser Tyr Asn Thr Ile Ile
    50                  55                  60

Ser Asn Ser Leu Ser Phe Asp Ile Val Asn Lys Ser Leu Gln Phe Lys
65                  70                  75                  80

Tyr Lys Thr Gln Lys Ala Thr Ile Leu Glu Ala Ser Leu Lys Lys Leu
                85                  90                  95

Ile Pro Ala Trp Glu Phe Thr Ile Ile Pro Tyr Asn Gly Gln Lys His
            100                 105                 110

Gln Ser Asp Ile Thr Asp Ile Val Ser Ser Leu Gln Leu Gln Phe Glu
        115                 120                 125

Ser Ser Glu Glu Ala Asp Lys Gly Asn Ser His Ser Lys Lys Met Leu
    130                 135                 140

Lys Ala Leu Leu Ser Glu Gly Glu Ser Ile Trp Glu Ile Thr Glu Lys
145                 150                 155                 160

Ile Leu Asn Ser Phe Glu Tyr Thr Ser Arg Phe Thr Lys Thr Lys Thr
                165                 170                 175

Leu Tyr Gln Phe Leu Phe Leu Ala Thr Phe Ile Asn Cys Gly Arg Phe
            180                 185                 190

Ser Asp Ile Lys Asn Val Asp Pro Lys Ser Phe Lys Leu Val Gln Asn
        195                 200                 205

Lys Tyr Leu Gly Val Ile Ile Gln Cys Leu Val Thr Glu Thr Lys Thr
    210                 215                 220

Ser Val Ser Arg His Ile Tyr Phe Phe Ser Ala Arg Gly Arg Ile Asp
225                 230                 235                 240

Pro Leu Val Tyr Leu Asp Glu Phe Leu Arg Asn Ser Glu Pro Val Leu
                245                 250                 255

Lys Arg Val Asn Arg Thr Gly Asn Ser Ser Asn Lys Gln Glu Tyr
            260                 265                 270

Gln Leu Leu Lys Asp Asn Leu Val Arg Ser Tyr Asn Lys Ala Leu Lys
        275                 280                 285

Lys Asn Ala Pro Tyr Pro Ile Phe Ala Ile Lys Asn Gly Pro Lys Ser
    290                 295                 300

His Ile Gly Arg His Leu Met Thr Ser Phe Leu Ser Met Lys Gly Leu
```

```
                305                 310                 315                 320
Thr Glu Leu Thr Asn Val Val Gly Asn Trp Ser Asp Lys Arg Ala Ser
                    325                 330                 335
Ala Val Ala Arg Thr Thr Tyr Thr His Gln Ile Thr Ala Ile Pro Asp
                340                 345                 350
His Tyr Phe Ala Leu Val Ser Arg Tyr Tyr Ala Tyr Asp Pro Ile Ser
            355                 360                 365
Lys Glu Met Ile Ala Leu Lys Asp Glu Thr Asn Pro Ile Glu Glu Trp
        370                 375                 380
Gln His Ile Glu Gln Leu Lys Gly Ser Ala Glu Gly
385                 390                 395

<210> SEQ ID NO 9
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ser Ile Arg Tyr Pro Ala Trp Asn Gly Ile Ile Ser Gln Glu Val Leu
1               5                   10                  15
Asp Tyr Leu Ser Ser Tyr Ile Asn Arg Arg Ile
            20                  25

<210> SEQ ID NO 10
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gaagttccta ttctctagaa agtataggaa cttc                              34

<210> SEQ ID NO 11
<211> LENGTH: 1269
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
atgagccagt tcgacatcct gtgcaagacc ccccccaagg tgctggtgcg gcagttcgtg    60
gagagattcg agaggcccag cggcgagaag atcgccagct gtgccgccga gctgacctac   120
ctgtgctgga tgatcaccca acggcaccg ccatcaaga gggccacctt catgagctac     180
aacaccatca tcagcaacag cctgagcttc gacatcgtga acaagagcct gcagttcaag   240
tacaagaccc agaaggccac catcctggag gccagcctga gaagctgat ccccgcctgg    300 gagttcacca tcatcccctta aacggccag aagcaccaga gcgacatcac cgacatcgtg   360
tccagcctgc agctgcagtt cgagagcagc gaggaggccg acaagggcaa cagccacagc   420
aagaagatgc tgaaggccct gctgtccgag ggcgagagca tctgggagat caccgagaag   480
atcctgaaca gcttcgagta caccagcagg ttcaccaaga ccaagaccct gtaccagttc   540
ctgttcctgg ccacattcat caactgcggc aggttcagcg acatcaagaa cgtgaccccc   600
aagagcttca gctggtgca gaacaagtac ctgggcgtga tcattcagtg cctggtgacc   660
```

```
gagaccaaga caagcgtgtc caggcacatc tacttttca gcgccagagg caggatcgac    720
cccctggtgt acctggacga gttcctgagg aacagcgagc ccgtgctgaa gagagtgaac    780
aggaccggca acagcagcag caacaagcag gagtaccagc tgctgaagga caacctggtg    840
cgcagctaca acaaggccct gaagaagaac gcccccctacc ccatcttcgc tatcaagaac    900
ggccctaaga gccacatcgg caggcacctg atgaccagct ttctgagcat gaagggcctg    960
accgagctga caaacgtggt gggcaactgg agcgacaaga gggcctccgc cgtggccagg   1020
accacctaca cccaccagat caccgccatc ccgaccact acttcgccct ggtgtccagg   1080
tactacgcct acgaccccat cagcaaggag atgatcgccc tgaaggacga gaccaacccc   1140
atcgaggagt ggcagcacat cgagcagctg aagggcagcg ccgagggcag catcagatac   1200
cccgcctgga acggcatcat cagccaggag gtgctggact acctgagcag ctacatcaac   1260
aggcggatc                                                            1269
```

<210> SEQ ID NO 12
<211> LENGTH: 605
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

```
Met Asp Thr Tyr Ala Gly Ala Tyr Asp Arg Gln Ser Arg Glu Arg Glu
1               5                   10                  15

Asn Ser Ser Ala Ala Ser Pro Ala Thr Gln Arg Ser Ala Asn Glu Asp
            20                  25                  30

Lys Ala Ala Asp Leu Gln Arg Glu Val Glu Arg Asp Gly Gly Arg Phe
        35                  40                  45

Arg Phe Val Gly His Phe Ser Glu Ala Pro Gly Thr Ser Ala Phe Gly
    50                  55                  60

Thr Ala Glu Arg Pro Glu Phe Glu Arg Ile Leu Asn Glu Cys Arg Ala
65                  70                  75                  80

Gly Arg Leu Asn Met Ile Ile Val Tyr Asp Val Ser Arg Phe Ser Arg
                85                  90                  95

Leu Lys Val Met Asp Ala Ile Pro Ile Val Ser Glu Leu Leu Ala Leu
            100                 105                 110

Gly Val Thr Ile Val Ser Thr Gln Glu Gly Val Phe Arg Gln Gly Asn
        115                 120                 125

Val Met Asp Leu Ile His Leu Ile Met Arg Leu Asp Ala Ser His Lys
    130                 135                 140

Glu Ser Ser Leu Lys Ser Ala Lys Ile Leu Asp Thr Lys Asn Leu Gln
145                 150                 155                 160

Arg Glu Leu Gly Gly Tyr Val Gly Gly Lys Ala Pro Tyr Gly Phe Glu
                165                 170                 175

Leu Val Ser Glu Thr Lys Glu Ile Thr Arg Asn Gly Arg Met Val Asn
            180                 185                 190

Val Val Ile Asn Lys Leu Ala His Ser Thr Thr Pro Leu Thr Gly Pro
        195                 200                 205

Phe Glu Phe Glu Pro Asp Val Ile Arg Trp Trp Arg Glu Ile Lys
    210                 215                 220

Thr His Lys His Leu Pro Phe Lys Pro Gly Ser Gln Ala Ala Ile His
225                 230                 235                 240
```

```
Pro Gly Ser Ile Thr Gly Leu Cys Lys Arg Met Asp Ala Asp Ala Val
            245                 250                 255
Pro Thr Arg Gly Glu Thr Ile Gly Lys Lys Thr Ala Ser Ser Ala Trp
        260                 265                 270
Asp Pro Ala Thr Val Met Arg Ile Leu Arg Asp Pro Arg Ile Ala Gly
        275                 280                 285
Phe Ala Ala Glu Val Ile Tyr Lys Lys Pro Asp Gly Thr Pro Thr
    290                 295                 300
Thr Lys Ile Glu Gly Tyr Arg Ile Gln Arg Asp Pro Ile Thr Leu Arg
305                 310                 315                 320
Pro Val Glu Leu Asp Cys Gly Pro Ile Ile Glu Pro Ala Glu Trp Tyr
                325                 330                 335
Glu Leu Gln Ala Trp Leu Asp Gly Arg Gly Arg Gly Lys Gly Leu Ser
                340                 345                 350
Arg Gly Gln Ala Ile Leu Ser Ala Met Asp Lys Leu Tyr Cys Glu Cys
            355                 360                 365
Gly Ala Val Met Thr Ser Lys Arg Gly Glu Ser Ile Lys Asp Ser
370                 375                 380
Tyr Arg Cys Arg Arg Lys Val Val Asp Pro Ser Ala Pro Gly Gln
385                 390                 395                 400
His Glu Gly Thr Cys Asn Val Ser Met Ala Ala Leu Asp Lys Phe Val
                405                 410                 415
Ala Glu Arg Ile Phe Asn Lys Ile Arg His Ala Glu Gly Asp Glu Glu
            420                 425                 430
Thr Leu Ala Leu Leu Trp Glu Ala Ala Arg Arg Phe Gly Lys Leu Thr
        435                 440                 445
Glu Ala Pro Glu Lys Ser Gly Glu Arg Ala Asn Leu Val Ala Glu Arg
    450                 455                 460
Ala Asp Ala Leu Asn Ala Leu Glu Glu Leu Tyr Glu Asp Arg Ala Ala
465                 470                 475                 480
Gly Ala Tyr Asp Gly Pro Val Gly Arg Lys His Phe Arg Lys Gln Gln
                485                 490                 495
Ala Ala Leu Thr Leu Arg Gln Gln Gly Ala Glu Glu Arg Leu Ala Glu
            500                 505                 510
Leu Glu Ala Ala Glu Ala Pro Lys Leu Pro Leu Asp Gln Trp Phe Pro
        515                 520                 525
Glu Asp Ala Asp Ala Asp Pro Thr Gly Pro Lys Ser Trp Trp Gly Arg
    530                 535                 540
Ala Ser Val Asp Asp Lys Arg Val Phe Val Gly Leu Phe Val Asp Lys
545                 550                 555                 560
Ile Val Val Thr Lys Ser Thr Thr Gly Arg Gly Gln Gly Thr Pro Ile
                565                 570                 575
Glu Lys Arg Ala Ser Ile Thr Trp Ala Lys Pro Pro Thr Asp Asp Asp
            580                 585                 590
Glu Asp Asp Ala Gln Asp Gly Thr Glu Asp Val Ala Ala
        595                 600                 605

<210> SEQ ID NO 13
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
```
tgcgggtgcc agggcgtgcc cttgggctcc ccgggcgcgt actcc                45

<210> SEQ ID NO 14
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gtgccccaac tggggtaacc tttgagttct ctcagttggg gg                   42

<210> SEQ ID NO 15
<211> LENGTH: 1815
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
atggatacct acgccggagc ctacgacaga cagagccggg agagagagaa cagcagcgcc    60
gccagccccg ccacccagag aagcgccaac gaggataagg ccgccgatct gcagagagag   120
gtggagaggg acggcggcag attcagattt gtgggccact tcagcgaggc ccctggcacc   180
agcgccttcg gcaccgccga gacccgag ttcgagaaa tcctgaacga gtgtagggcc      240
ggcaggctga acatgatcat cgtgtacgac gtgtcccggt tcagcaggct gaaggtgatg   300
gacgccatcc ctatcgtgtc cgagctgctg gccctgggcg tgaccatcgt gtccacccag   360
gaaggcgtct ttagacaggg caacgtgatg gacctgatcc acctgatcat gaggctggac   420
gccagccaca aggagagcag cctgaagagc gccaagatcc tggacaccaa gaacctgcag   480
agggagctgg gcggctatgt gggcggcaag gcccccctacg gcttcgagct ggtgtccgag   540
accaaggaga tcacccggaa cggcaggatg gtgaacgtgg tgatcaacaa gctggcccac   600
agcaccaccc ccctgaccgg cccettegag tttgagcccg acgtgatcag gtggtggtgg   660
cgggagatca agacccacaa gcacctgcct ttcaagcccg cagcaggc cgccatccac     720 cccggcagca tcaccggcct gtgtaagaga atggacgccg acgccgtgcc caccagaggc   780
gagaccatcg gcaagaaaac cgccagcagc gcctgggacc ccgccaccgt gatgagaatc   840
ctgagggacc ctaggatcgc cggcttcgcc gccgaggtga tctacaagaa gaagcccgac   900 ggcacccccca ccaccaagat cgagggctac agaatccaga gagaccccat caccctgaga   960
cctgtggagc tggactgtgg ccctatcatc gagcctgccg agtggtacga gctgcaggcc  1020
tggctggacg gcagaggcag aggcaagggc ctgagcagag gccaggccat cctgagcgcc  1080
atggacaagc tgtactgtga gtgtggcgcc gtgatgacca gcaagagagg cgaggagagc  1140
atcaaggaca gctaccggtg ccggagaaga aaggtggtgg accccagcgc ccctggccag  1200
cacgagggca cctgtaatgt gagcatggcc gccctggaca agttcgtggc cgagcggatc  1260
ttcaacaaga tccggcacgc cgagggcgac gaggagaccc tggccctgct gtgggaggcc  1320
gccagaagat cggcaagct gaccgaggcc ccgagaaga gcggcgagag ggccaacctg  1380
gtggccgaga gagccgacgc cctgaacgcc ctggaggagc tgtacgagga cagagccgcc  1440
ggagcctatg acgccctgtg ggcaggaag cacttcagaa agcagcaggc cgccctgacc  1500
ctgagacagc agggcgccga ggaaagactg gccgagctgg aggccgccga ggcccctaag  1560

```
ctgcccctgg atcagtggtt ccccgaggat gccgacgccg accccaccgg ccccaagtcc    1620
tggtggggca gagccagcgt ggacgacaag agggtgttcg tgggcctgtt cgtggataag    1680
atcgtggtga ccaagagcac caccggcagg ggccagggca cccccatcga agagagcc     1740 agcatcacct gggccaagcc tcccaccgac gacgacgagg atgacgccca ggacggcacc    1800
gaggacgtgg ccgcc                                                    1815
```

<210> SEQ ID NO 16
<211> LENGTH: 380
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 16

```
Met Ile Glu Asn Gln Leu Ser Leu Leu Gly Asp Phe Ser Gly Val Arg
1               5                   10                  15

Pro Asp Asp Val Lys Thr Ala Ile Gln Ala Ala Gln Lys Lys Gly Ile
            20                  25                  30

Asn Val Ala Glu Asn Glu Gln Phe Lys Ala Ala Phe Glu His Leu Leu
        35                  40                  45

Asn Glu Phe Lys Lys Arg Glu Glu Arg Tyr Ser Pro Asn Thr Leu Arg
    50                  55                  60

Arg Leu Glu Ser Ala Trp Thr Cys Phe Val Asp Trp Cys Leu Ala Asn
65                  70                  75                  80

His Arg His Ser Leu Pro Ala Thr Pro Asp Thr Val Glu Ala Phe Phe
                85                  90                  95

Ile Glu Arg Ala Glu Glu Leu His Arg Asn Thr Leu Ser Val Tyr Arg
            100                 105                 110

Trp Ala Ile Ser Arg Val His Arg Val Ala Gly Cys Pro Asp Pro Cys
        115                 120                 125

Leu Asp Ile Tyr Val Glu Asp Arg Leu Lys Ala Ile Ala Arg Lys Lys
    130                 135                 140

Val Arg Glu Gly Glu Ala Val Lys Gln Ala Ser Pro Phe Asn Glu Gln
145                 150                 155                 160

His Leu Leu Lys Leu Thr Ser Leu Trp Tyr Arg Ser Asp Lys Leu Leu
                165                 170                 175

Leu Arg Arg Asn Leu Ala Leu Leu Ala Val Ala Tyr Glu Ser Met Leu
            180                 185                 190

Arg Ala Ser Glu Leu Ala Asn Ile Arg Val Ser Asp Met Glu Leu Ala
        195                 200                 205

Gly Asp Gly Thr Ala Ile Leu Thr Ile Pro Ile Thr Lys Thr Asn His
    210                 215                 220

Ser Gly Glu Pro Asp Thr Cys Ile Leu Ser Gln Asp Val Val Ser Leu
225                 230                 235                 240

Leu Met Asp Tyr Thr Glu Ala Gly Lys Leu Asp Met Ser Ser Asp Gly
                245                 250                 255

Phe Leu Phe Val Gly Val Ser Lys His Asn Thr Cys Ile Lys Pro Lys
            260                 265                 270

Lys Asp Lys Gln Thr Gly Glu Val Leu His Lys Pro Ile Thr Thr Lys
        275                 280                 285

Thr Val Glu Gly Val Phe Tyr Ser Ala Trp Glu Thr Leu Asp Leu Gly
    290                 295                 300

Arg Gln Gly Val Lys Pro Phe Thr Ala His Ser Ala Arg Val Gly Ala
```

```
                    305                 310                 315                 320
Ala Gln Asp Leu Leu Lys Lys Gly Tyr Asn Thr Leu Gln Ile Gln Gln
                    325                 330                 335

Ser Gly Arg Trp Ser Ser Gly Ala Met Val Ala Arg Tyr Gly Arg Ala
                    340                 345                 350

Ile Leu Ala Arg Asp Gly Ala Met Ala His Ser Arg Val Lys Thr Arg
                    355                 360                 365

Ser Ala Pro Met Gln Trp Gly Lys Asp Glu Lys Asp
                    370                 375                 380

<210> SEQ ID NO 17
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tcaatttctg agaactgtca ttctcggaaa ttga                                      34

<210> SEQ ID NO 18
<211> LENGTH: 1140
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
atgatcgaga accagctgag cctgctgggc gacttttctg gcgtgcggcc cgacgatgtg        60
aaaaccgcca tcaggccgc ccagaaaaag ggcatcaacg tggccgagaa cgagcagttc       120
aaggccgcct tcgagcatct gctgaacgag ttcaagaagc gggaagagag atacagcccc       180
aacaccctgc ggcggctgga aagcgcctgg acctgcttcg tggattggtg cctggccaac       240
cacagacaca gcctgcctgc cacccccgat accgtggaag ccttcttcat cgagcgggcc       300
gaggaactgc accggaacac cctgagcgtg tacagatggg ccatcagccg ggtgcacaga       360
gtggccggat gccctgatcc ctgcctggac atctacgtgg aagatcggct gaaggccatt       420
gcccggaaga agtgcgggga aggcgaggcc gtgaagcagg ccagccccttt caacgagcag       480 catctgctga agctgaccag cctgtggtac agaagcgaca gctgctgct gcggcggaac       540 ctggctctgc tggctgtggc ctacgagagc atgctgagag ccagcgagct ggccaacatc       600
cgggtgtccg atatggaact ggccggcgac ggaaccgcca tcctgaccat ccctatcacc       660
aagaccaacc actccggcga gcccgatacc tgcatcctgt cccaggatgt ggtgtccctg       720
ctgatggact acaccgaggc cggcaagctg gatatgagca gcgacggctt cctgttcgtg       780
ggcgtgtcca gcacaacac ctgtatcaag cccaagaagg acaagcagac cggcgaggtg       840
ctgcacaagc ccatcaccac caagacagtg aaggcgtgt tctacagcgc ctgggagaca       900
ctggacctgg gcagacaggg cgtgaagcct ttcacagccc acagcgccag agtgggagcc       960
gctcaggacc tgctgaagaa gggctacaat accctgcaga tccagcagtc cggccggtgg      1020
tctagcggag ccatggtggc cagatacggc agagccatcc tggctaggga tggcgctatg      1080
gcccacagca gagtgaaaac cagatccgcc cccatgcagt ggggcaagga cgagaaggac      1140

<210> SEQ ID NO 19
<211> LENGTH: 568
```

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 19

Met Ser Ser Tyr Met Asp Leu Val Asp Glu Pro Ala Thr Leu Tyr
1               5                   10                  15

His Lys Phe Val Glu Cys Leu Lys Ala Gly Glu Asn Phe Cys Gly Asp
            20                  25                  30

Lys Leu Ser Gly Ile Ile Thr Met Ala Ile Leu Lys Ala Ile Lys Ala
            35                  40                  45

Leu Thr Glu Val Lys Lys Thr Thr Phe Asn Lys Tyr Lys Thr Thr Ile
50                  55                  60

Lys Gln Gly Leu Gln Tyr Asp Val Gly Ser Ser Thr Ile Ser Phe Val
65                  70                  75                  80

Tyr His Leu Lys Asp Cys Asp Glu Leu Ser Arg Gly Leu Ser Asp Ala
                85                  90                  95

Phe Glu Pro Tyr Lys Phe Lys Ile Lys Ser Asn Lys Glu Ala Thr Ser
            100                 105                 110

Phe Lys Thr Leu Phe Arg Gly Pro Ser Phe Gly Ser Gln Lys Asn Trp
        115                 120                 125

Arg Lys Lys Glu Val Asp Arg Glu Val Asp Asn Leu Phe His Ser Thr
130                 135                 140

Glu Thr Asp Glu Ser Ile Phe Lys Phe Ile Leu Asn Thr Leu Asp Ser
145                 150                 155                 160

Ile Glu Thr Gln Thr Asn Thr Asp Arg Gln Lys Thr Val Leu Thr Phe
                165                 170                 175

Ile Leu Leu Met Thr Phe Phe Asn Cys Cys Arg Asn Asn Asp Leu Met
            180                 185                 190

Asn Val Asp Pro Ser Thr Phe Lys Ile Val Lys Asn Lys Phe Val Gly
        195                 200                 205

Tyr Leu Leu Gln Ala Glu Val Lys Gln Thr Lys Thr Arg Lys Ser Arg
210                 215                 220

Asn Ile Phe Phe Phe Pro Ile Arg Glu Asn Arg Phe Asp Leu Phe Leu
225                 230                 235                 240

Ala Leu His Asp Phe Phe Arg Thr Cys Gln Pro Thr Pro Lys Ser Arg
                245                 250                 255

Leu Ser Asp Gln Val Ser Glu Gln Lys Trp Gln Leu Phe Arg Asp Ser
            260                 265                 270

Met Val Ile Asp Tyr Asn Arg Phe Phe Arg Lys Phe Pro Ala Ser Pro
        275                 280                 285

Ile Phe Ala Ile Lys His Gly Pro Lys Ser His Leu Gly Arg His Leu
290                 295                 300

Met Asn Ser Phe Leu His Lys Asn Glu Leu Asp Ser Trp Ala Asn Ser
305                 310                 315                 320

Leu Gly Asn Trp Ser Ser Ser Gln Asn Gln Arg Glu Ser Gly Ala Arg
                325                 330                 335

Leu Gly Tyr Thr His Gly Gly Arg Asp Leu Pro Gln Pro Leu Phe Gly
            340                 345                 350

Phe Leu Ala Gly Tyr Cys Val Arg Asn Glu Glu Gly His Ile Val Gly
        355                 360                 365

Leu Gly Leu Glu Lys Asp Ile Asn Asp Leu Phe Asp Gly Ile Met Asp
370                 375                 380

```
Pro Leu Asn Glu Lys Glu Asp Thr Glu Ile Cys Glu Ser Tyr Gly Glu
385                 390                 395                 400

Trp Ala Lys Ile Val Ser Lys Asp Val Leu Ile Phe Leu Lys Arg Tyr
            405                 410                 415

His Ser Lys Asn Ala Cys Arg Arg Tyr Gln Asn Ser Thr Leu Tyr Ala
        420                 425                 430

Arg Thr Phe Leu Lys Thr Glu Ser Val Thr Leu Ser Gly Ser Lys Gly
            435                 440                 445

Ser Glu Glu Pro Ser Ser Pro Val Arg Ile Pro Ile Leu Ser Met Gly
        450                 455                 460

Lys Ala Ser Pro Ser Glu Gly Arg Lys Leu Arg Ala Ser Glu His Ala
465                 470                 475                 480

Asn Asp Asp Asn Glu Ile Glu Lys Ile Asp Ser Asp Ser Ser Gln Ser
            485                 490                 495

Glu Glu Ile Pro Ile Glu Met Ser Asp Ser Glu Asp Glu Thr Thr Ala
        500                 505                 510

Ser Asn Ile Ser Gly Ile Tyr Leu Asp Met Ser Lys Ala Asn Ser Asn
        515                 520                 525

Val Val Tyr Ser Pro Pro Ser Gln Thr Gly Arg Ala Ala Gly Ala Gly
        530                 535                 540

Arg Lys Arg Gly Val Gly Gly Arg Arg Thr Val Glu Ser Lys Arg Arg
545                 550                 555                 560

Arg Val Leu Ala Pro Ile Asn Arg
                565

<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ggttgcttaa gaataagtaa ttcttaagca acc                              33

<210> SEQ ID NO 21
<211> LENGTH: 1704
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
atgtccagct acatggacct ggtggacgac gagcccgcca ccctgtacca caagttcgtg    60
gaatgcctga aggccggcga gaacttctgc ggcgataagc tgagcggcat catcaccatg   120
gccattctga aggccatcaa ggccctgacc gaagtgaaga aaaccacctt caacaagtac   180
aagaccacca tcaagcaggg cctgcagtac gacgtgggca gcagcaccat cagcttcgtg   240
taccacctga aggactgcga cgagctgagc agaggcctga gcgacgcctt cgagccctac   300
aagttcaaga tcaagagcaa caagaggcc accagcttca gaccctgtt caggggccct   360 agcttcggca gccagaagaa ctggcggaag aaagaggtgg accgcgaggt ggacaacctg   420
ttccacagca ccgagacaga cgagagcatc ttcaagttca tcctgaacac cctggacagc   480
atcgaaaccc agaccaacac cgaccggcag aaaaccgtgc tgacctttat cctgctgatg   540
```

```
accttcttca actgctgccg aacaacgac ctgatgaacg tggacccag caccttcaag      600 atcgtgaaga acaagtttgt gggctacctg ctgcaggctg aagtgaagca gaccaagacc      660
agaaagagcc ggaatatctt cttcttcccc atccgggaaa accgcttcga cctgttcctg      720
gccctgcacg acttcttcag aacctgccag cccacccca agagcagact gagcgatcag      780
gtgtccgagc agaagtggca gctgttccgg gacagcatgg tcatcgacta caaccggttc      840
tttcggaagt tccccgccag ccccatcttc gccattaagc acggcccaa gtcccacctg      900 ggccggcatc tgatgaacag cttctgcac aagaacgagc tggacagctg gccaacagc       960 ctgggcaatt ggagcagctc ccagaaccag agagagagcg cgccagact gggctacaca     1020 cacggcggaa gagatctgcc ccagcccctg tttggcttcc tggccggata ctgcgtgcgg     1080
aacgaagagg ccacatcgt gggcctgggc ctggaaaagg acatcaacga tctgttcgac     1140
ggcatcatgg acccctgaa cgagaaagag gacaccgaga tctgcgagag ctacggcgag     1200
tgggccaaga ttgtgtccaa ggacgtgctg atcttcctga agagatacca cagcaagaac     1260
gcctgtcgga gataccagaa cagcaccctg tatgcccgga ccttcctgaa aaccgagagc     1320
gtgaccctga gcggctccaa gggcagcgag gaaccttcta gccctgtgcg gatccccatc     1380
ctgagcatgg aaaggccag cccctccgag ggaagaaagc tgagagccag cgagcacgcc     1440
aacgacgaca acgagatcga aagatcgac agcgacagca gccagagcga agagatccct     1500
atcgagatga gcgactccga ggacgagaca accgccagca catcagcgg catctacctg     1560 gacatgagca aggccaactc caacgtggtg tacagccccc ctagccagac aggcagagct     1620
gctggcgccg aagaaaaag aggcgtggga ggcagacgga ccgtggaaag caagcggaga     1680
agagtgctgg cccccatcaa ccgg                                            1704
```

<210> SEQ ID NO 22
<211> LENGTH: 109
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 22

Ser Arg Gly Val Gln Val Glu Thr Ile Ser Pro Gly Asp Gly Arg Thr
1               5                   10                  15

Phe Pro Lys Arg Gly Gln Thr Cys Val Val His Tyr Thr Gly Met Leu
                20                  25                  30

Glu Asp Gly Lys Lys Phe Asp Ser Ser Arg Asp Arg Asn Lys Pro Phe
            35                  40                  45

Lys Phe Met Leu Gly Lys Gln Glu Val Ile Arg Gly Trp Glu Glu Gly
        50                  55                  60

Val Ala Gln Met Ser Val Gly Gln Arg Ala Lys Leu Thr Ile Ser Pro
65                  70                  75                  80

Asp Tyr Ala Tyr Gly Ala Thr Gly His Pro Gly Ile Ile Pro Pro His
                85                  90                  95

Ala Thr Leu Val Phe Asp Val Glu Leu Leu Lys Leu Glu
            100                 105

<210> SEQ ID NO 23
<211> LENGTH: 92
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 23

Ile Leu Trp His Glu Met Trp His Glu Gly Leu Glu Glu Ala Ser Arg
1               5                   10                  15

Leu Tyr Phe Gly Glu Arg Asn Val Lys Gly Met Phe Glu Val Leu Glu
            20                  25                  30

Pro Leu His Ala Met Met Glu Arg Gly Pro Gln Thr Leu Lys Glu Thr
        35                  40                  45

Ser Phe Asn Gln Ala Tyr Gly Arg Asp Leu Met Glu Ala Gln Glu Trp
    50                  55                  60

Cys Arg Lys Tyr Met Lys Ser Gly Asn Val Lys Asp Leu Leu Gln Ala
65                  70                  75                  80

Trp Asp Leu Tyr Tyr His Val Phe Arg Arg Ile Ser
                85                  90

<210> SEQ ID NO 24
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
tctagaggag tgcaggtgga aaccatctcc ccaggagacg ggcgcacctt ccccaagcgc    60
ggccagacct gcgtggtgca ctacaccggg atgcttgaag atggaaagaa atttgattcc   120
tcccgggaca gaaacaagcc ctttaagttt atgctaggca agcaggaggt gatccgaggc   180
tgggaagaag gggttgccca gatgagtgtg ggtcagagag ccaaactgac tatatctcca   240
gattatgcct atggtgccac tgggcaccca ggcatcatcc caccacatgc cactctcgtc   300
ttcgatgtgg agcttctaaa actggaa                                       327

<210> SEQ ID NO 25
<211> LENGTH: 276
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
atcctctggc atgagatgtg gcatgaaggc ctggaagagg catctcgttt gtactttggg    60
gaaaggaacg tgaaaggcat gtttgaggtg ctggagccct gcatgctat gatggaacgg   120 ggcccccaga ctctgaagga aacatccttt aatcaggcct atggtcgaga tttaatggag   180
gcccaagagt ggtgcaggaa gtacatgaaa tcagggaatg tcaaggacct cctccaagcc   240
tgggacctct attatcatgt gttccgacga atctca                             276

<210> SEQ ID NO 26
<211> LENGTH: 188
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Ala Pro Thr Gln Asp Glu Phe Thr Gln Leu Ser Gln Ser Ile Ala Glu
1               5                   10                  15

Phe His Thr Tyr Gln Leu Gly Asn Gly Arg Cys Ser Ser Leu Leu Ala
             20                  25                  30

Gln Arg Ile His Ala Pro Pro Glu Thr Val Trp Ser Val Val Arg Arg
         35                  40                  45

Phe Asp Arg Pro Gln Ile Tyr Lys His Phe Ile Lys Ser Cys Asn Val
 50                  55                  60

Ser Glu Asp Phe Glu Met Arg Val Gly Cys Thr Arg Asp Val Asn Val
 65                  70                  75                  80

Ile Ser Gly Leu Pro Ala Asn Thr Ser Arg Glu Arg Leu Asp Leu Leu
                 85                  90                  95

Asp Asp Asp Arg Arg Val Thr Gly Phe Ser Ile Thr Gly Gly Glu His
                100                 105                 110

Arg Leu Arg Asn Tyr Lys Ser Val Thr Val His Arg Phe Glu Lys
                115                 120                 125

Glu Glu Glu Glu Glu Arg Ile Trp Thr Val Val Leu Glu Ser Tyr Val
130                 135                 140

Val Asp Val Pro Glu Gly Asn Ser Glu Glu Asp Thr Arg Leu Phe Ala
145                 150                 155                 160

Asp Thr Val Ile Arg Leu Asn Leu Gln Lys Leu Ala Ser Ile Thr Glu
                165                 170                 175

Ala Met Asn Tyr Pro Tyr Asp Val Pro Asp Tyr Ala
                180                 185

<210> SEQ ID NO 27
<211> LENGTH: 305
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Pro Leu Tyr Gly Phe Thr Ser Ile Cys Gly Arg Pro Glu Met Glu
1               5                   10                  15

Asp Ala Val Ser Thr Ile Pro Arg Phe Leu Gln Ser Ser Gly Ser
            20                  25                  30

Met Leu Asp Gly Arg Phe Asp Pro Gln Ser Ala Ala His Phe Phe Gly
            35                  40                  45

Val Tyr Asp Gly His Gly Gly Ser Gln Val Ala Asn Tyr Cys Arg Glu
 50                  55                  60

Arg Met His Leu Ala Leu Ala Glu Glu Ile Ala Lys Glu Lys Pro Met
65                  70                  75                  80

Leu Cys Asp Gly Asp Thr Trp Leu Glu Lys Trp Lys Lys Ala Leu Phe
                85                  90                  95

Asn Ser Phe Leu Arg Val Asp Ser Glu Ile Gly Ser Val Ala Pro Glu
                100                 105                 110

Thr Val Gly Ser Thr Ser Val Val Ala Val Val Phe Pro Ser His Ile
            115                 120                 125

Phe Val Ala Asn Cys Gly Asp Ser Arg Ala Val Leu Cys Arg Gly Lys
130                 135                 140

Thr Ala Leu Pro Leu Ser Val Asp His Lys Pro Asp Arg Glu Asp Glu
145                 150                 155                 160

Ala Ala Arg Ile Glu Ala Ala Gly Gly Lys Val Ile Gln Trp Asn Gly
                165                 170                 175

Ala Arg Val Phe Gly Val Leu Ala Met Ser Arg Ser Ile Gly Asp Arg

```
                180             185             190
Tyr Leu Lys Pro Ser Ile Ile Pro Asp Pro Glu Val Thr Ala Val Lys
            195                 200                 205

Arg Val Lys Glu Asp Asp Cys Leu Ile Leu Ala Ser Asp Gly Val Trp
            210                 215                 220

Asp Val Met Thr Asp Glu Ala Cys Glu Met Ala Arg Lys Arg Ile
225                 230                 235                 240

Leu Leu Trp His Lys Lys Asn Ala Val Ala Gly Asp Ala Ser Leu Leu
                245                 250                 255

Ala Asp Glu Arg Arg Lys Glu Gly Lys Asp Pro Ala Ala Met Ser Ala
            260                 265                 270

Ala Glu Tyr Leu Ser Lys Leu Ala Ile Gln Arg Gly Ser Lys Asp Asn
            275                 280                 285

Ile Ser Val Val Val Val Asp Leu Lys Asp Tyr Lys Asp Asp Asp
            290                 295                 300

Lys
305

<210> SEQ ID NO 28
<211> LENGTH: 564
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
gcgccaactc aagacgagtt cacccaactc tcccaatcaa tcgccgagtt ccacacgtac    60
caactcggta acggccgttg ctcatctctc ctagctcagc gaatccacgc gccgccggaa   120
acagtatggt ccgtggtgag acgtttcgat aggccacaga tttacaaaca cttcatcaaa   180
agctgtaacg tgagtgaaga tttcgagatg cgagtgggat gcacgcgcga cgtgaacgtg   240
ataagtggat taccggcgaa tacgtctcga gagagattag atctgttgga cgatgatcgg   300
agagtgactg ggtttagtat aaccggtggt gaacataggc tgaggaatta taaatcggtt   360
acgacggttc atagatttga gaagaagaa gaagaagaaa ggatctggac cgttgttttg   420
gaatcttatg ttgttgatgt accggaaggt aattcggagg aagatacgag attgtttgct   480
gatacggtta ttagattgaa tcttcagaaa cttgcttcga tcactgaagc tatgaactac   540
ccatacgatg ttccagatta cgct                                          564

<210> SEQ ID NO 29
<211> LENGTH: 915
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
cctttgtatg gttttacttc gatttgtgga agaagacctg agatggaaga tgctgtttcg    60
actataccaa gattccttca atcttcctct ggttcgatgt tagatggtcg gtttgatcct   120
caatccgccg ctcatttctt cggtgtttac gacggccatg gcggttctca ggtagcgaac   180
tattgtagag agaggatgca tttggctttg gcggaggaga tagctaagga gaaaccgatg   240
ctctgcgatg tgatacgtg gctggagaag tggaagaaag ctcttttcaa ctcgttcctg   300
agagttgact cggagattgg gtcagttgcg ccggagacgg ttgggtcaac gtcggtggtt   360
```

```
gccgttgttt tcccgtctca catcttcgtc gctaactgcg gtgactctag agccgttctt    420
tgccgcggca aaactgcact tccattatcc gttgaccata aaccggatag agaagatgaa    480
gctgcgagga ttgaagccgc aggagggaaa gtgattcagt ggaatggagc tcgtgttttc    540
ggtgttctcg ccatgtcgag atccattggc gatagatact tgaaaccatc catcattcct    600
gatccggaag tgacggctgt gaagagagta aagaagatg attgtctgat tttggcgagt    660
gacgggtttt gggatgtaat gacggatgaa gaagcgtgtg agatggcaag gaagcggatt    720
ctcttgtggc acaagaaaaa cgcggtggct ggggatgcat cgttgctcgc ggatgagcgg    780
agaaaggaag ggaaagatcc tgcggcgatg tccgcggctg agtatttgtc aaagctggcg    840
atacagagag gaagcaaaga caacataagt gtggtggtgg ttgatttgaa ggattacaag    900
gacgatgacg ataag                                                    915
```

<210> SEQ ID NO 30
<211> LENGTH: 92
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 30

```
Met Lys Arg Asp His His His His His Gln Asp Lys Lys Thr Met
1               5                   10                  15

Met Met Asn Glu Glu Asp Asp Gly Asn Gly Met Asp Glu Leu Leu Ala
            20                  25                  30

Val Leu Gly Tyr Lys Val Arg Ser Ser Glu Met Ala Asp Val Ala Gln
        35                  40                  45

Lys Leu Glu Gln Leu Glu Val Met Met Ser Asn Val Gln Glu Asp Asp
    50                  55                  60

Leu Ser Gln Leu Ala Thr Glu Thr Val His Tyr Asn Pro Ala Glu Leu
65                  70                  75                  80

Tyr Thr Trp Leu Asp Ser Met Leu Thr Asp Leu Asn
                85                  90
```

<210> SEQ ID NO 31
<211> LENGTH: 345
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 31

```
Met Ala Ala Ser Asp Glu Val Asn Leu Ile Glu Ser Arg Thr Val Val
1               5                   10                  15

Pro Leu Asn Thr Trp Val Leu Ile Ser Asn Phe Lys Val Ala Tyr Asn
            20                  25                  30

Ile Leu Arg Arg Pro Asp Gly Thr Phe Asn Arg His Leu Ala Glu Tyr
        35                  40                  45

Leu Asp Arg Lys Val Thr Ala Asn Ala Asn Pro Val Asp Gly Val Phe
    50                  55                  60

Ser Phe Asp Val Leu Ile Asp Arg Arg Ile Asn Leu Leu Ser Arg Val
65                  70                  75                  80

Tyr Arg Pro Ala Tyr Ala Asp Gln Glu Gln Pro Pro Ser Ile Leu Asp
                85                  90                  95
```

Leu Glu Lys Pro Val Asp Gly Asp Ile Val Pro Val Ile Leu Phe Phe
            100                 105                 110

His Gly Gly Ser Phe Ala His Ser Ser Ala Asn Ser Ala Ile Tyr Asp
        115                 120                 125

Thr Leu Cys Arg Arg Leu Val Gly Leu Cys Lys Cys Val Val Ser
    130                 135                 140

Val Asn Tyr Arg Arg Ala Pro Glu Asn Pro Tyr Pro Cys Ala Tyr Asp
145                 150                 155                 160

Asp Gly Trp Ile Ala Leu Asn Trp Val Asn Ser Arg Ser Trp Leu Lys
                165                 170                 175

Ser Lys Lys Asp Ser Lys Val His Ile Phe Leu Ala Gly Asp Ser Ser
            180                 185                 190

Gly Gly Asn Ile Ala His Asn Val Ala Leu Arg Ala Gly Glu Ser Gly
        195                 200                 205

Ile Asp Val Leu Gly Asn Ile Leu Leu Asn Pro Met Phe Gly Gly Asn
210                 215                 220

Glu Arg Thr Glu Ser Glu Lys Ser Leu Asp Gly Lys Tyr Phe Val Thr
225                 230                 235                 240

Val Arg Asp Arg Asp Trp Tyr Trp Lys Ala Phe Leu Pro Glu Gly Glu
                245                 250                 255

Asp Arg Glu His Pro Ala Cys Asn Pro Phe Ser Pro Arg Gly Lys Ser
            260                 265                 270

Leu Glu Gly Val Ser Phe Pro Lys Ser Leu Val Val Ala Gly Leu
        275                 280                 285

Asp Leu Ile Arg Asp Trp Gln Leu Ala Tyr Ala Glu Gly Leu Lys Lys
290                 295                 300

Ala Gly Gln Glu Val Lys Leu Met His Leu Glu Lys Ala Thr Val Gly
305                 310                 315                 320

Phe Tyr Leu Leu Pro Asn Asn Asn His Phe His Asn Val Met Asp Glu
                325                 330                 335

Ile Ser Ala Phe Val Asn Ala Glu Cys
            340                 345

<210> SEQ ID NO 32
<211> LENGTH: 276
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
atgaagcggg accaccacca tcaccatcat caggacaaga aaaccatgat gatgaacgaa      60
gaggacgacg gcaacggcat ggacgagctg ctggctgtgc tgggctacaa agtgcggagc     120
agcgagatgg ccgacgtggc ccagaaactg gaacagctgg aagtgatgat gagcaacgtg     180
caggaagatg acctgtccca gctggccacc gagacagtgc actacaaccc cgccgagctg     240
tacacctggc tggactccat gctgaccgac ctgaac                               276

<210> SEQ ID NO 33
<211> LENGTH: 1035
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33

-continued

```
atggccgcca gcgacgaagt gaacctgatc gagagcagaa ccgtggtgcc cctgaacacc      60
tgggtgctga tctccaactt caaggtggcc tacaacatcc tgcggaggcc cgacggcacc     120
ttcaacagac acctggccga gtacctggac cggaaagtga ccgccaacgc caaccctgtg     180
gacggcgtgt tcagcttcga cgtgctgatc gaccggcgga tcaacctgct gagccgggtg     240
tacagacccg cctacgccga tcaggaacag ccccctcta tcctggatct ggaaaagccc      300
gtggatggcg acatcgtgcc cgtgatcctg ttcttccacg cggcagctt tgcccacagc      360 agcgccaata gcgccatcta cgacaccctg tgcagacggc tcgtgggcct gtgcaaatgc     420
gtggtggtgt ccgtgaacta ccgcagagcc cccgagaacc cttacccctg cgcctacgat     480
gatggctgga tcgccctgaa ctgggtcaac agcagaagct ggctgaagtc caagaaagac     540
agcaaggtgc acatctttct ggccggcgat agcagcggcg caatatcgc ccataacgtg      600 gccctgagag ccggcgagtc tggcatcgat gtgctgggca atatcctgct gaaccccatg     660
ttcggcggca cgagcggac cgagagcgag aagtctctgg acggcaagta cttcgtgacc      720
gtgcgggacc gggactggta ctggaaggcc tttctgcccg agggcgagga cagagagcac     780
cccgcctgca atcccttcag ccccagaggc aaaagcctgg aaggcgtgtc cttcccaaag     840
tccctggtgg tggtggccgg cctggacctg atcagagatt ggcagctggc ctatgccgag     900
ggcctgaaga aagccggcca ggaagtgaag ctgatgcacc tggaaaaggc caccgtgggc     960
ttctacctgc tgcccaacaa caaccacttc cacaacgtga tggacgagat cagcgccttc    1020
gtgaacgccg agtgc                                                    1035
```

<210> SEQ ID NO 34
<211> LENGTH: 7
<212> TYPE: PRT
<213> ORGANISM: Simian virus 40

<400> SEQUENCE: 34

Pro Lys Lys Lys Arg Lys Val
1               5

<210> SEQ ID NO 35
<211> LENGTH: 21
<212> TYPE: DNA
<213> ORGANISM: Simian virus 40

<400> SEQUENCE: 35
cccaagaaaa agcggaaggt g                                              21

<210> SEQ ID NO 36
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ser Gly Gly Ser Gly Ser Gly Ser Ser Gly Gly Ser Gly Thr
1               5                   10

<210> SEQ ID NO 37
<211> LENGTH: 42
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 37
tccggagggt ctggctccgg atcaagtggt ggcagcggta cc                42

<210> SEQ ID NO 38
<211> LENGTH: 722
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

```
Met Ser Gln Phe Asp Ile Leu Cys Lys Thr Pro Lys Val Leu Val
1               5                   10                  15

Arg Gln Phe Val Glu Arg Phe Glu Arg Pro Ser Gly Glu Lys Ile Ala
                20                  25                  30

Ser Cys Ala Ala Glu Leu Thr Tyr Leu Cys Trp Met Ile Thr His Asn
            35                  40                  45

Gly Thr Ala Ile Lys Arg Ala Thr Phe Met Ser Tyr Asn Thr Ile Ile
        50                  55                  60

Ser Asn Ser Leu Ser Phe Asp Ile Val Asn Lys Ser Leu Gln Phe Lys
65                  70                  75                  80

Tyr Lys Thr Gln Lys Ala Thr Ile Leu Glu Ala Ser Leu Lys Lys Leu
                85                  90                  95

Ile Pro Ala Trp Glu Phe Thr Ile Ile Pro Tyr Asn Gly Gln Lys His
            100                 105                 110

Gln Ser Asp Ile Thr Asp Ile Val Ser Ser Leu Gln Leu Gln Phe Glu
        115                 120                 125

Ser Ser Glu Glu Ala Asp Lys Gly Asn Ser His Ser Lys Lys Met Leu
130                 135                 140

Lys Ala Leu Leu Ser Glu Gly Glu Ser Ile Trp Glu Ile Thr Glu Lys
145                 150                 155                 160

Ile Leu Asn Ser Phe Glu Tyr Thr Ser Arg Phe Thr Lys Thr Lys Thr
                165                 170                 175

Leu Tyr Gln Phe Leu Phe Leu Ala Thr Phe Ile Asn Cys Gly Arg Phe
            180                 185                 190

Ser Asp Ile Lys Asn Val Asp Pro Lys Ser Phe Lys Leu Val Gln Asn
        195                 200                 205

Lys Tyr Leu Gly Val Ile Ile Gln Cys Leu Val Thr Glu Thr Lys Thr
210                 215                 220

Ser Val Ser Arg His Ile Tyr Phe Phe Ser Ala Arg Gly Arg Ile Asp
225                 230                 235                 240

Pro Leu Val Tyr Leu Asp Glu Phe Leu Arg Asn Ser Glu Pro Val Leu
                245                 250                 255

Lys Arg Val Asn Arg Thr Gly Asn Ser Ser Ser Asn Lys Gln Glu Tyr
            260                 265                 270

Gln Leu Leu Lys Asp Asn Leu Val Arg Ser Tyr Asn Lys Ala Leu Lys
        275                 280                 285

Lys Asn Ala Pro Tyr Pro Ile Phe Ala Ile Lys Asn Gly Pro Lys Ser
290                 295                 300

His Ile Gly Arg His Leu Met Thr Ser Phe Leu Ser Met Lys Gly Leu
305                 310                 315                 320

Thr Glu Leu Thr Asn Val Val Gly Asn Trp Ser Asp Lys Arg Ala Ser
                325                 330                 335
```

```
Ala Val Ala Arg Thr Thr Tyr Thr His Gln Ile Thr Ala Ile Pro Asp
            340                 345                 350

His Tyr Phe Ala Leu Val Ser Arg Tyr Tyr Ala Tyr Asp Pro Ile Ser
            355                 360                 365

Lys Glu Met Ile Ala Leu Lys Asp Glu Thr Asn Pro Ile Glu Glu Trp
370                 375                 380

Gln His Ile Glu Gln Leu Lys Gly Ser Ala Glu Gly Ser Gly Gly Ser
385                 390                 395                 400

Gly Ser Gly Ser Ser Gly Ser Gly Thr Pro Leu Tyr Gly Phe Thr
                405                 410                 415

Ser Ile Cys Gly Arg Arg Pro Glu Met Glu Asp Ala Val Ser Thr Ile
            420                 425                 430

Pro Arg Phe Leu Gln Ser Ser Ser Gly Ser Met Leu Asp Gly Arg Phe
            435                 440                 445

Asp Pro Gln Ser Ala Ala His Phe Phe Gly Val Tyr Asp Gly His Gly
            450                 455                 460

Gly Ser Gln Val Ala Asn Tyr Cys Arg Glu Arg Met His Leu Ala Leu
465                 470                 475                 480

Ala Glu Glu Ile Ala Lys Glu Lys Pro Met Leu Cys Asp Gly Asp Thr
                485                 490                 495

Trp Leu Glu Lys Trp Lys Lys Ala Leu Phe Asn Ser Phe Leu Arg Val
            500                 505                 510

Asp Ser Glu Ile Gly Ser Val Ala Pro Glu Thr Val Gly Ser Thr Ser
            515                 520                 525

Val Val Ala Val Val Phe Pro Ser His Ile Phe Val Ala Asn Cys Gly
            530                 535                 540

Asp Ser Arg Ala Val Leu Cys Arg Gly Lys Thr Ala Leu Pro Leu Ser
545                 550                 555                 560

Val Asp His Lys Pro Asp Arg Glu Asp Glu Ala Ala Arg Ile Glu Ala
                565                 570                 575

Ala Gly Gly Lys Val Ile Gln Trp Asn Gly Ala Arg Val Phe Gly Val
            580                 585                 590

Leu Ala Met Ser Arg Ser Ile Gly Asp Arg Tyr Leu Lys Pro Ser Ile
            595                 600                 605

Ile Pro Asp Pro Glu Val Thr Ala Val Lys Arg Val Lys Glu Asp Asp
610                 615                 620

Cys Leu Ile Leu Ala Ser Asp Gly Val Trp Asp Val Met Thr Asp Glu
625                 630                 635                 640

Glu Ala Cys Glu Met Ala Arg Lys Arg Ile Leu Leu Trp His Lys Lys
                645                 650                 655

Asn Ala Val Ala Gly Asp Ala Ser Leu Leu Ala Asp Glu Arg Arg Lys
            660                 665                 670

Glu Gly Lys Asp Pro Ala Ala Met Ser Ala Ala Glu Tyr Leu Ser Lys
            675                 680                 685

Leu Ala Ile Gln Arg Gly Ser Lys Asp Asn Ile Ser Val Val Val Val
            690                 695                 700

Asp Leu Lys Asp Tyr Lys Asp Asp Asp Lys Pro Lys Lys Lys Arg
705                 710                 715                 720

Lys Val

<210> SEQ ID NO 39
<211> LENGTH: 237
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 39

```
Met Ala Pro Thr Gln Asp Glu Phe Thr Gln Leu Ser Gln Ser Ile Ala
1               5                   10                  15

Glu Phe His Thr Tyr Gln Leu Gly Asn Gly Arg Cys Ser Ser Leu Leu
            20                  25                  30

Ala Gln Arg Ile His Ala Pro Pro Glu Thr Val Trp Ser Val Val Arg
        35                  40                  45

Arg Phe Asp Arg Pro Gln Ile Tyr Lys His Phe Ile Lys Ser Cys Asn
    50                  55                  60

Val Ser Glu Asp Phe Glu Met Arg Val Gly Cys Thr Arg Asp Val Asn
65                  70                  75                  80

Val Ile Ser Gly Leu Pro Ala Asn Thr Ser Arg Glu Arg Leu Asp Leu
                85                  90                  95

Leu Asp Asp Asp Arg Arg Val Thr Gly Phe Ser Ile Thr Gly Gly Glu
            100                 105                 110

His Arg Leu Arg Asn Tyr Lys Ser Val Thr Thr Val His Arg Phe Glu
        115                 120                 125

Lys Glu Glu Glu Glu Arg Ile Trp Thr Val Val Leu Glu Ser Tyr
    130                 135                 140

Val Val Asp Val Pro Glu Gly Asn Ser Glu Glu Asp Thr Arg Leu Phe
145                 150                 155                 160

Ala Asp Thr Val Ile Arg Leu Asn Leu Gln Lys Leu Ala Ser Ile Thr
                165                 170                 175

Glu Ala Met Asn Tyr Pro Tyr Asp Val Pro Asp Tyr Ala Ser Gly Gly
            180                 185                 190

Ser Gly Ser Gly Ser Ser Gly Gly Ser Gly Thr Ser Ile Arg Tyr Pro
        195                 200                 205

Ala Trp Asn Gly Ile Ile Ser Gln Glu Val Leu Asp Tyr Leu Ser Ser
    210                 215                 220

Tyr Ile Asn Arg Arg Ile Pro Lys Lys Lys Arg Lys Val
225                 230                 235
```

<210> SEQ ID NO 40
<211> LENGTH: 2166
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 40

```
atgagccagt tcgacatcct gtgcaagacc ccccccaagg tgctggtgcg gcagttcgtg     60
gagagattcg agaggcccag cggcgagaag atcgccagct gtgccgccga gctgacctac    120
ctgtgctgga tgatcaccca acggcaccgc catcaagag gccaccctt catgagctac      180 aacaccatca tcagcaacag cctgagcttc gacatcgtga acaagagcct gcagttcaag    240
tacaagaccc agaaggccac catcctggag gccagcctga gaagctgat ccccgcctgg    300 gagttcacca tcatccctta aacggccag aagcaccaga gcgacatcac cgacatcgtg    360
tccagcctgc agctgcagtt cgagagcagc gaggaggccg acaagggcaa cagccacagc    420
aagaagatgc tgaaggccct gctgtccgag ggcgagagca tctgggagat caccgagaag    480
```

| | |
|---|---|
| atcctgaaca gcttcgagta caccagcagg ttcaccaaga ccaagaccct gtaccagttc | 540 |
| ctgttcctgg ccacattcat caactgcggc aggttcagcg acatcaagaa cgtggacccc | 600 |
| aagagcttca agctggtgca gaacaagtac ctgggcgtga tcattcagtg cctggtgacc | 660 |
| gagaccaaga caagcgtgtc caggcacatc tacttttttca cgccagagg caggatcgac | 720 |
| cccctggtgt acctggacga gttcctgagg aacagcgagc ccgtgctgaa gagagtgaac | 780 |
| aggaccggca cagcagcag caacaagcag gagtaccagc tgctgaagga caacctggtg | 840 |
| cgcagctaca caaggccct gaagaagaac gccccctacc ccatcttcgc tatcaagaac | 900 |
| ggccctaaga gccacatcgg caggcacctg atgaccagct ttctgagcat gaagggcctg | 960 |
| accgagctga caaacgtggt gggcaactgg agcgacaaga gggcctccgc cgtggccagg | 1020 |
| accacctaca cccaccagat caccgccatc cccgaccact acttcgccct ggtgtccagg | 1080 |
| tactacgcct acgaccccat cagcaaggag atgatcgccc tgaaggacga gaccaacccc | 1140 |
| atcgaggagt ggcagcacat cgagcagctg aagggcagcg ccgagggctc cggagggtct | 1200 |
| ggctccggat caagtggtgg cagcggtacc cctttgtatg gttttacttc gatttgtgga | 1260 |
| agaagacctg agatggaaga tgctgttttcg actataccaa gattccttca atcttcctct | 1320 |
| ggttcgatgt tagatggtcg gtttgatcct caatccgccg ctcatttctt cggtgtttac | 1380 |
| gacggccatg gcggttctca ggtagcgaac tattgtagag agaggatgca tttggctttg | 1440 |
| gcggaggaga tagctaagga gaaaccgatg ctctgcgatg tgatacgtg gctggagaag | 1500 |
| tggaagaaag ctcttttcaa ctcgttcctg agagttgact cggagattgg gtcagttgcg | 1560 |
| ccggagacgt ttgggtcaac gtcggtggtt gccgttgttt tcccgtctca catcttcgtc | 1620 |
| gctaactgcg gtgactctag agccgttctt tgccgcggca aaactgcact tccattatcc | 1680 |
| gttgaccata aaccggatag agaagatgaa gctgcgagga ttgaagccgc aggagggaaa | 1740 |
| gtgattcagt ggaatggagc tcgtgttttc ggtgttctcg ccatgtcgag atccattggc | 1800 |
| gatagatact tgaaaccatc catcattcct gatccggaag tgacggctgt gaagagagta | 1860 |
| aaagaagatg attgtctgat tttggcgagt gacggggttt gggatgtaat gacggatgaa | 1920 |
| gaagcgtgtg agatggcaag gaagcggatt ctcttgtggc acaagaaaaa cgcggtggct | 1980 |
| ggggatgcat cgttgctcgc ggatgagcgg agaaaggaag gaaagatcc tgcggcgatg | 2040 |
| tccgcggctg agtatttgtc aaagctggcg atacagagag gaagcaaaga caacataagt | 2100 |
| gtggtggtgg ttgatttgaa ggattacaag gacgatgacg ataagcccaa gaaaaagcgg | 2160 |
| aaggtg | 2166 |

<210> SEQ ID NO 41
<211> LENGTH: 500
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Met Arg Ala Leu Val Val Ile Arg Leu Ser Arg Val Thr Asp Ala Thr
1               5                   10                  15

Thr Ser Pro Glu Arg Gln Leu Glu Ser Cys Gln Gln Leu Cys Ala Gln
            20                  25                  30

Arg Gly Trp Asp Val Val Gly Val Ala Glu Asp Leu Asp Val Ser Gly
        35                  40                  45

Ala Val Asp Pro Phe Asp Arg Lys Arg Arg Pro Asn Leu Ala Arg Trp

```
                50                  55                  60
Leu Ala Phe Glu Glu Gln Pro Phe Asp Val Ile Val Ala Tyr Arg Val
 65                  70                  75                  80

Asp Arg Leu Thr Arg Ser Ile Arg His Leu Gln Gln Leu Val His Trp
                     85                  90                  95

Ala Glu Asp His Lys Lys Leu Val Val Ser Ala Thr Glu Ala His Phe
                    100                 105                 110

Asp Thr Thr Thr Pro Phe Ala Ala Val Val Ile Ala Leu Met Gly Thr
                115                 120                 125

Val Ala Gln Met Glu Leu Glu Ala Ile Lys Glu Arg Asn Arg Ser Ala
                130                 135                 140

Ala His Phe Asn Ile Arg Ala Gly Lys Tyr Arg Gly Ser Leu Pro Pro
145                 150                 155                 160

Trp Gly Tyr Leu Pro Thr Arg Val Asp Gly Trp Arg Leu Val Pro
                    165                 170                 175

Asp Pro Val Gln Arg Glu Arg Ile Leu Glu Val Tyr His Arg Val Val
                180                 185                 190

Asp Asn His Glu Pro Leu His Leu Val Ala His Asp Leu Asn Arg Arg
                195                 200                 205

Gly Val Leu Ser Pro Lys Asp Tyr Phe Ala Gln Leu Gln Gly Arg Glu
                210                 215                 220

Pro Gln Gly Arg Glu Trp Ser Ala Thr Ala Leu Lys Arg Ser Met Ile
225                 230                 235                 240

Ser Glu Ala Met Leu Gly Tyr Ala Thr Leu Asn Gly Lys Thr Val Arg
                    245                 250                 255

Asp Asp Asp Gly Ala Pro Leu Val Arg Ala Glu Pro Ile Leu Thr Arg
                260                 265                 270

Glu Gln Leu Glu Ala Leu Arg Ala Glu Leu Val Lys Thr Ser Arg Ala
                275                 280                 285

Lys Pro Ala Val Ser Thr Pro Ser Leu Leu Leu Arg Val Leu Phe Cys
290                 295                 300

Ala Val Cys Gly Glu Pro Ala Tyr Lys Phe Ala Gly Gly Arg Lys
305                 310                 315                 320

His Pro Arg Tyr Arg Cys Arg Ser Met Gly Phe Pro Lys His Cys Gly
                    325                 330                 335

Asn Gly Thr Val Ala Met Ala Glu Trp Asp Ala Phe Cys Glu Glu Gln
                340                 345                 350

Val Leu Asp Leu Leu Gly Asp Ala Glu Arg Leu Glu Lys Val Trp Val
                355                 360                 365

Ala Gly Ser Asp Ser Ala Val Glu Leu Ala Glu Val Asn Ala Glu Leu
370                 375                 380

Val Asp Leu Thr Ser Leu Ile Gly Ser Pro Ala Tyr Arg Ala Gly Ser
385                 390                 395                 400

Pro Gln Arg Glu Ala Leu Asp Ala Arg Ile Ala Ala Leu Ala Ala Arg
                    405                 410                 415

Gln Glu Glu Leu Glu Gly Leu Glu Ala Arg Pro Ser Gly Trp Glu Trp
                420                 425                 430

Arg Glu Thr Gly Gln Arg Phe Gly Asp Trp Arg Glu Gln Asp Thr
                    435                 440                 445

Ala Ala Lys Asn Thr Trp Leu Arg Ser Met Asn Val Arg Leu Thr Phe
                450                 455                 460

Asp Val Arg Gly Gly Leu Thr Arg Thr Ile Asp Phe Gly Asp Leu Gln
465                 470                 475                 480
```

```
Glu Tyr Glu Gln His Leu Arg Leu Gly Ser Val Val Glu Arg Leu His
            485                 490                 495

Thr Gly Met Ser
            500

<210> SEQ ID NO 42
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
tcggccggct tgtcgacgac ggcggtctcc gtcgtcagga tcatccgggc                  50

<210> SEQ ID NO 43
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
gtcgtggttt gtctggtcaa ccaccgcggt ctcagtggtg tacggtacaa accccgac        58

<210> SEQ ID NO 44
<211> LENGTH: 1503
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
atgcgagccc tggtggtcat tcgcctgagc agagtcacag acgctactac aagccctgag      60
cggcagctgg agtcctgtca gcagctgtgc gcacagcgag gatgggatgt ggtcggagtg     120
gcagaggatc tggacgtgag cggggctgtc gatccattcg accgaaagcg agacccaac      180 ctggcacgat ggctggcttt cgaggaacag ccctttgatg tgatcgtcgc ctacagagtg     240
gacaggctga cacgctcaat cgacatctg cagcagctgg tgcattgggc cgaggatcac      300
aagaaactgg tggtcagcgc aactgaagcc cacttcgaca ccacaactcc ttttgccgct     360
gtggtcatcg cactgatggg caccgtggcc cagatggagc tggaagctat caaggagcga     420
aaccggagcg cagcccattt caatattcgg gccgggaaat acagaggcag cctgcccct      480 tggggctatc tgcctacccg ggtgatggg gagtggagac tggtgccaga ccccgtccag     540
agagagagga ttctggaagt gtaccacaga gtggtggaca ccacgaacc actgcatctg     600 gtggcccacg atctgaatag cgcggagtc ctgtctccaa aggactattt tgctcagctg      660
cagggaaggg agccacaggg acgagaatgg agtgctaccg cactgaagcg gtctatgatc     720
agtgaggcta tgctgggcta tgcaactctg aatgggaaaa ccgtgagaga cgatgacgga     780
gcaccactgg tgcgggctga gcctattctg acaagagagc agctgaagc tctgagggca      840 gaactggtga aaaccagtag ggccaagcct gctgtgtcaa caccaagcct gctgctgcga     900
gtgctgttct gcgcagtctg tggcgagcca gcatacaaat tgccggcgg gggaaggaag      960 catcccgct atcgatgccg gagcatgggg ttccctaagc actgtggaaa cggcactgtg    1020
gctatggccg aatgggacgc ctttgtgag gaacaggtgc tggatctgct ggggacgca    1080
```

```
gagcgcctgg aaaaagtgtg ggtcgctgga agcgattccg ctgtggagct ggcagaagtc      1140
aatgccgagc tggtggacct gacctccctg atcggatctc ctgcatacag gcaggctcc      1200 ccacagcgag aagctctgga tgcacgaatt gctgcactgg cagctcgaca ggaggaactg      1260
gaggggctga agccagacc ctctggatgg gagtggcgag aaacaggcca gcggtttggg      1320
gattggtgga gggagcagga cacagcagcc aagaacactt ggctgagatc catgaatgtc      1380
aggctgactt cgacgtgcg aggaggactg acccgaacaa tcgattttgg cgacctgcag      1440
gagtatgaac agcatctgcg cctgggaagt gtggtcgagc gactgcacac cggcatgtca      1500
taa                                                                   1503
```

<210> SEQ ID NO 45
<211> LENGTH: 1530
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 45

```
atggatccta agaaaaagcg aaaagtgatg cgagccctgg tggtcattcg cctgagcaga       60
gtcacagacg ctactacaag ccctgagcgg cagctggagt cctgtcagca gctgtgcgca      120
cagcgaggat gggatgtggt cggagtggca gaggatctgg acgtgagcgg ggctgtcgat      180
ccattcgacc gaaagcggag acccaacctg gcacgatggc tggctttcga ggaacagccc      240
tttgatgtga tcgtcgccta cagagtggac aggctgacac gctcaattcg acatctgcag      300
cagctggtgc attgggccga ggatcacaag aaactggtgg tcagcgcaac tgaagcccac      360
ttcgacacca caactccttt tgccgctgtg gtcatcgcac tgatgggcac cgtggcccag      420
atggagctgg aagctatcaa ggagcgaaac cggagcgcag cccatttcaa tattcgggcc      480
gggaaataca gaggcagcct gccccttgg ggctatctgc ctacccgggt ggatggggag      540
tggagactgg tgccagaccc cgtccagaga gagaggattc tggaagtgta ccacagagtg      600
gtggacaacc acgaaccact gcatctggtg gcccacgatc tgaataggcg cggagtcctg      660
tctccaaagg actatttgc tcagctgcag ggaagggagc cacagggacg agaatggagt      720
gctaccgcac tgaagcggtc tatgatcagt gaggctatgc tgggctatgc aactctgaat      780
gggaaaaccg tgagagacga tgacggagca ccactggtgc gggctgagcc tattctgaca      840
agagagcagc tggaagctct gagggcagaa ctggtgaaaa ccagtagggc caagcctgct      900
gtgtcaacac caagcctgct gctgcgagtg ctgttctgcg cagtctgtgg cgagccagca      960
tacaaatttg ccggcggggg aaggaagcat ccccgctatc gatgccggag catgggggtc     1020
cctaagcact gtggaaacgg cactgtggct atggccgaat gggacgcctt ttgtgaggaa     1080
caggtgctgg atctgctggg ggacgcagag cgcctgaaaa agtgtgggt cgctggaagc     1140 gattccgctg tggagctggc agaagtcaat gccgagctgg tggacctgac ctccctgatc     1200
ggatctcctg catacaggc aggctcccca cagcgagaag ctctggatgc acgaattgct     1260
gcactggcag ctcgacagga ggaactggag gggctgaag ccagaccctc tggatggag      1320 tggcgagaaa caggccagcg gtttggggat tggtgggg agcaggacac agcagccaag      1380
aacacttggc tgagatccat gaatgtcagg ctgactttcg acgtgcgagg aggactgacc      1440
cgaacaatcg attttggcga cctgcaggag tatgaacagc atctgcgcct gggaagtgtg      1500
gtcgagcgac tgcacaccgg catgtcataa                                     1530
```

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Met Asp Pro Lys Lys Lys Arg Lys Val
1               5

<210> SEQ ID NO 47

<400> SEQUENCE: 47

000

<210> SEQ ID NO 48

<400> SEQUENCE: 48

000

<210> SEQ ID NO 49

<400> SEQUENCE: 49

000

<210> SEQ ID NO 50
<211> LENGTH: 711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
atggcgccaa ctcaagacga gttcacccaa ctctcccaat caatcgccga gttccacacg      60
taccaactcg gtaacggccg ttgctcatct ctcctagctc agcgaatcca cgcgccgccg     120
gaaacagtat ggtccgtggt gagacgtttc gataggccac agatttacaa acacttcatc     180
aaaagctgta acgtgagtga agatttcgag atgcgagtgg gatgcacgcg cgacgtgaac     240
gtgataagtg gattaccggc gaatacgtct cgagagagat tagatctgtt ggacgatgat     300
cggagagtga ctgggtttag tataaccggt ggtgaacata ggctgaggaa ttataaatcg     360
gttacgacgg ttcatagatt tgagaaagaa gaagaagaag aaaggatctg gaccgttgtt     420
ttggaatctt atgttgttga tgtaccggaa ggtaattcgg aggaagatac gagattgttt     480
gctgatacgg ttattagatt gaatcttcag aaacttgctt cgatcactga agctatgaac     540
tacccatacg atgttccaga ttacgcttcc ggagggtctg gctccggatc aagtggtggc     600
agcggtacca gcatcagata ccccgcctgg aacggcatca tcagccagga ggtgctggac     660
tacctgagca gctacatcaa caggcggatc cccaagaaaa gcggaaggt g     711

<210> SEQ ID NO 51
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

```
His Thr Leu Tyr Ala Pro Gly Gly Tyr Asp Ile Met Gly Tyr Leu Asp
1               5                   10                  15

Gln Ile Gly Asn Arg Pro Asn Pro Gln Val Glu Leu Gly Pro Val Asp
            20                  25                  30

Thr Ser Cys Ala Leu Ile Leu Cys Asp Leu Lys Gln Lys Asp Thr Pro
        35                  40                  45

Ile Val Tyr Ala Ser Glu Ala Phe Leu Tyr Met Thr Gly Tyr Ser Asn
    50                  55                  60

Ala Glu Val Leu Gly Arg Asn Cys Arg Phe Leu Gln Ser Pro Asp Gly
65                  70                  75                  80

Met Val Lys Pro Lys Ser Thr Arg Lys Tyr Val Asp Ser Asn Thr Ile
                85                  90                  95

Asn Thr Met Arg Lys Ala Ile Asp Arg Asn Ala Glu Val Gln Val Glu
            100                 105                 110

Val Val Asn Phe Lys Lys Asn Gly Gln Arg Phe Val Asn Phe Leu Thr
        115                 120                 125

Met Ile Pro Val Arg Asp Glu Thr Gly Glu Tyr Arg Tyr Ser Met Gly
    130                 135                 140

Phe Gln Cys Glu Thr Glu
145                 150
```

<210> SEQ ID NO 52
<211> LENGTH: 150
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 52

```
His Thr Leu Tyr Ala Pro Gly Gly Tyr Asp Ile Met Gly Tyr Leu Arg
1               5                   10                  15

Gln Ile Arg Asn Arg Pro Asn Pro Gln Val Glu Leu Gly Pro Val Asp
            20                  25                  30

Thr Ser Cys Ala Leu Ile Leu Cys Asp Leu Lys Gln Lys Asp Thr Pro
        35                  40                  45

Ile Val Tyr Ala Ser Glu Ala Phe Leu Tyr Met Thr Gly Tyr Ser Asn
    50                  55                  60

Ala Glu Val Leu Gly Arg Asn Cys Arg Phe Leu Gln Ser Pro Asp Gly
65                  70                  75                  80

Met Val Lys Pro Lys Ser Thr Arg Lys Tyr Val Asp Ser Asn Thr Ile
                85                  90                  95

Asn Thr Met Arg Lys Ala Ile Asp Arg Asn Ala Glu Val Gln Val Glu
            100                 105                 110

Val Val Asn Phe Lys Lys Asn Gly Gln Arg Phe Val Asn Phe Leu Thr
        115                 120                 125

Met Ile Pro Val Arg Asp Glu Thr Gly Glu Tyr Arg Tyr Ser Met Gly
    130                 135                 140

Phe Gln Cys Glu Thr Glu
145                 150
```

<210> SEQ ID NO 53
<211> LENGTH: 450
<212> TYPE: DNA
<213> ORGANISM: Artificial Sequence -continued
<220> FEATURE:
<223> OTHER INFORMATION: Description of Artificial Sequence: Synthetic
      polynucleotide

<400> SEQUENCE: 53

```
catactcttt atgccccgg tggatatgac attatgggat atctggacca gatcggcaac    60
cggccaaacc cgcaggtgga actgggcccc gtggatacat cctgcgcctt gattctttgt   120
gacctgaaac agaaagacac cccgatagtt tacgcgagtg aagccttcct ctacatgaca   180
ggttacagca acgcagaggt gctgggccgg aattgccggt ttctgcaaag ccctgacggc   240
atggtgaagc ccaagagcac ccggaagtac gtggatagta acacaatcaa tactatgcgc   300
aaggcaatcg acaggaatgc cgaggtgcag gttgaagtag tcaattttaa aaagaatgga   360
cagcgatttg ttaatttcct gactatgata cctgttaggg acgaaacagg cgagtatcga   420
tactctatgg gattccagtg cgaaacagaa                                    450
```

<210> SEQ ID NO 54
<211> LENGTH: 450
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54

```
catactcttt atgccccgg tggatatgac attatgggat atctgaggca gatcaggaac    60
cggccaaacc cgcaggtgga actgggcccc gtggatacat cctgcgcctt gattctttgt   120
gacctgaaac agaaagacac cccgatagtt tacgcgagtg aagccttcct ctacatgaca   180
ggttacagca acgcagaggt gctgggccgg aattgccggt ttctgcaaag ccctgacggc   240
atggtgaagc ccaagagcac ccggaagtac gtggatagta acacaatcaa tactatgcgc   300
aaggcaatcg acaggaatgc cgaggtgcag gttgaagtag tcaattttaa aaagaatgga   360
cagcgatttg ttaatttcct gactatgata cctgttaggg acgaaacagg cgagtatcga   420
tactctatgg gattccagtg cgaaacagaa                                    450
```

<210> SEQ ID NO 55
<211> LENGTH: 171
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

```
Met Asn Gly Ala Ile Gly Gly Asp Leu Leu Leu Asn Phe Pro Asp Met
1               5                   10                  15

Ser Val Leu Glu Arg Gln Arg Ala His Leu Lys Tyr Leu Asn Pro Thr
            20                  25                  30

Phe Asp Ser Pro Leu Ala Gly Phe Phe Ala Asp Ser Ser Met Ile Thr
        35                  40                  45

Gly Gly Glu Met Asp Ser Tyr Leu Ser Thr Ala Gly Leu Asn Leu Pro
    50                  55                  60

Met Met Tyr Gly Glu Thr Thr Val Glu Gly Asp Ser Arg Leu Ser Ile
65                  70                  75                  80

Ser Pro Glu Thr Thr Leu Gly Thr Gly Asn Phe Lys Lys Arg Lys Phe
                85                  90                  95

Asp Thr Glu Thr Lys Asp Cys Asn Glu Lys Lys Lys Lys Met Thr Met
```

```
                    100                 105                 110
Asn Arg Asp Asp Leu Val Glu Glu Gly Glu Glu Lys Ser Lys Ile
            115                 120                 125
Thr Glu Gln Asn Asn Gly Ser Thr Lys Ser Ile Lys Lys Met Lys His
            130                 135                 140
Lys Ala Lys Lys Glu Glu Asn Asn Phe Ser Asn Asp Ser Ser Lys Val
145                 150                 155                 160
Thr Lys Glu Leu Glu Lys Thr Asp Tyr Ile His
                165                 170

<210> SEQ ID NO 56
<211> LENGTH: 612
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Met Lys Met Asp Lys Lys Thr Ile Val Trp Phe Arg Arg Asp Leu Arg
1               5                   10                  15
Ile Glu Asp Asn Pro Ala Leu Ala Ala Ala His Glu Gly Ser Val
            20                  25                  30
Phe Pro Val Phe Ile Trp Cys Pro Glu Glu Gly Gln Phe Tyr Pro
        35                  40                  45
Gly Arg Ala Ser Arg Trp Trp Met Lys Gln Ser Leu Ala His Leu Ser
    50                  55                  60
Gln Ser Leu Lys Ala Leu Gly Ser Asp Leu Thr Leu Ile Lys Thr His
65                  70                  75                  80
Asn Thr Ile Ser Ala Ile Leu Asp Cys Ile Arg Val Thr Gly Ala Thr
                85                  90                  95
Lys Val Val Phe Asn His Leu Tyr Asp Pro Val Ser Leu Val Arg Asp
            100                 105                 110
His Thr Val Lys Glu Lys Leu Val Glu Arg Gly Ile Ser Val Gln Ser
        115                 120                 125
Tyr Asn Gly Asp Leu Leu Tyr Glu Pro Trp Glu Ile Tyr Cys Glu Lys
    130                 135                 140
Gly Lys Pro Phe Thr Ser Phe Asn Ser Tyr Trp Lys Lys Cys Leu Asp
145                 150                 155                 160
Met Ser Ile Glu Ser Val Met Leu Pro Pro Pro Trp Arg Leu Met Pro
                165                 170                 175
Ile Thr Ala Ala Ala Glu Ala Ile Trp Ala Cys Ser Ile Glu Glu Leu
            180                 185                 190
Gly Leu Glu Asn Glu Ala Glu Lys Pro Ser Asn Ala Leu Leu Thr Arg
        195                 200                 205
Ala Trp Ser Pro Gly Trp Ser Asn Ala Asp Lys Leu Leu Asn Glu Phe
    210                 215                 220
Ile Glu Lys Gln Leu Ile Asp Tyr Ala Lys Asn Ser Lys Lys Val Val
225                 230                 235                 240
Gly Asn Ser Thr Ser Leu Leu Ser Pro Tyr Leu His Phe Gly Glu Ile
                245                 250                 255
Ser Val Arg His Val Phe Gln Cys Ala Arg Met Lys Gln Ile Ile Trp
            260                 265                 270
Ala Arg Asp Lys Asn Ser Glu Gly Glu Glu Ser Ala Asp Leu Phe Leu
        275                 280                 285
```

Arg Gly Ile Gly Leu Arg Glu Tyr Ser Arg Tyr Ile Cys Phe Asn Phe
    290                 295                 300

Pro Phe Thr His Glu Gln Ser Leu Leu Ser His Leu Arg Phe Phe Pro
305                 310                 315                 320

Trp Asp Ala Asp Val Asp Lys Phe Lys Ala Trp Arg Gln Gly Arg Thr
                325                 330                 335

Gly Tyr Pro Leu Val Asp Ala Gly Met Arg Glu Leu Trp Ala Thr Gly
            340                 345                 350

Trp Met His Asn Arg Ile Arg Val Ile Val Ser Ser Phe Ala Val Lys
            355                 360                 365

Phe Leu Leu Leu Pro Trp Lys Trp Gly Met Lys Tyr Phe Trp Asp Thr
370                 375                 380

Leu Leu Asp Ala Asp Leu Glu Cys Asp Ile Leu Gly Trp Gln Tyr Ile
385                 390                 395                 400

Ser Gly Ser Ile Pro Asp Gly His Glu Leu Asp Arg Leu Asp Asn Pro
                405                 410                 415

Ala Leu Gln Gly Ala Lys Tyr Asp Pro Glu Gly Glu Tyr Ile Arg Gln
            420                 425                 430

Trp Leu Pro Glu Leu Ala Arg Leu Pro Thr Glu Trp Ile His His Pro
            435                 440                 445

Trp Asp Ala Pro Leu Thr Val Leu Lys Ala Ser Gly Val Glu Leu Gly
450                 455                 460

Thr Asn Tyr Ala Lys Pro Ile Val Asp Ile Asp Thr Ala Arg Glu Leu
465                 470                 475                 480

Leu Ala Lys Ala Ile Ser Arg Thr Arg Glu Ala Gln Ile Met Ile Gly
                485                 490                 495

Ala Ala Pro Asp Glu Ile Val Ala Asp Ser Phe Glu Ala Leu Gly Ala
            500                 505                 510

Asn Thr Ile Lys Glu Pro Gly Leu Cys Pro Ser Val Ser Ser Asn Asp
            515                 520                 525

Gln Gln Val Pro Ser Ala Val Arg Tyr Asn Gly Ser Lys Arg Val Lys
530                 535                 540

Pro Glu Glu Glu Glu Arg Asp Met Lys Lys Ser Arg Gly Phe Asp
545                 550                 555                 560

Glu Arg Glu Leu Phe Ser Thr Ala Glu Ser Ser Ser Ser Ser Val
                565                 570                 575

Phe Phe Val Ser Gln Ser Cys Ser Leu Ala Ser Glu Gly Lys Asn Leu
            580                 585                 590

Glu Gly Ile Gln Asp Ser Ser Asp Gln Ile Thr Thr Ser Leu Gly Lys
            595                 600                 605

Asn Gly Cys Lys
    610

<210> SEQ ID NO 57
<211> LENGTH: 513
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
atgaatggag ctataggagg tgaccttttg ctcaattttc ctgacatgtc ggtcctagag     60
cgccaaaggg ctcacctcaa gtacctcaat cccacctttg attctcctct cgccggcttc    120
tttgccgatt cttcaatgat taccggcggc gagatggaca gctatctttc gactgccggt    180

```
ttgaatcttc cgatgatgta cggtgagacg acggtggaag gtgattcaag actctcaatt    240
tcgccggaaa cgacgcttgg gactggaaat ttcaagaaac ggaagtttga tacagagact    300
aaggattgta atgagaagaa gaagaagatg acgatgaaca gagatgacct agtagaagaa    360
ggagaagaag agaagtcgaa aataacagag caaaacaatg ggagcacaaa aagcatcaag    420
aagatgaaac acaaagccaa gaaagaagag aacaatttct ctaatgattc atctaaagtg    480
acgaaggaat tggagaaaac ggattatatt cat                                  513

<210> SEQ ID NO 58
<211> LENGTH: 1836
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
atgaagatgg acaaaaagac tatagtttgg tttagaagag acctaaggat tgaggataat     60
cctgcattag cagcagctgc tcacgaagga tctgtttttc ctgtcttcat ttggtgtcct    120
gaagaagaag gacagtttta tcctggaaga gcttcaagat ggtggatgaa acaatcactt    180
gctcacttat ctcaatcctt gaaggctctt ggatctgacc tcactttaat caaaacccac    240
aacacgattt cagcgatctt ggattgtatc cgcgttaccg tgctacaaa agtcgtcttt     300 aaccacctct atgatcctgt ttcgttagtt cgggaccata ccgtaaagga agctggtg     360 gaacgtggga tctctgtgca aagctacaat ggagatctat tgtatgaacc gtgggagata    420
tactgcgaaa agggcaaacc ttttacgagt ttcaattctt actggaagaa atgcttagat    480
atgtcgattg aatccgttat gcttcctcct ccttggcggt tgatgccaat aactgcagcg    540
gctgaagcga tttgggcgtg ttcgattgaa gaactagggc tggagaatga ggccgagaaa    600
ccgagcaatg cgttgttaac tagagcttgg tctccaggat ggagcaatgc tgataagtta    660
ctaaatgagt tcatcgagaa gcagttgata gattatgcaa agaacagcaa gaaagttgtt    720
ggaaattcta cttcactact ttctccgtat ctccatttcg gggaaataag cgtcagacac    780
gttttccagt gtgcccggat gaaacaaatt atatgggcaa gagataagaa cagtgaagga    840
gaagaaagtg cagatctttt tcttagggga atcggtttaa gagagtattc tcggtatata    900
tgtttcaact tcccgtttac tcacgagcaa tcgttgttga gtcatcttcg gttttttccct    960 tgggatgctg atgttgataa gttcaaggcc tggagacaag gcaggaccgg ttatccgttg   1020
gtggatgccg gaatgagaga gctttgggct accggatgga tgcataacag aataagagtg   1080
attgtttcaa gctttgctgt gaagtttctt ctccttccat ggaaatgggg aatgaagtat   1140
ttctgggata cacttttgga tgctgatttg gaatgtgaca tccttggctg gcagtatatc   1200
tctgggagta tccccgatgg ccacgagctt gatcgcttgg acaatcccgc gttacaaggc   1260
gccaaatatg acccagaagg tgagtacata aggcaatggc ttcccgagct tgcgagattg   1320
ccaactgaat ggatccatca tccatgggac gctccttttaa ccgtactcaa agcttctggt   1380
gtggaactcg gaacaaacta tgcgaaaccc attgtagaca tcgacacagc tcgtgagcta   1440
ctagctaaag ctatttcaag aaccgtgaa gcacagatca tgatcggagc agcacctgat   1500
gagattgtag cagatagctt cgaggcctta ggggctaata ccattaaaga acctggtctt   1560
tgcccatctg tgtcttctaa tgaccaacaa gtaccttcgg ctgttcgtta caacgggtca   1620
aagagagtga aacctgagga agaagaagag agagacatga agaaatctag gggattcgat   1680
```

```
gaaagggagt tgttttcgac tgctgaatct tcttcttctt cgagtgtgtt tttcgtttcg    1740
cagtcttgct cgttggcatc agaagggaag aatctggaag gtattcaaga ttcatctgat    1800
cagattacta caagtttggg aaaaaatggt tgcaaa                              1836
```

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59

```
atcgttctct atcactgata                                                  20
```

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60

```
ggcggtggcg ggggaggagg                                                  20
```

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61

```
gcgcccatga aattttaatg                                                  20
```

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62

```
tggcgccctg ccctctgctg                                                  20
```

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63

```
ccttggtgaa gtctcctttg                                                  20
```

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 64
catgtacgtt gctatccagg c                                              21

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
ctccttaatg tcacgcacga t                                              21

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
tgggtctggt acacgattgc                                                20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
gggtctcgat cttggtgagc                                                20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
tggctggggt ttgaaccttt                                                20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
aggaagctgt tccagactgc                                                20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 70
atgtgtgacg acgaggagac                                                    20

<210> SEQ ID NO 71
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
cacgatggac gggaagac                                                      18

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
tgttgccact ggtgctaaag                                                    20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
acagcagtct tctccgcttc                                                    20

<210> SEQ ID NO 74
<211> LENGTH: 343
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala Ala Trp Cys Lys Leu Asn Asn Arg Lys Trp Phe
    50                  55                  60

Pro Ala Glu Pro Glu Asp Val Arg Asp Tyr Leu Leu Tyr Leu Gln Ala
65                  70                  75                  80

Arg Gly Leu Ala Val Lys Thr Ile Gln Gln His Leu Gly Gln Leu Asn
                85                  90                  95

Met Leu His Arg Arg Ser Gly Leu Pro Arg Pro Ser Asp Ser Asn Ala
            100                 105                 110

Val Ser Leu Val Met Arg Arg Ile Arg Lys Glu Asn Val Asp Ala Gly
        115                 120                 125

```
Glu Arg Ala Lys Gln Ala Leu Ala Phe Glu Arg Thr Asp Phe Asp Gln
            130                 135                 140

Val Arg Ser Leu Met Glu Asn Ser Asp Arg Cys Gln Asp Ile Arg Asn
145                 150                 155                 160

Leu Ala Phe Leu Gly Ile Ala Tyr Asn Thr Leu Leu Arg Ile Ala Glu
                165                 170                 175

Ile Ala Arg Ile Arg Val Lys Asp Ile Ser Arg Thr Asp Gly Gly Arg
            180                 185                 190

Met Leu Ile His Ile Gly Arg Thr Lys Thr Leu Val Ser Thr Ala Gly
            195                 200                 205

Val Glu Lys Ala Leu Ser Leu Gly Val Thr Lys Leu Val Glu Arg Trp
210                 215                 220

Ile Ser Val Ser Gly Val Ala Asp Asp Pro Asn Asn Tyr Leu Phe Cys
225                 230                 235                 240

Arg Val Arg Lys Asn Gly Val Ala Ala Pro Ser Ala Thr Ser Gln Leu
                245                 250                 255

Ser Thr Arg Ala Leu Glu Gly Ile Phe Glu Ala Thr His Arg Leu Ile
                260                 265                 270

Tyr Gly Ala Lys Asp Asp Ser Gly Gln Arg Tyr Leu Ala Trp Ser Gly
            275                 280                 285

His Ser Ala Arg Val Gly Ala Ala Arg Asp Met Ala Arg Ala Gly Val
            290                 295                 300

Ser Ile Pro Glu Ile Met Gln Ala Gly Gly Trp Thr Asn Val Asn Ile
305                 310                 315                 320

Val Met Asn Tyr Ile Arg Asn Leu Asp Ser Glu Thr Gly Ala Met Val
                325                 330                 335

Arg Leu Leu Glu Asp Gly Asp
            340

<210> SEQ ID NO 75
<211> LENGTH: 422
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Ser Ser Tyr Met Asp Leu Val Asp Asp Glu Pro Ala Thr Leu Tyr His
1               5                   10                  15

Lys Phe Val Glu Cys Leu Lys Ala Gly Glu Asn Phe Cys Gly Asp Lys
                20                  25                  30

Leu Ser Gly Ile Ile Thr Met Ala Ile Leu Lys Ala Ile Lys Ala Leu
            35                  40                  45

Thr Glu Val Lys Lys Thr Thr Phe Asn Lys Tyr Lys Thr Thr Ile Lys
50                  55                  60

Gln Gly Leu Gln Tyr Asp Val Gly Ser Ser Thr Ile Ser Phe Val Tyr
65                  70                  75                  80

His Leu Lys Asp Cys Asp Glu Leu Ser Arg Gly Leu Ser Asp Ala Phe
                85                  90                  95

Glu Pro Tyr Lys Phe Lys Ile Lys Ser Asn Lys Glu Ala Thr Ser Phe
                100                 105                 110

Lys Thr Leu Phe Arg Gly Pro Ser Phe Gly Ser Gln Lys Asn Trp Arg
            115                 120                 125

Lys Lys Glu Val Asp Arg Glu Val Asp Asn Leu Phe His Ser Thr Glu
130                 135                 140
```

Thr Asp Glu Ser Ile Phe Lys Phe Ile Leu Asn Thr Leu Asp Ser Ile
145                 150                 155                 160

Glu Thr Gln Thr Asn Thr Asp Arg Gln Lys Thr Val Leu Thr Phe Ile
            165                 170                 175

Leu Leu Met Thr Phe Phe Asn Cys Cys Arg Asn Asn Asp Leu Met Asn
        180                 185                 190

Val Asp Pro Ser Thr Phe Lys Ile Val Lys Asn Lys Phe Val Gly Tyr
    195                 200                 205

Leu Leu Gln Ala Glu Val Lys Gln Thr Lys Thr Arg Lys Ser Arg Asn
210                 215                 220

Ile Phe Phe Phe Pro Ile Arg Glu Asn Arg Phe Asp Leu Phe Leu Ala
225                 230                 235                 240

Leu His Asp Phe Phe Arg Thr Cys Gln Pro Thr Pro Lys Ser Arg Leu
                245                 250                 255

Ser Asp Gln Val Ser Glu Gln Lys Trp Gln Leu Phe Arg Asp Ser Met
            260                 265                 270

Val Ile Asp Tyr Asn Arg Phe Phe Arg Lys Phe Pro Ala Ser Pro Ile
        275                 280                 285

Phe Ala Ile Lys His Gly Pro Lys Ser His Leu Gly Arg His Leu Met
    290                 295                 300

Asn Ser Phe Leu His Lys Asn Glu Leu Asp Ser Trp Ala Asn Ser Leu
305                 310                 315                 320

Gly Asn Trp Ser Ser Ser Gln Asn Gln Arg Glu Ser Gly Ala Arg Leu
                325                 330                 335

Gly Tyr Thr His Gly Gly Arg Asp Leu Pro Gln Pro Leu Phe Gly Phe
            340                 345                 350

Leu Ala Gly Tyr Cys Val Arg Asn Glu Glu Gly His Ile Val Gly Leu
        355                 360                 365

Gly Leu Glu Lys Asp Ile Asn Asp Leu Phe Asp Gly Ile Met Asp Pro
    370                 375                 380

Leu Asn Glu Lys Glu Asp Thr Glu Ile Cys Glu Ser Tyr Gly Glu Trp
385                 390                 395                 400

Ala Lys Ile Val Ser Lys Asp Val Leu Ile Phe Leu Lys Arg Tyr His
                405                 410                 415

Ser Lys Asn Ala Cys Arg
            420

<210> SEQ ID NO 76
<211> LENGTH: 421
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Pro Gln Phe Asp Ile Leu Cys Lys Thr Pro Lys Val Leu Val Arg
1               5                   10                  15

Gln Phe Val Glu Arg Phe Glu Arg Pro Ser Gly Glu Lys Ile Ala Ser
                20                  25                  30

Cys Ala Ala Glu Leu Thr Tyr Leu Cys Trp Met Ile Thr His Asn Gly
            35                  40                  45

Thr Ala Ile Lys Arg Ala Thr Phe Met Ser Tyr Asn Thr Ile Ile Ser
        50                  55                  60

Asn Ser Leu Ser Phe Asp Ile Val Asn Lys Ser Leu Gln Phe Lys Tyr

```
            65                  70                  75                  80
Lys Thr Gln Lys Ala Thr Ile Leu Glu Ala Ser Leu Lys Lys Leu Ile
                85                  90                  95

Pro Ala Trp Glu Phe Thr Ile Ile Pro Tyr Asn Gly Gln Lys His Gln
            100                 105                 110

Ser Asp Ile Thr Asp Ile Val Ser Leu Gln Leu Gln Phe Glu Ser
            115                 120                 125

Ser Glu Glu Ala Asp Lys Gly Asn Ser His Ser Lys Lys Met Leu Lys
        130                 135                 140

Ala Leu Leu Ser Glu Gly Glu Ser Ile Trp Glu Ile Thr Glu Lys Ile
145                 150                 155                 160

Leu Asn Ser Phe Glu Tyr Thr Ser Arg Phe Thr Lys Thr Lys Thr Leu
                165                 170                 175

Tyr Gln Phe Leu Phe Leu Ala Thr Phe Ile Asn Cys Gly Arg Phe Ser
            180                 185                 190

Asp Ile Lys Asn Val Asp Pro Lys Ser Phe Lys Leu Val Gln Asn Lys
            195                 200                 205

Tyr Leu Gly Val Ile Ile Gln Cys Leu Val Thr Glu Thr Lys Thr Ser
        210                 215                 220

Val Ser Arg His Ile Tyr Phe Phe Ser Ala Arg Gly Arg Ile Asp Pro
225                 230                 235                 240

Leu Val Tyr Leu Asp Glu Phe Leu Arg Asn Ser Glu Pro Val Leu Lys
                245                 250                 255

Arg Val Asn Arg Thr Gly Asn Ser Ser Ser Asn Lys Gln Glu Tyr Gln
            260                 265                 270

Leu Leu Lys Asp Asn Leu Val Arg Ser Tyr Asn Lys Ala Leu Lys Lys
        275                 280                 285

Asn Ala Pro Tyr Pro Ile Phe Ala Ile Lys Asn Gly Pro Lys Ser His
        290                 295                 300

Ile Gly Arg His Leu Met Thr Ser Phe Leu Ser Met Lys Gly Leu Thr
305                 310                 315                 320

Glu Leu Thr Asn Val Val Gly Asn Trp Ser Asp Lys Arg Ala Ser Ala
                325                 330                 335

Val Ala Arg Thr Thr Tyr Thr His Gln Ile Thr Ala Ile Pro Asp His
            340                 345                 350

Tyr Phe Ala Leu Val Ser Arg Tyr Tyr Ala Tyr Asp Pro Ile Ser Lys
        355                 360                 365

Glu Met Ile Ala Leu Lys Asp Glu Thr Asn Pro Ile Glu Glu Trp Gln
    370                 375                 380

His Ile Glu Gln Leu Lys Gly Ser Ala Glu Gly Ser Ile Arg Tyr Pro
385                 390                 395                 400

Ala Trp Asn Gly Ile Ile Ser Gln Glu Val Leu Asp Tyr Leu Ser Ser
                405                 410                 415

Tyr Ile Asn Arg Arg
            420

<210> SEQ ID NO 77
<211> LENGTH: 325
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77
```

-continued

```
Ala Ala Phe Glu His Leu Leu Asn Glu Phe Lys Lys Arg Glu Glu Arg
1               5                   10                  15

Tyr Ser Pro Asn Thr Leu Arg Arg Leu Glu Ser Ala Trp Thr Cys Phe
            20                  25                  30

Val Asp Trp Cys Leu Ala Asn His Arg His Ser Leu Pro Ala Thr Pro
                35                  40                  45

Asp Thr Val Glu Ala Phe Phe Ile Glu Arg Ala Glu Glu Leu His Arg
        50                  55                  60

Asn Thr Leu Ser Val Tyr Arg Trp Ala Ile Ser Arg Val His Arg Val
65                  70                  75                  80

Ala Gly Cys Pro Asp Pro Cys Leu Asp Ile Tyr Val Glu Asp Arg Leu
                85                  90                  95

Lys Ala Ile Ala Arg Lys Lys Val Arg Glu Gly Glu Ala Val Lys Gln
                100                 105                 110

Ala Ser Pro Phe Asn Glu Gln His Leu Leu Lys Leu Thr Ser Leu Trp
            115                 120                 125

Tyr Arg Ser Asp Lys Leu Leu Leu Arg Arg Asn Leu Ala Leu Leu Ala
        130                 135                 140

Val Ala Tyr Glu Ser Met Leu Arg Ala Ser Glu Leu Ala Asn Ile Arg
145                 150                 155                 160

Val Ser Asp Met Glu Leu Ala Gly Asp Gly Thr Ala Ile Leu Thr Ile
                165                 170                 175

Pro Ile Thr Lys Thr Asn His Ser Gly Glu Pro Asp Thr Cys Ile Leu
                180                 185                 190

Ser Gln Asp Val Val Ser Leu Leu Met Asp Tyr Thr Glu Ala Gly Lys
            195                 200                 205

Leu Asp Met Ser Ser Asp Gly Phe Leu Phe Val Gly Val Ser Lys His
        210                 215                 220

Asn Thr Cys Ile Lys Pro Lys Lys Asp Lys Gln Thr Gly Glu Val Leu
225                 230                 235                 240

His Lys Pro Ile Thr Thr Lys Thr Val Glu Gly Val Phe Tyr Ser Ala
                245                 250                 255

Trp Glu Thr Leu Asp Leu Gly Arg Gln Gly Val Lys Pro Phe Thr Ala
            260                 265                 270

His Ser Ala Arg Val Gly Ala Ala Gln Asp Leu Leu Lys Lys Gly Tyr
        275                 280                 285

Asn Thr Leu Gln Ile Gln Gln Ser Gly Arg Trp Ser Ser Gly Ala Met
        290                 295                 300

Val Ala Arg Tyr Gly Arg Ala Ile Leu Ala Arg Asp Gly Ala Met Ala
305                 310                 315                 320

His Ser Arg Val Lys
                325

<210> SEQ ID NO 78
<211> LENGTH: 321
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Asp Glu Val Arg Lys Asn Leu Met Asp Met Phe Arg Asp Arg Gln Ala
1               5                   10                  15

Phe Ser Glu His Thr Trp Lys Met Leu Leu Ser Val Cys Arg Ser Trp
            20                  25                  30
```

-continued

```
Ala Ala Trp Cys Lys Leu Asn Asn Arg Lys Trp Phe Pro Ala Glu Pro
        35                  40                  45
Glu Asp Val Arg Asp Tyr Leu Leu Tyr Leu Gln Ala Arg Gly Leu Ala
    50                  55                  60
Val Lys Thr Ile Gln Gln His Leu Gly Gln Leu Asn Met Leu His Arg
65                      70                  75                  80
Arg Ser Gly Leu Pro Arg Pro Ser Asp Ser Asn Ala Val Ser Leu Val
                85                  90                  95
Met Arg Arg Ile Arg Lys Glu Asn Val Asp Ala Gly Glu Arg Ala Lys
                100                 105                 110
Gln Ala Leu Ala Phe Glu Arg Thr Asp Phe Asp Gln Val Arg Ser Leu
            115                 120                 125
Met Glu Asn Ser Asp Arg Cys Gln Asp Ile Arg Asn Leu Ala Phe Leu
    130                 135                 140
Gly Ile Ala Tyr Asn Thr Leu Leu Lys Ile Ala Glu Ile Ala Arg Ile
145                 150                 155                 160
Arg Val Lys Asp Ile Ser Arg Thr Asp Gly Gly Arg Met Leu Ile His
                165                 170                 175
Ile Gly Arg Thr Lys Thr Leu Val Ser Thr Ala Gly Val Glu Lys Ala
            180                 185                 190
Leu Ser Leu Gly Val Thr Lys Leu Val Glu Arg Trp Ile Ser Val Ser
        195                 200                 205
Gly Val Ala Asp Asp Pro Asn Asn Tyr Leu Phe Cys Arg Val Arg Lys
    210                 215                 220
Asn Gly Val Ala Ala Pro Ser Ala Thr Ser Gln Leu Ser Thr Arg Ala
225                 230                 235                 240
Leu Glu Gly Ile Phe Glu Ala Thr His Arg Leu Ile Tyr Gly Ala Lys
                245                 250                 255
Asp Asp Ser Gly Gln Arg Tyr Leu Ala Trp Ser Gly His Ser Ala Arg
            260                 265                 270
Val Gly Ala Ala Arg Asp Met Ala Arg Ala Gly Val Ser Ile Pro Glu
        275                 280                 285
Ile Met Gln Ala Gly Gly Trp Thr Asn Val Asn Ile Val Met Asn Tyr
    290                 295                 300
Ile Arg Asn Leu Asp Ser Glu Thr Gly Ala Met Val Arg Leu Leu Glu
305                 310                 315                 320
Asp
```